US010125369B2

(12) United States Patent
Borodovsky et al.

(10) Patent No.: US 10,125,369 B2
(45) Date of Patent: Nov. 13, 2018

(54) PCSK9 IRNA COMPOSITIONS AND METHODS OF USE THEREOF

(71) Applicant: Alnylam Pharmaceuticals, Inc., Cambridge, MA (US)

(72) Inventors: Anna Borodovsky, Melrose, MA (US); Kallanthottathil G. Rajeev, Wayland, MA (US); Kevin Fitzgerald, Brookline, MA (US); Maria Frank-Kamenetsky, Brookline, MA (US); William Querbes, Boston, MA (US); Martin Maier, Belmont, MA (US); Klaus Charisse, Acton, MA (US); Satyanarayana Kuchimanchi, Acton, MA (US); Muthiah Manoharan, Weston, MA (US); Stuart Milstein, Arlington, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 203 days.

(21) Appl. No.: 14/650,128

(22) PCT Filed: Dec. 5, 2013

(86) PCT No.: PCT/US2013/073349
§ 371 (c)(1),
(2) Date: Jun. 5, 2015

(87) PCT Pub. No.: WO2014/089313
PCT Pub. Date: Jun. 12, 2014

(65) Prior Publication Data

US 2016/0017335 A1 Jan. 21, 2016

Related U.S. Application Data

(60) Provisional application No. 61/892,188, filed on Oct. 17, 2013, provisional application No. 61/886,916,
(Continued)

(51) Int. Cl.

| | |
|---|---|
| *C07H 21/04* | (2006.01) |
| *A61K 48/00* | (2006.01) |
| *C12N 15/11* | (2006.01) |
| *C12N 15/113* | (2010.01) |
| *A61K 31/713* | (2006.01) |
| *A61K 47/54* | (2017.01) |

(52) U.S. Cl.
CPC ........ *C12N 15/1137* (2013.01); *A61K 31/713* (2013.01); *A61K 47/549* (2017.08);
(Continued)

(58) Field of Classification Search
CPC ........ C12N 2310/315; C12N 2310/321; C12N 2310/3533; A61K 31/713
(Continued)

(56) References Cited

U.S. PATENT DOCUMENTS 7,150,970 B2 12/2006 Trask et al.
7,491,805 B2 2/2009 Vargeese et al.
(Continued)

FOREIGN PATENT DOCUMENTS

WO WO-2004/045543 A2 6/2004
WO WO 2005/003350 A2 1/2005
(Continued)

OTHER PUBLICATIONS

International Search Report and Written Opinion from PCT/US2013/073349, dated Mar. 6, 2014.
(Continued)

*Primary Examiner* — Terra C Gibbs
(74) *Attorney, Agent, or Firm* — McCarter & English, LLP; Maria Laccotripe Zacharakis; Deborah L. Nagle

(57) ABSTRACT

The invention relates to RNAi agents, e.g., double-stranded RNAi agents, targeting the PCSK9 gene, and methods of using such RNAi agents to inhibit expression of PCSK9 and methods of treating subjects having a lipid disorder, such as a hyperlipidemia.

85 Claims, 20 Drawing Sheets

Specification includes a Sequence Listing.

Related U.S. Application Data filed on Oct. 4, 2013, provisional application No. 61/793,530, filed on Mar. 15, 2013, provisional application No. 61/733,518, filed on Dec. 5, 2012.

(52) U.S. Cl.
CPC ........ *C12Y 304/21* (2013.01); *C12N 2310/14* (2013.01); *C12N 2310/312* (2013.01); *C12N 2310/315* (2013.01); *C12N 2310/321* (2013.01); *C12N 2310/322* (2013.01); *C12N 2310/343* (2013.01); *C12N 2310/351* (2013.01); *C12N 2310/3515* (2013.01); *C12N 2320/35* (2013.01)

(58) Field of Classification Search
USPC .................................. 536/23.1, 24.5; 514/44
See application file for complete search history.

(56) References Cited

U.S. PATENT DOCUMENTS

| | | | |
|---|---|---|---|
| 7,507,811 | B2 | 3/2009 | Khvorova et al. |
| 7,511,132 | B2 | 3/2009 | Khvorova et al. |
| 7,514,550 | B2 | 4/2009 | Khvorova et al. |
| 7,521,191 | B2 | 4/2009 | Khvorova et al. |
| 7,541,453 | B2 | 6/2009 | Khvorova et al. |
| 7,550,572 | B2 | 6/2009 | Khvorova et al. |
| 7,569,684 | B2 | 8/2009 | Khvorova et al. |
| 7,576,196 | B2 | 8/2009 | Khvorova et al. |
| 7,576,197 | B2 | 8/2009 | Khvorova et al. |
| 7,579,457 | B2 | 8/2009 | Khvorova et al. |
| 7,579,458 | B2 | 8/2009 | Khvorova et al. |
| 7,582,746 | B2 | 9/2009 | Khvorova et al. |
| 7,582,747 | B2 | 9/2009 | Khvorova et al. |
| 7,589,191 | B2 | 9/2009 | Khvorova et al. |
| 7,592,442 | B2 | 9/2009 | Khvorova et al. |
| 7,592,443 | B2 | 9/2009 | Khvorova et al. |
| 7,592,444 | B2 | 9/2009 | Khvorova et al. |
| 7,595,388 | B2 | 9/2009 | Khvorova et al. |
| 7,595,389 | B2 | 9/2009 | Khvorova et al. |
| 7,598,369 | B2 | 10/2009 | Khvorova et al. |
| 7,598,370 | B2 | 10/2009 | Khvorova et al. |
| 7,605,251 | B2 | 10/2009 | Tan et al. |
| 7,605,252 | B2 | 10/2009 | Khvorova et al. |
| 7,608,706 | B2 | 10/2009 | Khvorova et al. |
| 7,608,707 | B2 | 10/2009 | Khvorova et al. |
| 7,612,196 | B2 | 11/2009 | Khvorova et al. |
| 7,615,541 | B2 | 11/2009 | Khvorova et al. |
| 7,619,081 | B2 | 11/2009 | Khvorova et al. |
| 7,632,938 | B2 | 12/2009 | Khvorova et al. |
| 7,632,939 | B2 | 12/2009 | Khvorova et al. |
| 7,635,770 | B2 | 12/2009 | Khvorova et al. |
| 7,635,771 | B2 | 12/2009 | Khvorova et al. |
| 7,638,621 | B2 | 12/2009 | Khvorova et al. |
| 7,638,622 | B2 | 12/2009 | Khvorova et al. |
| 7,642,349 | B2 | 1/2010 | Khvorova et al. |
| 7,645,869 | B2 | 1/2010 | Khvorova et al. |
| 7,645,870 | B2 | 1/2010 | Khvorova et al. |
| 7,655,788 | B2 | 2/2010 | Khvorova et al. |
| 7,655,789 | B2 | 2/2010 | Khvorova et al. |
| 7,662,950 | B2 | 2/2010 | Khvorova et al. |
| 7,666,853 | B2 | 2/2010 | Khvorova et al. |
| 7,674,896 | B2 | 3/2010 | Khvorova et al. |
| 7,678,896 | B2 | 3/2010 | Khvorova et al. |
| 7,691,997 | B2 | 4/2010 | Khvorova et al. |
| 7,691,998 | B2 | 4/2010 | Khvorova et al. |
| 7,696,344 | B2 | 4/2010 | Khvorova et al. |
| 7,709,629 | B2 | 5/2010 | Khvorova et al. |
| 7,737,267 | B2 | 6/2010 | Khvorova et al. |
| 7,741,470 | B2 | 6/2010 | Khvorova et al. |
| 7,745,610 | B2 | 6/2010 | Khvorova et al. |
| 7,745,611 | B2 | 6/2010 | Khvorova et al. |
| 7,745,612 | B2 | 6/2010 | Khvorova et al. |
| 7,781,575 | B2 | 8/2010 | Khvorova et al. |
| 7,795,420 | B2 | 9/2010 | Khvorova et al. |
| 7,795,421 | B2 | 9/2010 | Khvorova et al. |
| 7,803,933 | B2 | 9/2010 | Khvorova et al. |
| 7,807,819 | B2 | 10/2010 | Khvorova et al. |
| 7,807,820 | B2 | 10/2010 | Khvorova et al. |
| 7,816,512 | B2 | 10/2010 | Khvorova et al. |
| 7,820,809 | B2 | 10/2010 | Khvorova et al. |
| 7,829,696 | B2 | 11/2010 | Khvorova et al. |
| 7,833,989 | B2 | 11/2010 | Khvorova et al. |
| 7,833,992 | B2 | 11/2010 | Vargeese et al. |
| 7,834,170 | B2 | 11/2010 | Khvorova et al. |
| 7,855,186 | B2 | 12/2010 | Khvorova et al. |
| 7,893,247 | B2 | 2/2011 | Khvorova et al. |
| 7,897,754 | B2 | 3/2011 | Khvorova et al. |
| 7,935,813 | B2 | 5/2011 | Khvorova et al. |
| 7,951,935 | B2 | 5/2011 | Khvorova et al. |
| 7,977,471 | B2 | 7/2011 | Khvorova et al. |
| 7,985,854 | B2 | 7/2011 | Khvorova et al. |
| 7,999,097 | B2 | 8/2011 | Khvorova et al. |
| 8,008,474 | B2 | 8/2011 | Khvorova et al. |
| 8,013,145 | B2 | 9/2011 | Khvorova et al. |
| 8,022,198 | B2 | 9/2011 | Khvorova et al. |
| 8,022,199 | B2 | 9/2011 | Khvorova et al. |
| 8,030,474 | B2 | 10/2011 | Khvorova et al. |
| 8,030,476 | B2 | 10/2011 | Khvorova et al. |
| 8,039,610 | B2 | 10/2011 | Khvorova et al. |
| 8,067,576 | B2 | 11/2011 | Khvorova et al. |
| 8,071,754 | B2 | 12/2011 | Khvorova et al. |
| 8,084,437 | B2 | 12/2011 | Freier et al. |
| 8,090,542 | B2 | 1/2012 | Khvorova et al. |
| 8,093,222 | B2 | 1/2012 | Freier et al. |
| 8,093,370 | B2 | 1/2012 | Khvorova et al. |
| 8,106,022 | B2 | 1/2012 | Manoharan et al. |
| 8,138,329 | B2 | 3/2012 | Khvorova et al. |
| 8,198,427 | B1 | 6/2012 | Khvorova et al. |
| 8,202,979 | B2 | 6/2012 | McSwiggen et al. |
| 8,217,162 | B2 | 7/2012 | Khvorova et al. |
| 8,222,222 | B2 | 7/2012 | Tan et al. |
| 8,222,395 | B2 | 7/2012 | Khvorova et al. |
| 8,222,396 | B2 | 7/2012 | Khvorova et al. |
| 8,232,385 | B2 | 7/2012 | Khvorova et al. |
| 8,232,386 | B2 | 7/2012 | Khvorova et al. |
| 8,236,942 | B2 | 8/2012 | Khvorova et al. |
| 8,247,169 | B2 | 8/2012 | Khvorova et al. |
| 8,268,985 | B2 | 9/2012 | Khvorova et al. |
| 8,273,866 | B2 | 9/2012 | McSwiggen et al. |
| 8,273,869 | B2 | 9/2012 | Fitzgerald et al. |
| 8,293,887 | B2 | 10/2012 | Khvorova et al. |
| 8,304,528 | B2 | 11/2012 | Khvorova et al. |
| 8,314,229 | B2 | 11/2012 | Khvorova et al. |
| 8,399,654 | B2 | 3/2013 | Khvorova et al. |
| 8,426,579 | B2 | 4/2013 | Khvorova et al. |
| 8,445,667 | B2 | 5/2013 | Khvorova et al. |
| 8,445,668 | B2 | 5/2013 | Khvorova et al. |
| 8,450,467 | B2 | 5/2013 | Manoharan et al. |
| 8,461,326 | B2 | 6/2013 | Khvorova et al. |
| 8,575,329 | B2 | 11/2013 | Khvorova et al. |
| 8,598,139 | B2 | 12/2013 | Fitzgerald et al. |
| 8,633,306 | B2 | 1/2014 | Khvorova et al. |
| 8,658,784 | B2 | 2/2014 | Khvorova et al. |
| 8,658,785 | B1 | 2/2014 | Khvorova et al. |
| 8,664,190 | B2 | 3/2014 | Freier et al. |
| 8,759,284 | B2 | 6/2014 | Imran |
| 8,809,292 | B2 | 8/2014 | Tan et al. |
| 8,828,956 | B2 | 9/2014 | Manoharan et al. |
| 8,883,998 | B2 | 11/2014 | Khvorava et al. |
| 8,907,077 | B2 | 12/2014 | Khvorova et al. |
| 8,937,172 | B2 | 1/2015 | Khvorova et al. |
| 9,228,186 | B2 | 1/2016 | Khvorova et al. |
| 9,260,718 | B2 | 2/2016 | Tan et al. |
| 9,370,582 | B2 | 6/2016 | Manoharan et al. |
| 9,399,775 | B2 | 7/2016 | Rajeev et al. |
| 9,513,606 | B1 | 12/2016 | Larsen et al. |
| 9,796,974 | B2 | 10/2017 | Rajeev et al. |
| 2005/0032733 | A1 | 2/2005 | McSwiggen et al. |
| 2005/0070497 | A1 | 3/2005 | McSwiggen et al. |
| 2005/0079610 | A1 | 4/2005 | Polisky et al. |
| 2005/0119211 | A1 | 6/2005 | Chowrira et al. |
| 2005/0119212 | A1 | 6/2005 | Haeberli et al. |
| 2005/0124566 | A1 | 6/2005 | Robin et al. |
| 2005/0124567 | A1 | 6/2005 | McSwiggen et al. |

(56) References Cited

U.S. PATENT DOCUMENTS

| | | | |
|---|---|---|---|
| 2005/0124568 | A1 | 6/2005 | Usman et al. |
| 2005/0124569 | A1 | 6/2005 | Guerciolini et al. |
| 2005/0130181 | A1 | 6/2005 | McSwiggen |
| 2005/0136436 | A1 | 6/2005 | McSwiggen et al. |
| 2005/0137153 | A1 | 6/2005 | McSwiggen et al. |
| 2005/0137155 | A1 | 6/2005 | McSwiggen et al. |
| 2005/0143333 | A1 | 6/2005 | Richards et al. |
| 2005/0153914 | A1 | 7/2005 | McSwiggen et al. |
| 2005/0153916 | A1 | 7/2005 | McSwiggen et al. |
| 2005/0158735 | A1 | 7/2005 | McSwiggen et al. |
| 2005/0159376 | A1 | 7/2005 | McSwiggen et al. |
| 2005/0159378 | A1 | 7/2005 | McSwiggen et al. |
| 2005/0159379 | A1 | 7/2005 | McSwiggen et al. |
| 2005/0159380 | A1 | 7/2005 | Guerciolini et al. |
| 2005/0159381 | A1 | 7/2005 | McSwiggen et al. |
| 2005/0159382 | A1 | 7/2005 | McSwiggen et al. |
| 2005/0164224 | A1 | 7/2005 | McSwiggen et al. |
| 2005/0164966 | A1 | 7/2005 | McSwiggen et al. |
| 2005/0164967 | A1 | 7/2005 | McSwiggen et al. |
| 2005/0164968 | A1 | 7/2005 | McSwiggen et al. |
| 2005/0170371 | A1 | 8/2005 | McSwiggen et al. |
| 2005/0171040 | A1 | 8/2005 | Polisky et al. |
| 2005/0176024 | A1 | 8/2005 | McSwiggen et al. |
| 2005/0176025 | A1 | 8/2005 | McSwiggen et al. |
| 2005/0176663 | A1 | 8/2005 | McSwiggen et al. |
| 2005/0176664 | A1 | 8/2005 | Richards et al. |
| 2005/0176665 | A1 | 8/2005 | McSwiggen |
| 2005/0176666 | A1 | 8/2005 | Richards et al. |
| 2005/0182006 | A1 | 8/2005 | McSwiggen et al. |
| 2005/0182007 | A1 | 8/2005 | McSwiggen et al. |
| 2005/0182008 | A1 | 8/2005 | McSwiggen et al. |
| 2005/0182009 | A1 | 8/2005 | McSwiggen et al. |
| 2005/0187174 | A1 | 8/2005 | Richards et al. |
| 2005/0191618 | A1 | 9/2005 | McSwiggen et al. |
| 2005/0196765 | A1 | 9/2005 | McSwiggen et al. |
| 2005/0196767 | A1 | 9/2005 | McSwiggen et al. |
| 2005/0196781 | A1 | 9/2005 | Robin et al. |
| 2005/0203040 | A1 | 9/2005 | Richards et al. |
| 2005/0209179 | A1 | 9/2005 | McSwiggen et al. |
| 2005/0209180 | A1 | 9/2005 | Jadhav et al. |
| 2005/0222064 | A1 | 10/2005 | Vargeese et al. |
| 2005/0222066 | A1 | 10/2005 | Richards et al. |
| 2005/0227935 | A1 | 10/2005 | McSwiggen et al. |
| 2005/0227936 | A1 | 10/2005 | McSwiggen et al. |
| 2005/0233344 | A1 | 10/2005 | McSwiggen et al. |
| 2005/0233997 | A1 | 10/2005 | Richards et al. |
| 2005/0233998 | A1 | 10/2005 | Jadhav et al. |
| 2005/0239731 | A1 | 10/2005 | McSwiggen et al. |
| 2005/0255487 | A1 | 11/2005 | Khvorova et al. |
| 2005/0256068 | A1 | 11/2005 | McSwiggen et al. |
| 2005/0260620 | A1 | 11/2005 | Christiano et al. |
| 2005/0261219 | A1 | 11/2005 | Richards et al. |
| 2005/0267058 | A1 | 12/2005 | McSwiggen et al. |
| 2005/0277133 | A1 | 12/2005 | McSwiggen |
| 2005/0277608 | A1 | 12/2005 | Guerciolini et al. |
| 2005/0282188 | A1 | 12/2005 | Haeberli et al. |
| 2005/0287128 | A1 | 12/2005 | Guerciolini et al. |
| 2005/0288242 | A1 | 12/2005 | McSwiggen |
| 2006/0019913 | A1 | 1/2006 | McSwiggen et al. |
| 2006/0019917 | A1 | 1/2006 | Guerciolini et al. |
| 2006/0025361 | A1 | 2/2006 | McSwiggen et al. |
| 2006/0142225 | A1 | 6/2006 | McSwiggen |
| 2006/0142226 | A1 | 6/2006 | Polisky et al. |
| 2006/0148743 | A1 | 7/2006 | Jadhav et al. |
| 2006/0211642 | A1 | 9/2006 | McSwiggen et al. |
| 2006/0216747 | A1 | 9/2006 | McSwiggen et al. |
| 2006/0217331 | A1 | 9/2006 | Vargeese et al. |
| 2006/0217332 | A1 | 9/2006 | Vargeese et al. |
| 2006/0241075 | A1 | 10/2006 | McSwiggen |
| 2006/0247194 | A1 | 11/2006 | McSwiggen et al. |
| 2006/0270623 | A1 | 11/2006 | McSwiggen |
| 2006/0276422 | A1 | 12/2006 | Usman et al. |
| 2006/0287267 | A1 | 12/2006 | Vaish et al. |
| 2007/0010561 | A1 | 1/2007 | Brown et al. |
| 2007/0032441 | A1 | 2/2007 | McSwiggen et al. |
| 2007/0039072 | A1 | 2/2007 | Khvorova et al. |
| 2007/0042983 | A1 | 2/2007 | Haeberli et al. |
| 2007/0042986 | A1 | 2/2007 | Trask et al. |
| 2007/0049543 | A1 | 3/2007 | McSwiggen et al. |
| 2007/0088155 | A1 | 4/2007 | Khvorova et al. |
| 2007/0093437 | A1 | 4/2007 | Chowrira et al. |
| 2007/0093653 | A1 | 4/2007 | Khvorova et al. |
| 2007/0128641 | A1 | 6/2007 | Khvorova et al. |
| 2007/0160980 | A1 | 7/2007 | Haeberli et al. |
| 2007/0161596 | A1 | 7/2007 | McSwiggen et al. |
| 2007/0173473 | A1 | 7/2007 | McSwiggen et al. |
| 2007/0179104 | A1 | 8/2007 | McSwiggen |
| 2007/0179286 | A1 | 8/2007 | Khvorova et al. |
| 2007/0185043 | A1 | 8/2007 | McSwiggen et al. |
| 2007/0185049 | A1 | 8/2007 | Jadhav et al. |
| 2007/0185317 | A1 | 8/2007 | Khvorova et al. |
| 2007/0213520 | A1 | 9/2007 | Khvorova et al. |
| 2007/0213521 | A1 | 9/2007 | Khvorova et al. |
| 2007/0219362 | A1 | 9/2007 | Khvorova et al. |
| 2007/0232797 | A1 | 10/2007 | Khvorova et al. |
| 2007/0238868 | A1 | 10/2007 | Khvorova et al. |
| 2007/0244312 | A1 | 10/2007 | Khvorova et al. |
| 2007/0249819 | A1 | 10/2007 | Khvorova et al. |
| 2007/0255046 | A1 | 11/2007 | Khvorova et al. |
| 2007/0255047 | A1 | 11/2007 | Khvorova et al. |
| 2007/0255048 | A1 | 11/2007 | Khvorova et al. |
| 2007/0255050 | A1 | 11/2007 | Khvorova et al. |
| 2007/0255051 | A1 | 11/2007 | Khvorova et al. |
| 2007/0255052 | A1 | 11/2007 | Khvorova et al. |
| 2007/0260047 | A1 | 11/2007 | Khvorova et al. |
| 2007/0260048 | A1 | 11/2007 | Khvorova et al. |
| 2007/0260049 | A1 | 11/2007 | Khvorova et al. |
| 2007/0260050 | A1 | 11/2007 | Khvorova et al. |
| 2007/0260051 | A1 | 11/2007 | Khvorova et al. |
| 2007/0260052 | A1 | 11/2007 | Khvorova et al. |
| 2007/0265437 | A1 | 11/2007 | Khvorova et al. |
| 2007/0270579 | A1 | 11/2007 | Jadhav et al. |
| 2007/0276135 | A1 | 11/2007 | Khvorova et al. |
| 2007/0287833 | A1 | 12/2007 | Khvorova et al. |
| 2007/0293664 | A1 | 12/2007 | Khvorova et al. |
| 2007/0299253 | A1 | 12/2007 | Khvorova et al. |
| 2008/0015114 | A1 | 1/2008 | Khvorova et al. |
| 2008/0027215 | A1 | 1/2008 | Khvorova et al. |
| 2008/0027216 | A1 | 1/2008 | Khvorova et al. |
| 2008/0033156 | A1 | 2/2008 | Vargeese et al. |
| 2008/0039617 | A1 | 2/2008 | Khvorova et al. |
| 2008/0045703 | A1 | 2/2008 | Khvorova et al. |
| 2008/0071073 | A1 | 3/2008 | Khvorova et al. |
| 2008/0076908 | A1 | 3/2008 | Khvorova et al. |
| 2008/0081904 | A1 | 4/2008 | Khvorova et al. |
| 2008/0085997 | A1 | 4/2008 | Khvorova et al. |
| 2008/0086002 | A1 | 4/2008 | Khvorova et al. |
| 2008/0091001 | A1 | 4/2008 | Khvorova et al. |
| 2008/0091002 | A1 | 4/2008 | Khvorova et al. |
| 2008/0091003 | A1 | 4/2008 | Khvorova et al. |
| 2008/0091004 | A1 | 4/2008 | Khvorova et al. |
| 2008/0097089 | A1 | 4/2008 | Khvorova et al. |
| 2008/0097091 | A1 | 4/2008 | Khvorova et al. |
| 2008/0097092 | A1 | 4/2008 | Khvorova et al. |
| 2008/0108802 | A1 | 5/2008 | Khvorova et al. |
| 2008/0108803 | A1 | 5/2008 | Khvorova et al. |
| 2008/0113371 | A1 | 5/2008 | Khvorova et al. |
| 2008/0113372 | A1 | 5/2008 | Khvorova et al. |
| 2008/0113374 | A1 | 5/2008 | Khvorova et al. |
| 2008/0113930 | A1 * | 5/2008 | Tan .................... C12N 15/1137 514/44 A |
| 2008/0114162 | A1 | 5/2008 | Khvorova et al. |
| 2008/0161256 | A1 | 7/2008 | Morrisey et al. |
| 2008/0161547 | A1 | 7/2008 | Khvorova et al. |
| 2008/0188430 | A1 | 8/2008 | Usman et al. |
| 2008/0188648 | A1 | 8/2008 | Khvorova et al. |
| 2008/0207884 | A1 | 8/2008 | Khvorova et al. |
| 2008/0221316 | A1 | 9/2008 | Khvorova et al. |
| 2008/0221317 | A1 | 9/2008 | Khvorova et al. |
| 2008/0249040 | A1 | 10/2008 | McSwiggen et al. |
| 2008/0249294 | A1 | 10/2008 | Haeberli et al. |
| 2008/0268457 | A1 | 10/2008 | Khvorova et al. |
| 2008/0293595 | A1 | 11/2008 | Khvorova et al. |
| 2008/0300395 | A1 | 12/2008 | Khvorova et al. |

(56) References Cited

U.S. PATENT DOCUMENTS

| | | | |
|---|---|---|---|
| 2008/0306015 | A1 | 12/2008 | Khvorova et al. |
| 2009/0005547 | A1 | 1/2009 | Khvorova et al. |
| 2009/0005548 | A1 | 1/2009 | Khvorova et al. |
| 2009/0023907 | A1 | 1/2009 | Khvorova et al. |
| 2009/0023908 | A1 | 1/2009 | Khvorova et al. |
| 2009/0030190 | A1 | 1/2009 | Khvorova et al. |
| 2009/0043084 | A1 | 2/2009 | Khvorova et al. |
| 2009/0093431 | A1 | 4/2009 | McSwiggen et al. |
| 2009/0093435 | A1 | 4/2009 | McSwiggen et al. |
| 2009/0093436 | A1 | 4/2009 | McSwiggen et al. |
| 2009/0093437 | A1 | 4/2009 | McSwiggen et al. |
| 2009/0093438 | A1 | 4/2009 | McSwiggen et al. |
| 2009/0093439 | A1 | 4/2009 | McSwiggen et al. |
| 2009/0099115 | A1 | 4/2009 | McSwiggen et al. |
| 2009/0099116 | A1 | 4/2009 | McSwiggen et al. |
| 2009/0099117 | A1 | 4/2009 | McSwiggen et al. |
| 2009/0099118 | A1 | 4/2009 | McSwiggen et al. |
| 2009/0099119 | A1 | 4/2009 | McSwiggen et al. |
| 2009/0099121 | A1 | 4/2009 | McSwiggen et al. |
| 2009/0105178 | A1 | 4/2009 | McSwiggen et al. |
| 2009/0137507 | A1 | 5/2009 | McSwiggen et al. |
| 2009/0137508 | A1 | 5/2009 | McSwiggen et al. |
| 2009/0137509 | A1 | 5/2009 | McSwiggen et al. |
| 2009/0137510 | A1 | 5/2009 | McSwiggen et al. |
| 2009/0137511 | A1 | 5/2009 | McSwiggen et al. |
| 2009/0137512 | A1 | 5/2009 | McSwiggen et al. |
| 2009/0137513 | A1 | 5/2009 | McSwiggen et al. |
| 2009/0143324 | A1 | 6/2009 | McSwiggen et al. |
| 2009/0143325 | A1 | 6/2009 | McSwiggen et al. |
| 2009/0149408 | A1 | 6/2009 | McSwiggen et al. |
| 2009/0156533 | A1 | 6/2009 | McSwiggen et al. |
| 2009/0163701 | A1 | 6/2009 | Khvorova et al. |
| 2009/0182134 | A1 | 7/2009 | Khvorova et al. |
| 2009/0190918 | A1 | 7/2009 | Chang |
| 2009/0192105 | A1 | 7/2009 | McSwiggen et al. |
| 2009/0227780 | A1 | 9/2009 | Khvorova et al. |
| 2009/0239931 | A1 | 9/2009 | McSwiggen et al. |
| 2009/0253772 | A1 | 10/2009 | McSwiggen et al. |
| 2009/0253773 | A1 | 10/2009 | McSwiggen et al. |
| 2009/0253774 | A1 | 10/2009 | McSwiggen et al. |
| 2009/0264504 | A1 | 10/2009 | McSwiggen et al. |
| 2009/0275640 | A1 | 11/2009 | Khvorova et al. |
| 2009/0281164 | A1 | 11/2009 | McSwiggen et al. |
| 2009/0291497 | A1 | 11/2009 | Khvorova et al. |
| 2009/0299045 | A1 | 12/2009 | Richards et al. |
| 2009/0306182 | A1 | 12/2009 | McSwiggen et al. |
| 2009/0306184 | A1 | 12/2009 | McSwiggen et al. |
| 2010/0004141 | A1 | 1/2010 | Khvorova et al. |
| 2010/0004142 | A1 | 1/2010 | Khvorova et al. |
| 2010/0056395 | A1 | 3/2010 | Khvorova et al. |
| 2010/0093835 | A1 | 4/2010 | McSwiggen et al. |
| 2010/0099578 | A1 | 4/2010 | Khvorova et al. |
| 2010/0099743 | A1 | 4/2010 | McSwiggen et al. |
| 2010/0099744 | A1 | 4/2010 | McSwiggen et al. |
| 2010/0113307 | A1 | 5/2010 | Khvorova et al. |
| 2010/0113564 | A1 | 5/2010 | McSwiggen et al. |
| 2010/0130592 | A1 | 5/2010 | McSwiggen et al. |
| 2010/0144842 | A1 | 6/2010 | McSwiggen et al. |
| 2010/0144851 | A1 | 6/2010 | McSwiggen et al. |
| 2010/0145038 | A1 | 6/2010 | McSwiggen et al. |
| 2010/0145039 | A1 | 6/2010 | Khvorova et al. |
| 2010/0152064 | A1 | 6/2010 | Khvorova et al. |
| 2010/0173976 | A1 | 7/2010 | McSwiggen et al. |
| 2010/0184824 | A1 | 7/2010 | McSwiggen et al. |
| 2010/0184825 | A1 | 7/2010 | McSwiggen et al. |
| 2010/0227911 | A1 | 9/2010 | McSwiggen et al. |
| 2010/0227912 | A1 | 9/2010 | McSwiggen et al. |
| 2010/0228018 | A1 | 9/2010 | McSwiggen et al. |
| 2010/0240730 | A1 | 9/2010 | Beigelman et al. |
| 2010/0248990 | A1 | 9/2010 | Khvorova et al. |
| 2010/0267587 | A1 | 10/2010 | Khvorova et al. |
| 2010/0311812 | A1 | 12/2010 | McSwiggen et al. |
| 2010/0317716 | A1 | 12/2010 | McSwiggen et al. |
| 2010/0317717 | A1 | 12/2010 | McSwiggen et al. |
| 2010/0331214 | A1 | 12/2010 | Khvorova et al. |
| 2011/0015251 | A1 | 1/2011 | McSwiggen et al. |
| 2011/0105363 | A1 | 5/2011 | Khvorova et al. |
| 2011/0160281 | A1 | 6/2011 | McSwiggen et al. |
| 2011/0313024 | A1 | 12/2011 | Beigelman et al. |
| 2011/0319297 | A1 | 12/2011 | Khvorova et al. |
| 2011/0319474 | A1 | 12/2011 | Khvorova et al. |
| 2012/0004403 | A1 | 1/2012 | Beigelman et al. |
| 2012/0015850 | A1 | 1/2012 | Khvorova et al. |
| 2012/0135892 | A1 | 5/2012 | Khvorova et al. |
| 2012/0252873 | A1 | 10/2012 | Khvorova et al. |
| 2012/0258888 | A1 | 10/2012 | Khvorova et al. |
| 2012/0258889 | A1 | 10/2012 | Khvorova et al. |
| 2012/0270751 | A1 | 10/2012 | Khvorova et al. |
| 2012/0283311 | A1 | 11/2012 | Khvorova et al. |
| 2013/0023446 | A1 | 1/2013 | Khvorova et al. |
| 2013/0059760 | A1 | 3/2013 | Khvorova et al. |
| 2013/0225447 | A1 | 8/2013 | Khvorova et al. |
| 2013/0225667 | A1 | 8/2013 | Khvorova et al. |
| 2013/0289094 | A1 | 10/2013 | Hinkle et al. |
| 2014/0121263 | A1 | 5/2014 | Fitzgerald et al. |
| 2014/0148362 | A1 | 5/2014 | Khvorova et al. |
| 2014/0194492 | A1 | 7/2014 | Freier et al. |
| 2014/0288158 | A1 | 9/2014 | Rajeev et al. |
| 2015/0167005 | A1 | 6/2015 | Freier et al. |
| 2016/0152973 | A1 | 6/2016 | Jadhav |
| 2016/0193242 | A1 | 7/2016 | Khvorova et al. |
| 2016/0194646 | A1 | 7/2016 | Khvorova et al. |
| 2016/0201058 | A1 | 7/2016 | Khvorova et al. |
| 2016/0201065 | A1 | 7/2016 | Khvorova et al. |
| 2016/0272975 | A1 | 9/2016 | Jadhav |
| 2016/0348117 | A1 | 12/2016 | Tan et al. |
| 2016/0354404 | A1 | 12/2016 | Hinkle et al. |
| 2016/0355817 | A1 | 12/2016 | Rajeev et al. |
| 2016/0369276 | A1 | 12/2016 | Khvorova et al. |
| 2016/0369278 | A1 | 12/2016 | Khvorova et al. |
| 2016/0369284 | A1 | 12/2016 | Khvorova et al. |
| 2017/0000815 | A1 | 1/2017 | Fitzgerald et al. |
| 2018/0008724 | A1 | 1/2018 | Rajeev et al. |

FOREIGN PATENT DOCUMENTS

| | | | | |
|---|---|---|---|---|
| WO | WO-2005/007854 | A2 | | 1/2005 |
| WO | WO-2005/007855 | A2 | | 1/2005 |
| WO | WO 2005/007859 | A2 | | 1/2005 |
| WO | WO-2005/014811 | A2 | | 2/2005 |
| WO | WO-2005/019453 | A2 | | 3/2005 |
| WO | WO-2005/028649 | A1 | | 3/2005 |
| WO | WO-2005/028650 | A2 | | 3/2005 |
| WO | WO-2005/035759 | A2 | | 4/2005 |
| WO | WO-2005/040379 | A2 | | 5/2005 |
| WO | WO-2005/044981 | A2 | | 5/2005 |
| WO | WO-2005/045032 | A2 | | 5/2005 |
| WO | WO-2005/045034 | A2 | | 5/2005 |
| WO | WO-2005/045035 | A2 | | 5/2005 |
| WO | WO-2005/045036 | A2 | | 5/2005 |
| WO | WO-2005/045037 | A2 | | 5/2005 |
| WO | WO 2005/045038 | A2 | | 5/2005 |
| WO | WO-2005/045039 | A2 | | 5/2005 |
| WO | WO-2005/045040 | A2 | | 5/2005 |
| WO | WO-2005/045041 | A2 | | 5/2005 |
| WO | WO-2005/105995 | A2 | | 11/2005 |
| WO | WO 2008049085 | A1 | * | 10/2007 |
| WO | WO-2008/066776 | A2 | | 6/2008 |
| WO | WO-2010/148013 | A2 | | 12/2010 |
| WO | WO-2012/058693 | A2 | | 5/2012 |
| WO | WO-2013/074974 | A2 | | 5/2013 |
| WO | WO 2017/035340 | A1 | | 3/2017 |

OTHER PUBLICATIONS

Positive Results from Alnylam's ALN-PCS Phase I Trial on Severe Hypercholesterolemia (Apr. 21, 2012) Retrieved from <https://www.news-medical.net/news/20120421/Positive-results-from-Alnylame28099s-ALN-PCS-Phase-I-trial-on-severe-hypercholesterolemia.aspx>.

* cited by examiner

| Duplex | Sense | | AS | | Chemistry |
|---|---|---|---|---|---|
| AD-53815.5 | A-110695.11 | CfuAfgAfcCfuGfUfUfuUfgCfuUfuUfgUfL96 | A-109545.18 | aCfaAfaAfgCfaAfaacAfgGfuCfuAfgsAfsa | 21/23 (Parent) |
| AD-56651.1 | A-115523.1 | (iC)uAfgAfcCfuGfUfUfuUfgCfuUfuUfgUfL96 | A-115524.1 | (iA)CfaAfaAfgCfaAfaacAfgGfuCfuAfgsAfs(iA) | 21/23 + inverted base |
| AD-56610.1 | A-115523.2 | (iC)uAfgAfcCfuGfUfUfuUfgCfuUfuUfgUfL96 | A-115525.1 | aCfaAfaAfgCfaAfaacAfgGfuCfuAfgsAfs(iA) | 21/23 + inverted base |
| AD-56634.1 | A-115529.1 | CbuAfgAfcCfuGfUfUfuUfgCfuUfuUfgUfL96 | A-115530.1 | AbCfaAfaAfgCfaAfaacAfgGfuCfuAfgsAfsAb | 21/23 + L-Sugar |
| AD-56652.1 | A-115533.1 | CbuAfgAfcCfuGfUfUfuUfgCfuUfuugUfL96 | A-115532.2 | acaAfaAfgcaAfaacAfgGfuCfuAfgsAfsAb | 21/23 + L-Sugar |
| AD-56663.1 | A-115552.1 | CfuAfgAfcCfuGfUfUfuUfgCfuuuUfgUfL96 | A-115553.1 | aCfaAfAfAfgCfaAfaacAfgGfuCfuAfgsAfsa | 21/23 |
| AD-56658.1 | A-115564.1 | CfuAfgAfcCfuGfUfUfuUfgCfuUfUfUfgUfL96 | A-115565.1 | aCfaaaAfgCfaAfaacAfgGfuCfuAfgsAfsa | 21/23 |
| AD-56676.1 | A-115584.1 | AfgAfcCfuGfUfUfuUfgCfuuuUfgUfL96 | A-115585.1 | aCfaAfAfAfgCfaAfaacAfgGfuCfusAfsg | 19/21 |
| AD-56666.1 | A-115596.1 | AfgAfcCfuGfUfUfuUfgCfuUfUfUfgUfL96 | A-115597.1 | aCfaaaAfgCfaAfaacAfgGfuCfusAfsg | 19/21 |
| AD-57928 | A-117428 | CfsusAfgAfcCfuGfUfUfuUfgCfuUfuUfgUfL96 | A-117429 | asCfsaAfaAfgCfaAfaacAfgGfuCfuAfgsasa | 6 PS version of parent |

| Duplex | Sense ID | Sense | AS ID | Antisense |
|---|---|---|---|---|
| AD-57928 (parent) | A-117428 | CfsusAfgAfcCfuGfUfUfuUfgCfuUfuUfgUfL96 | A-117429 | asCfsaAfaAfgCfaAfaacAfgGfuCfuAfgsasa |
| AD-59849 | A-121244 | CfsusAfgAfcCfuGfUfUfuUfgcuuuuguL96 | A-121239 | asCfsaAfaagCfaAfaacAfgGfucuAfgsasa |
| AD-60688 | A-120188 | csusagacCfuGfuuuugcuuuuguL96 | A-121239 | asCfsaAfaagCfaAfaacAfgGfucuAfgsasa |
| AD-59223 | A-120188 | csusagacCfuGfuuuugcuuuuguL96 | A-120190 | asCfsaAfAfAfgCfaAfaAfcAfgGfuCfuagsasa |
| AD-60212 | A-122088 | csusagacCfuGfudTuugcuuuuguL96 | A-120190 | asCfsaAfAfAfgCfaAfaAfcAfgGfuCfuagsasa |
| AD-59228 | A-120197 | CfsusAfgAfcCfuGfUfUfuUfgCfsuUfsuUfsgsUfsL96 | A-120202 | asCfsaAfaAfsgCfaAfaacAfgGfuCfsuAfgsasa |

B.

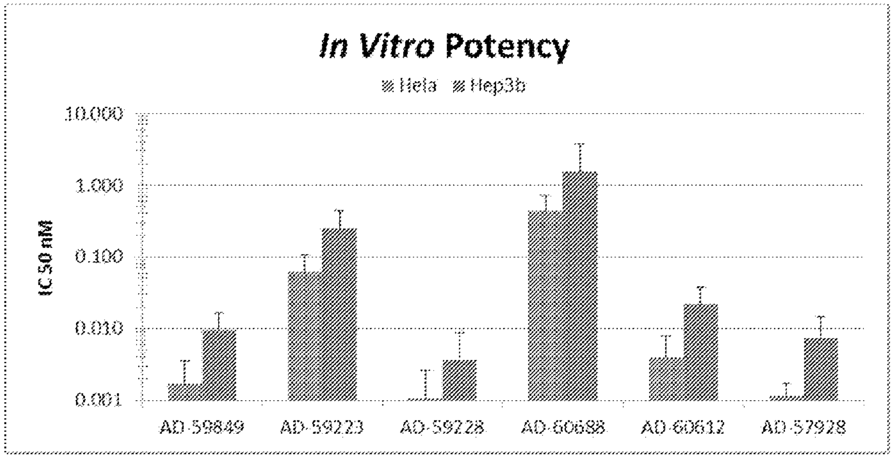

Figure 12

SEQUENCE LISTING

```
<160> NUMBER OF SEQ ID NOS: 1666

<210> SEQ ID NO 1
<211> LENGTH: 16
<212> TYPE: PRT
<213> ORGANISM: Unknown
<220> FEATURE:
<223> OTHER INFORMATION: Description of Unknown: Exemplary hydrophobic
      membrane translocation peptide

<400> SEQUENCE: 1

Ala Ala Val Ala Leu Leu Pro Ala Val Leu Leu Ala Leu Leu Ala Pro
1               5                   10                  15


<210> SEQ ID NO 2
<211> LENGTH: 11
<212> TYPE: PRT
<213> ORGANISM: Unknown
<220> FEATURE:
<223> OTHER INFORMATION: Description of Unknown: RFGF
      analogue peptide

<400> SEQUENCE: 2

Ala Ala Leu Leu Pro Val Leu Leu Ala Ala Pro
1               5                   10
```

<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Arg Pro Pro Gln
1 5 10

<210> SEQ ID NO 4
<211> LENGTH: 16
<212> TYPE: PRT
<213> ORGANISM: Drosophila sp.

<400> SEQUENCE: 4

Arg Gln Ile Lys Ile Trp Phe Gln Asn Arg Arg Met Lys Trp Lys Lys
1 5 10 15

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gcatcctggg ctacactga 19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgggtgtcgc tgttgaagtc 20

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic probe

<400> SEQUENCE: 7
ccaggtggtc tcctcc 16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
acgtggctgg cattgca 17

<210> SEQ ID NO 9
<211> LENGTH: 23
<212> TYPE: DNA

<213> ORGANISM: Artificial Sequence
<220> FEATURE:
<223> OTHER INFORMATION: Description of Artificial Sequence: Synthetic
primer

<400> SEQUENCE: 9
aagtggatca gtctctgcct caa 23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 10
catgatgctg tctgccgagc cg 22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 11
cuuacgcuga guacuucgat t 21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 12
ucgaaguacu cagcguaagt t 21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
cgaggacggc gacuacgagg a 21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
accgcugcgc caaggauccg u 21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
gcugcgccaa ggauccgugg a 21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
cuacguggug gugcugaagg a 21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
cccgccgggg auaccucacc a 21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 18
ccgccgggga uaccucacca a 21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 19
gccggggaua ccucaccaag a 21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
ccggggauac cucaccaaga u 21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
auaccucacc aagauccugc a 21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
caccaagauc cugcaugucu u 21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
caagauccug caugucuucc a 21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24
guugccccau gucgacuaca u 21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25
gccccauguc gacuacaucg a 21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 26
ccaugucgac uacaucgagg a 21

-continued

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
ucgacuacau cgaggaggac u 21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
acuacaucga ggaggacucc u 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
uacaucgagg aggacuccuc u 21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
ucgaggagga cuccucuguc u 21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 31
cgaggaggac uccucugucu u 21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 32
guaccgggcg gaugaauacc a 21

<210> SEQ ID NO 33

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
ccugguggag guguaucucc u 21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
cugguggagg uguaucuccu a 21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
gguggaggug uaucuccuag a 21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
uggaggugua ucuccuagac a 21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37
agguguaucu ccuagacacc a 21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38
guaucuccua gacaccagca u 21

<210> SEQ ID NO 39
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
uaucuccuag acaccagcau a 21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
ucuccuagac accagcauac a 21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
uccuagacac cagcauacag a 21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 42
agacaccagc auacagagug a 21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 43
caccagcaua cagagugacc a 21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 44
uacagaguga ccaccgggaa a 21

<210> SEQ ID NO 45
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 45
acagagugac caccgggaaa u 21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
gagugaccac cgggaaaucg a 21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
ggaaaucgag ggcaggguca u 21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
aaucgagggc agggucaugg u 21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49
gcagggucau ggucaccgac u 21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50
cagggucaug gucaccgacu u 21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51
ggucaugguc accgacuucg a 21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
ucauggucac cgacuucgag a 21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
aggacgggac ccgcuuccac a 21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54
cgggacccgc uuccacagac a 21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 55
uccacagaca ggccagcaag u 21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 56
ccugcgcgug cucaacugcc a 21

<210> SEQ ID NO 57
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 57
cugcgcgugc ucaacugcca a 21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 58
cgugcucaac ugccaaggga a 21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 59
cacccucaua ggccuggagu u 21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 60
acccucauag gccuggaguu u 21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 61
cccucauagg ccuggaguuu a 21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 62
ccucauaggc cuggaguuua u 21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
cucauaggcc uggaguuuau u 21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64
uaggccugga guuuauucgg a 21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 65
aggccuggag uuuauucgga a 21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 66
ggccuggagu uuauucggaa a 21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 67
gccuggaguu uauucggaaa a 21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 68
ggaguuuauu cggaaaagcc a 21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 69
guuuauucgg aaaagccagc u 21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 70
gggcuggggu cgugcugguc a 21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
ggucaccgcu gccggcaacu u 21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
gggacgaugc cugccucuac u 21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
caacuuuggc cgcugugugg a 21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
uuggccgcug uguggaccuc u 21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
uggccgcugu guggaccucu u 21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
ggccgcugug uggaccucuu u 21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
uguguggacc ucuuugcccc a 21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
gggaggacau cauuggugcc u 21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
acugcagcac cugcuuugug u 21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80
gcauugcagc caugaugcug u 21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 81
guugaggcag agacugaucc a 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 82
ugaggcagag acugauccac u 21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 83
gaggcagaga cugauccacu u 21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 84
ggcagagacu gauccacuuc u 21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 85
cagagacuga uccacuucuc u 21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 86
acugauccac uucucugcca a 21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
auccacuucu cugccaaaga u 21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
ggccugguuc ccugaggacc a 21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
gguacugacc cccaaccugg u 21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 90
guuggcagcu guuuugcagg a 21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
uggcagcugu uuugcaggac u 21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 92
gcagcuguuu ugcaggacug u 21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
ucugccgggc ccacaacgcu u 21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 94
cugccgggcc cacaacgcuu u 21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
gcccacaacg cuuuuggggg u 21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 96
cgcuuuuggg ggugagggug u 21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 97
cuuuuggggg ugagggugucc u 21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
uuuugggggu gagggugucu a 21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
ggggugaggg ugucuacgcc a 21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 100
gggugagggu gucuacgcca u 21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 101
ggugagggug ucuacgccau u 21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 102
agggugucua cgccauugcc a 21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 103
gugucuacgc cauugccagg u 21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104
ugcagcgucc acacagcucc a 21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
gcauggggac ccguguccac u 21

-continued

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106
cccacaagcc gccugugcug a 21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 107
gaggccacga ggucagccca a 21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 108
cacgagguca gcccaaccag u 21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 109
gggaggccag cauccacgcu u 21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 110
auccacgcuu ccugcugcca u 21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 111
ggaaugcaaa gucaaggagc a 21

<210> SEQ ID NO 112

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 112
aaucccggcc ccucaggagc a 21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 113
gcuggggcug agcuuuaaaa u 21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114
ggaggugcca ggaagcuccc u 21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
acuguggggc auuucaccau u 21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
ccaccaagga ggcaggauuc u 21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
caccaaggag gcaggauucu u 21

<210> SEQ ID NO 118
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
accaaggagg caggauucuu u 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
ggaggcagga uucuucccau u 21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
gaggcaggau ucuucccaug a 21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121
ugauggcccu caucuccagc u 21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 122
cuuucuggau ggcaucuagc a 21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123
uuucuggaug gcaucuagcc a 21

<210> SEQ ID NO 124
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 124

uucuggaugg caucuagcca a                                               21


<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125

ucuggauggc aucuagccag a                                               21


<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126

cuggauggca ucuagccaga a                                               21


<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127

cuuuacucug cucuaugcca a                                               21


<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128

uuuacucugc ucuaugccag a                                               21


<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129

gcucuaugcc aggcugugcu a                                               21


<210> SEQ ID NO 130
<211> LENGTH: 21
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 130
cucagccaac ccgcuccacu a 21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
ucagccaacc cgcuccacua a 21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
ccugccaagc ucacacagca a 21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
gccaagcuca cacagcagga a 21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 134
ccaagcucac acagcaggaa a 21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
caagcucaca cagcaggaac u 21

<210> SEQ ID NO 136
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 136
aagcucacac agcaggaacu u 21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
cugaagccaa gccucuucuu a 21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ugaagccaag ccucuucuua a 21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gaagccaagc cucuucuuac u 21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aagccaagcc ucuucuuacu u 21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
agugaggcug ggaaggggaa a 21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 142
gugaggcugg gaaggggaac a 21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 143
ggcugggaag gggaacacag a 21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 144
gaaggggaac acagaccagg a 21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 145
aaggggaaca cagaccagga a 21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 146
aggggaacac agaccaggaa a 21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
gggaacacag accaggaagc u 21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
acugucccuc cuugagcacc a 21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 149
ccagccccac ccaagcaagc a 21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
ccccacccaa gcaagcagac a 21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
cccacccaag caagcagaca u 21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
ccacccaagc aagcagacau u 21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
cacccaagca agcagacauu u 21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
acccaagcaa gcagacauuu a 21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
cccaagcaag cagacauuua u 21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
ccaagcaagc agacauuuau u 21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
caagcaagca gacauuuauc u 21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
aagcaagcag acauuuaucu u 21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
agcaagcaga cauuuaucuu u 21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 160
caagcagaca uuuaucuuuu u 21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 161
aagcagacau uuaucuuuug a 21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 162
agcagacauu uaucuuuugg a 21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 163
gcagacauuu aucuuuuggg u 21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 164
agacauuuau cuuuugggguc u 21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 165
gacauuuauc uuuuggggucu u 21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
acauuuaucu uuugggucug u 21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
uuuaucuuuu gggucugucc u 21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
uuaucuuuug ggucuguccu u 21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
uaucuuuugg gucuguccuc u 21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
aucuuuuggg ucuguccucu u 21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 171
ucuuuugggu cuguccucuc u 21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 172
uuuggggucu guccucucug u 21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
uuugggucug uccucucugu u 21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 174
uugggucugu ccucucuguu u 21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 175
ugggucuguc cucucuguug a 21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 176
gggucugucc ucucuguugc a 21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 177
ggucuguccu cucuguugcc u 21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 178
gucuguccuc ucuguugccu u 21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 179
ucuguccucu cuguugccuu u 21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 180
cuguccucuc uguugccuuu u 21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 181
uguccucucu guugccuuuu u 21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 182
guccucucug uugccuuuuu a 21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 183
uuuucuagac cuguuuugcu u 21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 184
uuucuagacc uguuuugcuu u 21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 185
uucuagaccu guuuugcuuu u 21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 186
ucuagaccug uuuugcuuuu u 21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 187
cuagaccugu uuugcuuuug u 21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 188
uagaccuguu uugcuuuugu a 21

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 189
agaccuguuu ugcuuuugu 19

<210> SEQ ID NO 190
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 190
gaccuguuuu gcuuuugu 18

<210> SEQ ID NO 191

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
agaccuguuu ugcuuuugu 19

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 192
uuuuguaacu ugaagauauu u 21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 193
uuuguaacuu gaagauauuu a 21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 194
uuguaacuug aagauauuua u 21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 195
uguaacuuga agauauuuau u 21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 196
guaacuugaa gauauuuauu u 21

<210> SEQ ID NO 197
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 197
cuagaccugu uuugcuuuug u 21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 198
cuagaccugu uuugcuuuug u 21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 199
cuagaccugu uuugcuuuug u 21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 200
cuagaccugu uuugcuuuug u 21

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 201
agaccuguuu ugcuuuugu 19

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 202
cuagaccugu uuugcuuuug u 21

<210> SEQ ID NO 203
<211> LENGTH: 20
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 203
uagaccuguu uugcuuuugu 20

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 204
agaccuguuu ugcuuuugu 19

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 205
uagaccuguu uugcuuuugu 20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 206
uagaccuguu uugcuuuugu 20

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 207
cuagaccugu uuugcuuuug u 21

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 208
uagaccuguu uugcuuuugu 20

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 209
agaccuguuu ugcuuuugu 19

<210> SEQ ID NO 210
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 210
gaccuguuuu gcuuuugu 18

<210> SEQ ID NO 211
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 211
gaccuguuuu gcuuuugu 18

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 212
agaccuguuu ugcuuuugu 19

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 213
uagaccuguu uugcuuuugu 20

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 214
agaccuguuu ugcuuuugu 19

<210> SEQ ID NO 215
<211> LENGTH: 20
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 215
uagaccuguu uugcuuuugu 20

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 216
cuagaccugu uuugcuuuug u 21

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 217
uagaccuguu uugcuuuugu 20

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 218
agaccuguuu ugcuuuugu 19

<210> SEQ ID NO 219
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 219
ucuagaccug uuuugcuuuu gu 22

<210> SEQ ID NO 220
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 220
uucuagaccu guuuugcuuu ugu 23

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 221
caagcagaca uuuaucuuuu u 21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 222
uuuucuagac cuguuuugcu u 21

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 223
agaccuguuu ugcuuuugu 19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 224
agaccuguuu ugcuuuugu 19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 225
agaccuguuu ugcuuuugu 19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 226
agaccuguuu ugcuuuugu 19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 227
agaccuguuu ugcuuuugu 19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 228
agaccuguuu ugcuuuugu 19

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 229
cuagaccugu uuugcuuuug u 21

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 230
agaccuguuu ugcuuuugu 19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 231
agaccuguuu ugcuuuugu 19

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
cuagaccugu uuugcuuuug u 21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 233
cuagaccugu uuugcuuuug u 21

<210> SEQ ID NO 234
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 234
uccucguagu cgccguccuc guc 23

<210> SEQ ID NO 235
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 235
acggauccuu ggcgcagcgg ugg 23

<210> SEQ ID NO 236
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 236
uccacggauc cuuggcgcag cgg 23

<210> SEQ ID NO 237
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 237
uccuucagca ccaccacgua ggu 23

<210> SEQ ID NO 238
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 238
uggugaggua uccccggcgg gca 23

<210> SEQ ID NO 239
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 239
uuggugaggu auccccggcg ggc 23

<210> SEQ ID NO 240
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 240
ucuuggugag guauccccgg cgg 23

<210> SEQ ID NO 241
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 241
aucuugguga gguaucccccg gcg 23

<210> SEQ ID NO 242
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 242
ugcaggaucu uggugaggua ucc 23

<210> SEQ ID NO 243
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 243
aagacaugca ggaucuuggu gag 23

<210> SEQ ID NO 244
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 244
uggaagacau gcaggaucuu ggu 23

<210> SEQ ID NO 245
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 245

-continued auguagucga cauggggcaa cuu 23

<210> SEQ ID NO 246
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 246
ucgauguagu cgacaugggg caa 23

<210> SEQ ID NO 247
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 247
uccucgaugu agucgacaug ggg 23

<210> SEQ ID NO 248
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 248
aguccuccuc gauguagucg aca 23

<210> SEQ ID NO 249
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 249
aggaguccuc cucgauguag ucg 23

<210> SEQ ID NO 250
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 250
agaggagucc uccucgaugu agu 23

<210> SEQ ID NO 251
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 251
agacagagga guccuccucg aug 23

<210> SEQ ID NO 252
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 252
aagacagagg aguccuccuc gau 23

<210> SEQ ID NO 253
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 253
ugguauucau ccgcccggua ccg 23

<210> SEQ ID NO 254
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 254
aggagauaca ccuccaccag gcu 23

<210> SEQ ID NO 255
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 255
uaggagauac accuccacca ggc 23

<210> SEQ ID NO 256
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 256
ucuaggagau acaccuccac cag 23

<210> SEQ ID NO 257
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 257
ugucuaggag auacaccucc acc 23

<210> SEQ ID NO 258
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 258
uggugucuag gagauacacc ucc 23

<210> SEQ ID NO 259
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 259
augcuggugu cuaggagaua cac 23

<210> SEQ ID NO 260
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 260
uaugcuggug ucuaggagau aca 23

<210> SEQ ID NO 261
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 261
uguaugcugg ugucuaggag aua 23

<210> SEQ ID NO 262
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 262
ucuguaugcu ggugucuagg aga 23

<210> SEQ ID NO 263
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 263
ucacucugua ugcugguguc uag 23

<210> SEQ ID NO 264
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 264
uggucacucu guaugcuggu guc 23

<210> SEQ ID NO 265
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 265
uuucccggug gucacucugu aug 23

<210> SEQ ID NO 266
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 266
auuucccggu ggucacucug uau 23

<210> SEQ ID NO 267
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 267
ucgauuuccc gguggucacu cug 23

<210> SEQ ID NO 268
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 268
augacccugc ccucgauuuc ccg 23

<210> SEQ ID NO 269
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 269
accaugaccc ugcccucgau uuc 23

<210> SEQ ID NO 270

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 270
agucggugac caugacccug ccc 23

<210> SEQ ID NO 271
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 271
aagucgguga ccaugacccu gcc 23

<210> SEQ ID NO 272
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 272
ucgaagucgg ugaccaugac ccu 23

<210> SEQ ID NO 273
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 273
ucucgaaguc ggugaccaug acc 23

<210> SEQ ID NO 274
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 274
uguggaagcg ggucccgucc ucc 23

<210> SEQ ID NO 275
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 275
ugucugugga agcggguccc guc 23

<210> SEQ ID NO 276
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
acuugcuggc cugucugugg aag 23

<210> SEQ ID NO 277
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
uggcaguuga gcacgcgcag gcu 23

<210> SEQ ID NO 278
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
uuggcaguug agcacgcgca ggc 23

<210> SEQ ID NO 279
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279
uucccuuggc aguugagcac gcg 23

<210> SEQ ID NO 280
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 280
aacuccaggc cuaugagggu gcc 23

<210> SEQ ID NO 281
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 281
aaacuccagg ccuaugaggg ugc 23

<210> SEQ ID NO 282
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 282
uaaacuccag gccuaugagg gug 23

<210> SEQ ID NO 283
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 283
auaaacucca ggccuaugag ggu 23

<210> SEQ ID NO 284
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 284
aauaaacucc aggccuauga ggg 23

<210> SEQ ID NO 285
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 285
uccgaauaaa cuccaggccu aug 23

<210> SEQ ID NO 286
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 286
uuccgaauaa acuccaggcc uau 23

<210> SEQ ID NO 287
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 287
uuuccgaaua aacuccaggc cua 23

<210> SEQ ID NO 288
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
uuuuccgaau aaacuccagg ccu 23

<210> SEQ ID NO 289
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 289
uggcuuuucc gaauaaacuc cag 23

<210> SEQ ID NO 290
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 290
agcuggcuuu uccgaauaaa cuc 23

<210> SEQ ID NO 291
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 291
ugaccagcac gaccccagcc cuc 23

<210> SEQ ID NO 292
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 292
aaguugccgg cagcggugac cag 23

<210> SEQ ID NO 293
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 293
aguagaggca ggcaucgucc cgg 23

<210> SEQ ID NO 294
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 294
uccacacagc ggccaaaguu ggu 23

<210> SEQ ID NO 295
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 295
agagguccac acagcggcca aag 23

<210> SEQ ID NO 296
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 296
aagaggucca cacagcggcc aaa 23

<210> SEQ ID NO 297
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 297
aaagaggucc acacagcggc caa 23

<210> SEQ ID NO 298
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 298
uggggcaaag agguccacac agc 23

<210> SEQ ID NO 299
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 299
aggcaccaau gauguccucc ccu 23

<210> SEQ ID NO 300
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
acacaaagca ggugcugcag ucg 23

<210> SEQ ID NO 301
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301
acagcaucau ggcugcaaug cca 23

<210> SEQ ID NO 302
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302
uggaucaguc ucugccucaa cuc 23

<210> SEQ ID NO 303
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303
aguggaucag ucucugccuc aac 23

<210> SEQ ID NO 304
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304
aaguggauca gucucugccu caa 23

<210> SEQ ID NO 305
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305
agaaguggau cagucucugc cuc 23

<210> SEQ ID NO 306
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
agagaagugg aucagucucu gcc 23

<210> SEQ ID NO 307
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 307
uuggcagaga aguggaucag ucu 23

<210> SEQ ID NO 308
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 308
aucuuuggca gagaagugga uca 23

<210> SEQ ID NO 309
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 309
ugguccucag ggaaccaggc cuc 23

<210> SEQ ID NO 310
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 310
accagguugg gggucaguac ccg 23

<210> SEQ ID NO 311
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 311
uccugcaaaa cagcugccaa ccu 23

<210> SEQ ID NO 312
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 312
aguccugcaa aacagcugcc aac 23

<210> SEQ ID NO 313
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 313
acaguccugc aaaacagcug cca 23

<210> SEQ ID NO 314
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 314
aagcguugug ggcccggcag acc 23

<210> SEQ ID NO 315
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 315
aaagcguugu gggcccggca gac 23

<210> SEQ ID NO 316
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 316
acccccaaaa gcguuguggg ccc 23

<210> SEQ ID NO 317
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 317
acacccucac ccccaaaagc guu 23

<210> SEQ ID NO 318
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 318
agacacccuc acccccaaaa gcg 23

<210> SEQ ID NO 319
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
uagacacccu cacccccaaa agc 23

<210> SEQ ID NO 320
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
uggcguagac acccucaccc cca 23

<210> SEQ ID NO 321
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
auggcguaga cacccucacc ccc 23

<210> SEQ ID NO 322
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
aauggcguag acacccucac ccc 23

<210> SEQ ID NO 323
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 323
uggcaauggc guagacaccc uca 23

<210> SEQ ID NO 324
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 324
accuggcaau ggcguagaca ccc 23

<210> SEQ ID NO 325
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
uggagcugug uggacgcugc agu 23

<210> SEQ ID NO 326
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
aguggacacg gguccccaug cug 23

<210> SEQ ID NO 327
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
ucagcacagg cggcuugugg gug 23

<210> SEQ ID NO 328
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
uugggcugac cucguggccu cag 23

<210> SEQ ID NO 329
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329
acugguuggg cugaccucgu ggc 23

<210> SEQ ID NO 330
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330
aagcguggau gcuggccucc cug 23

<210> SEQ ID NO 331
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 331
auggcagcag gaagcgugga ugc 23

<210> SEQ ID NO 332
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 332
ugcuccuuga cuuugcauuc cag 23

<210> SEQ ID NO 333
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 333
ugcuccugag ggccgggau ucc 23

<210> SEQ ID NO 334
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 334
auuuuaaagc ucagccccag ccc 23

<210> SEQ ID NO 335
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
agggagcuuc cuggcaccuc cac 23

<210> SEQ ID NO 336
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 336
aauggugaaa ugccccacag uga 23

<210> SEQ ID NO 337
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 337
agaauccugc cuccuuggug gag 23

<210> SEQ ID NO 338
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
aagaauccug ccuccuuggu gga 23

<210> SEQ ID NO 339
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 339
aaagaauccu gccuccuugg ugg 23

<210> SEQ ID NO 340
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 340
aaugggaaga auccugccuc cuu 23

<210> SEQ ID NO 341
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 341
ucaugggaag aauccugccu ccu 23

<210> SEQ ID NO 342
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 342
agcuggagau gagggccauc agc 23

```
<210> SEQ ID NO 343
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343

ugcuagaugc cauccagaaa gcu                                            23


<210> SEQ ID NO 344
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344

uggcuagaug ccauccagaa agc                                            23


<210> SEQ ID NO 345
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345

uuggcuagau gccauccaga aag                                            23


<210> SEQ ID NO 346
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346

ucuggcuaga ugccauccag aaa                                            23


<210> SEQ ID NO 347
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347

uucuggcuag augccaucca gaa                                            23


<210> SEQ ID NO 348
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348

uuggcauaga gcagaguaaa ggu                                            23


<210> SEQ ID NO 349
```

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 349
ucuggcauag agcagaguaa agg 23

<210> SEQ ID NO 350
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 350
uagcacagcc uggcauagag cag 23

<210> SEQ ID NO 351
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 351
uaguggagcg gguuggcuga gac 23

<210> SEQ ID NO 352
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 352
uuaguggagc ggguuggcug aga 23

<210> SEQ ID NO 353
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 353
uugcugugug agcuuggcag gca 23

<210> SEQ ID NO 354
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 354
uuccugcugu gugagcuugg cag 23

<210> SEQ ID NO 355
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 355
uuuccugcug ugugagcuug gca 23

<210> SEQ ID NO 356
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 356
aguuccugcu gugugagcuu ggc 23

<210> SEQ ID NO 357
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
aaguuccugc ugugugagcu ugg 23

<210> SEQ ID NO 358
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
uaagaagagg cuuggcuuca gag 23

<210> SEQ ID NO 359
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
uuaagaagag gcuuggcuuc aga 23

<210> SEQ ID NO 360
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
aguaagaaga ggcuuggcuu cag 23

<210> SEQ ID NO 361
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 361
aaguaagaag aggcuuggcu uca 23

<210> SEQ ID NO 362
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 362
uuuccccuuc ccagccucac ugu 23

<210> SEQ ID NO 363
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363
uguuccccuu cccagccuca cug 23

<210> SEQ ID NO 364
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364
ucuguguucc ccuucccagc cuc 23

<210> SEQ ID NO 365
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365
uccuggucug uguuccccuu ccc 23

<210> SEQ ID NO 366
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366
uuccuggucu guguuccccu ucc 23

<210> SEQ ID NO 367
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367
uuuccugguc uguguucccc uuc 23

<210> SEQ ID NO 368
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
agcuuccugg ucuguguucc ccu 23

<210> SEQ ID NO 369
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
uggugcucaa ggagggacag uug 23

<210> SEQ ID NO 370
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
ugcuugcuug gguggggcug gug 23

<210> SEQ ID NO 371
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
ugucugcuug cuuggguggg gcu 23

<210> SEQ ID NO 372
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372
augucugcuu gcuugggugg ggc 23

<210> SEQ ID NO 373
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 373
aaugucugcu ugcuugggug ggg 23

<210> SEQ ID NO 374
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
aaaugucugc uugcuugggu ggg 23

<210> SEQ ID NO 375
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
uaaaugucug cuugcuuggg ugg 23

<210> SEQ ID NO 376
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
auaaaugucu gcuugcuugg gug 23

<210> SEQ ID NO 377
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
aauaaauguc ugcuugcuug ggu 23

<210> SEQ ID NO 378
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
agauaaaugu cugcuugcuu ggg 23

<210> SEQ ID NO 379
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
aagauaaaug ucugcuugcu ugg 23

<210> SEQ ID NO 380
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
aaagauaaau gucugcuugc uug 23

<210> SEQ ID NO 381
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381
aaaaagauaa augucugcuu gcu 23

<210> SEQ ID NO 382
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
ucaaaagaua aaugucugcu ugc 23

<210> SEQ ID NO 383
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
uccaaaagau aaaugucugc uug 23

<210> SEQ ID NO 384
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
acccaaaaga uaaaugucug cuu 23

<210> SEQ ID NO 385
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
agacccaaaa gauaaauguc ugc 23

<210> SEQ ID NO 386
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
aagacccaaa agauaaaugu cug 23

<210> SEQ ID NO 387
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
acagacccaa aagauaaaug ucu 23

<210> SEQ ID NO 388
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
aggacagacc caaaagauaa aug 23

<210> SEQ ID NO 389
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389
aaggacagac ccaaaagaua aau 23

<210> SEQ ID NO 390
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
agaggacaga cccaaaagau aaa 23

<210> SEQ ID NO 391
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
aagaggacag acccaaaaga uaa 23

<210> SEQ ID NO 392
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 392
agagaggaca gacccaaaag aua 23

<210> SEQ ID NO 393
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 393
acagagagga cagacccaaa aga 23

<210> SEQ ID NO 394
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 394
aacagagagg acagacccaa aag 23

<210> SEQ ID NO 395
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 395
aaacagagag gacagaccca aaa 23

<210> SEQ ID NO 396
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 396
ucaacagaga ggacagaccc aaa 23

<210> SEQ ID NO 397
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 397
ugcaacagag aggacagacc caa 23

<210> SEQ ID NO 398
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 398
aggcaacaga gaggacagac cca 23

<210> SEQ ID NO 399
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 399
aaggcaacag agaggacaga ccc 23

<210> SEQ ID NO 400
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
aaaggcaaca gagaggacag acc 23

<210> SEQ ID NO 401
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
aaaaggcaac agagaggaca gac 23

<210> SEQ ID NO 402
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 402
aaaaaggcaa cagagaggac aga 23

<210> SEQ ID NO 403
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 403
uaaaaaggca acagagagga cag 23

<210> SEQ ID NO 404
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 404
aagcaaaaca ggucuagaaa agu 23

<210> SEQ ID NO 405
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 405
aaagcaaaac aggucuagaa aag 23

<210> SEQ ID NO 406
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 406
aaaagcaaaa caggucuaga aaa 23

<210> SEQ ID NO 407
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 407
aaaaagcaaa acaggucuag aaa 23

<210> SEQ ID NO 408
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 408
acaaaagcaa aacaggucua gaa 23

<210> SEQ ID NO 409
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
uacaaaagca aaacaggucu aga 23

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
acaaaagcaa aacaggucua g 21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
acaaaagcaa aacaggucau a 21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
acaaaagcaa aacaggucua g 21

<210> SEQ ID NO 413
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 413
aaauaucuuc aaguuacaaa agc 23

<210> SEQ ID NO 414
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 414
uaaauaucuu caaguuacaa aag 23

<210> SEQ ID NO 415
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
auaaauaucu ucaaguuaca aaa 23

<210> SEQ ID NO 416
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416 aauaaaauauc uucaaguuac aaa 23

<210> SEQ ID NO 417
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417
aaauaaauau cuucaaguua caa 23

<210> SEQ ID NO 418
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
acaaaagcaa aacaggucua gaa 23

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419
acaaaagcaa aacaggucua gaa 23

<210> SEQ ID NO 420
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 420
acaaaagcaa aacaggucua gaa 23

<210> SEQ ID NO 421
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421
acaaaagcaa aacaggucua gaa 23

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 422
acaaaagcaa aacaggucua g 21

<210> SEQ ID NO 423
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 423
acaaaagcaa aacaggucua ga 22

<210> SEQ ID NO 424
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 424
acaaaagcaa aacaggucua ga 22

<210> SEQ ID NO 425
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 425
acaaaagcaa aacaggucua ga 22

<210> SEQ ID NO 426
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 426
acaaaagcaa aacaggucua ga 22

<210> SEQ ID NO 427
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 427
acaaaagcaa aacaggucua ga 22

<210> SEQ ID NO 428

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 428
acaaaagcaa aacaggucua g 21

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
acaaaagcaa aacaggucua 20

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
acaaaagcaa aacaggucu 19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 431
acaaaagcaa aacaggucu 19

<210> SEQ ID NO 432
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 432
acaaaagcaa aacaggucua 20

<210> SEQ ID NO 433
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 433
acaaaagcaa aacaggucua 20

<210> SEQ ID NO 434
<211> LENGTH: 20

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 434
acaaaagcaa aacaggucua 20

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435
acaaaagcaa aacaggucua g 21

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436
acaaaagcaa aacaggucua g 21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 437
acaaaagcaa aacaggucua g 21

<210> SEQ ID NO 438
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438
acaaaagcaa aacaggucua gaa 23

<210> SEQ ID NO 439
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
acaaaagcaa aacaggucua gaa 23

<210> SEQ ID NO 440
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 440
acaaaagcaa aacaggucua gaa 23

<210> SEQ ID NO 441
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441
acaaaagcaa aacaggucua gaa 23

<210> SEQ ID NO 442
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442
aaaaagauaa augucugcuu gcu 23

<210> SEQ ID NO 443
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443
aagcaaaaca ggucuagaaa agu 23

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 444
acaaaagcaa aacaggucua g 21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 445
acaaaagcaa aacaggucua g 21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 446
acaaaagcaa aacaggucua g 21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 447
acaaaagcaa aacaggucua g 21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 448
acaaaagcaa aacaggucua g 21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 449
acaaaagcaa aacaggucua g 21

<210> SEQ ID NO 450
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 450
acaaaagcaa aacaggucua gaa 23

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 451
acaaaagcaa aacaggucua g 21

<210> SEQ ID NO 452
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 452
acaaaagcaa aacaggucua g                                              21

<210> SEQ ID NO 453
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
acaaaagcaa aacaggucua gaa                                            23

<210> SEQ ID NO 454
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
acaaaagcaa aacaggucua gaa                                            23

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
cgaggacggc gacuacgagg a                                              21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
gccggggaua ccucaccaag a                                              21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
gccccauguc gacuacaucg a                                              21

<210> SEQ ID NO 458
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 458
ccugguggag guguaucucc u 21

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 459
uccuagacac cagcauacag a 21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 460
gcagggucau ggucaccgac u 21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 461
ccugcgcgug cucaacugcc a 21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 462
uaggccugga guuuauucgg a 21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 463
gggacgaugc cugccucuac u 21

<210> SEQ ID NO 464
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 464
gcauugcagc caugaugcug u 21

<210> SEQ ID NO 465
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
ggccugguuc ccugaggacc a 21

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
cgcuuuuggg ggugagggug u 21

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
uuuucuagac cuguuuugcu u 21

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
ccggggauac cucaccaaga u 21

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
ccaugucgac uacaucgagg a 21

<210> SEQ ID NO 470
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 470
cugguggagg uguaucuccu a 21

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 471
agacaccagc auacagagug a 21

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 472
cagggucaug gucaccgacu u 21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 473
cugcgcgugc ucaacugcca a 21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 474
aggccuggag uuuauucgga a 21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 475
caacuuuggc cgcugugugg a 21

<210> SEQ ID NO 476
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 476
guugaggcag agacugaucc a 21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
gguacugacc cccaaccugg u 21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
cuuuuggggg ugagggguguc u 21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
accgcugcgc caaggauccg u 21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 480
ucgacuacau cgaggaggac u 21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 481
gguggaggug uaucuccuag a 21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 482

-continued caccagcaua cagagugacc a 21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 483
ggucaugguc accgacuucg a 21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 484
cgugcucaac ugccaaggga a 21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 485
ggccuggagu uuauucggaa a 21

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 486
uuggccgcug uguggaccuc u 21

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
ugaggcagag acugauccac u 21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 488
guuggcagcu guuuugcagg a 21

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
uuuugggggu gagggugucu a 21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
gcugcgccaa ggauccgugg a 21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
auaccucacc aagauccugc a 21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
acuacaucga ggaggacucc u 21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
uggaggugua ucuccuagac a 21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
uacagaguga ccaccgggaa a 21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 495
ucauggucac cgacuucgag a 21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 496
cacccucaua ggccuggagu u 21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 497
gccuggaguu uauucggaaa a 21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 498
uggccgcugu guggaccucu u 21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 499
gaggcagaga cugauccacu u 21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 500
uggcagcugu uuugcaggac u 21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 501
ggggugaggg ugucuacgcc a 21

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
caccaagauc cugcaugucu u 21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 503
uacaucgagg aggacuccuc u 21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 504
agguguaucu ccuagacacc a 21

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 505
acagagugac caccgggaaa u 21

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 506
aggacgggac ccgcuuccac a 21

<210> SEQ ID NO 507

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 507
acccucauag gccuggaguu u 21

<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 508
ggaguuuauu cggaaaagcc a 21

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 509
ggccgcugug uggaccucuu u 21

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 510
ggcagagacu gauccacuuc u 21

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 511
gcagcuguuu ugcaggacug u 21

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 512
gggugagggu gucuacgcca u 21

<210> SEQ ID NO 513
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 513
cuacguggug gugcugaagg a 21

<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 514
caagauccug caugucuucc a 21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 515
ucgaggagga cuccucuguc u 21

<210> SEQ ID NO 516
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 516
guaucuccua gacaccagca u 21

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 517
gagugaccac cgggaaaucg a 21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 518
cgggacccgc uuccacagac a 21

<210> SEQ ID NO 519
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 519
cccucauagg ccuggaguuu a 21

<210> SEQ ID NO 520
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 520
guuuauucgg aaaagccagc u 21

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 521
ugugnggacc ucuuugcccc a 21

<210> SEQ ID NO 522
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 522
cagagacuga uccacuucuc u 21

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 523
ucugccgggc ccacaacgcu u 21

<210> SEQ ID NO 524
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 524
ggugagggug ucuacgccau u 21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 525
cccgccgggg auaccucacc a 21

<210> SEQ ID NO 526
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 526
cgaggaggac uccucugucu u 21

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 527
uaucuccuag acaccagcau a 21

<210> SEQ ID NO 528
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 528
ggaaaucgag ggcaggguca u 21

<210> SEQ ID NO 529
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 529
uccacagaca ggccagcaag u 21

<210> SEQ ID NO 530
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 530
ccucauaggc cuggaguuua u 21

<210> SEQ ID NO 531
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 531
gggcuggggu cgugcugguc a 21

<210> SEQ ID NO 532
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 532
gggaggacau cauuggugcc u 21

<210> SEQ ID NO 533
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 533
acugauccac uucucugcca a 21

<210> SEQ ID NO 534
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 534
cugccgggcc cacaacgcuu u 21

<210> SEQ ID NO 535
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 535
agggugucua cgccauugcc a 21

<210> SEQ ID NO 536
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 536
ccgccgggga uaccucacca a 21

<210> SEQ ID NO 537
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 537
guugccccau gucgacuaca u 21

<210> SEQ ID NO 538
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 538
guaccgggcg gaugaauacc a 21

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 539
ucuccuagac accagcauac a 21

<210> SEQ ID NO 540
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 540
aaucgagggc agggucaugg u 21

<210> SEQ ID NO 541
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 541
cucauaggcc uggaguuuau u 21

<210> SEQ ID NO 542
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 542
ggucaccgcu gccggcaacu u 21

<210> SEQ ID NO 543
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 543
acugcagcac cugcuuugug u 21

<210> SEQ ID NO 544
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 544
auccacuucu cugccaaaga u 21

<210> SEQ ID NO 545
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 545
gcccacaacg cuuuuggggg u 21

<210> SEQ ID NO 546
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 546
gugucuacgc cauugccagg u 21

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 547
ggaaugcaaa gucaaggagc a 21

<210> SEQ ID NO 548
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 548
ugauggcccu caucuccagc u 21

<210> SEQ ID NO 549
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 549
cugaagccaa gccucuucuu a 21

<210> SEQ ID NO 550
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 550
acugucccuc cuugagcacc a 21

<210> SEQ ID NO 551
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 551
caagcaagca gacauuuauc u 21

<210> SEQ ID NO 552
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 552
uaucuuuugg gucuguccuc u 21

<210> SEQ ID NO 553
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 553
uguccucucu guugccuuuu u 21

<210> SEQ ID NO 554
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 554
uuguaacuug aagauauuua u 21

<210> SEQ ID NO 555
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 555
cuuuacucug cucuaugcca a 21

<210> SEQ ID NO 556
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 556
aggggaacac agaccaggaa a 21

<210> SEQ ID NO 557
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 557
uugggucugu ccucucuguu u 21

<210> SEQ ID NO 558
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 558
ugcagcgucc acacagcucc a 21

<210> SEQ ID NO 559
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 559
aaucccggcc ccucaggagc a 21

<210> SEQ ID NO 560
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 560
uuucuggaug gcaucuagcc a 21

<210> SEQ ID NO 561
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 561
gaagccaagc cucuucuuac u 21

<210> SEQ ID NO 562
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
ccagccccac ccaagcaagc a 21

<210> SEQ ID NO 563
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
aagcaagcag acauuuaucu u 21

<210> SEQ ID NO 564
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
ucuuuugggu cuguccucuc u 21

<210> SEQ ID NO 565
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
guccucucug uugccuuuuu a 21

<210> SEQ ID NO 566
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 566
uguaacuuga agauauuuau u 21

<210> SEQ ID NO 567
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
uuuacucugc ucuaugccag a 21

<210> SEQ ID NO 568
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 568
ccaagcaagc agacauuuau u 21

<210> SEQ ID NO 569
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 569
ugggucuguc cucucuguug a 21

<210> SEQ ID NO 570
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 570
gcauggggac ccguguccac u 21

<210> SEQ ID NO 571
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 571
ucuggauggc aucuagccag a 21

<210> SEQ ID NO 572
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 572
aagccaagcc ucuucuuacu u 21

<210> SEQ ID NO 573
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 573
ccccacccaa gcaagcagac a 21

<210> SEQ ID NO 574
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 574
agcaagcaga cauuuaucuu u 21

<210> SEQ ID NO 575
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 575
uuuugggucu guccucucug u 21

<210> SEQ ID NO 576
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 576
uuucuagacc uguuuugcuu u 21

<210> SEQ ID NO 577
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 577
accaaggagg caggauucuu u 21

<210> SEQ ID NO 578
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 578
ucagccaacc cgcuccacua a 21

<210> SEQ ID NO 579
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 579
caagcagaca uuuaucuuuu u 21

<210> SEQ ID NO 580
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 580
gggucugucc ucucuguugc a 21

<210> SEQ ID NO 581
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 581
cccacaagcc gccugugcug a 21

<210> SEQ ID NO 582
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 582
gcuggggcug agcuuuaaaa u 21

<210> SEQ ID NO 583
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 583
gcucuaugcc aggcugugcu a 21

<210> SEQ ID NO 584
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 584
gugaggcugg gaaggggaac a 21

<210> SEQ ID NO 585
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 585
cccacccaag caagcagaca u 21

<210> SEQ ID NO 586

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 586
gcagacauuu aucuuuuggg u 21

<210> SEQ ID NO 587
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 587
uuugggucug uccucucugu u 21

<210> SEQ ID NO 588
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 588
uucuagaccu guuuugcuuu u 21

<210> SEQ ID NO 589
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 589
ggaggcagga uucuucccau u 21

<210> SEQ ID NO 590
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 590
ccugccaagc ucacacagca a 21

<210> SEQ ID NO 591
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 591
aagcagacau uuaucuuuug a 21

<210> SEQ ID NO 592
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 592
ucuagaccug uuuugcuuuu u 21

<210> SEQ ID NO 593
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 593
gaggccacga ggucagccca a 21

<210> SEQ ID NO 594
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 594
ggaggugcca ggaagcuccc u 21

<210> SEQ ID NO 595
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 595
cucagccaac ccgcuccacu a 21

<210> SEQ ID NO 596
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 596
ggcugggaag gggaacacag a 21

<210> SEQ ID NO 597
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 597
ccacccaagc aagcagacau u 21

<210> SEQ ID NO 598
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 598
agacauuuau cuuuugggu cu 21

<210> SEQ ID NO 599
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 599
ggucuguccu cucuguugcc u 21

<210> SEQ ID NO 600
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 600
cuagaccugu uuugcuuuug u 21

<210> SEQ ID NO 601
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 601
gaggcaggau ucuucccaug a 21

<210> SEQ ID NO 602
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 602
ccaagcucac acagcaggaa a 21

<210> SEQ ID NO 603
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 603
agcagacauu uaucuuuugg a 21

<210> SEQ ID NO 604
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 604
guaacuugaa gauauuuauu u 21

<210> SEQ ID NO 605
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 605
cacgagguca gcccaaccag u 21

<210> SEQ ID NO 606
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 606
acuguggggc auuucaccau u 21

<210> SEQ ID NO 607
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 607
gaaggggaac acagaccagg a 21

<210> SEQ ID NO 608
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 608
cacccaagca agcagacauu u 21

<210> SEQ ID NO 609
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 609
acauuuaucu uuugggucug u 21

<210> SEQ ID NO 610
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 610
gucuguccuc ucuguugccu u 21

<210> SEQ ID NO 611
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
uagaccuguu uugcuuuugu a 21

<210> SEQ ID NO 612
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
cuuucuggau ggcaucuagc a 21

<210> SEQ ID NO 613
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
aagcucacac agcaggaacu u 21

<210> SEQ ID NO 614
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
gacauuuauc uuuugggucu u 21

<210> SEQ ID NO 615
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
uuuucuagac cuguuuugcu u 21

<210> SEQ ID NO 616
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 616
gggaggccag cauccacgcu u 21

<210> SEQ ID NO 617
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 617
ccaccaagga ggcaggauuc u 21

<210> SEQ ID NO 618
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 618
gccaagcuca cacagcagga a 21

<210> SEQ ID NO 619
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 619
aaggggaaca cagaccagga a 21

<210> SEQ ID NO 620
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 620
acccaagcaa gcagacauuu a 21

<210> SEQ ID NO 621
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 621
uuuaucuuuu gggucugucc u 21

<210> SEQ ID NO 622
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 622
ucuguccucu cuguugccuu u 21

<210> SEQ ID NO 623
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 623
uuuuguaacu ugaagauauu u 21

<210> SEQ ID NO 624
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 624
uucuggaugg caucuagcca a 21

<210> SEQ ID NO 625
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 625
ugaagccaag ccucuucuua a 21

<210> SEQ ID NO 626
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 626
uuaucuuuug ggucuguccu u 21

<210> SEQ ID NO 627
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
uuuucuagac cuguuuugcu u 21

<210> SEQ ID NO 628
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
auccacgcuu ccugcugcca u 21

<210> SEQ ID NO 629
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 629
caccaaggag gcaggauucu u 21

<210> SEQ ID NO 630
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 630
caagcucaca cagcaggaac u 21

<210> SEQ ID NO 631
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 631
gggaacacag accaggaagc u 21

<210> SEQ ID NO 632
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 632
cccaagcaag cagacauuua u 21

<210> SEQ ID NO 633
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 633
cuguccucuc uguugccuuu u 21

<210> SEQ ID NO 634
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 634
uuuguaacuu gaagauauuu a 21

<210> SEQ ID NO 635
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 635
cuggauggca ucuagccaga a 21

<210> SEQ ID NO 636
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 636
agugaggcug ggaaggggaa a 21

<210> SEQ ID NO 637
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 637
aucuuuuggg ucuguccucu u 21

<210> SEQ ID NO 638
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 638
cacuuacgcu gaguacuucg a 21

<210> SEQ ID NO 639
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 639
cuagaccugu uuugcuuuug u 21

<210> SEQ ID NO 640
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 640
cuagaccugu uuugcuuuug u 21

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 641
cuagaccugu uuugcuuuug u 21

<210> SEQ ID NO 642
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 642
cuagaccugu uuugcuuuug u 21

<210> SEQ ID NO 643
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 643
cuagaccugu uuugcuuuug u 21

<210> SEQ ID NO 644
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 644
cuagaccugu uuugcuuuug u 21

<210> SEQ ID NO 645
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 645
cuagaccugu uuugcuuuug u 21

<210> SEQ ID NO 646
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 646
cuagaccugu uuugcuuuug u 21

<210> SEQ ID NO 647
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 647
cuagaccugu uuugcuuuug u 21

<210> SEQ ID NO 648
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 648
cuagaccugu uuugcuuuug u 21

<210> SEQ ID NO 649
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 649
cuagaccugu uuugcuuuug u 21

<210> SEQ ID NO 650
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 650
cuagaccugu uuugcuuuug u 21

<210> SEQ ID NO 651
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 651
cuagaccugu uuugcuuuug u 21

<210> SEQ ID NO 652
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 652
cuagaccugu uuugcuuuug u 21

<210> SEQ ID NO 653
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 653
cuagaccugu uuugcuuuug u 21

<210> SEQ ID NO 654
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 654
cuagaccugu uuugcuuuug u 21

<210> SEQ ID NO 655
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 655
cuagaccugu uuugcuuuug u 21

<210> SEQ ID NO 656
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 656
cuagaccugu uuugcuuuug u 21

<210> SEQ ID NO 657
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 657
cuagaccugu uuugcuuuug u 21

<210> SEQ ID NO 658
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 658
cuagaccugu uuugcuuuug u 21

<210> SEQ ID NO 659
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 659
cuagaccugu uuugcuuuug u 21

<210> SEQ ID NO 660
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 660
cuagaccugu uuugcuuuug u 21

<210> SEQ ID NO 661
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 661
cuagaccugu uuugcuuuug u 21

<210> SEQ ID NO 662
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 662
cuagaccugu uuugcuuuug u 21

<210> SEQ ID NO 663
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 663
cuagaccugu uuugcuuuug u 21

<210> SEQ ID NO 664
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 664
cuagaccugu uuugcuuuug u 21

<210> SEQ ID NO 665

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 665
cuagaccugu uuugcuuuug u 21

<210> SEQ ID NO 666
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 666
cuagaccugu uuugcuuuug u 21

<210> SEQ ID NO 667
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 667
cuagaccugu uuugcuuuug u 21

<210> SEQ ID NO 668
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 668
cuagaccugu uuugcuuuug u 21

<210> SEQ ID NO 669
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 669
cuagaccugu uuugcuuuug u 21

<210> SEQ ID NO 670
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 670
cuagaccugu uuugcuuuug u 21

<210> SEQ ID NO 671
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 671
cuagaccugu uuugcuuuug u 21

<210> SEQ ID NO 672
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 672
cuagaccugu uuugcuuuug u 21

<210> SEQ ID NO 673
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 673
cuagaccugu uuugcuuuug u 21

<210> SEQ ID NO 674
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 674
cuagaccugu uuugcuuuug u 21

<210> SEQ ID NO 675
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 675
cuagaccugu uuugcuuuug u 21

<210> SEQ ID NO 676
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 676
cuagaccugu uuugcuuuug u 21

<210> SEQ ID NO 677
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 677
cuagaccugu uuugcuuuug u 21

<210> SEQ ID NO 678
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 678
cuagaccugu uuugcuuuug u 21

<210> SEQ ID NO 679
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 679
cuagaccugu uuugcuuuug u 21

<210> SEQ ID NO 680
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 680
cuagaccugu uuugcuuuug u 21

<210> SEQ ID NO 681
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 681
cuagaccugu uuugcuuuug u 21

<210> SEQ ID NO 682
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682
cuagaccugu uuugcuuuug u 21

<210> SEQ ID NO 683
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 683
cuagaccugu uuugcuuuug u 21

<210> SEQ ID NO 684
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 684
cuagaccugu uuugcuuuug u 21

<210> SEQ ID NO 685
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 685
cuagaccugu uuugcuuuug u 21

<210> SEQ ID NO 686
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 686
cuagaccugu uuugcuuuug u 21

<210> SEQ ID NO 687
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 687
cuagaccugu uuugcuuuug u 21

<210> SEQ ID NO 688
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 688
cuagaccugu uuugcuuuug u 21

<210> SEQ ID NO 689
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 689
cuagaccugu uuugcuuuug u 21

<210> SEQ ID NO 690
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
cuagaccugu uuugcuuuug u 21

<210> SEQ ID NO 691
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
cuagaccugu uuugcuuuug u 21

<210> SEQ ID NO 692
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
cuagaccugu uuugcuuuug u 21

<210> SEQ ID NO 693
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
cuagaccugu uuugcuuuug u 21

<210> SEQ ID NO 694
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
cuagaccugu uuugcuuuug u 21

<210> SEQ ID NO 695
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 695
cuagaccugu uuugcuuuug u 21

<210> SEQ ID NO 696
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 696
cuagaccugu uuugcuuuug u 21

<210> SEQ ID NO 697
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 697
cuagaccugu uuugcuuuug u 21

<210> SEQ ID NO 698
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 698
cuagaccugu uuugcuuuug u 21

<210> SEQ ID NO 699
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 699
cuagaccugu uuugcuuuug u 21

<210> SEQ ID NO 700
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 700
cuagaccugu uuugcuuuug u 21

<210> SEQ ID NO 701
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 701
cuagaccugu uuugcuuuug u 21

<210> SEQ ID NO 702
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 702
cuagaccugu uuugcuuuug u 21

<210> SEQ ID NO 703
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 703
cuagaccugu uuugcuuuug u 21

<210> SEQ ID NO 704
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 704
cuagaccugu uuugcuuuug u 21

<210> SEQ ID NO 705
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 705
cuagaccugu uuugcuuuug u 21

<210> SEQ ID NO 706
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 706
cuagaccugu uuugcuuuug u 21

<210> SEQ ID NO 707
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 707
cuagaccugu uuugcuuuug u 21

<210> SEQ ID NO 708
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 708
cuagaccugu uuugcuuuug u 21

<210> SEQ ID NO 709
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 709
cuagaccugu uuugcuuuug u 21

<210> SEQ ID NO 710
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 710
agaccuguuu ugcuuuugu 19

<210> SEQ ID NO 711
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 711
agaccuguuu ugcuuuugu 19

<210> SEQ ID NO 712
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 712
agaccuguuu ugcuuuugu 19

<210> SEQ ID NO 713
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 713
agaccuguuu ugcuuuugu 19

<210> SEQ ID NO 714
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 714
agaccuguuu ugcuuuugu 19

<210> SEQ ID NO 715
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 715
agaccuguuu ugcuuuugu 19

<210> SEQ ID NO 716
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 716
agaccuguuu ugcuuuugu 19

<210> SEQ ID NO 717
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 717
agaccuguuu ugcuuuugu 19

<210> SEQ ID NO 718
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 718
agaccuguuu ugcuuuugu 19

<210> SEQ ID NO 719
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 719
agaccuguuu ugcuuuugu 19

<210> SEQ ID NO 720
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
agaccuguuu ugcuuuugu 19

<210> SEQ ID NO 721
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721
agaccuguuu ugcuuuugu 19

<210> SEQ ID NO 722
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 722
agaccuguuu ugcuuuugu 19

<210> SEQ ID NO 723
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 723
agaccuguuu ugcuuuugu 19

<210> SEQ ID NO 724
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 724
agaccuguuu ugcuuuugu 19

<210> SEQ ID NO 725
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 725
agaccuguuu ugcuuuugu 19

<210> SEQ ID NO 726
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 726
gaccuguuuu gcuuuugu 18

<210> SEQ ID NO 727
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 727
caagcagaca uuuaucuuuu u 21

<210> SEQ ID NO 728
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 728
caagcagaca uuuaucuuuu u 21

<210> SEQ ID NO 729
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 729
caagcagaca uuuaucuuuu u 21

<210> SEQ ID NO 730
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 730
caagcagaca uuuaucuuuu u 21

<210> SEQ ID NO 731
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 731
caagcagaca uuuaucuuuu u 21

<210> SEQ ID NO 732
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 732
caagcagaca uuuaucuuuu u 21

<210> SEQ ID NO 733
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 733
caagcagaca uuuaucuuuu u 21

<210> SEQ ID NO 734
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 734
caagcagaca uuuaucuuuu u 21

<210> SEQ ID NO 735
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 735
caagcagaca uuuaucuuuu u 21

<210> SEQ ID NO 736
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 736
caagcagaca uuuaucuuuu u 21

<210> SEQ ID NO 737
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 737
caagcagaca uuuaucuuuu u 21

<210> SEQ ID NO 738
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 738
caagcagaca uuuaucuuuu u 21

<210> SEQ ID NO 739
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 739
caagcagaca uuuaucuuuu u 21

<210> SEQ ID NO 740
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
caagcagaca uuuaucuuuu u 21

<210> SEQ ID NO 741
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 741
caagcagaca uuuaucuuuu u 21

<210> SEQ ID NO 742
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 742
caagcagaca uuuaucuuuu u 21

<210> SEQ ID NO 743
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 743
caagcagaca uuuaucuuuu u 21

<210> SEQ ID NO 744

<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
caagcagaca uuuaucuuuu u 21

<210> SEQ ID NO 745
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
caagcagaca uuuaucuuuu u 21

<210> SEQ ID NO 746
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
caagcagaca uuuaucuuuu u 21

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
caagcagaca uuuaucuuuu u 21

<210> SEQ ID NO 748
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
caagcagaca uuuaucuuuu u 21

<210> SEQ ID NO 749
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
caagcagaca uuuaucuuuu u 21

<210> SEQ ID NO 750
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 750
caagcagaca uuuaucuuuu u 21

<210> SEQ ID NO 751
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 751
caagcagaca uuuaucuuuu u 21

<210> SEQ ID NO 752
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 752
caagcagaca uuuaucuuuu u 21

<210> SEQ ID NO 753
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 753
caagcagaca uuuaucuuuu u 21

<210> SEQ ID NO 754
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 754
caagcagaca uuuaucuuuu u 21

<210> SEQ ID NO 755
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 755
caagcagaca uuuaucuuuu u 21

<210> SEQ ID NO 756
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 756

caagcagaca uuuaucuuuu u                                              21


<210> SEQ ID NO 757
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757

caagcagaca uuuaucuuuu u                                              21


<210> SEQ ID NO 758
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758

caagcagaca uuuaucuuuu u                                              21


<210> SEQ ID NO 759
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759

caagcagaca uuuaucuuuu u                                              21


<210> SEQ ID NO 760
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760

caagcagaca uuuaucuuuu u                                              21


<210> SEQ ID NO 761
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761

caagcagaca uuuaucuuuu u                                              21


<210> SEQ ID NO 762
<211> LENGTH: 21
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 762
caagcagaca uuuaucuuuu u 21

<210> SEQ ID NO 763
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 763
caagcagaca uuuaucuuuu u 21

<210> SEQ ID NO 764
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 764
caagcagaca uuuaucuuuu u 21

<210> SEQ ID NO 765
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 765
caagcagaca uuuaucuuuu u 21

<210> SEQ ID NO 766
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 766
caagcagaca uuuaucuuuu u 21

<210> SEQ ID NO 767
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 767
caagcagaca uuuaucuuuu u 21

<210> SEQ ID NO 768
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 768
caagcagaca uuuaucuuuu u 21

<210> SEQ ID NO 769
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
caagcagaca uuuaucuuuu u 21

<210> SEQ ID NO 770
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
caagcagaca uuuaucuuuu u 21

<210> SEQ ID NO 771
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
caagcagaca uuuaucuuuu u 21

<210> SEQ ID NO 772
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
caagcagaca uuuaucuuuu u 21

<210> SEQ ID NO 773
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
caagcagaca uuuaucuuuu u 21

<210> SEQ ID NO 774
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 774
caagcagaca uuuaucuuuu u 21

<210> SEQ ID NO 775
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 775
caagcagaca uuuaucuuuu u 21

<210> SEQ ID NO 776
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 776
caagcagaca uuuaucuuuu u 21

<210> SEQ ID NO 777
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 777
caagcagaca uuuaucuuuu u 21

<210> SEQ ID NO 778
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 778
caagcagaca uuuaucuuuu u 21

<210> SEQ ID NO 779
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 779
caagcagaca uuuaucuuuu u 21

<210> SEQ ID NO 780
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 780
caagcagaca uuuaucuuuu u 21

<210> SEQ ID NO 781
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 781
caagcagaca uuuaucuuuu u 21

<210> SEQ ID NO 782
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 782
caagcagaca uuuaucuuuu u 21

<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 783
caagcagaca uuuaucuuuu u 21

<210> SEQ ID NO 784
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 784
caagcagaca uuuaucuuuu u 21

<210> SEQ ID NO 785
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 785
caagcagaca uuuaucuuuu u 21

<210> SEQ ID NO 786
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 786
caagcagaca uuuaucuuuu u 21

<210> SEQ ID NO 787
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 787
caagcagaca uuuaucuuuu u 21

<210> SEQ ID NO 788
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 788
caagcagaca uuuaucuuuu u 21

<210> SEQ ID NO 789
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 789
caagcagaca uuuaucuuuu u 21

<210> SEQ ID NO 790
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 790
caagcagaca uuuaucuuuu u 21

<210> SEQ ID NO 791
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 791
caagcagaca uuuaucuuuu u 21

<210> SEQ ID NO 792
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 792
caagcagaca uuuaucuuuu u 21

<210> SEQ ID NO 793
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 793
caagcagaca uuuaucuuuu u 21

<210> SEQ ID NO 794
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 794
caagcagaca uuuaucuuuu u 21

<210> SEQ ID NO 795
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 795
caagcagaca uuuaucuuuu u 21

<210> SEQ ID NO 796
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 796
caagcagaca uuuaucuuuu u 21

<210> SEQ ID NO 797
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 797
caagcagaca uuuaucuuuu u 21

<210> SEQ ID NO 798
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 798
caagcagaca uuuaucuuuu u 21

<210> SEQ ID NO 799
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 799
caagcagaca uuuaucuuuu u 21

<210> SEQ ID NO 800
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 800
caagcagaca uuuaucuuuu u 21

<210> SEQ ID NO 801
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 801
caagcagaca uuuaucuuuu u 21

<210> SEQ ID NO 802
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 802
caagcagaca uuuaucuuuu u 21

<210> SEQ ID NO 803
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 803
caagcagaca uuuaucuuuu u 21

<210> SEQ ID NO 804
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 804
caagcagaca uuuaucuuuu u 21

<210> SEQ ID NO 805
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 805
caagcagaca uuuaucuuuu u 21

<210> SEQ ID NO 806
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 806
caagcagaca uuuaucuuuu u 21

<210> SEQ ID NO 807
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 807
caagcagaca uuuaucuuuu u 21

<210> SEQ ID NO 808
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 808
caagcagaca uuuaucuuuu u 21

<210> SEQ ID NO 809
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 809
caagcagaca uuuaucuuuu u 21

<210> SEQ ID NO 810
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 810
caagcagaca uuuaucuuuu u 21

<210> SEQ ID NO 811
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 811
caagcagaca uuuaucuuuu u 21

<210> SEQ ID NO 812
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 812
caagcagaca uuuaucuuuu u 21

<210> SEQ ID NO 813
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 813
caagcagaca uuuaucuuuu u 21

<210> SEQ ID NO 814
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 814
caagcagaca uuuaucuuuu u 21

<210> SEQ ID NO 815
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 815
caagcagaca uuuaucuuuu u 21

<210> SEQ ID NO 816
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 816
caagcagaca uuuaucuuuu u 21

<210> SEQ ID NO 817
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
cuagaccugu uuugcuuuug u 21

<210> SEQ ID NO 818
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818
cuagaccugu uuugcuuuug u 21

<210> SEQ ID NO 819
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
cuagaccugu uuugcuuuug u 21

<210> SEQ ID NO 820
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 820
cuagaccugu uuugcuuuug u 21

<210> SEQ ID NO 821
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 821
cuagaccugu uuugcuuuug u 21

<210> SEQ ID NO 822
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 822
cuagaccugu uuugcuuuug u 21

<210> SEQ ID NO 823

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 823
cuagaccugu uuugcuuuug u 21

<210> SEQ ID NO 824
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 824
cuagaccugu uuugcuuuug u 21

<210> SEQ ID NO 825
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 825
cuagaccugu uuugcuuuug u 21

<210> SEQ ID NO 826
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 826
cuagaccugu uuugcuuuug u 21

<210> SEQ ID NO 827
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 827
cuagaccugu uuugcuuuug u 21

<210> SEQ ID NO 828
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 828
cuagaccugu uuugcuuuug u 21

<210> SEQ ID NO 829
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829
cuagaccugu uuugcuuuug u 21

<210> SEQ ID NO 830
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830
cuagaccugu uuugcuuuug u 21

<210> SEQ ID NO 831
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831
cuagaccugu uuugcuuuug u 21

<210> SEQ ID NO 832
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 832
cuagaccugu uuugcuuuug u 21

<210> SEQ ID NO 833
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 833
cuagaccugu uuugcuuuug u 21

<210> SEQ ID NO 834
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 834
cuagaccugu uuugcuuuug u 21

<210> SEQ ID NO 835
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 835
cuagaccugu uuugcuuuug u 21

<210> SEQ ID NO 836
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 836
cuagaccugu uuugcuuuug u 21

<210> SEQ ID NO 837
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 837
cuagaccugu uuugcuuuug u 21

<210> SEQ ID NO 838
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 838
cuagaccugu uuugcuuuug u 21

<210> SEQ ID NO 839
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 839
cuagaccugu uuugcuuuug u 21

<210> SEQ ID NO 840
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 840
cuagaccugu uuugcuuuug u 21

<210> SEQ ID NO 841
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 841
cuagaccugu uuugcuuuug u 21

<210> SEQ ID NO 842
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 842
cuagaccugu uuugcuuuug u 21

<210> SEQ ID NO 843
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 843
cuagaccugu uuugcuuuug u 21

<210> SEQ ID NO 844
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 844
cuagaccugu uuugcuuuug u 21

<210> SEQ ID NO 845
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 845
cuagaccugu uuugcuuuug u 21

<210> SEQ ID NO 846
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 846
cuagaccugu uuugcuuuug u 21

<210> SEQ ID NO 847
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 847
cuagaccugu uuugcuuuug u 21

<210> SEQ ID NO 848
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
cuagaccugu uuugcuuuug u 21

<210> SEQ ID NO 849
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
cuagaccugu uuugcuuuug u 21

<210> SEQ ID NO 850
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
cuagaccugu uuugcuuuug u 21

<210> SEQ ID NO 851
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
cuagaccugu uuugcuuuug u 21

<210> SEQ ID NO 852
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
cuagaccugu uuugcuuuug u 21

<210> SEQ ID NO 853
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 853
cuagaccugu uuugcuuuug u 21

<210> SEQ ID NO 854
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 854
cuagaccugu uuugcuuuug u 21

<210> SEQ ID NO 855
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 855
cuagaccugu uuugcuuuug u 21

<210> SEQ ID NO 856
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 856
agaccuguuu ugcuuuugu 19

<210> SEQ ID NO 857
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 857
cuagaccugu uuugcuuuug u 21

<210> SEQ ID NO 858
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 858
cuagaccugu uuugcuuuug u 21

<210> SEQ ID NO 859
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 859
cuagaccugu uuugcuuuug u 21

<210> SEQ ID NO 860
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 860
cuagaccugu uuugcuuuug u 21

<210> SEQ ID NO 861
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 861
cuagaccugu uuugcuuuug u 21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 862
ctagaccugu uuugcuuuug u 21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 863
ctagaccugu uuugcuuuug u 21

<210> SEQ ID NO 864
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 864
cuagaccugu uuugcuuuug u 21

<210> SEQ ID NO 865
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 865
cuagaccugu uuugcuuuug u 21

<210> SEQ ID NO 866
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 866
cuagaccugu uuugcuuuug u 21

<210> SEQ ID NO 867
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 867
cuagaccugu uuugcuuuug u 21

<210> SEQ ID NO 868
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 868
cuagaccugu uuugcuuuug u 21

<210> SEQ ID NO 869
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 869
cuagaccugu uuugcuuuug u 21

<210> SEQ ID NO 870
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 870
cuagaccugu uuugcuuuug u 21

<210> SEQ ID NO 871
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 871
cuagaccugu uuugcuuuug u 21

<210> SEQ ID NO 872
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 872
cuagaccugu uuugcuuuug u 21

<210> SEQ ID NO 873
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 873
cuagaccugu uuugcuuuug u 21

<210> SEQ ID NO 874
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 874
cuagaccugu uuugcuuuug u 21

<210> SEQ ID NO 875
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 875
cuagaccugu uuugcuuuug u 21

<210> SEQ ID NO 876
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 876
uagaccuguu uugcuuuugu 20

<210> SEQ ID NO 877
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 877
agaccuguuu ugcuuuugu 19

<210> SEQ ID NO 878
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 878
uagaccuguu uugcuuuugu 20

<210> SEQ ID NO 879
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 879
uagaccuguu uugcuuuugu 20

<210> SEQ ID NO 880
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 880
cuagaccugu uuugcuuuug u 21

<210> SEQ ID NO 881
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 881
uagaccuguu uugcuuuugu 20

<210> SEQ ID NO 882
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 882
agaccuguuu ugcuuuugu 19

<210> SEQ ID NO 883
<211> LENGTH: 18
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 883
gaccuguuuu gcuuuugu 18

<210> SEQ ID NO 884
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
gaccuguuuu gcuuuugu 18

<210> SEQ ID NO 885
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
agaccuguuu ugcuuuugu 19

<210> SEQ ID NO 886
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
uagaccuguu uugcuuuugu 20

<210> SEQ ID NO 887
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
agaccuguuu ugcuuuugu 19

<210> SEQ ID NO 888
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
uagaccuguu uugcuuuugu 20

<210> SEQ ID NO 889
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 889
cuagaccugu uuugcuuuug u 21

<210> SEQ ID NO 890
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 890
uagaccuguu uugcuuuugu 20

<210> SEQ ID NO 891
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 891
agaccuguuu ugcuuuugu 19

<210> SEQ ID NO 892
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 892
ucuagaccug uuuugcuuuu gu 22

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 893
uucuagaccu guuuugcuuu ugu 23

<210> SEQ ID NO 894
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
cuagaccugu uuugcuuuug u 21

<210> SEQ ID NO 895
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 895
cuagaccugu uuugcuuuug u 21

<210> SEQ ID NO 896
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 896
cuagaccugu uuugcuuuug u 21

<210> SEQ ID NO 897
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 897
cuagaccugu uuugcuuuug u 21

<210> SEQ ID NO 898
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 898
cuagaccugu uuugcuuuug u 21

<210> SEQ ID NO 899
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 899
cuagaccugu uuugcuuuug u 21

<210> SEQ ID NO 900
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 900
cuagaccugu uuugcuuuug u 21

<210> SEQ ID NO 901
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 901
cuagaccugu uuugcuuuug u 21

<210> SEQ ID NO 902
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 902
cuagaccugu uuugcuuuug u 21

<210> SEQ ID NO 903
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 903
cuagaccugu uuugcuuuug u 21

<210> SEQ ID NO 904
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 904
cuagaccugu uuugcuuuug u 21

<210> SEQ ID NO 905
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 905
cuagaccugu uuugcuuuug u 21

<210> SEQ ID NO 906
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906
cuagaccugu uuugcuuuug u 21

<210> SEQ ID NO 907
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 907
cuagaccugu uuugcuuuug u 21

<210> SEQ ID NO 908
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 908
cuagaccugu uuugcuuuug u 21

<210> SEQ ID NO 909
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 909
cuagaccugu uuugcuuuug u 21

<210> SEQ ID NO 910
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 910
cuagaccugu uuugcuuuug u 21

<210> SEQ ID NO 911
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 911
cuagaccugu uuugcuuuug u 21

<210> SEQ ID NO 912
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 912
caagcagaca uuuaucuuuu u 21

<210> SEQ ID NO 913
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 913
uuuucuagac cuguuuugcu u 21

<210> SEQ ID NO 914
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 914
agaccuguuu ugcuuuugu 19

<210> SEQ ID NO 915
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 915
agaccuguuu ugcuuuugu 19

<210> SEQ ID NO 916
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 916
agaccuguuu ugcuuuugu 19

<210> SEQ ID NO 917
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 917
agaccuguuu ugcuuuugu 19

<210> SEQ ID NO 918
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 918
agaccuguuu ugcuuuugu 19

<210> SEQ ID NO 919
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 919
agaccuguuu ugcuuuugu 19

<210> SEQ ID NO 920
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 920
cuagaccugu uuugcuuuug u 21

<210> SEQ ID NO 921
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 921
cuagaccugu uuugcuuuug u 21

<210> SEQ ID NO 922
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 922
cuagaccugu uuugcuuuug u 21

<210> SEQ ID NO 923
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 923
cuagaccugu uuugcuuuug u 21

<210> SEQ ID NO 924
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 924
cuagaccugu uuugcuuuug u 21

<210> SEQ ID NO 925
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 925
cuagaccugu uuugcuuuug u 21

<210> SEQ ID NO 926
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 926
cuagaccugu uuugcuuuug u 21

<210> SEQ ID NO 927
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 927
cuagaccugu uuugcuuuug u 21

<210> SEQ ID NO 928
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 928
cuagaccugu uuugcuuuug u 21

<210> SEQ ID NO 929
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 929
cuagaccugu uuugcuuuug u 21

<210> SEQ ID NO 930
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 930
cuagaccugu uuugcuuuug u 21

<210> SEQ ID NO 931
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 931
cuagaccugu uuugcuuuug u 21

<210> SEQ ID NO 932
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 932
agaccuguuu ugcuuuugu 19

<210> SEQ ID NO 933
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 933
agaccuguuu ugcuuuugu 19

<210> SEQ ID NO 934
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 934
cuagaccugu uuugcuuuug u 21

<210> SEQ ID NO 935
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 935
cuagaccugu uuugcuuuug u 21

<210> SEQ ID NO 936
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 936
cuagaccugu uuugcuuuug u 21

<210> SEQ ID NO 937
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 937
cuagaccugu uuugcuuuug u 21

<210> SEQ ID NO 938

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 938
cuagaccugu uuugcuuuug u 21

<210> SEQ ID NO 939
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 939
cuagaccugu uuugcuuuug u 21

<210> SEQ ID NO 940
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 940
cuagaccugu uuugcuuuug u 21

<210> SEQ ID NO 941
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 941
cuagaccugu uuugcuuuug u 21

<210> SEQ ID NO 942
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 942
cuagaccugu uuugctuuug u 21

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
cuagaccugu uuugcuuuug u 21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 944
cuagaccugu uuugcutuug u 21

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 945
cuagaccugu uuugcuutug u 21

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 946
cuagaccugu uuugcuuuug u 21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 947
cuagaccugu uuugcuuutg u 21

<210> SEQ ID NO 948
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948
cuagaccugu uuugcuuuug u 21

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 949
cuagaccugu uuugcuuuug u 21

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 950
cuagaccugu uuugcuuuug t 21

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 951
cuagaccugu uuugcuuuug u 21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 952
cuagaccugu uuugcuuuug u 21

<210> SEQ ID NO 953
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 953
cuagaccugu uuugcuuuug u 21

<210> SEQ ID NO 954
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 954
cuagaccugu uuugcuuuug u 21

<210> SEQ ID NO 955
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 955
cuagaccugu uuugcuuuug u 21

<210> SEQ ID NO 956
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 956
cuagaccugu uuugcuuuug u 21

<210> SEQ ID NO 957
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 957
cuagaccugu uuugcuuuug u 21

<210> SEQ ID NO 958
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 958
cuagaccugu uuugcuuuug u 21

<210> SEQ ID NO 959
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 959
cuagaccugu uuugcuuuug u 21

<210> SEQ ID NO 960
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 960
cuagaccugu uuugcuuuug u 21

<210> SEQ ID NO 961
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 961
cuagaccugu uuugcuuuug u 21

<210> SEQ ID NO 962
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 962
cuagaccugu uuugcuuuug u 21

<210> SEQ ID NO 963
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 963
cuagaccugu uuugcuuuug u 21

<210> SEQ ID NO 964
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 964
cuagaccugu uuugcuuuug u 21

<210> SEQ ID NO 965
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 965
cuagaccugu uuugcuuuug u 21

<210> SEQ ID NO 966
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 966
cuagaccugu uuugcuuuug u 21

<210> SEQ ID NO 967
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 967
cuagaccugu uuugcuuuug u 21

<210> SEQ ID NO 968
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 968
cuagaccugu uuugcuuuug u 21

<210> SEQ ID NO 969
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 969
cuagaccugu uuugcuuuug u 21

<210> SEQ ID NO 970
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 970
cuagaccugu uuugcuuuug u 21

<210> SEQ ID NO 971
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971
cuagaccugu uuugcuuuug u 21

<210> SEQ ID NO 972
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 972
cuagaccugu uuugcuuuug u 21

<210> SEQ ID NO 973
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 973
cuagaccugu uuugcuuuug u 21

<210> SEQ ID NO 974
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
cuagaccugu uuugcuuuug u 21

<210> SEQ ID NO 975
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
cuagaccugu uuugcuuuug u 21

<210> SEQ ID NO 976
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
cuagaccugu uuugcuuuug u 21

<210> SEQ ID NO 977
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
cuagaccugu uuugcuuuug u 21

<210> SEQ ID NO 978
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
cuagaccugu uuugcuuuug u 21

<210> SEQ ID NO 979
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 979
cuagaccugu uuugcuuuug u 21

<210> SEQ ID NO 980
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 980
cuagaccugu uuugcuuuug u 21

<210> SEQ ID NO 981
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 981
cuagaccugu uuugcuuuug u 21

<210> SEQ ID NO 982
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 982
cuagaccugu uuugcuuuug u 21

<210> SEQ ID NO 983
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 983
cuagaccugu uuugcuuuug u 21

<210> SEQ ID NO 984
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 984
cuagaccugu uuugcuuuug u 21

<210> SEQ ID NO 985
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 985
cuagaccugu uuugcuuuug u 21

<210> SEQ ID NO 986
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
cuagaccugu uuugcuuuug u 21

<210> SEQ ID NO 987
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 987
cuagaccugu uuugcuuuug u 21

<210> SEQ ID NO 988
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 988
cuagaccugu uuugcuuuug u 21

<210> SEQ ID NO 989
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 989
cuagaccugu uuugcuuuug u 21

<210> SEQ ID NO 990
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 990
cuagaccugu uuugcuuuug u 21

<210> SEQ ID NO 991
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 991
cuagaccugu uuugcuuuug u 21

<210> SEQ ID NO 992
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 992
cuagaccugu uuugcuuuug u 21

<210> SEQ ID NO 993
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 993
cuagaccugu uuugcuuuug u 21

<210> SEQ ID NO 994
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 994
cuagaccugu uuugcuuuug u 21

<210> SEQ ID NO 995
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 995
cuagaccugu uuugcuuuug u 21

<210> SEQ ID NO 996
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 996
cuagaccugu uuugcuuuug u 21

<210> SEQ ID NO 997
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 997
cuagaccugu uuugcuuuug u 21

<210> SEQ ID NO 998
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
cuagaccugu uuugcuuuug u 21

<210> SEQ ID NO 999
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
cuagaccugu uuugcuuuug u 21

<210> SEQ ID NO 1000
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000
cuagaccugu uuugcuuuug u 21

<210> SEQ ID NO 1001
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
cuagaccugu uuuguuuuug u 21

<210> SEQ ID NO 1002
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002
cuagaccugu uuucuuuuu 19

<210> SEQ ID NO 1003
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003
cuagaccugu uuucuuuuu 19

<210> SEQ ID NO 1004
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1004
cuagaccugu uuucuuuuu 19

<210> SEQ ID NO 1005
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1005
cuaaccuguu uucuuuuu 18

<210> SEQ ID NO 1006
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1006
uccucguagu cgccguccuc guc 23

<210> SEQ ID NO 1007
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1007
ucuuggugag guauccccgg cgg 23

<210> SEQ ID NO 1008
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1008
ucgauguagu cgacaugggg caa 23

<210> SEQ ID NO 1009
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1009
aggagauaca ccuccaccag gcu 23

<210> SEQ ID NO 1010
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1010
ucuguaugcu ggugucuagg aga 23

<210> SEQ ID NO 1011
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1011
agucggugac caugacccug ccc 23

<210> SEQ ID NO 1012
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1012
uggcaguuga gcacgcgcag gcu 23

<210> SEQ ID NO 1013
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1013
uccgaauaaa cuccaggccu aug 23

<210> SEQ ID NO 1014
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1014
aguagaggca ggcaucgucc cgg 23

<210> SEQ ID NO 1015
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1015
acagcaucau ggcugcaaug cca 23

<210> SEQ ID NO 1016
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1016 uggucucag ggaaccaggc cuc 23

<210> SEQ ID NO 1017
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1017
acacccucac ccccaaaagc guu 23

<210> SEQ ID NO 1018
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1018
aagcaaaaca ggucuagaaa agu 23

<210> SEQ ID NO 1019
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1019
aucuugguga gguauccccg gcg 23

<210> SEQ ID NO 1020
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1020
uccucgaugu agucgacaug ggg 23

<210> SEQ ID NO 1021
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1021
uaggagauac accuccacca ggc 23

<210> SEQ ID NO 1022
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022
ucacucugua ugcugguguc uag 23

<210> SEQ ID NO 1023
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1023
aagucgguga ccaugacccu gcc 23

<210> SEQ ID NO 1024
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1024
uuggcaguug agcacgcgca ggc 23

<210> SEQ ID NO 1025
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1025
uuccgaauaa acuccaggcc uau 23

<210> SEQ ID NO 1026
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1026
uccacacagc ggccaaaguu ggu 23

<210> SEQ ID NO 1027
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1027
uggaucaguc ucugccucaa cuc 23

<210> SEQ ID NO 1028

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1028
accagguugg gggucaguac ccg 23

<210> SEQ ID NO 1029
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1029
agacacccuc acccccaaaa gcg 23

<210> SEQ ID NO 1030
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1030
acggauccuu ggcgcagcgg ugg 23

<210> SEQ ID NO 1031
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1031
aguccuccuc gauguagucg aca 23

<210> SEQ ID NO 1032
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1032
ucuaggagau acaccuccac cag 23

<210> SEQ ID NO 1033
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1033
uggucacucu guaugcuggu guc 23

<210> SEQ ID NO 1034
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1034
ucgaagucgg ugaccaugac ccu 23

<210> SEQ ID NO 1035
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1035
uucccuuggc aguugagcac gcg 23

<210> SEQ ID NO 1036
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1036
uuuccgaaua aacuccaggc cua 23

<210> SEQ ID NO 1037
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1037
agagguccac acagcggcca aag 23

<210> SEQ ID NO 1038
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1038
aguggaucag ucucugccuc aac 23

<210> SEQ ID NO 1039
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1039
uccugcaaaa cagcugccaa ccu 23

<210> SEQ ID NO 1040
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1040
uagacacccu cacccccaaa agc 23

<210> SEQ ID NO 1041
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1041
uccacggauc cuuggcgcag cgg 23

<210> SEQ ID NO 1042
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1042
ugcaggaucu uggugaggua ucc 23

<210> SEQ ID NO 1043
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1043
aggaguccuc cucgauguag ucg 23

<210> SEQ ID NO 1044
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1044
ugucuaggag auacaccucc acc 23

<210> SEQ ID NO 1045
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1045
uuucccggug gucacucugu aug 23

<210> SEQ ID NO 1046
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
ucucgaaguc ggugaccaug acc 23

<210> SEQ ID NO 1047
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
aacuccaggc cuaugagggu gcc 23

<210> SEQ ID NO 1048
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048
uuuuccgaau aaacuccagg ccu 23

<210> SEQ ID NO 1049
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049
aagaggucca cacagcggcc aaa 23

<210> SEQ ID NO 1050
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050
aaguggauca gucucugccu caa 23

<210> SEQ ID NO 1051
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051
aguccugcaa aacagcugcc aac 23

<210> SEQ ID NO 1052
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1052
uggcguagac acccucaccc cca 23

<210> SEQ ID NO 1053
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1053
aagacaugca ggaucuuggu gag 23

<210> SEQ ID NO 1054
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054
agaggagucc uccucgaugu agu 23

<210> SEQ ID NO 1055
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1055
uggugucuag gagauacacc ucc 23

<210> SEQ ID NO 1056
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056
auuucccggu ggucacucug uau 23

<210> SEQ ID NO 1057
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1057
uguggaagcg ggucccgucc ucc 23

<210> SEQ ID NO 1058
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1058
aaacuccagg ccuaugaggg ugc 23

<210> SEQ ID NO 1059
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1059
uggcuuuucc gaauaaacuc cag 23

<210> SEQ ID NO 1060
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1060
aaagaggucc acacagcggc caa 23

<210> SEQ ID NO 1061
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1061
agaaguggau cagucucugc cuc 23

<210> SEQ ID NO 1062
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1062
acaguccugc aaaacagcug cca 23

<210> SEQ ID NO 1063
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1063
auggcguaga cacccucacc ccc 23

<210> SEQ ID NO 1064
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1064
uccuucagca ccaccacgua ggu 23

<210> SEQ ID NO 1065
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1065
uggaagacau gcaggaucuu ggu 23

<210> SEQ ID NO 1066
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1066
agacagagga guccuccucg aug 23

<210> SEQ ID NO 1067
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1067
augcuggugu cuaggagaua cac 23

<210> SEQ ID NO 1068
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1068
ucgauuuccc gguggucacu cug 23

<210> SEQ ID NO 1069
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
ugucugugga agcggguccc guc 23

<210> SEQ ID NO 1070
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
uaaacuccag gccuaugagg gug 23

<210> SEQ ID NO 1071
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1071
agcuggcuuu uccgaauaaa cuc 23

<210> SEQ ID NO 1072
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1072
uggggcaaag agguccacac agc 23

<210> SEQ ID NO 1073
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1073
agagaagugg aucagucucu gcc 23

<210> SEQ ID NO 1074
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1074
aagcguugug ggcccggcag acc 23

<210> SEQ ID NO 1075
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1075
aauggcguag acacccucac ccc 23

<210> SEQ ID NO 1076
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1076
uggugaggua uccccggcgg gca 23

<210> SEQ ID NO 1077
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
aagacagagg aguccuccuc gau 23

<210> SEQ ID NO 1078
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
uaugcuggug ucuaggagau aca 23

<210> SEQ ID NO 1079
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
augacccugc ccucgauuuc ccg 23

<210> SEQ ID NO 1080
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
acuugcuggc cugucugugg aag 23

<210> SEQ ID NO 1081
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
auaaacucca ggccuaugag ggu 23

<210> SEQ ID NO 1082
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
ugaccagcac gaccccagcc cuc 23

<210> SEQ ID NO 1083
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1083
aggcaccaau gauguccucc ccu 23

<210> SEQ ID NO 1084
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1084
uuggcagaga aguggaucag ucu 23

<210> SEQ ID NO 1085
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1085
aaagcguugu gggcccggca gac 23

<210> SEQ ID NO 1086
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1086
uggcaauggc guagacaccc uca 23

<210> SEQ ID NO 1087
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1087
uuggugaggu auccccggcg ggc 23

<210> SEQ ID NO 1088
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1088
auguagucga cauggggcaa cuu 23

<210> SEQ ID NO 1089
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1089
ugguauucau ccgcccggua ccg 23

<210> SEQ ID NO 1090
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1090
uguaugcugg ugucuaggag aua 23

<210> SEQ ID NO 1091
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1091
accaugaccc ugcccucgau uuc 23

<210> SEQ ID NO 1092
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1092
aauaaacucc aggccuauga ggg 23

<210> SEQ ID NO 1093
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1093
aaguugccgg cagcggugac cag 23

<210> SEQ ID NO 1094
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1094
acacaaagca ggugcugcag ucg 23

<210> SEQ ID NO 1095
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1095
aucuuuggca gagaagugga uca 23

<210> SEQ ID NO 1096
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1096
acccccaaaa gcguuguggg ccc 23

<210> SEQ ID NO 1097
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1097
accuggcaau ggcguagaca ccc 23

<210> SEQ ID NO 1098
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1098
ugcuccuuga cuuugcauuc cag 23

<210> SEQ ID NO 1099
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1099
agcuggagau gagggccauc agc 23

<210> SEQ ID NO 1100
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1100
uaagaagagg cuuggcuuca gag 23

<210> SEQ ID NO 1101
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1101
uggugcucaa ggagggacag uug 23

<210> SEQ ID NO 1102
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1102
agauaaaugu cugcuugcuu ggg 23

<210> SEQ ID NO 1103
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1103
agaggacaga cccaaaagau aaa 23

<210> SEQ ID NO 1104
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1104
aaaaaggcaa cagagaggac aga 23

<210> SEQ ID NO 1105
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
auaaauaucu ucaaguuaca aaa 23

<210> SEQ ID NO 1106
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
uuggcauaga gcagaguaaa ggu 23

<210> SEQ ID NO 1107

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1107
uuuccugguc uguguucccc uuc 23

<210> SEQ ID NO 1108
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1108
aaacagagag gacagaccca aaa 23

<210> SEQ ID NO 1109
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1109
uggagcugug uggacgcugc agu 23

<210> SEQ ID NO 1110
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1110
ugcuccugag gggccgggau ucc 23

<210> SEQ ID NO 1111
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1111
uggcuagaug ccauccagaa agc 23

<210> SEQ ID NO 1112
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1112
aguaagaaga ggcuuggcuu cag 23

<210> SEQ ID NO 1113
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1113
ugcuugcuug gguggggcug gug 23

<210> SEQ ID NO 1114
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1114
aagauaaaug ucugcuugcu ugg 23

<210> SEQ ID NO 1115
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1115
agagaggaca gacccaaaag aua 23

<210> SEQ ID NO 1116
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1116
uaaaaaggca acagagagga cag 23

<210> SEQ ID NO 1117
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1117
aauaaauauc uucaaguuac aaa 23

<210> SEQ ID NO 1118
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1118
ucuggcauag agcagaguaa agg 23

<210> SEQ ID NO 1119
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1119
aauaaauguc ugcuugcuug ggu 23

<210> SEQ ID NO 1120
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1120
ucaacagaga ggacagaccc aaa 23

<210> SEQ ID NO 1121
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1121
aguggacacg gguccccaug cug 23

<210> SEQ ID NO 1122
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1122
ucuggcuaga ugccauccag aaa 23

<210> SEQ ID NO 1123
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1123
aaguaagaag aggcuuggcu uca 23

<210> SEQ ID NO 1124
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1124
ugucugcuug cuuggguggg gcu 23

<210> SEQ ID NO 1125
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1125
aaagauaaau gucugcuugc uug 23

<210> SEQ ID NO 1126
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1126
acagagagga cagacccaaa aga 23

<210> SEQ ID NO 1127
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1127
aaagcaaaac aggucuagaa aag 23

<210> SEQ ID NO 1128
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1128
aaagaauccu gccuccuugg ugg 23

<210> SEQ ID NO 1129
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
uuaguggagc ggguuggcug aga 23

<210> SEQ ID NO 1130
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
aaaaagauaa augucugcuu gcu 23

<210> SEQ ID NO 1131
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 1131
ugcaacagag aggacagacc caa 23

<210> SEQ ID NO 1132
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1132
ucagcacagg cggcuugugg gug 23

<210> SEQ ID NO 1133
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1133
auuuuaaagc ucagccccag ccc 23

<210> SEQ ID NO 1134
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1134
uagcacagcc uggcauagag cag 23

<210> SEQ ID NO 1135
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1135
uguuccccuu cccagccuca cug 23

<210> SEQ ID NO 1136
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1136
augucugcuu gcuugggugg ggc 23

<210> SEQ ID NO 1137
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1137
acccaaaaga uaaaugucug cuu 23

<210> SEQ ID NO 1138
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1138
aacagagagg acagacccaa aag 23

<210> SEQ ID NO 1139
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1139
aaaagcaaaa caggucuaga aaa 23

<210> SEQ ID NO 1140
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1140
aaugggaaga auccugccuc cuu 23

<210> SEQ ID NO 1141
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1141
uugcugugug agcuuggcag gca 23

<210> SEQ ID NO 1142
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1142
ucaaaagaua aaugucugcu ugc 23

<210> SEQ ID NO 1143
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1143
aaaaagcaaa acaggucuag aaa 23

<210> SEQ ID NO 1144
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1144
uugggcugac cucguggccu cag 23

<210> SEQ ID NO 1145
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1145
agggagcuuc cuggcaccuc cac 23

<210> SEQ ID NO 1146
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1146
uaguggagcg gguuggcuga gac 23

<210> SEQ ID NO 1147
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1147
ucuguguucc ccuucccagc cuc 23

<210> SEQ ID NO 1148
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1148
aaugucugcu ugcuugggug ggg 23

<210> SEQ ID NO 1149
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1149
agacccaaaa gauaaauguc ugc 23

<210> SEQ ID NO 1150
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1150
aggcaacaga gaggacagac cca 23

<210> SEQ ID NO 1151
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1151
acaaaagcaa aacaggucua gaa 23

<210> SEQ ID NO 1152
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1152
ucaugggaag aauccugccu ccu 23

<210> SEQ ID NO 1153
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1153
uuuccugcug ugugagcuug gca 23

<210> SEQ ID NO 1154
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1154
uccaaaagau aaaugucugc uug 23

<210> SEQ ID NO 1155
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1155
aaauaaauau cuucaaguua caa 23

<210> SEQ ID NO 1156
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1156
acugguuggg cugaccucgu ggc 23

<210> SEQ ID NO 1157
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1157
aauggugaaa ugccccacag uga 23

<210> SEQ ID NO 1158
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1158
uccuggucug uguuccccuu ccc 23

<210> SEQ ID NO 1159
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1159
aaaugucugc uugcuugggu ggg 23

<210> SEQ ID NO 1160
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1160
acagacccaa aagauaaaug ucu 23

<210> SEQ ID NO 1161
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1161
aaggcaacag agaggacaga ccc 23

<210> SEQ ID NO 1162
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1162
uacaaaagca aaacaggucu aga 23

<210> SEQ ID NO 1163
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1163
ugcuagaugc cauccagaaa gcu 23

<210> SEQ ID NO 1164
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1164
aaguuccugc ugugugagcu ugg 23

<210> SEQ ID NO 1165
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1165
aagacccaaa agauaaaugu cug 23

<210> SEQ ID NO 1166
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1166
aagcaaaaca ggucuagaaa agu 23

<210> SEQ ID NO 1167
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1167
aagcguggau gcuggccucc cug 23

<210> SEQ ID NO 1168
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1168
agaauccugc cuccuuggug gag 23

<210> SEQ ID NO 1169
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1169
uuccugcugu gugagcuugg cag 23

<210> SEQ ID NO 1170
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1170
uuccuggucu guguuccccu ucc 23

<210> SEQ ID NO 1171
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1171
uaaaugucug cuugcuuggg ugg 23

<210> SEQ ID NO 1172
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1172
aggacagacc caaaagauaa aug 23

<210> SEQ ID NO 1173
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1173
aaaggcaaca gagaggacag acc 23

<210> SEQ ID NO 1174
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1174
aaauaucuuc aaguuacaaa agc 23

<210> SEQ ID NO 1175
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1175
uuggcuagau gccauccaga aag 23

<210> SEQ ID NO 1176
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1176
uuaagaagag gcuuggcuuc aga 23

<210> SEQ ID NO 1177
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1177
aaggacagac ccaaaagaua aau 23

<210> SEQ ID NO 1178
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1178
aagcaaaaca ggucuagaaa agu 23

<210> SEQ ID NO 1179
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1179
auggcagcag gaagcgugga ugc 23

<210> SEQ ID NO 1180
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1180
aagaauccug ccuccuuggu gga 23

<210> SEQ ID NO 1181
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1181
aguuccugcu gugugagcuu ggc 23

<210> SEQ ID NO 1182
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1182
agcuuccugg ucuguguucc ccu 23

<210> SEQ ID NO 1183
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1183
auaaaugucu gcuugcuugg gug 23

<210> SEQ ID NO 1184
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1184
aaaaggcaac agagaggaca gac 23

<210> SEQ ID NO 1185
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1185
uaaauaucuu caaguuacaa aag 23

<210> SEQ ID NO 1186

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1186
uucuggcuag augccaucca gaa 23

<210> SEQ ID NO 1187
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1187
uuuccccuuc ccagccucac ugu 23

<210> SEQ ID NO 1188
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1188
aagaggacag acccaaaaga uaa 23

<210> SEQ ID NO 1189
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1189
ucgaaguacu cagcguaagu gau 23

<210> SEQ ID NO 1190
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1190
acaaaagcaa aacaggucua gaa 23

<210> SEQ ID NO 1191
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1191
acaaaagcaa aacaggucua gaa 23

<210> SEQ ID NO 1192
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1192
acaaaagcaa aacaggucua gaa 23

<210> SEQ ID NO 1193
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1193
acaaaagcaa aacaggucua gaa 23

<210> SEQ ID NO 1194
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1194
acaaaagcaa aacaggucua gaa 23

<210> SEQ ID NO 1195
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1195
acaaaagcaa aacaggucua gaa 23

<210> SEQ ID NO 1196
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1196
acaaaagcaa aacaggucua gaa 23

<210> SEQ ID NO 1197
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1197
acaaaagcaa aacaggucua gaa 23

<210> SEQ ID NO 1198
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1198
acaaaagcaa aacaggucua gaa 23

<210> SEQ ID NO 1199
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199
acaaaagcaa aacaggucua gaa 23

<210> SEQ ID NO 1200
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200
acaaaagcaa aacaggucua gaa 23

<210> SEQ ID NO 1201
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201
acaaaagcaa aacaggucua gaa 23

<210> SEQ ID NO 1202
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1202
acaaaagcaa aacaggucua gaa 23

<210> SEQ ID NO 1203
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1203
acaaaagcaa aacaggucua gaa 23

<210> SEQ ID NO 1204
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1204
acaaaagcaa aacaggucua gaa 23

<210> SEQ ID NO 1205
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1205
acaaaagcaa aacaggucua gaa 23

<210> SEQ ID NO 1206
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1206
acaaaagcaa aacaggucua gaa 23

<210> SEQ ID NO 1207
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1207
acaaaagcaa aacaggucua gaa 23

<210> SEQ ID NO 1208
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1208
acaaaagcaa aacaggucua gaa 23

<210> SEQ ID NO 1209
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1209
acaaaagcaa aacaggucua gaa 23

<210> SEQ ID NO 1210
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1210
acaaaagcaa aacaggucua gaa 23

<210> SEQ ID NO 1211
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1211
acaaaagcaa aacaggucua gaa 23

<210> SEQ ID NO 1212
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1212
acaaaagcaa aacaggucua gaa 23

<210> SEQ ID NO 1213
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1213
acaaaagcaa aacaggucua gaa 23

<210> SEQ ID NO 1214
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1214
acaaaagcaa aacaggucua gaa 23

<210> SEQ ID NO 1215
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1215
acaaaagcaa aacaggucua gaa 23

<210> SEQ ID NO 1216
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1216
acaaaagcaa aacaggucua gaa 23

<210> SEQ ID NO 1217
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1217
acaaaagcaa aacaggucua gaa 23

<210> SEQ ID NO 1218
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1218
acaaaagcaa aacaggucua gaa 23

<210> SEQ ID NO 1219
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1219
acaaaagcaa aacaggucua gaa 23

<210> SEQ ID NO 1220
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1220
acaaaagcaa aacaggucua gaa 23

<210> SEQ ID NO 1221
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1221
acaaaagcaa aacaggucua gaa 23

<210> SEQ ID NO 1222
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1222
acaaaagcaa aacaggucua gaa 23

<210> SEQ ID NO 1223
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1223
acaaaagcaa aacaggucua gaa 23

<210> SEQ ID NO 1224
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1224
acaaaagcaa aacaggucua gaa 23

<210> SEQ ID NO 1225
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1225
acaaaagcaa aacaggucua gaa 23

<210> SEQ ID NO 1226
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1226
acaaaagcaa aacaggucua gaa 23

<210> SEQ ID NO 1227
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1227
acaaaagcaa aacaggucua gaa 23

<210> SEQ ID NO 1228
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1228
acaaaagcaa aacaggucua gaa 23

<210> SEQ ID NO 1229
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1229
acaaaagcaa aacaggucua gaa 23

<210> SEQ ID NO 1230
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1230
acaaaagcaa aacaggucua gaa 23

<210> SEQ ID NO 1231
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1231
acaaaagcaa aacaggucua gaa 23

<210> SEQ ID NO 1232
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1232
acaaaagcaa aacaggucua gaa 23

<210> SEQ ID NO 1233
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1233
acaaaagcaa aacaggucua gaa 23

<210> SEQ ID NO 1234
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1234
acaaaagcaa aacaggucua gaa 23

<210> SEQ ID NO 1235
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1235
acaaaagcaa aacaggucua gaa 23

<210> SEQ ID NO 1236
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1236
acaaaagcaa aacaggucua gaa 23

<210> SEQ ID NO 1237
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1237
acaaaagcaa aacaggucua gaa 23

<210> SEQ ID NO 1238
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1238
acaaaagcaa aacaggucua gaa 23

<210> SEQ ID NO 1239
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1239
acaaaagcaa aacaggucua gaa 23

<210> SEQ ID NO 1240
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1240
acaaaagcaa aacaggucua gaa 23

<210> SEQ ID NO 1241
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1241
acaaaagcaa aacaggucua gaa 23

<210> SEQ ID NO 1242
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1242
acaaaagcaa aacaggucua gaa 23

<210> SEQ ID NO 1243
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1243
acaaaagcaa aacaggucua gaa 23

<210> SEQ ID NO 1244
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1244
acaaaagcaa aacaggucua gaa 23

<210> SEQ ID NO 1245
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1245
acaaaagcaa aacaggucua gaa 23

<210> SEQ ID NO 1246
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1246
acaaaagcaa aacaggucua gaa 23

<210> SEQ ID NO 1247
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1247
acaaaagcaa aacaggucua gaa 23

<210> SEQ ID NO 1248
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1248
acaaaagcaa aacaggucua gaa 23

<210> SEQ ID NO 1249
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1249
acaaaagcaa aacaggucua gaa 23

<210> SEQ ID NO 1250
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1250
acaaaagcaa aacaggucua gaa 23

<210> SEQ ID NO 1251
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1251
acaaaagcaa aacaggucua gaa 23

<210> SEQ ID NO 1252
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1252
acaaaagcaa aacaggucua gaa 23

<210> SEQ ID NO 1253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
acaaaagcaa aacaggucua gaa 23

<210> SEQ ID NO 1254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
acaaaagcaa aacaggucua gaa 23

<210> SEQ ID NO 1255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1255
acaaaagcaa aacaggucua gaa 23

<210> SEQ ID NO 1256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
acaaaagcaa aacaggucua gaa 23

<210> SEQ ID NO 1257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
acaaaagcaa aacaggucua gaa 23

<210> SEQ ID NO 1258
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
acaaaagcaa aacaggucua gaa 23

<210> SEQ ID NO 1259
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1259
acaaaagcaa aacaggucua gaa 23

<210> SEQ ID NO 1260
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1260
acaaaagcaa aacaggucua gaa 23

<210> SEQ ID NO 1261
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1261
acaaaagcaa aacaggucua g 21

<210> SEQ ID NO 1262
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1262
acaaaagcaa aacaggucua g 21

<210> SEQ ID NO 1263
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1263
acaaaagcaa aacaggucua g 21

<210> SEQ ID NO 1264
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1264
acaaaagcaa aacaggucua g 21

<210> SEQ ID NO 1265

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1265
acaaaagcaa aacaggucua g 21

<210> SEQ ID NO 1266
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1266
acaaaagcaa aacaggucua g 21

<210> SEQ ID NO 1267
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1267
acaaaagcaa aacaggucua g 21

<210> SEQ ID NO 1268
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1268
acaaaagcaa aacaggucua g 21

<210> SEQ ID NO 1269
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1269
acaaaagcaa aacaggucua g 21

<210> SEQ ID NO 1270
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1270
acaaaagcaa aacaggucua g 21

<210> SEQ ID NO 1271
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1271
acaaaagcaa aacaggucua g 21

<210> SEQ ID NO 1272
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1272
acaaaagcaa aacaggucua g 21

<210> SEQ ID NO 1273
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1273
acaaaagcaa aacaggucua g 21

<210> SEQ ID NO 1274
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1274
acaaaagcaa aacaggucua g 21

<210> SEQ ID NO 1275
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1275
acaaaagcaa aacaggucua g 21

<210> SEQ ID NO 1276
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1276
acaaaagcaa aacaggucua g 21

<210> SEQ ID NO 1277
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1277
acaaaagcaa aacaggucau a                                                21

<210> SEQ ID NO 1278
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
aaaaagauaa augucugcuu gcu                                              23

<210> SEQ ID NO 1279
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
aaaaagauaa augucugcuu gcu                                              23

<210> SEQ ID NO 1280
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
aaaaagauaa augucugcuu gcu                                              23

<210> SEQ ID NO 1281
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
aaaaagauaa augucugcuu gcu                                              23

<210> SEQ ID NO 1282
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
aaaaagauaa augucugcuu gcu                                              23

<210> SEQ ID NO 1283
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1283
aaaaagauaa augucugcuu gcu 23

<210> SEQ ID NO 1284
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1284
aaaaagauaa augucugcuu gcu 23

<210> SEQ ID NO 1285
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1285
aaaaagauaa augucugcuu gcu 23

<210> SEQ ID NO 1286
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1286
aaaaagauaa augucugcuu gcu 23

<210> SEQ ID NO 1287
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1287
aaaaagauaa augucugcuu gcu 23

<210> SEQ ID NO 1288
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1288
aaaaagauaa augucugcuu gcu 23

<210> SEQ ID NO 1289
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1289
aaaaagauaa augucugcuu gcu 23

<210> SEQ ID NO 1290
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1290
aaaaagauaa augucugcuu gcu 23

<210> SEQ ID NO 1291
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1291
aaaaagauaa augucugcuu gcu 23

<210> SEQ ID NO 1292
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
aaaaagauaa augucugcuu gcu 23

<210> SEQ ID NO 1293
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293
aaaaagauaa augucugcuu gcu 23

<210> SEQ ID NO 1294
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1294
aaaaagauaa augucugcuu gcu 23

<210> SEQ ID NO 1295
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1295
aaaaagauaa augucugcuu gcu 23

<210> SEQ ID NO 1296
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1296
aaaaagauaa augucugcuu gcu 23

<210> SEQ ID NO 1297
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1297
aaaaagauaa augucugcuu gcu 23

<210> SEQ ID NO 1298
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1298
aaaaagauaa augucugcuu gcu 23

<210> SEQ ID NO 1299
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1299
aaaaagauaa augucugcuu gcu 23

<210> SEQ ID NO 1300
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1300
aaaaagauaa augucugcuu gcu 23

<210> SEQ ID NO 1301
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1301
aaaaagauaa augucugcuu gcu 23

<210> SEQ ID NO 1302
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1302
aaaaagauaa augucugcuu gcu 23

<210> SEQ ID NO 1303
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1303
aaaaagauaa augucugcuu gcu 23

<210> SEQ ID NO 1304
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1304
aaaaagauaa augucugcuu gcu 23

<210> SEQ ID NO 1305
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1305
aaaaagauaa augucugcuu gcu 23

<210> SEQ ID NO 1306
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1306
aaaaagauaa augucugcuu gcu 23

<210> SEQ ID NO 1307
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1307
aaaaagauaa augucugcuu gcu 23

<210> SEQ ID NO 1308
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1308
aaaaagauaa augucugcuu gcu 23

<210> SEQ ID NO 1309
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1309
aaaaagauaa augucugcuu gcu 23

<210> SEQ ID NO 1310
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1310
aaaaagauaa augucugcuu gcu 23

<210> SEQ ID NO 1311
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1311
aaaaagauaa augucugcuu gcu 23

<210> SEQ ID NO 1312
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1312
aaaaagauaa augucugcuu gcu 23

<210> SEQ ID NO 1313
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1313
aaaaagauaa augucugcuu gcu 23

<210> SEQ ID NO 1314
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1314
aaaaagauaa augucugcuu gcu 23

<210> SEQ ID NO 1315
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1315
aaaaagauaa augucugcuu gcu 23

<210> SEQ ID NO 1316
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1316
aaaaagauaa augucugcuu gcu 23

<210> SEQ ID NO 1317
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1317
aaaaagauaa augucugcuu gcu 23

<210> SEQ ID NO 1318
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1318
aaaaagauaa augucugcuu gcu 23

<210> SEQ ID NO 1319
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1319
aaaaagauaa augucugcuu gcu 23

<210> SEQ ID NO 1320
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1320
aaaaagauaa augucugcuu gcu 23

<210> SEQ ID NO 1321
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1321
aaaaagauaa augucugcuu gcu 23

<210> SEQ ID NO 1322
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1322
aaaaagauaa augucugcuu gcu 23

<210> SEQ ID NO 1323
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1323
aaaaagauaa augucugcuu gcu 23

<210> SEQ ID NO 1324
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1324
aaaaagauaa augucugcuu gcu 23

<210> SEQ ID NO 1325
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1325
aaaaagauaa augucugcuu gcu 23

<210> SEQ ID NO 1326
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1326
aaaaagauaa augucugcuu gcu 23

<210> SEQ ID NO 1327
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1327
aaaaagauaa augucugcuu gcu 23

<210> SEQ ID NO 1328
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1328
aaaaagauaa augucugcuu gcu 23

<210> SEQ ID NO 1329
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1329
aaaaagauaa augucugcuu gcu 23

<210> SEQ ID NO 1330
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1330
aaaaagauaa augucugcuu gcu 23

<210> SEQ ID NO 1331
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1331
aaaaagauaa augucugcuu gcu 23

<210> SEQ ID NO 1332
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1332
aaaaagauaa augucugcuu gcu 23

<210> SEQ ID NO 1333
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1333
aaaaagauaa augucugcuu gcu 23

<210> SEQ ID NO 1334
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1334
aaaaagauaa augucugcuu gcu 23

<210> SEQ ID NO 1335
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1335
aaaaagauaa augucugcuu gcu 23

<210> SEQ ID NO 1336
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1336
aaaaagauaa augucugcuu gcu 23

<210> SEQ ID NO 1337
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1337
aaaaagauaa augucugcuu gcu 23

<210> SEQ ID NO 1338
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1338
aaaaagauaa augucugcuu gcu 23

<210> SEQ ID NO 1339
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1339
aaaaagauaa augucugcuu gcu 23

<210> SEQ ID NO 1340
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1340
aaaaagauaa augucugcuu gcu 23

<210> SEQ ID NO 1341
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1341
aaaaagauaa augucugcuu gcu 23

<210> SEQ ID NO 1342
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1342
aaaaagauaa augucugcuu gcu 23

<210> SEQ ID NO 1343
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1343
aaaaagauaa augucugcuu gcu 23

<210> SEQ ID NO 1344

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1344
aaaaagauaa augucugcuu gcu 23

<210> SEQ ID NO 1345
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1345
aaaaagauaa augucugcuu gcu 23

<210> SEQ ID NO 1346
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1346
aaaaagauaa augucugcuu gcu 23

<210> SEQ ID NO 1347
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1347
aaaaagauaa augucugcuu gcu 23

<210> SEQ ID NO 1348
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1348
aaaaagauaa augucugcuu gcu 23

<210> SEQ ID NO 1349
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1349
aaaaagauaa augucugcuu gcu 23

<210> SEQ ID NO 1350
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1350
aaaaagauaa augucugcuu gcu 23

<210> SEQ ID NO 1351
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1351
aaaaagauaa augucugcuu gcu 23

<210> SEQ ID NO 1352
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1352
aaaaagauaa augucugcuu gcu 23

<210> SEQ ID NO 1353
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1353
aaaaagauaa augucugcuu gcu 23

<210> SEQ ID NO 1354
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1354
aaaaagauaa augucugcuu gcu 23

<210> SEQ ID NO 1355
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1355
aaaaagauaa augucugcuu gcu 23

<210> SEQ ID NO 1356
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1356
aaaaagauaa augucugcuu gcu 23

<210> SEQ ID NO 1357
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1357
aaaaagauaa augucugcuu gcu 23

<210> SEQ ID NO 1358
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1358
aaaaagauaa augucugcuu gcu 23

<210> SEQ ID NO 1359
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1359
aaaaagauaa augucugcuu gcu 23

<210> SEQ ID NO 1360
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1360
aaaaagauaa augucugcuu gcu 23

<210> SEQ ID NO 1361
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1361
aaaaagauaa augucugcuu gcu 23

<210> SEQ ID NO 1362
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1362
aaaaagauaa augucugcuu gcu 23

<210> SEQ ID NO 1363
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1363
aaaaagauaa augucugcuu gcu 23

<210> SEQ ID NO 1364
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1364
aaaaagauaa augucugcuu gcu 23

<210> SEQ ID NO 1365
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1365
aaaaagauaa augucugcuu gcu 23

<210> SEQ ID NO 1366
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1366
aaaaagauaa augucugcuu gcu 23

<210> SEQ ID NO 1367
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1367
aaaaagauaa augucugcuu gcu 23

<210> SEQ ID NO 1368
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1368
acaaaagcaa aacaggucua gaa 23

<210> SEQ ID NO 1369
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1369
acaaaagcaa aacaggucua gaa 23

<210> SEQ ID NO 1370
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1370
acaaaagcaa aacaggucua gaa 23

<210> SEQ ID NO 1371
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
acaaaagcaa aacaggucua gaa 23

<210> SEQ ID NO 1372
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
acaaaagcaa aacaggucua gaa 23

<210> SEQ ID NO 1373
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373
acaaaagcaa aacaggucua gaa 23

<210> SEQ ID NO 1374
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1374
acaaaagcaa aacaggucua gaa 23

<210> SEQ ID NO 1375
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1375
acaaaagcaa aacaggucua gaa 23

<210> SEQ ID NO 1376
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1376
acaaaagcaa aacaggucua gaa 23

<210> SEQ ID NO 1377
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1377
acaaaagcaa aacaggucua gaa 23

<210> SEQ ID NO 1378
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1378
acaaaagcaa aacaggucua gaa 23

<210> SEQ ID NO 1379
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1379
acaaaagcaa aacaggucua gaa 23

<210> SEQ ID NO 1380
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1380
acaaaagcaa aacaggucua gaa 23

<210> SEQ ID NO 1381
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1381
acaaaagcaa aacaggucua gaa 23

<210> SEQ ID NO 1382
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1382
acaaaagcaa aacaggucua gaa 23

<210> SEQ ID NO 1383
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1383
acaaaagcaa aacaggucua gaa 23

<210> SEQ ID NO 1384
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1384
acaaaagcaa aacaggucua gaa 23

<210> SEQ ID NO 1385
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1385
acaaaagcaa aacaggucua gaa 23

<210> SEQ ID NO 1386
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1386
acaaaagcaa aacaggucua gaa 23

<210> SEQ ID NO 1387
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1387
acaaaagcaa aacaggucua gaa 23

<210> SEQ ID NO 1388
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1388
acaaaagcaa aacaggucua gaa 23

<210> SEQ ID NO 1389
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1389
acaaaagcaa aacaggucua gaa 23

<210> SEQ ID NO 1390
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1390
acaaaagcaa aacaggucua gaa 23

<210> SEQ ID NO 1391
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1391
acaaaagcaa aacaggucua gaa 23

<210> SEQ ID NO 1392
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1392
acaaaagcaa aacaggucua gaa 23

<210> SEQ ID NO 1393
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1393
acaaaagcaa aacaggucua gaa 23

<210> SEQ ID NO 1394
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1394
acaaaagcaa aacaggucua gaa 23

<210> SEQ ID NO 1395
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1395
acaaaagcaa aacaggucua gaa 23

<210> SEQ ID NO 1396
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1396
acaaaagcaa aacaggucua gaa 23

<210> SEQ ID NO 1397
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1397
acaaaagcaa aacaggucua gaa 23

<210> SEQ ID NO 1398
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1398
acaaaagcaa aacaggucua gaa 23

<210> SEQ ID NO 1399
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1399
acaaaagcaa aacaggucua gaa 23

<210> SEQ ID NO 1400
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1400
acaaaagcaa aacaggucua gaa 23

<210> SEQ ID NO 1401
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1401
acaaaagcaa aacaggucua gaa 23

<210> SEQ ID NO 1402
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1402
acaaaagcaa aacaggucua gaa 23

<210> SEQ ID NO 1403
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1403
acaaaagcaa aacaggucua gaa 23

<210> SEQ ID NO 1404
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1404
acaaaagcaa aacaggucua gaa 23

<210> SEQ ID NO 1405
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1405
acaaaagcaa aacaggucua gaa 23

<210> SEQ ID NO 1406
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1406
acaaaagcaa aacaggucua gaa 23

<210> SEQ ID NO 1407
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1407
acaaaagcaa aacaggucua g 21

<210> SEQ ID NO 1408
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1408
acaaaagcaa aacaggucua gaa 23

<210> SEQ ID NO 1409
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1409
acaaaagcaa aacaggucua gaa 23

<210> SEQ ID NO 1410
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1410
acaaaagcaa aacaggucua gaa 23

<210> SEQ ID NO 1411
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1411
acaaaagcaa aacaggucua gaa 23

<210> SEQ ID NO 1412
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1412
acaaaagcaa aacaggucua gaa 23

<210> SEQ ID NO 1413
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1413
acaaaagcaa aacaggucua gaa 23

<210> SEQ ID NO 1414
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1414
acaaaagcaa aacaggucua gaa 23

<210> SEQ ID NO 1415
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1415
acaaaagcaa aacaggucua gaa 23

<210> SEQ ID NO 1416
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1416
acaaaagcaa aacaggucua gaa 23

<210> SEQ ID NO 1417
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1417
acaaaagcaa aacaggucua gaa 23

<210> SEQ ID NO 1418
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1418
acaaaagcaa aacaggucua gaa 23

<210> SEQ ID NO 1419
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1419
acaaaagcaa aacaggucua gaa 23

<210> SEQ ID NO 1420
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1420
acaaaagcaa aacaggucua gaa 23

<210> SEQ ID NO 1421
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1421
acaaaagcaa aacaggucua gaa 23

<210> SEQ ID NO 1422
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1422
acaaaagcaa aacaggucua gaa 23

<210> SEQ ID NO 1423

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1423
acaaaagcaa aacaggucua gaa 23

<210> SEQ ID NO 1424
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1424
acaaaagcaa aacaggucua gaa 23

<210> SEQ ID NO 1425
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1425
acaaaagcaa aacaggucua gaa 23

<210> SEQ ID NO 1426
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1426
acaaaagcaa aacaggucua ga 22

<210> SEQ ID NO 1427
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1427
acaaaagcaa aacaggucua ga 22

<210> SEQ ID NO 1428
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1428
acaaaagcaa aacaggucua ga 22

<210> SEQ ID NO 1429
<211> LENGTH: 22

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1429
acaaaagcaa aacaggucua ga 22

<210> SEQ ID NO 1430
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1430
acaaaagcaa aacaggucua ga 22

<210> SEQ ID NO 1431
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1431
acaaaagcaa aacaggucua g 21

<210> SEQ ID NO 1432
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1432
acaaaagcaa aacaggucua 20

<210> SEQ ID NO 1433
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1433
acaaaagcaa aacaggucu 19

<210> SEQ ID NO 1434
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1434
acaaaagcaa aacaggucu 19

<210> SEQ ID NO 1435
<211> LENGTH: 20
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1435
acaaaagcaa aacaggucua 20

<210> SEQ ID NO 1436
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1436
acaaaagcaa aacaggucua 20

<210> SEQ ID NO 1437
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1437
acaaaagcaa aacaggucua 20

<210> SEQ ID NO 1438
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1438
acaaaagcaa aacaggucua g 21

<210> SEQ ID NO 1439
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1439
acaaaagcaa aacaggucua g 21

<210> SEQ ID NO 1440
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1440
acaaaagcaa aacaggucua g 21

<210> SEQ ID NO 1441
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1441
acaaaagcaa aacaggucua gaa 23

<210> SEQ ID NO 1442
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1442
acaaaagcaa aacaggucua gaa 23

<210> SEQ ID NO 1443
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1443
acaaaagcaa aacaggucua gaa 23

<210> SEQ ID NO 1444
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1444
acaaaagcaa aacaggucua gaa 23

<210> SEQ ID NO 1445
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1445
acaaaagcaa aacaggucua gaa 23

<210> SEQ ID NO 1446
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1446
acaaaagcaa aacaggucua gaa 23

<210> SEQ ID NO 1447
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1447
acaaaagcaa aacaggucua gaa 23

<210> SEQ ID NO 1448
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1448
acaaaagcaa aacaggucua gaa 23

<210> SEQ ID NO 1449
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1449
acaaaagcaa aacaggucua gaa 23

<210> SEQ ID NO 1450
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1450
acaaaagcaa aacaggucua gaa 23

<210> SEQ ID NO 1451
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1451
acaaaagcaa aacaggucua gaa 23

<210> SEQ ID NO 1452
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1452
acaaaagcaa aacaggucua gaa 23

<210> SEQ ID NO 1453
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1453
acaaaagcaa aacaggucua gaa 23

<210> SEQ ID NO 1454
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1454
acaaaagcaa aacaggucua gaa 23

<210> SEQ ID NO 1455
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1455
acaaaagcaa aacaggucua gaa 23

<210> SEQ ID NO 1456
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1456
acaaaagcaa aacaggucua gaa 23

<210> SEQ ID NO 1457
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1457
acaaaagcaa aacaggucua gaa 23

<210> SEQ ID NO 1458
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1458
acaaaagcaa aacaggucua gaa 23

<210> SEQ ID NO 1459
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1459
acaaaagcaa aacaggucua gaa 23

<210> SEQ ID NO 1460
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1460
acaaaagcaa aacaggucua gaa 23

<210> SEQ ID NO 1461
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1461
acaaaagcaa aacaggucua gaa 23

<210> SEQ ID NO 1462
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1462
acaaaagcaa aacaggucua gaa 23

<210> SEQ ID NO 1463
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1463
aaaaagauaa augucugcuu gcu 23

<210> SEQ ID NO 1464
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1464
aagcaaaaca ggucuagaaa agu 23

<210> SEQ ID NO 1465
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1465
acaaaagcaa aacaggucua g 21

<210> SEQ ID NO 1466
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1466
acaaaagcaa aacaggucua g 21

<210> SEQ ID NO 1467
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1467
acaaaagcaa aacaggucua g 21

<210> SEQ ID NO 1468
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1468
acaaaagcaa aacaggucua g 21

<210> SEQ ID NO 1469
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1469
acaaaagcaa aacaggucua g 21

<210> SEQ ID NO 1470
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1470
acaaaagcaa aacaggucua g 21

<210> SEQ ID NO 1471
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1471
acaaaagcaa aacaggucua gaa 23

<210> SEQ ID NO 1472
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1472
acaaaagcaa aacaggucua gaa 23

<210> SEQ ID NO 1473
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1473
acaaaagcaa aacaggucua gaa 23

<210> SEQ ID NO 1474
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1474
acaaaagcaa aacaggucua gaa 23

<210> SEQ ID NO 1475
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1475
acaaaagcaa aacaggucua gaa 23

<210> SEQ ID NO 1476
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1476
acaaaagcaa aacaggucua gaa 23

<210> SEQ ID NO 1477
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1477
acaaaagcaa aacaggucua gaa 23

<210> SEQ ID NO 1478
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1478
acaaaagcaa aacaggucua gaa 23

<210> SEQ ID NO 1479
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1479
acaaaagcaa aacaggucua gaa 23

<210> SEQ ID NO 1480
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1480
acaaaagcaa aacaggucua gaa 23

<210> SEQ ID NO 1481
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1481
acaaaagcaa aacaggucua gaa 23

<210> SEQ ID NO 1482
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1482
acaaaagcaa aacaggucua gaa 23

<210> SEQ ID NO 1483
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1483
acaaaagcaa aacaggucua g 21

<210> SEQ ID NO 1484
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1484
acaaaagcaa aacaggucua g 21

<210> SEQ ID NO 1485
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1485
acaaaagcaa aacaggucua gaa 23

<210> SEQ ID NO 1486
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1486
acaaaagcaa aacaggucua gaa 23

<210> SEQ ID NO 1487
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1487
acaaaagcaa aacaggucua gaa 23

<210> SEQ ID NO 1488
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1488
acaaaagcaa aacaggucua gaa 23

<210> SEQ ID NO 1489
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1489
acaaaagcaa aacaggucua gaa 23

<210> SEQ ID NO 1490
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1490
acaaaagcaa aacaggucua gaa 23

<210> SEQ ID NO 1491
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1491
acaaaagcaa aacaggucua gaa 23

<210> SEQ ID NO 1492
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1492
acaaaagcaa aacaggucua gaa 23

<210> SEQ ID NO 1493
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1493
acaaaagcaa aacaggucua gaa 23

<210> SEQ ID NO 1494
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1494
acaaaagcaa aacaggucua gaa 23

<210> SEQ ID NO 1495
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1495
acaaaagcaa aacaggucua gaa 23

<210> SEQ ID NO 1496
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1496
acaaaagcaa aacaggucua gaa 23

<210> SEQ ID NO 1497
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1497
acaaaagcaa aacaggucua gaa 23

<210> SEQ ID NO 1498
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1498
acaaaagcaa aacaggucua gaa 23

<210> SEQ ID NO 1499
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1499
acaaaagcaa aacaggucua gaa 23

<210> SEQ ID NO 1500
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1500
acaaaagcaa aacaggucua gaa 23

<210> SEQ ID NO 1501
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1501
acaaaagcaa aacaggucua gaa 23

<210> SEQ ID NO 1502

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1502
acaaaagcaa aacaggucua gaa 23

<210> SEQ ID NO 1503
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1503
acaaaagcaa aacaggucua gaa 23

<210> SEQ ID NO 1504
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1504
acaaaagcaa aacaggucua gaa 23

<210> SEQ ID NO 1505
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1505
acaaaagcaa aacaggucua gaa 23

<210> SEQ ID NO 1506
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1506
acaaaagcaa aacaggucua gaa 23

<210> SEQ ID NO 1507
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1507
acaaaagcaa aacaggucua gaa 23

<210> SEQ ID NO 1508
<211> LENGTH: 23

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1508
acaaaagcaa aacaggucua gaa 23

<210> SEQ ID NO 1509
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1509
acaaaagcaa aacaggucua gaa 23

<210> SEQ ID NO 1510
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1510
acaaaagcaa aacaggucua gaa 23

<210> SEQ ID NO 1511
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1511
acaaaagcaa aacaggucua gaa 23

<210> SEQ ID NO 1512
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1512
acaaaagcaa aacaggucua gaa 23

<210> SEQ ID NO 1513
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1513
acaaaagcaa aacaggucua gaa 23

<210> SEQ ID NO 1514
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1514
acaaaagcaa aacaggucua gaa 23

<210> SEQ ID NO 1515
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1515
acaaaagcaa aacaggucua gaa 23

<210> SEQ ID NO 1516
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1516
acaaaagcaa aacaggucua gaa 23

<210> SEQ ID NO 1517
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1517
acaaaagcaa aacaggucua gaa 23

<210> SEQ ID NO 1518
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1518
acaaaagcaa aacaggucua gaa 23

<210> SEQ ID NO 1519
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1519
acaaaacaaa acagucuaaa 20

<210> SEQ ID NO 1520
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1520
acaaaagcaa aacaggucua gaa 23

<210> SEQ ID NO 1521
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1521
acaaaagcaa aacaggucua gaa 23

<210> SEQ ID NO 1522
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1522
acaaaagcaa aacaggucua gaa 23

<210> SEQ ID NO 1523
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1523
acaaaagcaa aacaggucua gaa 23

<210> SEQ ID NO 1524
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1524
acaaaagcaa aacaggucua gaa 23

<210> SEQ ID NO 1525
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1525
acaaaagcaa aacaggucua gaa 23

<210> SEQ ID NO 1526
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1526
acaaaagcaa aacaggucua gaa 23

<210> SEQ ID NO 1527
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1527
acaaaagcaa aacaggucua gaa 23

<210> SEQ ID NO 1528
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1528
acaaaagcaa aacaggucua gaa 23

<210> SEQ ID NO 1529
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1529
acaaaagcaa aacaggucua gaa 23

<210> SEQ ID NO 1530
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1530
acaaaagcaa aacaggucua gaa 23

<210> SEQ ID NO 1531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1531
acaaaagcaa aacaggucua gaa 23

<210> SEQ ID NO 1532
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1532
acaaaagcaa aacaggucua gaa 23

<210> SEQ ID NO 1533
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1533
acaaaagcaa aacaggucua gaa 23

<210> SEQ ID NO 1534
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1534
acaaaagcaa aacaggucua gaa 23

<210> SEQ ID NO 1535
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1535
acaaaagcaa aacaggucua ga 22

<210> SEQ ID NO 1536
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1536
acaaaagcaa aacaggucua ga 22

<210> SEQ ID NO 1537
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1537
acaaaagcaa aacaggucua ga 22

<210> SEQ ID NO 1538
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1538
acaaaagcaa aacaggucua gaa 23

<210> SEQ ID NO 1539
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1539
acaaaagcaa aacaggucua gaa 23

<210> SEQ ID NO 1540
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1540
acaaaagcaa aacaggucua gaa 23

<210> SEQ ID NO 1541
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1541
acaaaagcaa aacaggucua gaa 23

<210> SEQ ID NO 1542
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1542
acaaaagcaa aacaggucua gaa 23

<210> SEQ ID NO 1543
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1543
acaaaagcaa aacaggucua gaa 23

<210> SEQ ID NO 1544
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1544
acaaaagcaa aacaggucua gaa 23

<210> SEQ ID NO 1545
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1545
acaaaagcaa aacaggucua gaa 23

<210> SEQ ID NO 1546
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1546
acaaaagcaa aacaggucua gaa 23

<210> SEQ ID NO 1547
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1547
acaaaagcaa aacaggucua gaa 23

<210> SEQ ID NO 1548
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1548
acaaaagcaa aacaggucua gaa 23

<210> SEQ ID NO 1549
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1549
acaaaagcaa aacaggucua gaa 23

<210> SEQ ID NO 1550
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1550
acaaaagcaa aacaggucua gaa 23

<210> SEQ ID NO 1551
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1551
acaaaagcaa aacaggucua gaa 23

<210> SEQ ID NO 1552
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1552
acaaaagcaa aacaggucua gaa 23

<210> SEQ ID NO 1553
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1553
acaaaagcaa aacaggucua gaa 23

<210> SEQ ID NO 1554
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1554
acaaaacaaa acaggucuag aa 22

<210> SEQ ID NO 1555
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1555
acaaaacaaa acagucuaaa 20

<210> SEQ ID NO 1556
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1556
acaaaacaaa acagucuaaa 20

<210> SEQ ID NO 1557
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1557
cuagaccugu uuugcuuuug u 21

<210> SEQ ID NO 1558
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1558
cuagaccugu uuugcuuuug u 21

<210> SEQ ID NO 1559
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1559
cuagaccugu uuugcuuuug u 21

<210> SEQ ID NO 1560
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1560
cuagaccugu uuugcuuuug u 21

<210> SEQ ID NO 1561
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1561
cuagaccugu uuugcuuuug u 21

<210> SEQ ID NO 1562
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1562
cuagaccugu uuugcuuuug u 21

<210> SEQ ID NO 1563
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1563
cuagaccugu uuugcuuuug u 21

<210> SEQ ID NO 1564
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1564
cuagaccugu uuugcuuuug u 21

<210> SEQ ID NO 1565
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1565
caagcagaca uuuaucuuuu u 21

<210> SEQ ID NO 1566
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1566
uuuucuagac cuguuuugcu u 21

<210> SEQ ID NO 1567
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1567
acaaaagcaa aacaggucua gaa 23

<210> SEQ ID NO 1568
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1568
acaaaagcaa aacaggucua gaa 23

<210> SEQ ID NO 1569
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1569
acaaaagcaa aacaggucua gaa 23

<210> SEQ ID NO 1570
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1570
acaaaagcaa aacaggucua gaa 23

<210> SEQ ID NO 1571
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1571
acaaaagcaa aacaggucua gaa 23

<210> SEQ ID NO 1572
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1572
acaaaagcaa aacaggucua gaa 23

<210> SEQ ID NO 1573
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1573
acaaaagcaa aacaggucua gaa 23

<210> SEQ ID NO 1574
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1574
acaaaagcaa aacaggucua gaa 23

<210> SEQ ID NO 1575
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1575
aaaaagauaa augucugcuu gcu 23

<210> SEQ ID NO 1576
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1576
aagcaaaaca ggucuagaaa agu 23

<210> SEQ ID NO 1577
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1577
cuagaccugu uuugcuuuug u 21

<210> SEQ ID NO 1578
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1578
cuagaccugu uuugcuuuug a 21

<210> SEQ ID NO 1579
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1579
guagaccugu uuugcuuuug u 21

<210> SEQ ID NO 1580
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1580
gaagaccugu uuugcuuuug u 21

<210> SEQ ID NO 1581

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1581
gaugaccugu uuugcuuuug u 21

<210> SEQ ID NO 1582
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1582
gaugaccugu uuugcuuuug u 21

<210> SEQ ID NO 1583
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1583
caucaccugu uuugcuuuug u 21

<210> SEQ ID NO 1584
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1584
cuucuccugu uuugcuuuug u 21

<210> SEQ ID NO 1585
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1585
cuacugcugu uuugcuuuug u 21

<210> SEQ ID NO 1586
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1586
cuagaccugu uuugcuuuug u 21

<210> SEQ ID NO 1587
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1587
cuagaccugu uuugcuuuug u 21

<210> SEQ ID NO 1588
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1588
cuagaccugu uuugcuuuug u 21

<210> SEQ ID NO 1589
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1589
cuagaccugu uuugcuuuug u 21

<210> SEQ ID NO 1590
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1590
cuagaccugu uuugcuuuug u 21

<210> SEQ ID NO 1591
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1591
cuagaccugu uuugcuuuug u 21

<210> SEQ ID NO 1592
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1592
cuagaccugu uuugcuuuug u 21

<210> SEQ ID NO 1593
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1593

cuagaccugu uuugcuuuug u                                              21


<210> SEQ ID NO 1594
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1594

cuagaccugu uuugcuuuug u                                              21


<210> SEQ ID NO 1595
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1595

cuagaccugu uuugcuuuug u                                              21


<210> SEQ ID NO 1596
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1596

cuagaccugu uuugcuuuug u                                              21


<210> SEQ ID NO 1597
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1597

cuagaccugu uuugcuuuug u                                              21


<210> SEQ ID NO 1598
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1598

cuagaccugu uuugcuuuug u                                              21


<210> SEQ ID NO 1599
<211> LENGTH: 21
<212> TYPE: RNA
<213> ORGANISM: Artificial Sequence
```

<220> FEATURE:
<223> OTHER INFORMATION: Description of Artificial Sequence: Synthetic
oligonucleotide

<400> SEQUENCE: 1599
cuagaccugu uuugcuuuug u 21

<210> SEQ ID NO 1600
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1600
cuagaccugu uuugcuuuug u 21

<210> SEQ ID NO 1601
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1601
cuagaccugu uuugcuuuug u 21

<210> SEQ ID NO 1602
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1602
cuagaccugu uuugcuuuug u 21

<210> SEQ ID NO 1603
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1603
cuagaccugu uuugcuuuug u 21

<210> SEQ ID NO 1604
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1604
cuagaccugu uuugcuuuug u 21

<210> SEQ ID NO 1605
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 1605
acaaaagcaa aacaggucua gaa 23

<210> SEQ ID NO 1606
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1606
ucaaaagcaa aacaggucua gaa 23

<210> SEQ ID NO 1607
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1607
acaaaagcaa aacaggucua cuu 23

<210> SEQ ID NO 1608
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1608
acaaaagcaa aacaggucuu cuu 23

<210> SEQ ID NO 1609
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1609
acaaaagcaa aacaggucau cuu 23

<210> SEQ ID NO 1610
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1610
acaaaagcaa aacaggucau caa 23

<210> SEQ ID NO 1611
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1611
acaaaagcaa aacaggugau gaa 23

<210> SEQ ID NO 1612
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1612
acaaaagcaa aacaggagaa gaa 23

<210> SEQ ID NO 1613
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1613
acaaaagcaa aacagcagua gaa 23

<210> SEQ ID NO 1614
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1614
acaaaagcaa aacaggucua gaa 23

<210> SEQ ID NO 1615
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1615
acaaaagcaa aacaggucua gaa 23

<210> SEQ ID NO 1616
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1616
acaaaagcaa aacaggucua gaa 23

<210> SEQ ID NO 1617
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1617
acaaaagcaa aacaggucua gaa 23

<210> SEQ ID NO 1618
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1618
acaaaagcaa aacaggucua gaa 23

<210> SEQ ID NO 1619
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1619
acaaaagcaa aacaggucua gaa 23

<210> SEQ ID NO 1620
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1620
acaaaagcaa aacaggucua gaa 23

<210> SEQ ID NO 1621
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1621
acaaaagcaa aacaggucua gaa 23

<210> SEQ ID NO 1622
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1622
acaaaagcaa aacaggucua gaa 23

<210> SEQ ID NO 1623
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1623
acaaaagcaa aacaggucua gaa 23

<210> SEQ ID NO 1624
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1624
acaaaagcaa aacaggucua gaa 23

<210> SEQ ID NO 1625
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1625
acaaaagcaa aacaggucua gaa 23

<210> SEQ ID NO 1626
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1626
acaaaagcaa aacaggucua gaa 23

<210> SEQ ID NO 1627
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1627
acaaaagcaa aacaggucua gaa 23

<210> SEQ ID NO 1628
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1628
acaaaagcaa aacaggucua gaa 23

<210> SEQ ID NO 1629
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1629
acaaaagcaa aacaggucua gaa 23

<210> SEQ ID NO 1630
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1630
acaaaagcaa aacaggucua gaa 23

<210> SEQ ID NO 1631
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1631
acaaaagcaa aacaggucua gaa 23

<210> SEQ ID NO 1632
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1632
acaaaagcaa aacaggucua gaa 23

<210> SEQ ID NO 1633
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1633
cuagaccugu uuugcuuuug u 21

<210> SEQ ID NO 1634
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1634
cuagaccugu uuugcuuuug u 21

<210> SEQ ID NO 1635
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1635
cuagaccugu uuugcuuuug u 21

<210> SEQ ID NO 1636
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1636
cuagaccugu uuugcuuuug u 21

<210> SEQ ID NO 1637
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1637
cuagaccugu uuugcuuuug u 21

<210> SEQ ID NO 1638
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1638
cuagaccugu uuugcuuuug u 21

<210> SEQ ID NO 1639
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1639
cuagaccugu uuugcuuuug u 21

<210> SEQ ID NO 1640
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1640
agaccuguuu ugcuuuugu 19

<210> SEQ ID NO 1641
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1641
agaccuguuu ugcuuuugu 19

<210> SEQ ID NO 1642
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1642
cuagaccugu uuugcuuuug u 21

<210> SEQ ID NO 1643
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1643
acaaaagcaa aacaggucua gaa 23

<210> SEQ ID NO 1644
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1644
acaaaagcaa aacaggucua gaa 23

<210> SEQ ID NO 1645
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1645
acaaaagcaa aacaggucua gaa 23

<210> SEQ ID NO 1646
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1646
acaaaagcaa aacaggucua gaa 23

<210> SEQ ID NO 1647
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1647
acaaaagcaa aacaggucua gaa 23

<210> SEQ ID NO 1648
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1648
acaaaagcaa aacaggucua gaa 23

<210> SEQ ID NO 1649
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1649
acaaaagcaa aacaggucua gaa 23

<210> SEQ ID NO 1650
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1650
acaaaagcaa aacaggucua g 21

<210> SEQ ID NO 1651
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1651
acaaaagcaa aacaggucua g 21

<210> SEQ ID NO 1652
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1652
acaaaagcaa aacaggucua gaa 23

<210> SEQ ID NO 1653
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1653
cuagaccugu uuugcuuuug u 21

<210> SEQ ID NO 1654
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1654
cuagaccugu uuugcuuuug u 21

<210> SEQ ID NO 1655
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1655
cuagaccugu uuugcuuuug u 21

<210> SEQ ID NO 1656
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1656
cuagaccugu uuugcuuuug u 21

<210> SEQ ID NO 1657
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1657
cuagaccugu tuugcuuuug u 21

<210> SEQ ID NO 1658
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1658
cuagaccugu uuugcuuuug u 21

<210> SEQ ID NO 1659
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1659
acaaaagcaa aacaggucua gaa 23

<210> SEQ ID NO 1660
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1660
acaaaagcaa aacaggucua gaa 23

<210> SEQ ID NO 1661
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1661
acaaaagcaa aacaggucua gaa 23

<210> SEQ ID NO 1662
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1662
acaaaagcaa aacaggucua gaa 23

<210> SEQ ID NO 1663
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1663
acaaaagcaa aacaggucua gaa 23

<210> SEQ ID NO 1664
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1664
acaaaagcaa aacaggucua gaa 23

<210> SEQ ID NO 1665
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1665

-continued

```
cuagaccugu tuugcuuuu gu                                              21


<210> SEQ ID NO 1666
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1666

acaaaagcaa aacaggucua gaa                                            23
```

PCSK9 IRNA COMPOSITIONS AND METHODS OF USE THEREOF

RELATED APPLICATIONS

This application is a 35 U.S.C. § 371 national stage filing of International Application No. PCT/US2013/073349, filed on Dec. 5, 2013, which, in turn, claims priority to U.S. Provisional Application No. 61/733,518, filed on Dec. 5, 2012; U.S. Provisional Application No. 61/793,530, filed on Mar. 15, 2013; U.S. Provisional Application No. 61/886,916, filed on Oct. 4, 2013; and U.S. Provisional Application No. 61/892,188, filed on Oct. 17, 2013. This application is also related to U.S. Provisional Application No. 61/561,710, filed on Nov. 18, 2011. The entire contents of each of the foregoing patent applications are hereby incorporated herein by reference.

SEQUENCE LISTING

The instant application contains a Sequence Listing which has been submitted electronically in ASCII format and is hereby incorporated by reference in its entirety. Said ASCII copy, created on Aug. 24, 2015, is named 121301_00405_SL.txt and is 397,560 bytes in size.

BACKGROUND OF THE INVENTION

Proprotein convertase subtilisin kexin 9 (PCSK9) is a member of the subtilisin serine protease family. The other eight mammalian subtilisin proteases, PCSK1-PCSK8 (also called PC1/3, PC2, furin, PC4, PC5/6, PACE4, PC7, and S1P/SKI-1) are proprotein convertases that process a wide variety of proteins in the secretory pathway and play roles in diverse biological processes (Bergeron, F. (2000) *J. Mol. Endocrinol.* 24, 1-22, Gensberg, K., (1998) *Semin. Cell Dev. Biol.* 9, 11-17, Seidah, N. G. (1999) *Brain Res.* 848, 45-62, Taylor, N. A., (2003) *FASEB J.* 17, 1215-1227, and Zhou, A., (1999) *J. Biol. Chem.* 274, 20745-20748).

PCSK9 has been proposed to play a role in cholesterol metabolism. PCSK9 mRNA expression is down-regulated by dietary cholesterol feeding in mice (Maxwell, K. N., (2003) *J. Lipid Res.* 44, 2109-2119), up-regulated by statins in HepG2 cells (Dubuc, G., (2004) *Arterioscler. Thromb. Vasc. Biol.* 24, 1454-1459), and up-regulated in sterol regulatory element binding protein (SREBP) transgenic mice (Horton, J. D., (2003) *Proc. Natl. Acad. Sci. USA* 100, 12027-12032), similar to the cholesterol biosynthetic enzymes and the low-density lipoprotein receptor (LDLR). Furthermore, PCSK9 missense mutations have been found to be associated with a form of autosomal dominant hypercholesterolemia (Hchola3) (Abifadel, M., et al. (2003) *Nat. Genet.* 34, 154-156, Timms, K. M., (2004) *Hum. Genet.* 114, 349-353, Leren, T. P. (2004) *Clin. Genet.* 65, 419-422). PCSK9 may also play a role in determining LDL cholesterol levels in the general population, because single-nucleotide polymorphisms (SNPs) have been associated with cholesterol levels in a Japanese population (Shioji, K., (2004) *J. Hum. Genet.* 49, 109-114).

Autosomal dominant hypercholesterolemias (ADHs) are monogenic diseases in which patients exhibit elevated total and LDL cholesterol levels, tendon xanthomas, and premature atherosclerosis (Rader, D. J., (2003) *J. Clin. Invest.* 111, 1795-1803). The pathogenesis of ADHs and a recessive form, autosomal recessive hypercholesterolemia (ARH) (Cohen, J. C., (2003) *Curr. Opin. Lipidol.* 14, 121-127), is due to defects in LDL uptake by the liver. ADH may be caused by LDLR mutations, which prevent LDL uptake, or by mutations in the protein on LDL, apolipoprotein B, which binds to the LDLR. ARH is caused by mutations in the ARH protein that are necessary for endocytosis of the LDLR-LDL complex via its interaction with clathrin. Therefore, if PCSK9 mutations are causative in Hchola3 families, it seems likely that PCSK9 plays a role in receptor-mediated LDL uptake.

Overexpression studies point to a role for PCSK9 in controlling LDLR levels and, hence, LDL uptake by the liver (Maxwell, K. N. (2004) *Proc. Natl. Acad. Sci. USA* 101, 7100-7105, Benjannet, S., et al. (2004) *J. Biol. Chem.* 279, 48865-48875, Park, S. W., (2004) *J. Biol. Chem.* 279, 50630-50638). Adenoviral-mediated overexpression of mouse or human PCSK9 for 3 or 4 days in mice results in elevated total and LDL cholesterol levels; this effect is not seen in LDLR knockout animals (Maxwell, K. N. (2004) *Proc. Natl. Acad. Sci. USA* 101, 7100-7105, Benjannet, S., et al. (2004) *J. Biol. Chem.* 279, 48865-48875, Park, S. W., (2004) *J. Biol. Chem.* 279, 50630-50638). In addition, PCSK9 overexpression results in a severe reduction in hepatic LDLR protein, without affecting LDLR mRNA levels, SREBP protein levels, or SREBP protein nuclear to cytoplasmic ratio.

While hypercholesterolemia itself is asymptomatic, longstanding elevation of serum cholesterol can lead to atherosclerosis. Over a period of decades, chronically elevated serum cholesterol contributes to formation of atheromatous plaques in the arteries which can lead to progressive stenosis or even complete occlusion of the involved arteries. In addition, smaller plaques may rupture and cause a clot to form and obstruct blood flow resulting in, for example, myocardial infarction and/or stroke. If the formation of the stenosis or occlusion is gradual, blood supply to the tissues and organs slowly diminishes until organ function becomes impaired.

Accordingly, there is a need in the art for effective treatments for PCSK9-associated diseases, such as a hyperlipidemia, e.g., hypercholesterolemia.

SUMMARY OF THE INVENTION

As described in more detail below, disclosed herein are compositions comprising RNAi agents, e.g., double-stranded iRNA agents, targeting PCSK9. Also disclosed are methods using the compositions of the invention for inhibiting PCSK9 expression and for treating pathologies related to PCSK9 expression, e.g., hypercholesterolemia.

Accordingly, in one aspect, the present invention provides RNAi agents, e.g., double-stranded RNAi agents, capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense:

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$$

antisense:

$$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'\quad \text{(III)}$$

wherein:

i, j, k, and l are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$, each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b'$ differ from the modification on Y'; and wherein the sense strand is conjugated to at least one ligand.

In one embodiment, i is 0; j is 0; i is 1; j is 1; both i and j are 0; or both i and j are 1. In another embodiment, k is 0; l is 0; k is 1; l is 1; both k and l are 0; or both k and l are 1.

In one embodiment, XXX is complementary to X'X'X', YYY is complementary to Y'Y'Y', and ZZZ is complementary to Z'Z'Z'.

In one embodiment, YYY motif occurs at or near the cleavage site of the sense strand.

In one embodiment, Y'Y'Y' motif occurs at the 11, 12 and 13 positions of the antisense strand from the 5'-end.

In one embodiment, Y' is 2'-O-methyl.

In one embodiment, formula (III) is represented by formula (IIIa):

sense: 5' $n_p$-$N_a$-Y Y Y-$N_a$-$n_q$ 3' antisense: 3' $n_{p'}$-$N_{a'}$-Y'Y'Y'-$N_{a'}$-$n_{q'}$ 5' (IIIa).

In another embodiment, formula (III) is represented by formula (IIIb):

sense:
5' $n_p$-$N_a$-Y Y Y-$N_b$-Z Z Z-$N_a$-$n_q$ 3' antisense:
3' $n_{p'}$-$N_{a'}$-Y'Y'Y'-$N_{b'}$-Z'Z'Z'-$N_{a'}$-$n_{q'}$ 5' (IIIb)

wherein each $N_b$ and $N_b'$ independently represents an oligonucleotide sequence comprising 1-5 modified nucleotides.

In yet another embodiment, formula (III) is represented by formula (IIIc):

sense:
5' $n_p$-$N_a$-X X X-$N_b$-Y Y Y-$N_a$-$n_q$ 3' antisense:
3' $n_{p'}$-$N_{a'}$-X'X'X'-$N_{b'}$-Y'Y'Y'-$N_{a'}$-$n_{q'}$ 5' (IIIc)

wherein each $N_b$ and $N_b'$ independently represents an oligonucleotide sequence comprising 1-5 modified nucleotides.

In one embodiment, formula (III) is represented by formula (IIId):

sense:
5' $n_p$-$N_a$-X X X-$N_b$-Y Y Y-$N_b$-Z Z Z-$N_a$-$n_q$ 3' antisense:
3' $n_{p'}$-$N_{a'}$-X'X'X'-$N_{b'}$-Y'Y'Y'-$N_{b'}$-Z'Z'Z'-$N_{a'}$-$n_{q'}$ 5' (IIId)

wherein each $N_b$ and $N_b'$ independently represents an oligonucleotide sequence comprising 1-5 modified nucleotides and each $N_a$ and $N_a'$ independently represents an oligonucleotide sequence comprising 2-10 modified nucleotides.

In one embodiment, the double-stranded region is 15-30 nucleotide pairs in length. In another embodiment, the double-stranded region is 17-23 nucleotide pairs in length. In yet another embodiment, the double-stranded region is 17-25 nucleotide pairs in length. In one embodiment, the double-stranded region is 23-27 nucleotide pairs in length. In another embodiment, the double-stranded region is 19-21 nucleotide pairs in length. In another embodiment, the double-stranded region is 21-23 nucleotide pairs in length. In one embodiment, each strand has 15-30 nucleotides.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof. In another embodiment, the modifications on the nucleotides are 2'-O-methyl or 2'-fluoro modifications.

In one embodiment, the ligand is one or more GalNAc derivatives attached through a bivalent or trivalent branched linker. In another embodiment, the ligand is

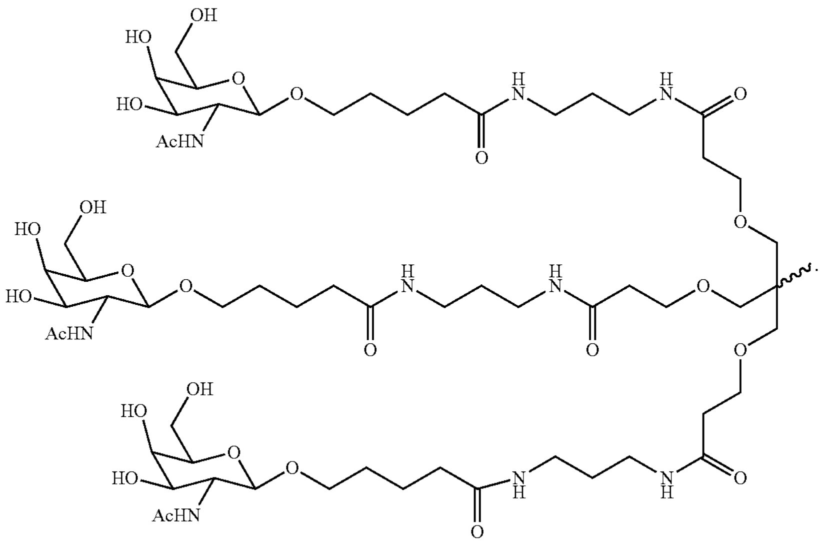 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ligand is attached to the 3' end of the sense strand.

In one embodiment, the RNAi agent is conjugated to the ligand as shown in the following schematic In one embodiment, the RNAi agent is selected from the group of RNAi agents listed in Table 1, Table 2, Table 9, Table 10, Table 12, and FIG. 12.

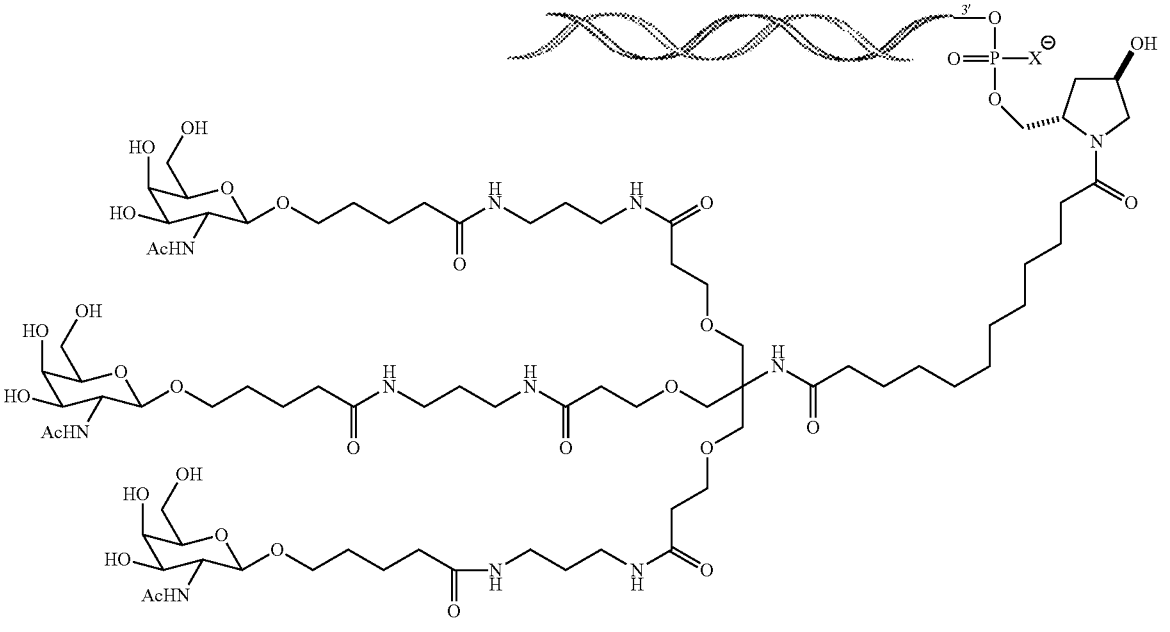

wherein X is O or S. In a specific embodiment, X is O.

In one embodiment, the agent further comprises at least one phosphorothioate or methylphosphonate internucleotide linkage.

In one embodiment, the phosphorothioate or methylphosphonate internucleotide linkage is at the 3'-terminus of one strand. In one embodiment, the strand is the antisense strand. In another embodiment, the strand is the sense strand.

In one embodiment, the phosphorothioate or methylphosphonate internucleotide linkage is at the 5'-terminus of one strand. In one embodiment, the strand is the antisense strand. In another embodiment, the strand is the sense strand.

In one embodiment, the phosphorothioate or methylphosphonate internucleotide linkage is at the both the 5'- and 3'-terminus of one strand. In one embodiment, the strand is the antisense strand.

In one embodiment, the base pair at the 1 position of the 5'-end of the antisense strand of the duplex is an AU base pair.

In one embodiment, the Y nucleotides contain a 2'-fluoro modification.

In one embodiment, the Y' nucleotides contain a 2'-O-methyl modification.

In one embodiment, p'>0. In another embodiment, p'=2.

In one embodiment, q'=0, p=0, q=0, and p' overhang nucleotides are complementary to the target mRNA. In another embodiment, q'=0, p=0, q=0, and p' overhang nucleotides are non-complementary to the target mRNA.

In one embodiment, the sense strand has a total of 21 nucleotides and the antisense strand has a total of 23 nucleotides.

In one embodiment, at least one $n_p$' is linked to a neighboring nucleotide via a phosphorothioate linkage.

In one embodiment, all $n_p$' are linked to neighboring nucleotides via phosphorothioate linkages.

In one embodiment, the RNAi agent is selected from the group consisting of AD-53815, AD-56663, AD-56658, AD-56676, AD-56666, AD-57928, and AD-60212.

In another aspect, the present invention provides RNAi agents, e.g., double stranded RNAi agents, capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense:
$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}$ $N_a'\text{-}n_q'\ 5'$ (III)

wherein:

i, j, k, and l are each independently 0 or 1;

p, p', q, and q' are each independently 0-6;

each $N_a$ and $N_a$' independently represents an oligonucleotide sequence comprising 0-25 nucleotides which are either modified or unmodified or combinations thereof, each sequence comprising at least two differently modified nucleotides;

each $N_b$ and $N_b$' independently represents an oligonucleotide sequence comprising 0-10 nucleotides which are either modified or unmodified or combinations thereof;

each $n_p$, $n_p$', $n_q$, and $n_q$', each of which may or may not be present independently represents an overhang nucleotide;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In yet another aspect, the present invention provides RNAi agents, e.g., double stranded RNAi agents, capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' (III)

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In a further aspect, the present invention provides RNAi agents, e.g., double stranded RNAi agents, capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense:
5' $n_p$-$N_a$-(X X X)$_i$-$N_b$-Y Y Y-$N_b$-(Z Z Z)$_j$-$N_a$-$n_q$ 3'

-continued antisense:
3' $n_p'$-$N_a'$-(X'X'X')$_k$-$N_b'$-Y'Y'Y'-$N_b'$-(Z'Z'Z')$_l$-$N_a'$-$n_q'$ 5' (III)

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand, wherein the ligand is one or more GalNAc derivatives attached through a bivalent or trivalent branched linker.

In another aspect, the present invention provides RNAi agents, e.g., double stranded RNAi agents capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' (III)

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In yet another aspect, the present invention provides RNAi agents, e.g., double stranded RNAi agents, capable of inhibiting the expression of Proprotein Convertase Subtilisin Kexin 9 (PCSK9) in a cell, wherein the double stranded RNAi agent comprises a sense strand complementary to an antisense strand, wherein the antisense strand comprises a region complementary to part of an mRNA encoding PCSK9, wherein each strand is about 14 to about 30 nucleotides in length, wherein the double stranded RNAi agent is represented by formula (III):

sense: 5' $n_p$-$N_a$-Y Y Y-$N_a$-$n_q$ 3' antisense: 3' $n_p$'-$N_a$'-Y'Y'Y'-$N_a$'-$n_q$' 5' (IIIa)

wherein:

each $n_p$, $n_q$, and $n_q$', each of which may or may not be present, independently represents an overhang nucleotide;

p, q, and q' are each independently 0-6;

$n_p$'>0 and at least one $n_p$' is linked to a neighboring nucleotide via a phosphorothioate linkage;

each $N_a$ and $N_a$' independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

The present invention also provides cells, vectors, host cells, and pharmaceutical compositions comprising the double stranded RNAi agents of the invention.

In one embodiment, the present invention provides RNAi agent selected from the group of RNAi agents listed in Table 1, Table 2, Table 9, Table 10, Table 12, and FIG. 12.

In some embodiments, the RNAi agent is administered using a pharmaceutical composition.

In preferred embodiments, the RNAi agent is administered in a solution. In some such embodiments, the siRNA is administered in an unbuffered solution. In one embodiment, the siRNA is administered in water. In other embodiments, the siRNA is administered with a buffer solution, such as an acetate buffer, a citrate buffer, a prolamine buffer, a carbonate buffer, or a phosphate buffer or any combination thereof. In some embodiments, the buffer solution is phosphate buffered saline (PBS).

In one embodiment, the pharmaceutical compositions further comprise a lipid formulation. In one embodiment, the lipid formulation comprises a LNP, or XTC. In another embodiment, the lipid formulation comprises a MC3.

In one aspect, the present invention provides methods of inhibiting PCSK9 expression in a cell. The methods include contacting the cell with an RNAi agent, e.g., a double stranded RNAi agent, or vector of the invention; and maintaining the cell produced in step (a) for a time sufficient to obtain degradation of the mRNA transcript of a PCSK9 gene, thereby inhibiting expression of the PCSK9 gene in the cell.

In one embodiment, the cell is within a subject.

In one embodiment, the subject is a human.

In one embodiment, the PCSK9 expression is inhibited by at least about 30% 35%, 40%, 45%, 50%, 55%, 60%, 65%, 70%, 75%, 80%, 85%, 90% or 95%.

In another aspect, the present invention provides methods of treating a subject having a disorder mediated by PCSK9 expression. The methods include administering to the subject a therapeutically effective amount of an RNAi agent, e.g., a double stranded RNAi agent, or the vector of the invention, thereby treating the subject.

In one embodiment, the subject is a human.

In one embodiment, the human has hypercholesterolemia.

In one embodiment, the RNAi agent, e.g., double stranded RNAi agent, is administered at a dose of about 0.01 mg/kg to about 10 mg/kg, about 0.5 mg/kg to about 50 mg/kg, about 10 mg/kg to about 30 mg/kg, about 10 mg/kg to about 20 mg/kg, about 15 mg/kg to about 20 mg/kg, about 15 mg/kg to about 25 mg/kg, about 15 mg/kg to about 30 mg/kg, or about 20 mg/kg to about 30 mg/kg.

In one embodiment, the RNAi agent, e.g., double stranded RNAi agent, is administered subcutaneously or intravenously.

In one embodiment, the RNAi agent is administered in a dosing regimen that includes a loading phase followed by a maintenance phase, wherein the loading phase comprises administering a dose of 2 mg/kg, 1 mg/kg or 0.5 mg/kg five times a week, and wherein the maintenance phase comprises administering a dose of 2 mg/kg, 1 mg/kg or 0.5 mg/kg once, twice, or three times weekly, once every two weeks, once every three weeks, once a month, once every two months, once every three months, once every four months, once every five months, or once every six months.

In one embodiment, the RNAi agent is administered in two or more doses. In a specific embodiment, the RNAi agent is administered at intervals selected from the group consisting of once every about 12 hours, once every about 24 hours, once every about 48 hours, once every about 72 hours, and once every about 96 hours.

In yet another aspect, the present invention provides methods of treating hypercholesterolemia in a subject. The methods include administering to the subject a therapeutically effective amount of an RNAi agent, e.g., a double stranded RNAi agent, or the vector of the invention, thereby treating the subject.

In one embodiment, the subject is a primate or rodent. In another embodiment, the subject is a human.

In one embodiment, the RNAi agent, e.g., double stranded RNAi agent, is administered at a dose of about 0.01 mg/kg to about 10 mg/kg or about 0.5 mg/kg to about 50 mg/kg. In another embodiment, the double stranded RNAi agent is administered at a dose of about 10 mg/kg to about 30 mg/kg.

In one embodiment, the RNAi agent, e.g., double stranded RNAi agent, is administered subcutaneously or intravenously.

In one embodiment, the RNAi agent is administered in a dosing regimen that includes a loading phase followed by a maintenance phase, wherein the loading phase comprises administering a dose of 2 mg/kg, 1 mg/kg or 0.5 mg/kg five times a week, and wherein the maintenance phase comprises administering a dose of 2 mg/kg, 1 mg/kg or 0.5 mg/kg once, twice, or three times weekly, once every two weeks, once every three weeks, once a month, once every two months, once every three months, once every four months, once every five months, or once every six months.

In one embodiment, the RNAi agent is administered in two or more doses. In a specific embodiment, the RNAi agent is administered at intervals selected from the group consisting of once every about 12 hours, once every about 24 hours, once every about 48 hours, once every about 72 hours, and once every about 96 hours.

In one embodiment, the methods further comprise determining an LDLR genotype or phenotype of the subject.

In one embodiment, administering results in a decrease in serum cholesterol in the subject.

In one embodiment, the methods further comprise determining the serum cholesterol level in the subject.

The present invention is further illustrated by the following detailed description and drawings.

BRIEF DESCRIPTION OF THE DRAWINGS

FIG. 3 is a Table showing the sequences of the sense (SEQ ID NOS 1633-1642, respectively, in order of appearance) and antisense (SEQ ID NOS 1643-1652, respectively, in order of appearance) stands of the duplexes analyzed for in vivo efficacy and lead optimization.

FIG. 12A is a Table depicting iRNA agents of the invention containing optimized sequences as compared to AD-57928 sequences. FIG. 12A discloses the "Sense" sequences as SEQ ID NOS 1653-1658, respectively, in order of appearance, and the "Antisense" sequences as SEQ ID NOS 1659-1664, respectively, in order of appearance.

FIG. 12B is a graph showing the $IC_{50}$ values of the indicated iRNA agents.

DETAILED DESCRIPTION OF THE INVENTION

Figure 1:
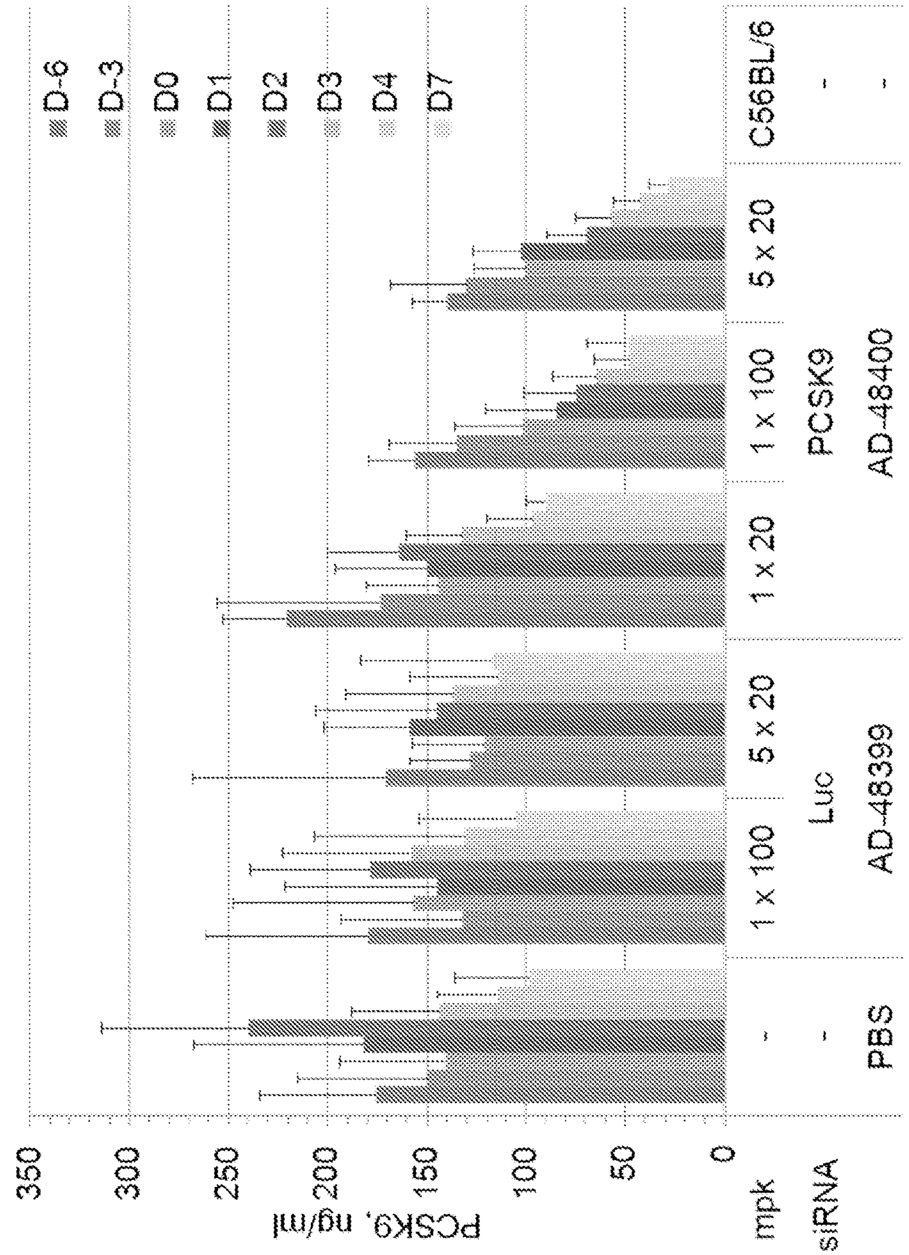
FIG. 1 is a graph depicting that there is a dose response effect with AD-48400 conjugated to GalNAc at all three dosages tested. AD-48399, conjugated to GalNAc, serves as a control.

The present invention provides compositions comprising RNAi agents, e.g., double-stranded iRNA agents, targeting PCSK9. Also disclosed are methods using the compositions of the invention for inhibiting PCSK9 expression and for treating pathologies related to PCSK9 expression, e.g., hypercholesterolemia.

I. DEFINITIONS

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "PCSK9" refers to the proprotein convertase subtilisin kexin 9 gene or protein. PCSK9 is also known as FH3, HCHOLA3, NARC-1, or NARC1. The term PCSK9 includes human PCSK9, the amino acid and nucleotide sequence of which may be found in, for example, GenBank Accession No. GI:299523249; mouse PCSK9, the amino acid and nucleotide sequence of which may be found in, for example, GenBank Accession No. GI:163644257; rat PCSK9, the amino acid and nucleotide sequence of which may be found in, for example, GenBank Accession No. GI:77020249. Additional examples of PCSK9 mRNA sequences are readily available using, e.g., GenBank.

As used herein, "target sequence" refers to a contiguous portion of the nucleotide sequence of an mRNA molecule formed during the transcription of a PCSK9 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of PCSK9 in a cell, e.g., a cell within a subject, such as a mammalian subject.

In one embodiment, an RNAi agent of the invention includes a single stranded RNA that interacts with a target RNA sequence, e.g., a PCSK9 target mRNA sequence, to direct the cleavage of the target RNA. Without wishing to be bound by theory, it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a PCSK9 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a PCSK9 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs.

In one embodiment, an RNAi agent of the invention is a dsRNA of 24-30 nucleotides that interacts with a target RNA sequence, e.g., a PCSK9 target mRNA sequence, to direct the cleavage of the target RNA. Without wishing to be bound by theory, long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). As used herein, a "nucleotide overhang" refers to the unpaired nucleotide or nucleotides that protrude from the duplex structure of an RNAi agent when a 3'-end of one strand of the RNAi agent extends beyond the 5'-end of the other strand, or vice versa. "Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" refers to the strand of a double stranded RNAi agent which includes a region that is substantially complementary to a target sequence (e.g., a human PCSK9 mRNA). As used herein, the term "region complementary to part of an mRNA encoding transthyretin" refers to a region on the antisense strand that is substantially complementary to part of a PCSK9 mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding PCSK9) including a 5' UTR, an open reading frame (ORF), or a 3' UTR. For example, a polynucleotide is complementary to at least a part of a PCSK9 mRNA if the sequence is substantially complementary to a non-interrupted portion of an mRNA encoding PCSK9.

The term "inhibiting," as used herein, is used interchangeably with "reducing," "silencing," "downregulating," "suppressing" and other similar terms, and includes any level of inhibition.

The phrase "inhibiting expression of a PCSK9," as used herein, includes inhibition of expression of any PCSK9 gene (such as, e.g., a mouse PCSK9 gene, a rat PCSK9 gene, a monkey PCSK9 gene, or a human PCSK9 gene) as well as variants, (e.g., naturally occurring variants), or mutants of a PCSK9 gene. Thus, the PCSK9 gene may be a wild-type PCSK9 gene, a mutant PCSK9 gene, or a transgenic PCSK9 gene in the context of a genetically manipulated cell, group of cells, or organism.

"Inhibiting expression of a PCSK9 gene" includes any level of inhibition of a PCSK9 gene, e.g., at least partial suppression of the expression of a PCSK9 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

The expression of a PCSK9 gene may be assessed based on the level of any variable associated with PCSK9 gene expression, e.g., PCSK9 mRNA level, PCSK9 protein level, or serum lipid levels. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "contacting a cell with a double stranded RNAi agent," as used herein, includes contacting a cell by any possible means. Contacting a cell with a double stranded RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, the bloodstream or the subcutaneous space, such that the agent will subsequently reach the tissue where the cell to be contacted is located. For example, the RNAi agent may contain and/or be coupled to a ligand, e.g., a GalNAc3 ligand, that directs the RNAi agent to a site of interest, e.g., the liver. Combinations of in vitro and in vivo methods of contacting are also possible. In connection with the methods of the invention, a cell might also be contacted in vitro with an RNAi agent and subsequently transplanted into a subject.

A "patient" or "subject," as used herein, is intended to include either a human or non-human animal, preferably a mammal, e.g., a monkey. Most preferably, the subject or patient is a human.

A "PCSK9-associated disease," as used herein, is intended to include any disease associated with the PCSK9 gene or protein. Such a disease may be caused, for example, by excess production of the PCSK9 protein, by PCSK9 gene mutations, by abnormal cleavage of the PCSK9 protein, by abnormal interactions between PCSK9 and other proteins or other endogenous or exogenous substances. Exemplary PCSK9-associated diseases include lipidemias, e.g., a hyperlipidemias, and other forms of lipid imbalance such as hypercholesterolemia, hypertriglyceridemia and the pathological conditions associated with these disorders such as heart and circulatory diseases.

"Therapeutically effective amount," as used herein, is intended to include the amount of an RNAi agent that, when administered to a patient for treating a PCSK9 associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by PCSK9 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a PCSK9-associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAS OF THE INVENTION

Described herein are improved double-stranded RNAi agents which inhibit the expression of a PCSK9 gene in a cell, such as a cell within a subject, e.g., a mammal, such as a human having a lipid disorder, e.g., hypercholesterolemia and uses of such double-stranded RNAi agents.

The double-stranded RNAi agents of the invention include agents with chemical modifications as disclosed, for example, in U.S. Provisional Application No. 61/561,710, filed on Nov. 18, 2011, the entire contents of which are incorporated herein by reference.

As shown herein and in Provisional Application No. 61/561,710, a superior result may be obtained by introducing one or more motifs of three identical modifications on three consecutive nucleotides into a sense strand and/or antisense strand of a RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are completely modified to have one or more motifs of three identical modifications on three consecutive nucleotides at or near the cleavage site of at least one strand of an RNAi agent, the gene silencing activity of the RNAi agent was superiorly enhanced.

Accordingly, the invention provides double-stranded RNAi agents capable of inhibiting the expression of a target gene (i.e., a Proprotein concertase subtilisin kexin 9 (PCSK9) gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably $GalNAc_3$).

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisenese strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5' end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one embodiment, the sense strand sequence may be represented by formula (I):

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3' \quad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5'\ n_p\text{-}N_a\text{-}YYY\text{-}N_b\text{-}ZZZ\text{-}N_a\text{-}n_q\ 3' \quad (Ib);$$

$$5'\ n_p\text{-}N_a\text{-}XXX\text{-}N_b\text{-}YYY\text{-}N_a\text{-}n_q\ 3' \quad (Ic);$$

or $$5'\ n_p\text{-}N_a\text{-}XXX\text{-}N_b\text{-}YYY\text{-}N_b\text{-}ZZZ\text{-}N_a\text{-}n_q\ 3' \quad (Id).$$

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'n_p\text{-}N_a\text{—}YYY\text{—}N_a\text{-}n_q3' \quad (Ia).$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'\ n_{q'}\text{-}N_a'\text{-}(Z'Z'Z')_k\text{-}N_b'\text{-}Y'Y'Y'\text{-}N_b'\text{-}(X'X'X')_l\text{-}N'_a\text{-}n_p'\ 3' \quad \text{(II)}$$

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the $1^{st}$ nucleotide, from the 5'-end; or optionally, the count starting at the $1^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

$$5'\ n_{q'}\text{-}N_a'\text{-}Z'Z'Z'\text{-}N_b'\text{-}Y'Y'Y'\text{-}N_a'\text{-}n_{p'}\ 3' \quad \text{(IIb);}$$

$$5'\ n_{q'}\text{-}N_a'\text{-}Y'Y'Y'\text{-}N_b'\text{-}X'X'X'\text{-}n_{p'}\ 3' \quad \text{(IIc);}$$

or $$5'\ n_{q'}\text{-}N_a'\text{-}Z'Z'Z'\text{-}N_b'\text{-}Y'Y'Y'\text{-}N_b'\text{-}X'X'X'\text{-}N_a'\text{-}n_{p'}\ 3' \quad \text{(IId).}$$

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

$$5'\ n_{p'}\text{-}N_{a'}\text{-}Y'Y'Y'\text{-}N_{a'}\text{-}n_{q'}\ 3' \quad \text{(Ia).}$$

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the $1^{st}$ nucleotide from the 5'-end, or optionally, the count starting at the $1^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the $1^{st}$ nucleotide from the 5'-end, or optionally, the count starting at the $1^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

sense:

$$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$$

antisense:

$$3'\ n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q'\ 5'$$

(III)

wherein:

i, j, k, and l are each independently 0 or 1;

p, p', q, and q' are each independently 0-6;

each $N_a$ and $N_a$ independently represents an oligonucleotide sequence comprising 0-25 modified nucleotides, each sequence comprising at least two differently modified nucleotides;

each $N_b$ and $N_b$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

$5'\ n_p\text{-}N_a\text{-}Y\ Y\ Y\text{-}N_a\text{-}n_q\ 3'$ $3'\ n_p'\text{-}N_a'\text{-}Y'Y'Y'\text{-}N_a'n_q'\ 5'$
(IIIa)

$5'\ n_p\text{-}N_a\text{-}Y\ Y\ Y\text{-}N_b\text{-}Z\ Z\ Z\text{-}N_a\text{-}n_q\ 3'$ $3'\ n_p'\text{-}N_a'\text{-}Y'Y'Y'\text{-}N_b'\text{-}Z'Z'Z'\text{-}N_a'n_q'\ 5'$
(IIIb)

$5'\ n_p\text{-}N_a\text{-}X\ X\ X\text{-}N_b\text{-}Y\ Y\ Y\text{-}N_a\text{-}n_q\ 3'$ $3'\ n_p'\text{-}N_a'\text{-}X'X'X'\text{-}N_b'\text{-}Y'Y'Y'\text{-}N_a'\text{-}n_q'\ 5'$
(IIIc)

$5'\ n_p\text{-}N_a\text{-}X\ X\ X\text{-}N_b\text{-}Y\ Y\ Y\text{-}N_b\text{-}Z\ Z\ Z\text{-}N_a\text{-}n_q\ 3'$ $3'\ n_p'\text{-}N_a'\text{-}X'X'X'\text{-}N_b'\text{-}Y'Y'Y'\text{-}N_b'\text{-}Z'Z'Z'\text{-}$ $N_a\text{-}n_q'\ 5'$
(IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker. In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

The RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is an agent selected from the group of agents listed in Table 1 and Table 2.

These agents may further comprise a ligand.

A. Ligands

The double-stranded RNA (dsRNA) agents of the invention may optionally be conjugated to one or more ligands. The ligand can be attached to the sense strand, antisense strand or both strands, at the 3'-end, 5'-end or both ends. For instance, the ligand may be conjugated to the sense strand. In preferred embodiments, the ligand is conjugated to the 3'-end of the sense strand. In one preferred embodiment, the ligand is a GalNAc ligand. In particularly preferred embodiments, the ligand is $GalNAc_3$:

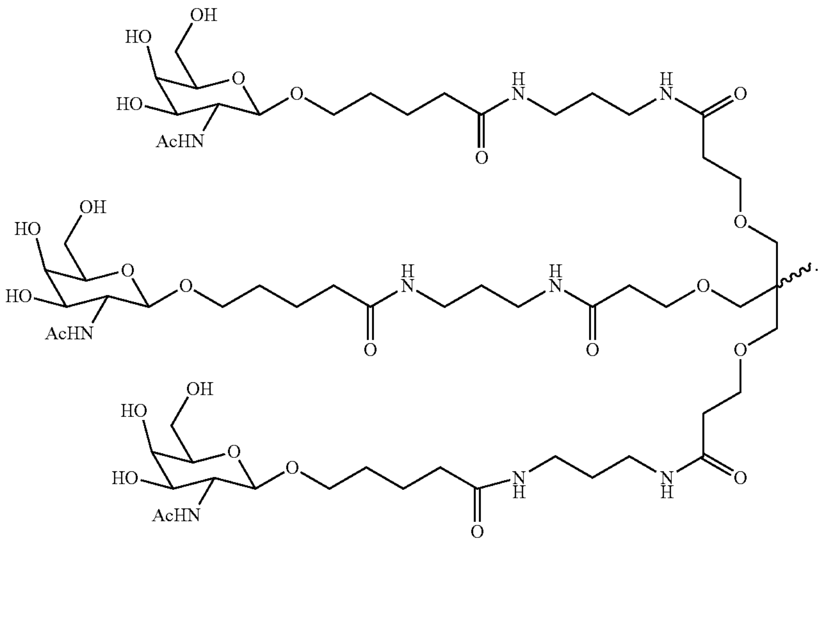 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the ligand, e.g., GalNAc ligand, is attached to the 3' end of the RNAi agent. In one embodiment, the RNAi agent is conjugated to the ligand, e.g., GalNAc ligand, as shown in the following schematic

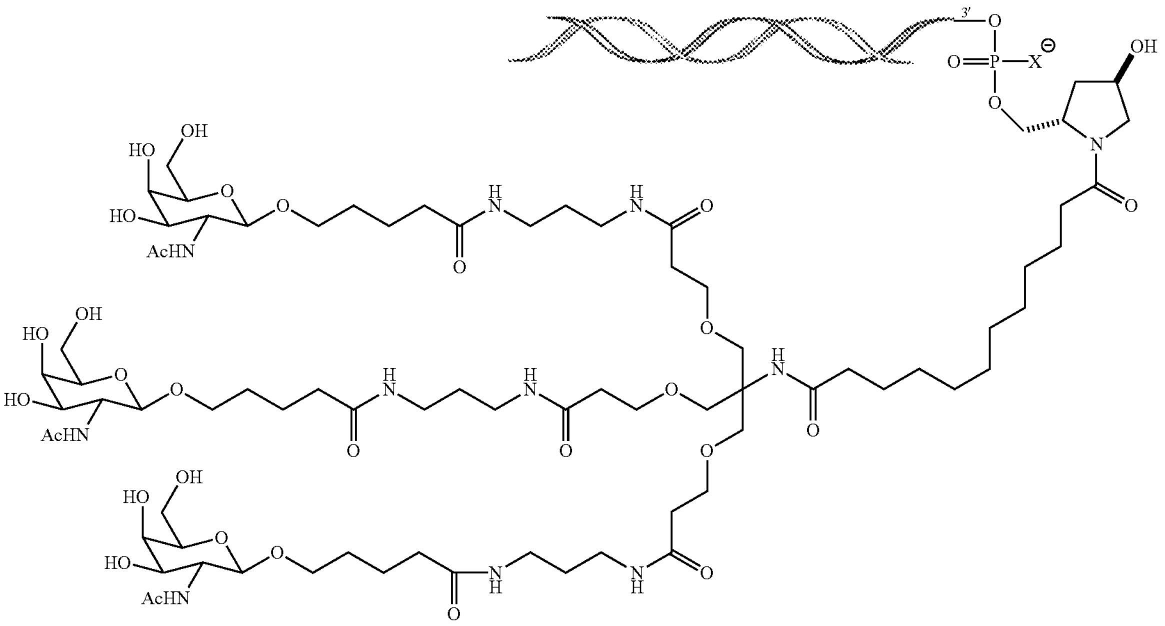

wherein X is O or S. In one embodiment, X is O.

A wide variety of entities can be coupled to the RNAi agents of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., *Biochemistry,* 1987, 26: 2964-2972), the EALA peptide (Vogel et al., *J. Am. Chem. Soc.,* 1996, 118: 1581-1586), and their derivatives (Turk et al., *Biochem. Biophys. Acta,* 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by, for example, activating an inflammatory response. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 1). An RFGF analogue (e.g., amino acid sequence AALLPVLLAAP (SEQ ID NO: 2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 3)) and the Drosophila Antennapedia protein (RQIKIWFQNRRMKWKK (SEQ ID NO: 4)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., *Cancer Res.,* 62:5139-43, 2002). An RGD peptide can facilitate targeting of an iRNA agent to tumors of a variety of other tissues, including the lung, kidney, spleen, or liver (Aoki et al., *Cancer Gene Therapy* 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_V\beta_3$ (Haubner et al., *Jour. Nucl. Med.,* 42:326-336, 2001). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type of ligand target PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as ligands (e.g., as PK modulating ligands).

In addition, aptamers that bind serum components (e.g., serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g., a carrier described herein. The ligand or tethered ligand may be present on a monomer when the monomer is incorporated into the growing strand. In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., TAP-$(CH_2)_nNH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated, e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

Formula (IV)

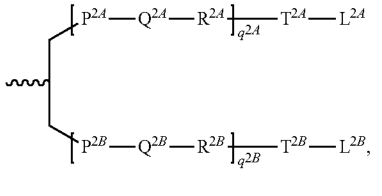

Formula (V)

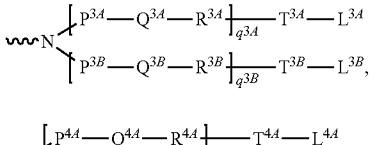

Formula (VI)

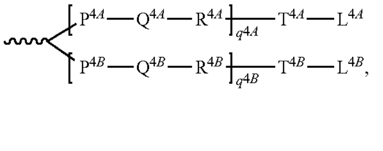

or

-continued

Formula (VII)

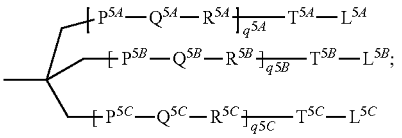

wherein:

$q^{2A}$, $q^{2B}$, $q^{3A}$, $q^{3B}$, $q^{4A}$, $q^{4B}$, $q^{5A}$, $q^{5B}$, and $q^{5C}$ represent independently for each occurrence 0-20 and wherein the repeating unit can be the same or different; $P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N—O,

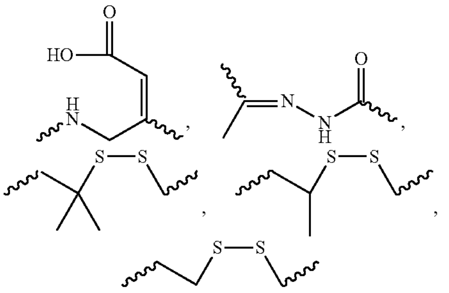

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

Formula (VII)

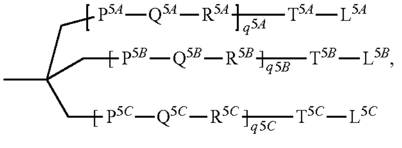

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the following compounds:

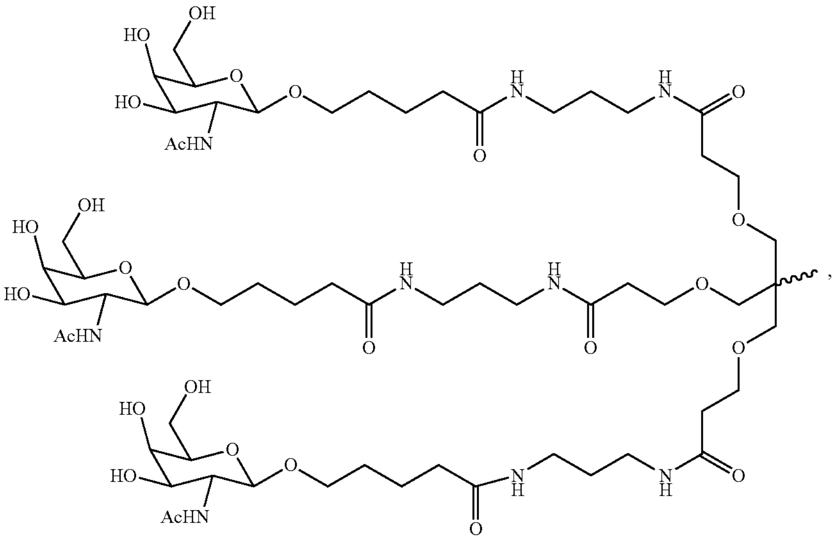
,
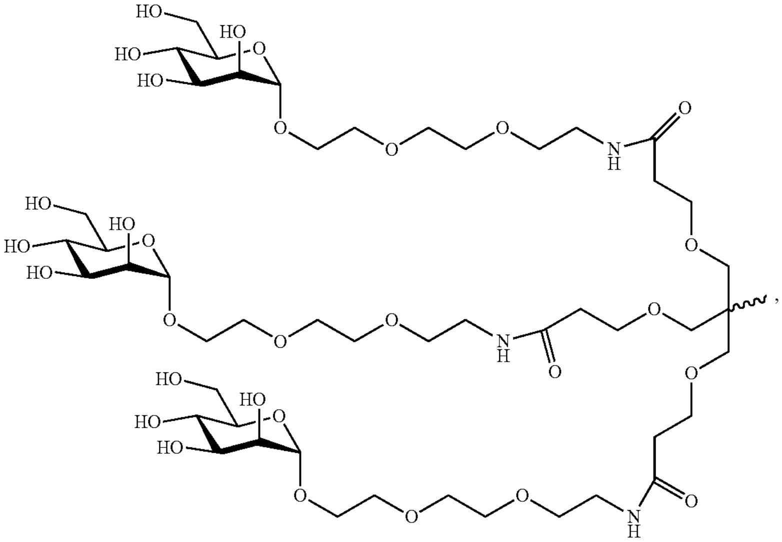
,
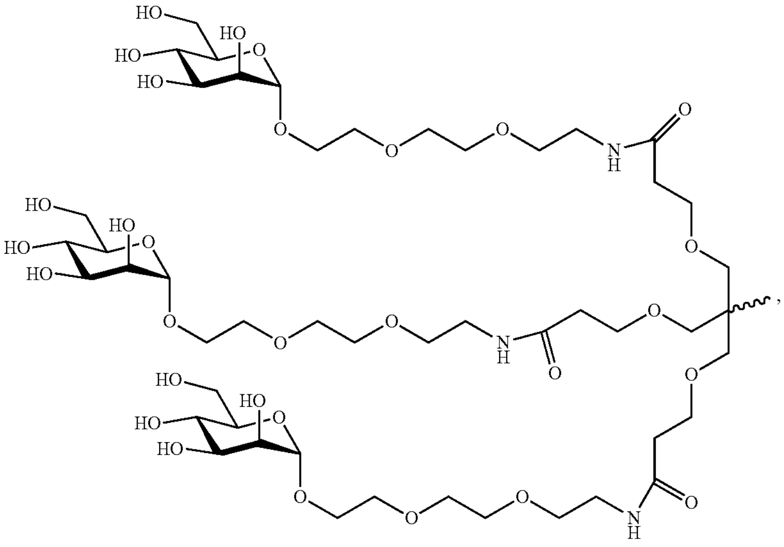
,

-continued
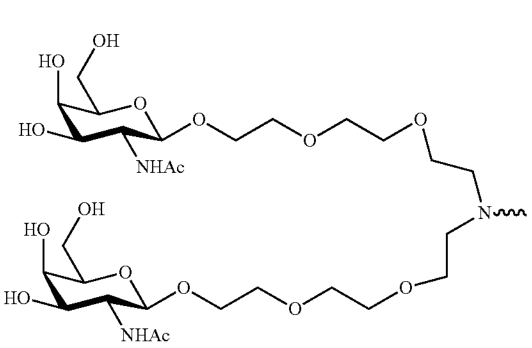
,
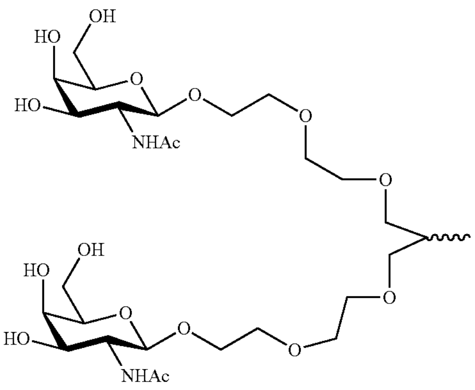
,
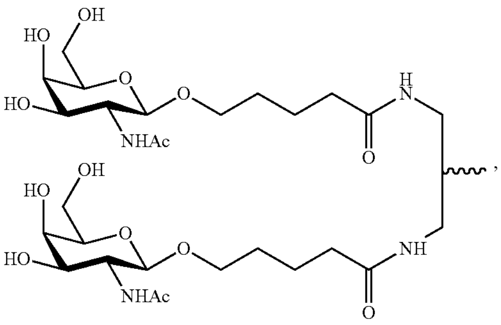
,
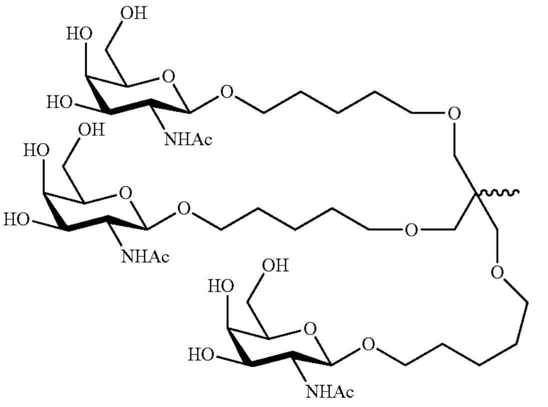
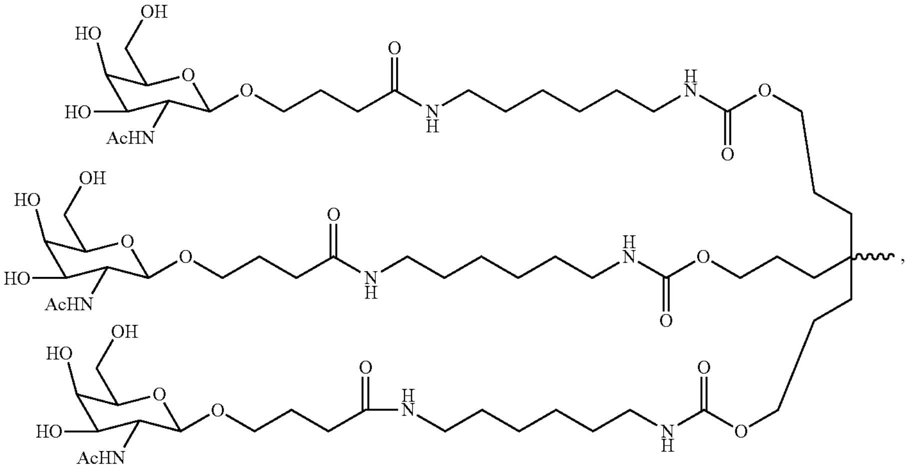
,

-continued

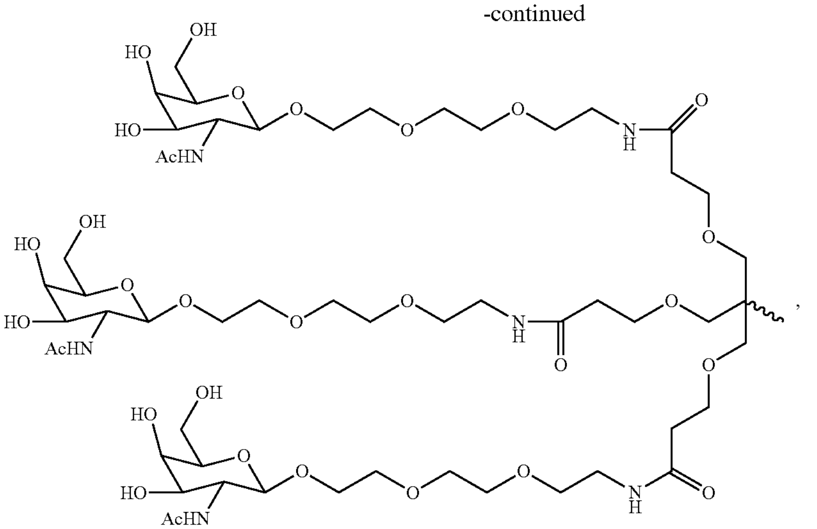

, or

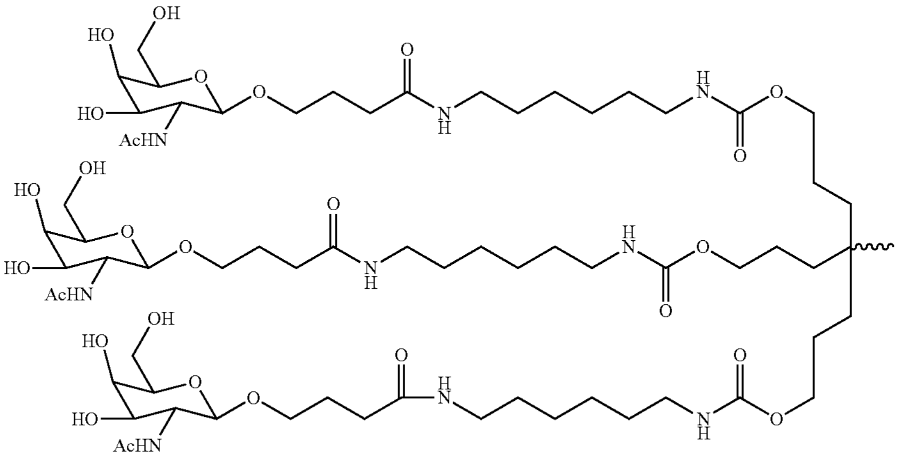

.

In other embodiments, the RNAi agent for use in the methods of the invention is an agent selected from the group consisting of AD-53815, AD-56663, AD-56658, AD-56676, AD-56666, AD-57928, and AD-60212.

III. DELIVERY OF AN iRNA OF THE INVENTION

The delivery of an iRNA agent of the invention to a cell e.g., a cell within a subject, such as a human subject (e.g., a subject in need thereof, such as a subject having a lipid disorder, such as a hyperlipidemia) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in *cynomolgus* monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the PCSK9 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference. Adenoviruses are also contemplated for use in delivery of iRNAs of the invention.

Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. PHARMACEUTICAL COMPOSITIONS OF THE INVENTION

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a PCSK9 gene, e.g. a lipid disorder. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions comprising RNAi agents of the invention may be, for example, solutions with or without a buffer, or compositions containing pharmaceutically acceptable carriers. Such compositions include, for example, aqueous or crystalline compositions, liposomal formulations, micellar formulations, emulsions, and gene therapy vectors.

In the methods of the invention, the RNAi agent may be administered in a solution. A free RNAi agent may be administered in an unbuffered solution, e.g., in saline or in water. Alternatively, the free siRNA may also be administered in a suitable buffer solution. The buffer solution may comprise acetate, citrate, prolamine, carbonate, or phosphate, or any combination thereof. In a preferred embodiment, the buffer solution is phosphate buffered saline (PBS). The pH and osmolarity of the buffer solution containing the RNAi agent can be adjusted such that it is suitable for administering to a subject.

In some embodiments, the buffer solution further comprises an agent for controlling the osmolarity of the solution, such that the osmolarity is kept at a desired value, e.g., at the physiologic values of the human plasma. Solutes which can be added to the buffer solution to control the osmolarity include, but are not limited to, proteins, peptides, amino acids, non-metabolized polymers, vitamins, ions, sugars, metabolites, organic acids, lipids, or salts. In some embodiments, the agent for controlling the osmolarity of the solution is a salt. In certain embodiments, the agent for controlling the osmolarity of the solution is sodium chloride or potassium chloride.

The pharmaceutical compositions of the invention may be administered in dosages sufficient to inhibit expression of a PCSK9 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the RNAi agent, e.g., dsRNA, may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the RNAi agent, e.g., dsRNA, may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.5 to about 50 mg/kg, about 0.75 to about 50 mg/kg, about 1 to about 50 mg/mg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered a therapeutic amount of iRNA, such as about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a bleeding disorder that would benefit from reduction in the expression of PCSK9. Such models can be used for in vivo testing of iRNA, as well as for determining a therapeutically effective dose. Suitable mouse models are known in the art and include, for example, a mouse containing a transgene expressing human PCSK9.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release,* 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P.Pharma. Sci.,* 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2, 405-410 and du Plessis et al., *Antiviral Research,* 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. Nos. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

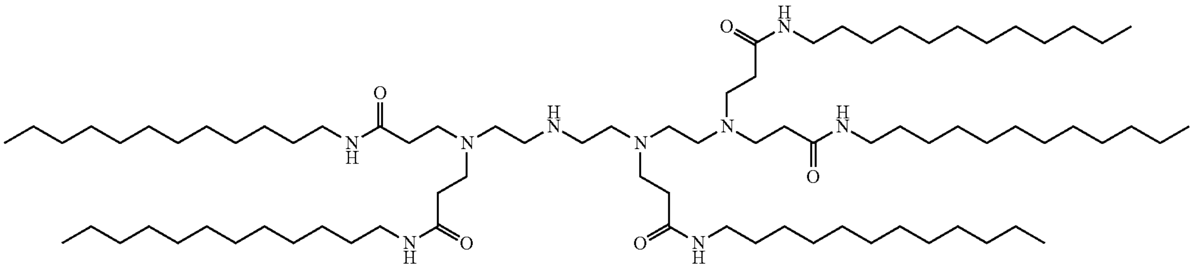

ND98 Isomer I

LNP01 formulations are described, e.g., in International Application Publication No. WO 2008/042973, which is hereby incorporated by reference.

Additional exemplary lipid-dsRNA formulations are described in Table A.

TABLE A

| | Ionizable/Cationic Lipid | cationic lipid/non-cationic lipid/cholesterol/PEG-lipid conjugate Lipid:siRNA ratio |
|---|---|---|
| LNP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine(ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |

TABLE A-continued

| | Ionizable/Cationic Lipid | cationic lipid/non-cationic lipid/cholesterol/PEG-lipid conjugate Lipid:siRNA ratio |
|---|---|---|
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (CIS-PEG, or PEG-CIS) (PEG with avg mol wt of 2000)

PEG-cDMA: PEG-carbamoyl-1,2-dimyristyloxypropylamine (PEG with avg mol wt of 2000)

LNP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Pub. No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

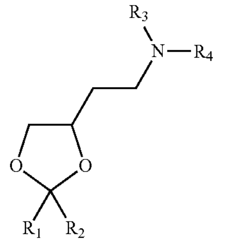

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

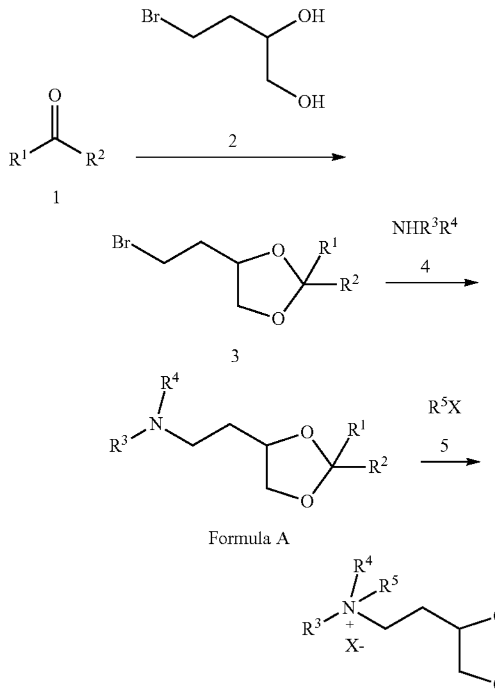

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

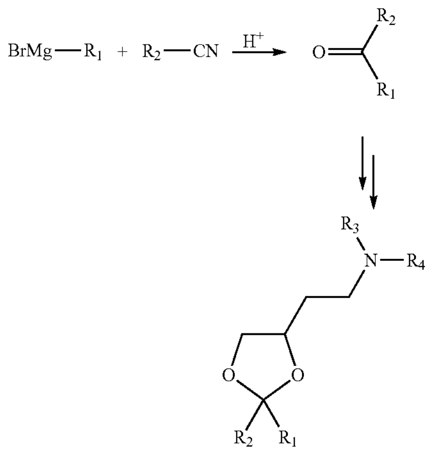

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g). Synthesis of ALNY-100

Synthesis of ketal 519 [ALNY-100] was performed using the following scheme 3:

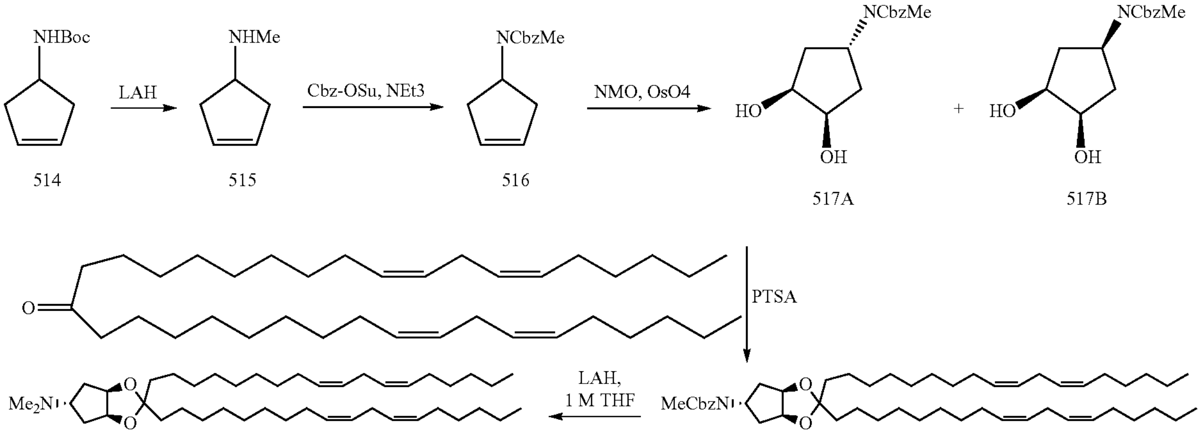

514 515 516 517A 517B 519 518

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0 OC under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an.Na2SO4 and solvent was removed in vacuum. Silica gel column chromatographic purification of the crude material was afforded a mixture of diastereomers, which were separated by prep HPLC.

Yield: —6 g crude

517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For LNP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles

An RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, M A, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass[a] D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by PCSK9 expression. In any event, the administering physician can adjust the amount and timing of iRNA administration on the basis of results observed using standard measures of efficacy known in the art or described herein.

IV. METHODS FOR INHIBITING PCSK9 EXPRESSION

The present invention provides methods of inhibiting expression of a Proprotein Convertase Subtilisin Kexin 9 (PCSK9) in a cell. The methods include contacting a cell with an RNAi agent, e.g., a double stranded RNAi agent, in an amount effective to inhibit expression of the PCSK9 in the cell, thereby inhibiting expression of the PCSK9 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a PCSK9" is intended to refer to inhibition of expression of any PCSK9 gene (such as, e.g., a mouse PCSK9 gene, a rat PCSK9 gene, a monkey PCSK9 gene, or a human PCSK9 gene) as well as variants or mutants of a PCSK9 gene. Thus, the PCSK9 gene may be a wild-type PCSK9 gene, a mutant PCSK9 gene, or a transgenic PCSK9 gene in the context of a genetically manipulated cell, group of cells, or organism.

"Inhibiting expression of a PCSK9 gene" includes any level of inhibition of a PCSK9 gene, e.g., at least partial suppression of the expression of a PCSK9 gene. The expression of the PCSK9 gene may be assessed based on the level, or the change in the level, of any variable associated with PCSK9 gene expression, e.g., PCSK9 mRNA level, PCSK9 protein level, or lipid levels. This level may be assessed in an individual cell or in a group of cells, including, for example, a sample derived from a subject.

Inhibition may be assessed by a decrease in an absolute or relative level of one or more variables that are associated with PCSK9 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a PCSK9 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a PCSK9 gene may be manifested by a reduction of the amount of mRNA expressed by a first cell or group of cells (such cells may be present, for example, in a sample derived from a subject) in which a PCSK9 gene is transcribed and which has or have been treated (e.g., by contacting the cell or cells with an RNAi agent of the invention, or by administering an RNAi agent of the invention to a subject in which the cells are or were present) such that the expression of a PCSK9 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA\text{ in control cells}) - (mRNA\text{ in treated cells})}{(mRNA\text{ in control cells})} \cdot 100\%$$

Alternatively, inhibition of the expression of a PCSK9 gene may be assessed in terms of a reduction of a parameter that is functionally linked to PCSK9 gene expression, e.g., PCSK9 protein expression, such as lipid levels, cholesterol levels, e.g., LDLc levels. PCSK9 gene silencing may be determined in any cell expressing PCSK9, either constitutively or by genomic engineering, and by any assay known in the art. The liver is the major site of PCSK9 expression. Other significant sites of expression include the pancreas, kidney, and intestines.

Inhibition of the expression of a PCSK9 protein may be manifested by a reduction in the level of the PCSK9 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a PCSK9 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of PCSK9 mRNA that is expressed by a cell or group of cells may be determined using any method known in the art for assessing mRNA expression. In one embodiment, the level of expression of PCSK9 in a sample is determined by detecting a transcribed polynucleotide, or portion thereof, e.g., mRNA of the PCSK9 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of PCSK9 is determined using a nucleic acid probe. The term "probe", as used herein, refers to any molecule that is capable of selectively binding to a specific PCSK9. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to PCSK9 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of PCSK9 mRNA.

An alternative method for determining the level of expression of PCSK9 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of PCSK9 is determined by quantitative fluorogenic RT-PCR (i.e., the TaqMan™ System).

The expression levels of PCSK9 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of PCSK9 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of PCSK9 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of PCSK9 may be assessed using measurements of the level or change in the level of PCSK9 mRNA or PCSK9 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

V. METHODS FOR TREATING OR PREVENTING A PCSK9-ASSOCIATED DISEASE

The present invention also provides methods for treating or preventing diseases and conditions that can be modulated by down regulating PCSK9 gene expression. For example, the compositions described herein can be used to treat lipidemia, e.g., a hyperlipidemia and other forms of lipid imbalance such as hypercholesterolemia, hypertriglyceridemia and the pathological conditions associated with these disorders such as heart and circulatory diseases. Other diseases and conditions that can be modulated by down regulating PCSK9 gene expression include lysosomal storage diseases including, but not limited to, Niemann-Pick disease, Tay-Sachs disease, Lysosomal acid lipase deficiency, and Gaucher Disease. The methods include administering to the subject a therapeutically effective amount or prophylactically effective amount of an RNAi agent of the invention. In some embodiments, the method includes administering an effective amount of a PCSK9 siRNA to a patient having a heterozygous LDLR genotype.

The effect of the decreased PCSK9 gene preferably results in a decrease in LDLc (low density lipoprotein cholesterol) levels in the blood, and more particularly in the serum, of the mammal. In some embodiments, LDLc levels are decreased by at least 10%, 15%, 20%, 25%, 30%, 40%, 50%, 60%, 70%, 80%, 90% or more, as compared to pretreatment levels.

As used herein, a "subject" includes a human or non-human animal, preferably a vertebrate, and more preferably a mammal. A subject may include a transgenic organism. Most preferably, the subject is a human, such as a human suffering from or predisposed to developing a PCSK9-associated disease.

In some embodiments of the methods of the invention, PCSK9 expression is decreased for an extended duration, e.g., at least one week, two weeks, three weeks, or four weeks or longer. For example, in certain instances, expression of the PCSK9 gene is suppressed by at least about 5%, 10%, 15%, 20%, 25%, 30%, 35%, 40%, 45%, or 50% by administration of an iRNA agent described herein. In some embodiments, the PCSK9 gene is suppressed by at least about 60%, 70%, or 80% by administration of the iRNA agent. In some embodiments, the PCSK9 gene is suppressed by at least about 85%, 90%, or 95% by administration of the double-stranded oligonucleotide.

The RNAi agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the agents are administered subcutaneously.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of PCSK9, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

The method includes administering an iRNA agent, e.g., a dose sufficient to depress levels of PCSK9 mRNA for at least 5, more preferably 7, 10, 14, 21, 25, 30 or 40 days; and optionally, administering a second single dose of dsRNA, wherein the second single dose is administered at least 5, more preferably 7, 10, 14, 21, 25, 30 or 40 days after the first single dose is administered, thereby inhibiting the expression of the PCSK9 gene in a subject.

In one embodiment, doses of iRNA agent of the invention are administered not more than once every four weeks, not more than once every three weeks, not more than once every two weeks, or not more than once every week. In another embodiment, the administrations can be maintained for one, two, three, or six months, or one year or longer.

In another embodiment, administration can be provided when Low Density Lipoprotein cholesterol (LDLc) levels reach or surpass a predetermined minimal level, such as greater than 70 mg/dL, 130 mg/dL, 150 mg/dL, 200 mg/dL, 300 mg/dL, or 400 mg/dL.

In general, the iRNA agent does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control dsRNA, such as a dsRNA that does not target PCSK9.

For example, a subject can be administered a therapeutic amount of an iRNA agent, such as 0.5 mg/kg, 1.0 mg/kg, 1.5 mg/kg, 2.0 mg/kg, or 2.5 mg/kg dsRNA. The iRNA agent can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA agent can reduce PCSK9 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA agent, patients can be administered a smaller dose, such as a 5%> infusion reaction, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA agent of the invention or formulation of that iRNA agent can also be judged using an experimental animal model for the given disease as known in the art. When using an experimental animal model, efficacy of treatment is evidenced when a statistically significant reduction in a marker or symptom is observed.

In one embodiment, the RNAi agent is administered at a dose of between about 0.25 mg/kg to about 50 mg/kg, e.g., between about 0.25 mg/kg to about 0.5 mg/kg, between about 0.25 mg/kg to about 1 mg/kg, between about 0.25 mg/kg to about 5 mg/kg, between about 0.25 mg/kg to about 10 mg/kg, between about 1 mg/kg to about 10 mg/kg, between about 5 mg/kg to about 15 mg/kg, between about 10 mg/kg to about 20 mg/kg, between about 15 mg/kg to about 25 mg/kg, between about 20 mg/kg to about 30 mg/kg, between about 25 mg/kg to about 35 mg/kg, or between about 40 mg/kg to about 50 mg/kg.

In some embodiments, the RNAi agent is administered at a dose of about 0.25 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg or about 50 mg/kg. In one embodiment, iRNA agent is administered at a dose of about 25 mg/kg.

The dose of an RNAi agent that is administered to a subject may be tailored to balance the risks and benefits of a particular dose, for example, to achieve a desired level of PCSK9 gene suppression (as assessed, e.g., based on PCSK9 mRNA suppression, PCSK9 protein expression, or a reduction in lipid levels) or a desired therapeutic or prophylactic effect, while at the same time avoiding undesirable side effects.

In some embodiments, the RNAi agent is administered in two or more doses. If desired to facilitate repeated or frequent infusions, implantation of a delivery device, e.g., a pump, semi-permanent stent (e.g., intravenous, intraperitoneal, intracisternal or intracapsular), or reservoir may be advisable. In some embodiments, the number or amount of subsequent doses is dependent on the achievement of a desired effect, e.g., the suppression of a PCSK9 gene, or the achievement of a therapeutic or prophylactic effect, e.g., reducing reducing a symptom of hypercholesterolemia. In some embodiments, the RNAi agent is administered according to a schedule. For example, the RNAi agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly. In other embodiments, the schedule involves closely spaced administrations followed by a longer period of time during which the agent is not administered. For example, the schedule may involve an initial set of doses that are administered in a relatively short period of time (e.g., about every 6 hours, about every 12 hours, about every 24 hours, about every 48 hours, or about every 72 hours) followed by a longer time period (e.g., about 1 week, about 2 weeks, about 3 weeks, about 4 weeks, about 5 weeks, about 6 weeks, about 7 weeks, or about 8 weeks) during which the RNAi agent is not administered. In one embodiment, the RNAi agent is initially administered hourly and is later administered at a longer interval (e.g., daily, weekly, biweekly, or monthly). In another embodiment, the RNAi agent is initially administered daily and is later administered at a longer interval (e.g., weekly, biweekly, or monthly). In certain embodiments, the longer interval increases over time or is determined based on the achievement of a desired effect. In a specific embodiment, the RNAi agent is administered once daily during a first week, followed by weekly dosing starting on the eighth day of administration. In another specific embodiment, the RNAi agent is administered every other day during a first week followed by weekly dosing starting on the eighth day of administration.

In one embodiment, the iRNA agent is administered two times per week. In one embodiment, iRNA agent is administered two times per week at a dose of 1 mg/kg. In another embodiment, iRNA agent is administered two times per week at a dose of 2 mg/kg.

In one embodiment, the iRNA agent is administered once every two weeks. In one embodiment, iRNA agent is administered once every two week at a dose of 1 mg/kg. In another embodiment, iRNA agent is administered once every two week at a dose of 2 mg/kg.

In one embodiment, the iRNA agent is administered once a week. In one embodiment, iRNA agent is administered once a week at a dose of 0.5 mg/kg. In one embodiment, iRNA agent is administered once a week at a dose of 1 mg/kg. In another embodiment, iRNA agent is administered once a week at a dose of 2 mg/kg.

In some embodiments, the RNAi agent is administered in a dosing regimen that includes a "loading phase" of closely spaced administrations that may be followed by a "maintenance phase", in which the RNAi agent is administered at longer spaced intervals. In one embodiment, the loading phase comprises five daily administrations of the RNAi agent during the first week. In another embodiment, the maintenance phase comprises one or two weekly administrations of the RNAi agent. In a further embodiment, the maintenance phase lasts for 5 weeks. In one embodiment, the loading phase comprises administration of a dose of 2 mg/kg, 1 mg/kg or 0.5 mg/kg five times a week. In another embodiment, the maintenance phase comprises administration of a dose of 2 mg/kg, 1 mg/kg or 0.5 mg/kg once, twice, or three times weekly, once every two weeks, once every three weeks, once a month, once every two months, once every three months, once every four months, once every five months, or once every six months.

Any of these schedules may optionally be repeated for one or more iterations. The number of iterations may depend on the achievement of a desired effect, e.g., the suppression of a PCSK9 gene, and/or the achievement of a therapeutic or prophylactic effect, e.g., reducing serum cholesterol levels or reducing a symptom of hypercholesterolemia.

In further embodiments, administration of a siRNA is administered in combination an additional therapeutic agent. The siRNA and an additional therapeutic agent can be administered in combination in the same composition, e.g., parenterally, or the additional therapeutic agent can be administered as part of a separate composition or by another method described herein.

Examples of additional therapeutic agents include those known to treat an agent known to treat a lipid disorders, such as hypercholesterolemia, atherosclerosis or dyslipidemia. For example, a siRNA featured in the invention can be administered with, e.g., an HMG-CoA reductase inhibitor (e.g., a statin), a fibrate, a bile acid sequestrant, niacin, an antiplatelet agent, an angiotensin converting enzyme inhibitor, an angiotensin II receptor antagonist (e.g., losartan potassium, such as Merck & Co.'s Cozaar®), an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR)

agonist, a gene-based therapy, a composite vascular protectant (e.g., AGI-1067, from Atherogenics), a glycoprotein IIb/IIIa inhibitor, aspirin or an aspirin-like compound, an IBAT inhibitor (e.g., S-8921, from Shionogi), a squalene synthase inhibitor, or a monocyte chemoattractant protein (MCP)-I inhibitor. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis). Exemplary fibrates include, e.g., bezafibrate (e.g., Roche's Befizal®/Cedur®/Bezalip®, Kissei's Bezatol), clofibrate (e.g., Wyeth's Atromid-S®), fenofibrate (e.g., Fournier's Lipidil/Lipantil, Abbott's Tricor®, Takeda's Lipantil, generics), gemfibrozil (e.g., Pfizer's Lopid/Lipur) and ciprofibrate (Sanofi-Synthelabo's Modalim®). Exemplary bile acid sequestrants include, e.g., cholestyramine (Bristol-Myers Squibb's Questran® and Questran Light™), colestipol (e.g., Pharmacia's Colestid), and colesevelam (Genzyme/Sankyo's WelChol™). Exemplary niacin therapies include, e.g., immediate release formulations, such as Aventis' Nicobid, Upsher-Smith's Niacor, Aventis' Nicolar, and Sanwakagaku's Perycit. Niacin extended release formulations include, e.g., Kos Pharmaceuticals' Niaspan and Upsher-Smith's SIo-Niacin. Exemplary antiplatelet agents include, e.g., aspirin (e.g., Bayer's aspirin), clopidogrel (Sanofi-Synthelabo/Bristol-Myers Squibb's Plavix), and ticlopidine (e.g., Sanofi-Synthelabo's Ticlid and Daiichi's Panaldine). Other aspirin-like compounds useful in combination with a dsRNA targeting PCSK9 include, e.g., Asacard (slow-release aspirin, by Pharmacia) and Pamicogrel (Kanebo/Angelini Ricerche/CEPA). Exemplary angiotensin-converting enzyme inhibitors include, e.g., ramipril (e.g., Aventis' Altace) and enalapril (e.g., Merck & Co.'s Vasotec). Exemplary acyl CoA cholesterol acetyltransferase (AC AT) inhibitors include, e.g., avasimibe (Pfizer), eflucimibe (BioMsrieux Pierre Fabre/Eli Lilly), CS-505 (Sankyo and Kyoto), and SMP-797 (Sumito). Exemplary cholesterol absorption inhibitors include, e.g., ezetimibe (Merck/Schering-Plough Pharmaceuticals Zetia®) and Pamaqueside (Pfizer). Exemplary CETP inhibitors include, e.g., Torcetrapib (also called CP-529414, Pfizer), JTT-705 (Japan Tobacco), and CETi-I (Avant Immunotherapeutics). Exemplary microsomal triglyceride transfer protein (MTTP) inhibitors include, e.g., implitapide (Bayer), R-103757 (Janssen), and CP-346086 (Pfizer). Other exemplary cholesterol modulators include, e.g., NO-1886 (Otsuka/TAP Pharmaceutical), CI-1027 (Pfizer), and WAY-135433 (Wyeth-Ayerst).

Exemplary bile acid modulators include, e.g., HBS-107 (Hisamitsu/Banyu), Btg-511 (British Technology Group), BARI-1453 (Aventis), S-8921 (Shionogi), SD-5613 (Pfizer), and AZD-7806 (AstraZeneca). Exemplary peroxisome proliferation activated receptor (PPAR) agonists include, e.g., tesaglitazar (AZ-242) (AstraZeneca), Netoglitazone (MCC-555) (Mitsubishi/Johnson & Johnson), GW-409544 (Ligand Pharmaceuticals/GlaxoSmithKline), GW-501516 (Ligand Pharmaceuticals/GlaxoSmithKline), LY-929 (Ligand Pharmaceuticals and Eli Lilly), LY-465608 (Ligand Pharmaceuticals and Eli Lilly), LY-518674 (Ligand Pharmaceuticals and Eli Lilly), and MK-767 (Merck and Kyorin). Exemplary gene-based therapies include, e.g., AdGWEGF 121.10 (GenVec), ApoA1 (UCB Pharma/Groupe Fournier), EG-004 (Trinam) (Ark Therapeutics), and ATP-binding cassette transporter-A1 (ABCA1) (CV Therapeutics/Incyte, Aventis, Xenon). Exemplary Glycoprotein IIb/IIIa inhibitors include, e.g., roxifiban (also called DMP754, Bristol-Myers Squibb), Gantofiban (Merck KGaA/Yamanouchi), and Cromafiban (Millennium Pharmaceuticals). Exemplary squalene synthase inhibitors include, e.g., BMS-1884941 (Bristol-Myers Squibb), CP-210172 (Pfizer), CP-295697 (Pfizer), CP-294838 (Pfizer), and TAK-475 (Takeda). An exemplary MCP-I inhibitor is, e.g., RS-504393 (Roche Bioscience). The anti-atherosclerotic agent BO-653 (Chugai Pharmaceuticals), and the nicotinic acid derivative Nyclin (Yamanouchi Pharmaceuticals) are also appropriate for administering in combination with a dsRNA featured in the invention. Exemplary combination therapies suitable for administration with a dsRNA targeting PCSK9 include, e.g., advicor (Niacin/lovastatin from Kos Pharmaceuticals), amlodipine/atorvastatin (Pfizer), and ezetimibe/simvastatin (e.g., Vytorin® 10/10, 10/20, 10/40, and 10/80 tablets by Merck/Schering-Plough Pharmaceuticals). Agents for treating hypercholesterolemia, and suitable for administration in combination with a dsRNA targeting PCSK9 include, e.g., lovastatin, niacin Altoprev® Extended-Release Tablets (Andrx Labs), lovastatin Caduet® Tablets (Pfizer), amlodipine besylate, atorvastatin calcium Crestor® Tablets (AstraZeneca), rosuvastatin calcium Lescol® Capsules (Novartis), fluvastatin sodium Lescol® (Reliant, Novartis), fluvastatin sodium Lipitor® Tablets (Parke-Davis), atorvastatin calcium Lofibra® Capsules (Gate), Niaspan Extended-Release Tablets (Kos), niacin Pravachol Tablets (Bristol-Myers Squibb), pravastatin sodium TriCor® Tablets (Abbott), fenofibrate Vytorin® 10/10 Tablets (Merck/Schering-Plough Pharmaceuticals), ezetimibe, simvastatin WelChol™ Tablets (Sankyo), colesevelam hydrochloride Zetia® Tablets (Schering), ezetimibe Zetia® Tablets (Merck/Schering-Plough Pharmaceuticals), and ezetimibe Zocor® Tablets (Merck).

In one embodiment, an iRNA agent is administered in combination with an ezetimibe/simvastatin combination (e.g., Vytorin® (Merck/Schering-Plough Pharmaceuticals)). In one embodiment, the iRNA agent is administered to the patient, and then the additional therapeutic agent is administered to the patient (or vice versa). In another embodiment, the iRNA agent and the additional therapeutic agent are administered at the same time.

In another aspect, the invention features, a method of instructing an end user, e.g., a caregiver or a subject, on how to administer an iRNA agent described herein. The method includes, optionally, providing the end user with one or more doses of the iRNA agent, and instructing the end user to administer the iRNA agent on a regimen described herein, thereby instructing the end user.

In one aspect, the invention provides a method of treating a patient by selecting a patient on the basis that the patient is in need of LDL lowering, LDL lowering without lowering of HDL, ApoB lowering, or total cholesterol lowering. The method includes administering to the patient a siRNA in an amount sufficient to lower the patient's LDL levels or ApoB levels, e.g., without substantially lowering HDL levels.

Genetic predisposition plays a role in the development of target gene associated diseases, e.g., hyperlipidemia. Therefore, a patient in need of a siRNA can be identified by taking a family history, or, for example, screening for one or more genetic markers or variants. Examples of genes involved in hyperlipidemia include but are not limited to, e.g., LDL receptor (LDLR), the apoliproteins (ApoA1, ApoB, ApoE, and the like), Cholesteryl ester transfer protein (CETP), Lipoprotein lipase (LPL), hepatic lipase (LIPC), Endothelial lipase (EL), Lecithinxholesteryl acyltransferase (LCAT).

A healthcare provider, such as a doctor, nurse, or family member, can take a family history before prescribing or administering an iRNA agent of the invention. In addition, a test may be performed to determine a genotype or phenotype. For example, a DNA test may be performed on a sample from the patient, e.g., a blood sample, to identify the PCSK9 genotype and/or phenotype before a PCSK9 dsRNA is administered to the patient. In another embodiment, a test is performed to identify a related genotype and/or phenotype, e.g., a LDLR genotype. Example of genetic variants with the LDLR gene can be found in the art, e.g., in the following publications which are incorporated by reference: Costanza et al (2005) *Am J Epidemiol.* 15; 161(8):714-24; Yamada et al. (2008) *J Med Genet*. January; 45(1):22-8, Epub 2007 Aug. 31; and Boes et al (2009) *Exp. Gerontol* 44: 136-160, Epub 2008 Nov. 17.

VI. KITS

The present invention also provides kits for using any of the iRNA agents and/or performing any of the methods of the invention. Such kits include one or more RNAi agent(s) and instructions for use, e.g., instructions for inhibiting expression of a PCSK9 in a cell by contacting the cell with the RNAi agent(s) in an amount effective to inhibit expression of the PCSK9. The kits may optionally further comprise means for contacting the cell with the RNAi agent (e.g., an injection device), or means for measuring the inhibition of PCSK9 (e.g., means for measuring the inhibition of PCSK9 mRNA or TTR protein). Such means for measuring the inhibition of PCSK9 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Materials and Methods

The following materials and methods were used in the Examples.

cDNA Synthesis Using ABI High Capacity cDNA Reverse Transcription Kit (Applied Biosystems, Foster City, Calif., Cat #4368813)

A master mix of 2 μl 10× Buffer, 0.8 μl 25× dNTPs, 2 μl Random primers, 1 μl Reverse Transcriptase, 1 μl RNase inhibitor and 3.2 μl of $H_2O$ per reaction was added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Cell Culture and Transfections

Hep3B, HepG2 or HeLa cells (ATCC, Manassas, Va.) were grown to near confluence at 37° C. in an atmosphere of 5% $CO_2$ in recommended media (ATCC) supplemented with 10% FBS and glutamine (ATCC) before being released from the plate by trypsinization. For duplexes screened in 96-well format, transfection was carried out by adding 44.75 μl of Opti-MEM plus 0.25 μl of Lipofectamine RNAiMax per well (Invitrogen, Carlsbad Calif. cat #13778-150) to 5 μl of each siRNA duplex to an individual well in a 96-well plate. The mixture was then incubated at room temperature for 15 minutes. Fifty μl of complete growth media without antibiotic containing ~$2\times10^4$ cells were then added to the siRNA mixture. For duplexes screened in 384-well format, 5 μl of Opti-MEM plus 0.1 μl of Lipofectamine RNAiMax (Invitrogen, Carlsbad Calif. cat #13778-150) was mixed with 5 μl of each siRNA duplex per an individual well. The mixture was then incubated at room temperature for 15 minutes followed by addition of 40 μl of complete growth media without antibiotic containing ~$8\times10^3$ cells. Cells were incubated for 24 hours prior to RNA purification. Single dose experiments were performed at 10 nM and 0.1 nM final duplex concentration and dose response experiments were done using 8×5-fold serial dilutions starting from 2 nM.

Free Uptake Transfection

Five μl of each GalNac conjugated siRNA in PBS was combined with $3\times10^4$ freshly thawed cryopreserved *Cynomolgus* monkey hepatocytes (In Vitro Technologies-Celsis, Baltimore, Md.; lot#JQD) resuspended in 95111 of In Vitro Gro CP media (In Vitro Technologies-Celsis, Baltimore, Md.) in each well of a 96-well plate or 5 ul siRNA and 45 media containing $1.2\times10^3$ cells for 384 well plate format. The mixture was incubated for about 24 hours at 37° C. in an atmosphere of 5% $CO_2$. siRNAs were tested at multiple concentrations between 500 and 0.1 nM for single dose experiments and using 8×5-fold serial dilutions starting from 500 nM for dose response experiments.

Total RNA Isolation Using DYNABEADS mRNA Isolation Kit (Invitrogen, Part #: 610-12)

Cells were harvested and lysed in 150 μl of Lysis/Binding Buffer then mixed for 5 minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using magnetic stand and the supernatant was removed without disturbing the beads. After removing the supernatant, the lysed cells were added to the remaining beads and mixed for 5 minutes. After removing the supernatant, magnetic beads were washed 2 times with 150 μl Wash Buffer A and mixed for 1 minute. Beads were captured again and the supernatant removed. Beads were then washed with 150 μl Wash Buffer B, captured and the supernatant was removed. Beads were next washed with 150 μl Elution Buffer, captured and the supernatant removed. Beads were allowed to dry for 2 minutes. After drying, 50 μl of Elution Buffer was added and mixed for 5 minutes at 70° C. Beads were captured on a magnet for 5 minutes. Fifty μl of supernatant was removed and added to another 96-well plate.

For 384-well format, the cells were lysed for one minute by addition of 50 μl Lysis/Binding buffer. Two μl of magnetic beads per well was used. The required volume of beads was aliquoted, captured on a magnetic stand, and the bead storage solution was removed. The beads were then resuspended in the required volume of Lysis/Binding buffer (25 μl per well) and 25 μl of bead suspension was added to the lysed cells. The lysate-bead mixture was incubated for 10 minutes on VibraTransaltor at setting #7 (UnionScientific Corp., Randallstown, Md.). Subsequently beads were captured using a magnetic stand, the supernatant removed and the beads are washed once with 90 μl Buffer A, followed by single washing steps with 90 μl Buffer B and 100 μl of Elution buffer. The beads were soaked in each washing buffer for ~1 minute (no mixing involved). After the final wash step, the beads were resuspended in 15 μl of elution buffer for 5 minutes at 70° C., followed by bead capture and the removal of the supernatant (up to 8 μl) for cDNA synthesis and/or purified RNA storage (−20° C.).

Real Time PCR

Two μl of cDNA was added to a master mix containing 0.5 μl human GAPDH TaqMan Probe (Applied Biosystems Cat #4326317E), 0.5 μl human PCSK9 TaqMan probe (Applied Biosystems cat #Hs03037355_m1) for human cells or 0.5 μl *Cynomolgus* GAPDH custom TaqMan Assay (150 nM cyno GAP F primer-5'GCATCCTGGGCTACACTGA (SEQ ID NO: 5); 150 nM cyno GAP R primer-5'-TGGGTGTCGCTGTTGAAGTC (SEQ ID NO: 6) 250 nM cyno GAP probe-5'-5HEX-CCAGGTGGTCTCCTCC-BHQ1-Q-3' (SEQ ID NO: 7)), 0.5 μl *Cynomolgus* PCSK9 custom TaqMan Assay (900 nM cyno PCSK9 F primer 5'-ACGTGGCTGGCATTGCA (SEQ ID NO: 8); 900 nM cyno PCSK9 R primer 5'-AAGTGGATCAGTCTCTGCCTCAA (SEQ ID NO: 9); 250 nM cyno PCSK9 probe 5'-6FAM-CATGATGCTGTCTGCCGAGCCG-BHQ1-Q-3' (SEQ ID NO: 10)) for *Cynomolgus* cells and 5 μl Lightcycler 480 probe master mix (Roche Cat #04887301001) per well in a 384 well plate (Roche cat #04887301001). Real time PCR was performed in a Roche LC480 Real Time PCR system (Roche) using the ΔΔCt(RQ) assay. Each duplex was tested in two independent transfections and each transfection was assayed in duplicate, unless otherwise noted.

To calculate relative fold change, real time data were analyzed using the ΔΔCt method and normalized to assays performed with cells transfected with 10 nM AD-1955, or mock transfected cells. For free uptake assays the data were normalized to PBS or GalNAc-1955 (highest concentration used for experimental compounds) treated cells. $IC_{50}$s were calculated using a 4 parameter fit model using XLFit and normalized to cells transfected with AD-1955 over the same dose range, or to its own lowest dose.

The sense and antisense sequences of AD-1955 are: SENSE: 5'-cuuAcGcuGAGuAcuucGAdTsdT-3' (SEQ ID NO: 11); and ANTISENSE: 5'-UCGAAGuACUcAGCGuAAGdTsdT-3' (SEQ ID NO: 12).

TABLE B

Abbreviations of nucleotide monomers used in nucleic acid sequence representation.

| Abbreviation | Nucleotide(s) |
|---|---|
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |

TABLE B-continued

Abbreviations of nucleotide monomers used in nucleic acid sequence representation.

| Abbreviation | Nucleotide(s) |
|---|---|
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxyethylphosphorothioate |
| (Uhd) | 2'-O-hexadecyl-uridine-3'-phosphate |
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| (Uyh) | 2'-O-(1-hexyl-4-methylene-1,2,3-triazolyl)-uridine-3'-phosphate |
| (Ayh) | 2'-O-(1-hexyl-4-methylene-1,2,3-triazolyl)-adenosine-3'-phosphate |
| (Gyh) | 2'-O-(1-hexyl-4-methylene-1,2,3-triazolyl)-guanosine-3'-phosphate |
| (Cyh) | 2'-O-(1-hexyl-4-methylene-1,2,3-triazolyl)-cytidine-3'-phosphate |

Example 1. Synthesis of GalNAc-Conjugated Oligonucleotides

A series of siRNA duplexes spanning the sequence of PCSK9 mRNA were designed, synthesized, and conjugated with a trivalent GalNAc at the 3-end of the sense strand using the techniques described above. The sequences of these duplexes are shown in Table 1. These same sequences were also synthesized with various nucleotide modifications and conjugated with a trivalent GalNAc. The sequences of the modified duplexes are shown n Table 2.

TABLE 1

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53649.1 | A-110542.1 | CGAGGACGGCGACUACGAGGA | 13 | A-109239.2 | UCCUCGUAGUCGCCGUCCUCGUC | 234 | 459 | 481 |
| AD-53661.1 | A-110544.1 | ACCGCUGCGCCAAGGAUCCGU | 14 | A-109243.2 | ACGGAUCCUUGGCGCAGCGGUGG | 235 | 554 | 576 |
| AD-53667.1 | A-110545.1 | GCUGCGCCAAGGAUCCGUGGA | 15 | A-109245.2 | UCCACGGAUCCUUGGCGCAGCGG | 236 | 557 | 579 |
| AD-53679.1 | A-110547.1 | CUACGUGGUGGUGCUGAAGGA | 16 | A-109249.2 | UCCUUCAGCACCACCACGUAGGU | 237 | 591 | 613 |
| AD-53685.1 | A-110548.1 | CCCGCCGGGGAUACCUCACCA | 17 | A-109251.2 | UGGUGAGGUAUCCCCGGCGGGCA | 238 | 668 | 690 |
| AD-53691.1 | A-110549.1 | CCGCCGGGGAUACCUCACCAA | 18 | A-109253.2 | UUGGUGAGGUAUCCCCGGCGGGC | 239 | 669 | 691 |
| AD-53650.1 | A-110550.1 | GCCGGGGAUACCUCACCAAGA | 19 | A-109255.2 | UCUUGGUGAGGUAUCCCCGGCGG | 240 | 671 | 693 |
| AD-53656.1 | A-110551.1 | CCGGGGAUACCUCACCAAGAU | 20 | A-109257.2 | AUCUUGGUGAGGUAUCCCCGGCG | 241 | 672 | 694 |
| AD-53668.1 | A-110553.1 | AUACCUCACCAAGAUCCUGCA | 21 | A-109261.2 | UGCAGGAUCUUGGUGAGGUAUCC | 242 | 678 | 700 |
| AD-53674.1 | A-110554.1 | CACCAAGAUCCUGCAUGUCUU | 22 | A-109263.2 | AAGACAUGCAGGAUCUUGGUGAG | 243 | 684 | 706 |
| AD-53680.1 | A-110555.1 | CAAGAUCCUGCAUGUCUUCCA | 23 | A-109265.2 | UGGAAGACAUGCAGGAUCUUGGU | 244 | 687 | 709 |
| AD-53692.1 | A-110557.1 | GUUGCCCCAUGUCGACUACAU | 24 | A-109269.2 | AUGUAGUCGACAUGGGGCAACUU | 245 | 768 | 790 |
| AD-53651.1 | A-110558.1 | GCCCCAUGUCGACUACAUCGA | 25 | A-109271.2 | UCGAUGUAGUCGACAUGGGGCAA | 246 | 771 | 793 |
| AD-53657.1 | A-110559.1 | CCAUGUCGACUACAUCGAGGA | 26 | A-109273.2 | UCCUCGAUGUAGUCGACAUGGGG | 247 | 774 | 796 |
| AD-53663.1 | A-110560.1 | UCGACUACAUCGAGGAGGACU | 27 | A-109275.2 | AGUCCUCCUCGAUGUAGUCGACA | 248 | 779 | 801 |
| AD-53669.1 | A-110561.1 | ACUACAUCGAGGAGGACUCCU | 28 | A-109277.2 | AGGAGUCCUCCUCGAUGUAGUCG | 249 | 782 | 804 |
| AD-53675.1 | A-110562.1 | UACAUCGAGGAGGACUCCUCU | 29 | A-109279.2 | AGAGGAGUCCUCCUCGAUGUAGU | 250 | 784 | 806 |
| AD-53681.1 | A-110563.1 | UCGAGGAGGACUCCUCUGUCU | 30 | A-109281.2 | AGACAGAGGAGUCCUCCUCGAUG | 251 | 788 | 810 |
| AD-53687.1 | A-110564.1 | CGAGGAGGACUCCUCUGUCUU | 31 | A-109283.2 | AAGACAGAGGAGUCCUCCUCGAU | 252 | 789 | 811 |
| AD-53693.1 | A-110565.1 | GUACCGGGCGGAUGAAUACCA | 32 | A-109285.2 | UGGUAUUCAUCCGCCCGGUACCG | 253 | 855 | 877 |
| AD-53652.1 | A-110566.1 | CCUGGUGGAGGUGUAUCUCCU | 33 | A-109287.2 | AGGAGAUACACCUCCACCAGGCU | 254 | 894 | 916 |
| AD-53658.1 | A-110567.1 | CUGGUGGAGGUGUAUCUCCUA | 34 | A-109289.2 | UAGGAGAUACACCUCCACCAGGC | 255 | 895 | 917 |
| AD-53664.1 | A-110568.1 | GGUGGAGGUGUAUCUCCUAGA | 35 | A-109291.2 | UCUAGGAGAUACACCUCCACCAG | 256 | 897 | 919 |
| AD-53670.1 | A-110569.1 | UGGAGGUGUAUCUCCUAGACA | 36 | A-109293.2 | UGUCUAGGAGAUACACCUCCACC | 257 | 899 | 921 |
| AD-53676.1 | A-110570.1 | AGGUGUAUCUCCUAGACACCA | 37 | A-109295.2 | UGGUGUCUAGGAGAUACACCUCC | 258 | 902 | 924 |
| AD-53682.1 | A-110571.1 | GUAUCUCCUAGACACCAGCAU | 38 | A-109297.2 | AUGCUGGUGUCUAGGAGAUACAC | 259 | 906 | 928 |
| AD-53688.1 | A-110572.1 | UAUCUCCUAGACACCAGCAUA | 39 | A-109299.2 | UAUGCUGGUGUCUAGGAGAUACA | 260 | 907 | 929 |
| AD-53694.1 | A-110573.1 | UCUCCUAGACACCAGCAUACA | 40 | A-109301.2 | UGUAUGCUGGUGUCUAGGAGAUA | 261 | 909 | 931 |
| AD-53653.1 | A-110574.1 | UCCUAGACACCAGCAUACAGA | 41 | A-109303.2 | UCUGUAUGCUGGUGUCUAGGAGA | 262 | 911 | 933 |
| AD-53659.1 | A-110575.1 | AGACACCAGCAUACAGAGUGA | 42 | A-109305.2 | UCACUCUGUAUGCUGGUGUCUAG | 263 | 915 | 937 |
| AD-53665.1 | A-110576.1 | CACCAGCAUACAGAGUGACCA | 43 | A-109307.2 | UGGUCACUCUGUAUGCUGGUGUC | 264 | 918 | 940 |
| AD-53671.1 | A-110577.1 | UACAGAGUGACCACCGGGAAA | 44 | A-109309.2 | UUUCCCGGUGGUCACUCUGUAUG | 265 | 926 | 948 |
| AD-53677.1 | A-110578.1 | ACAGAGUGACCACCGGGAAAU | 45 | A-109311.2 | AUUUCCCGGUGGUCACUCUGUAU | 266 | 927 | 949 |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53683.1 | A-110579.1 | GAGUGACCACCGGGAAAUCGA | 46 | A-109313.2 | UCGAUUUCCCGGUGGUCACUCUG | 267 | 930 | 952 |
| AD-53689.1 | A-110580.1 | GGAAAUCGAGGGCAGGGUCAU | 47 | A-109315.2 | AUGACCCUGCCCUCGAUUUCCCG | 268 | 942 | 964 |
| AD-53695.1 | A-110581.1 | AAUCGAGGGCAGGGUCAUGGU | 48 | A-109317.2 | ACCAUGACCCUGCCCUCGAUUUC | 269 | 945 | 967 |
| AD-53654.1 | A-110582.1 | GCAGGGUCAUGGUCACCGACU | 49 | A-109319.2 | AGUCGGUGACCAUGACCCUGCCC | 270 | 953 | 975 |
| AD-53660.1 | A-110583.1 | CAGGGUCAUGGUCACCGACUU | 50 | A-109321.2 | AAGUCGGUGACCAUGACCCUGCC | 271 | 954 | 976 |
| AD-53666.1 | A-110584.1 | GGUCAUGGUCACCGACUUCGA | 51 | A-109323.2 | UCGAAGUCGGUGACCAUGACCCU | 272 | 957 | 979 |
| AD-53672.1 | A-110585.1 | UCAUGGUCACCGACUUCGAGA | 52 | A-109325.2 | UCUCGAAGUCGGUGACCAUGACC | 273 | 959 | 981 |
| AD-53678.1 | A-110586.1 | AGGACGGGACCCGCUUCCACA | 53 | A-109327.2 | UGUGGAAGCGGGUCCCGUCCUCC | 274 | 992 | 1014 |
| AD-53684.1 | A-110587.1 | CGGGACCCGCUUCCACAGACA | 54 | A-109329.2 | UGUCUGUGGAAGCGGGUCCCGUC | 275 | 996 | 1018 |
| AD-53690.1 | A-110588.1 | UCCACAGACAGGCCAGCAAGU | 55 | A-109331.2 | ACUUGCUGGCCUGUCUGUGGAAG | 276 | 1007 | 1029 |
| AD-53696.1 | A-110589.1 | CCUGCGCGUGCUCAACUGCCA | 56 | A-109333.2 | UGGCAGUUGAGCACGCGCAGGCU | 277 | 1107 | 1129 |
| AD-53702.1 | A-110590.1 | CUGCGCGUGCUCAACUGCCAA | 57 | A-109335.2 | UUGGCAGUUGAGCACGCGCAGGC | 278 | 1108 | 1130 |
| AD-53708.1 | A-110591.1 | CGUGCUCAACUGCCAAGGGAA | 58 | A-109337.2 | UUCCCUUGGCAGUUGAGCACGCG | 279 | 1113 | 1135 |
| AD-53714.1 | A-110592.1 | CACCCUCAUAGGCCUGGAGUU | 59 | A-109339.2 | AACUCCAGGCCUAUGAGGGUGCC | 280 | 1149 | 1171 |
| AD-53720.1 | A-110593.1 | ACCCUCAUAGGCCUGGAGUUU | 60 | A-109341.2 | AAACUCCAGGCCUAUGAGGGUGC | 281 | 1150 | 1172 |
| AD-53726.1 | A-110594.1 | CCCUCAUAGGCCUGGAGUUUA | 61 | A-109343.2 | UAAACUCCAGGCCUAUGAGGGUG | 282 | 1151 | 1173 |
| AD-53732.1 | A-110595.1 | CCUCAUAGGCCUGGAGUUUAU | 62 | A-109345.2 | AUAAACUCCAGGCCUAUGAGGGU | 283 | 1152 | 1174 |
| AD-53738.1 | A-110596.1 | CUCAUAGGCCUGGAGUUUAUU | 63 | A-109347.2 | AAUAAACUCCAGGCCUAUGAGGG | 284 | 1153 | 1175 |
| AD-53697.1 | A-110597.1 | UAGGCCUGGAGUUUAUUCGGA | 64 | A-109349.2 | UCCGAAUAAACUCCAGGCCUAUG | 285 | 1157 | 1179 |
| AD-53703.1 | A-110598.1 | AGGCCUGGAGUUUAUUCGGAA | 65 | A-109351.2 | UUCCGAAUAAACUCCAGGCCUAU | 286 | 1158 | 1180 |
| AD-53709.1 | A-110599.1 | GGCCUGGAGUUUAUUCGGAAA | 66 | A-109353.2 | UUUCCGAAUAAACUCCAGGCCUA | 287 | 1159 | 1181 |
| AD-53715.1 | A-110600.1 | GCCUGGAGUUUAUUCGGAAAA | 67 | A-109355.2 | UUUUCCGAAUAAACUCCAGGCCU | 288 | 1160 | 1182 |
| AD-53721.1 | A-110601.1 | GGAGUUUAUUCGGAAAAGCCA | 68 | A-109357.2 | UGGCUUUUCCGAAUAAACUCCAG | 289 | 1164 | 1186 |
| AD-53727.1 | A-110602.1 | GUUUAUUCGGAAAAGCCAGCU | 69 | A-109359.2 | AGCUGGCUUUUCCGAAUAAACUC | 290 | 1167 | 1189 |
| AD-53733.1 | A-110603.1 | GGGCUGGGGUCGUGCUGGUCA | 70 | A-109361.2 | UGACCAGCACGACCCCAGCCCUC | 291 | 1277 | 1299 |
| AD-53739.1 | A-110604.1 | GGUCACCGCUGCCGGCAACUU | 71 | A-109363.2 | AAGUUGCCGGCAGCGGUGACCAG | 292 | 1293 | 1315 |
| AD-53698.1 | A-110605.1 | GGGACGAUGCCUGCCUCUACU | 72 | A-109365.2 | AGUAGAGGCAGGCAUCGUCCCGG | 293 | 1316 | 1338 |
| AD-53704.1 | A-110606.1 | CAACUUUGGCCGCUGUGUGGA | 73 | A-109367.2 | UCCACACAGCGGCCAAAGUUGGU | 294 | 1419 | 1441 |
| AD-53710.1 | A-110607.1 | UUGGCCGCUGUGUGGACCUCU | 74 | A-109369.2 | AGAGGUCCACACAGCGGCCAAAG | 295 | 1424 | 1446 |
| AD-53716.1 | A-110608.1 | UGGCCGCUGUGUGGACCUCUU | 75 | A-109371.2 | AAGAGGUCCACACAGCGGCCAAA | 296 | 1425 | 1447 |
| AD-53722.1 | A-110609.1 | GGCCGCUGUGUGGACCUCUUU | 76 | A-109373.2 | AAAGAGGUCCACACAGCGGCCAA | 297 | 1426 | 1448 |
| AD-53728.1 | A-110610.1 | UGUGUGGACCUCUUUGCCCCA | 77 | A-109375.2 | UGGGGCAAAGAGGUCCACACAGC | 298 | 1432 | 1454 |
| AD-53734.1 | A-110611.1 | GGGAGGACAUCAUUGGUGCCU | 78 | A-109377.2 | AGGCACCAAUGAUGUCCUCCCCU | 299 | 1454 | 1476 |
| AD-53740.1 | A-110612.1 | ACUGCAGCACCUGCUUUGUGU | 79 | A-109379.2 | ACACAAAGCAGGUGCUGCAGUCG | 300 | 1481 | 1503 |
| AD-53699.1 | A-110613.1 | GCAUUGCAGCCAUGAUGCUGU | 80 | A-109381.2 | ACAGCAUCAUGGCUGCAAUGCCA | 301 | 1541 | 1563 |
| AD-53705.1 | A-110614.1 | GUUGAGGCAGAGACUGAUCCA | 81 | A-109383.2 | UGGAUCAGUCUCUGCCUCAACUC | 302 | 1590 | 1612 |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53711.1 | A-110615.1 | UGAGGCAGAGACUGAUCCACU | 82 | A-109385.2 | AGUGGAUCAGUCUCUGCCUCAAC | 303 | 1592 | 1614 |
| AD-53717.1 | A-110616.1 | GAGGCAGAGACUGAUCCACUU | 83 | A-109387.2 | AAGUGGAUCAGUCUCUGCCUCAA | 304 | 1593 | 1615 |
| AD-53723.1 | A-110617.1 | GGCAGAGACUGAUCCACUUCU | 84 | A-109389.2 | AGAAGUGGAUCAGUCUCUGCCUC | 305 | 1595 | 1617 |
| AD-53729.1 | A-110618.1 | CAGAGACUGAUCCACUUCUCU | 85 | A-109391.2 | AGAGAAGUGGAUCAGUCUCUGCC | 306 | 1597 | 1619 |
| AD-53735.1 | A-110619.1 | ACUGAUCCACUUCUCUGCCAA | 86 | A-109393.2 | UUGGCAGAGAAGUGGAUCAGUCU | 307 | 1602 | 1624 |
| AD-53741.1 | A-110620.1 | AUCCACUUCUCUGCCAAAGAU | 87 | A-109395.2 | AUCUUUGGCAGAGAAGUGGAUCA | 308 | 1606 | 1628 |
| AD-53700.1 | A-110621.1 | GGCCUGGUUCCCUGAGGACCA | 88 | A-109397.2 | UGGUCCUCAGGGAACCAGGCCUC | 309 | 1638 | 1660 |
| AD-53706.1 | A-110622.1 | GGUACUGACCCCCAACCUGGU | 89 | A-109399.2 | ACCAGGUUGGGGGUCAGUACCCG | 310 | 1662 | 1684 |
| AD-53712.1 | A-110623.1 | GUUGGCAGCUGUUUUGCAGGA | 90 | A-109401.2 | UCCUGCAAAACAGCUGCCAACCU | 311 | 1715 | 1737 |
| AD-53718.1 | A-110624.1 | UGGCAGCUGUUUUGCAGGACU | 91 | A-109403.2 | AGUCCUGCAAAACAGCUGCCAAC | 312 | 1717 | 1739 |
| AD-53724.1 | A-110625.1 | GCAGCUGUUUUGCAGGACUGU | 92 | A-109405.2 | ACAGUCCUGCAAAACAGCUGCCA | 313 | 1719 | 1741 |
| AD-53730.1 | A-110626.1 | UCUGCCGGGCCCACAACGCUU | 93 | A-109407.2 | AAGCGUUGUGGGCCCGGCAGACC | 314 | 1883 | 1905 |
| AD-53736.1 | A-110627.1 | CUGCCGGGCCCACAACGCUUU | 94 | A-109409.2 | AAAGCGUUGUGGGCCCGGCAGAC | 315 | 1884 | 1906 |
| AD-53742.1 | A-110628.1 | GCCCACAACGCUUUUGGGGGU | 95 | A-109411.2 | ACCCCCAAAAGCGUUGUGGGCCC | 316 | 1891 | 1913 |
| AD-53701.1 | A-110629.1 | CGCUUUUGGGGGUGAGGGUGU | 96 | A-109413.2 | ACACCCUCACCCCCAAAAGCGUU | 317 | 1899 | 1921 |
| AD-53707.1 | A-110630.1 | CUUUUGGGGGUGAGGGUGUCU | 97 | A-109415.2 | AGACACCCUCACCCCCAAAAGCG | 318 | 1901 | 1923 |
| AD-53713.1 | A-110631.1 | UUUUGGGGGUGAGGGUGUCUA | 98 | A-109417.2 | UAGACACCCUCACCCCCAAAAGC | 319 | 1902 | 1924 |
| AD-53719.1 | A-110632.1 | GGGGUGAGGGUGUCUACGCCA | 99 | A-109419.2 | UGGCGUAGACACCCUCACCCCCA | 320 | 1907 | 1929 |
| AD-53725.1 | A-110633.1 | GGGUGAGGGUGUCUACGCCAU | 100 | A-109421.2 | AUGGCGUAGACACCCUCACCCCC | 321 | 1908 | 1930 |
| AD-53731.1 | A-110634.1 | GGUGAGGGUGUCUACGCCAUU | 101 | A-109423.2 | AAUGGCGUAGACACCCUCACCCC | 322 | 1909 | 1931 |
| AD-53737.1 | A-110635.1 | AGGGUGUCUACGCCAUUGCCA | 102 | A-109425.2 | UGGCAAUGGCGUAGACACCCUCA | 323 | 1913 | 1935 |
| AD-53743.1 | A-110636.1 | GUGUCUACGCCAUUGCCAGGU | 103 | A-109427.2 | ACCUGGCAAUGGCGUAGACACCC | 324 | 1916 | 1938 |
| AD-53749.1 | A-110637.1 | UGCAGCGUCCACACAGCUCCA | 104 | A-109429.2 | UGGAGCUGUGUGGACGCUGCAGU | 325 | 1960 | 1982 |
| AD-53755.1 | A-110638.1 | GCAUGGGGACCCGUGUCCACU | 105 | A-109431.2 | AGUGGACACGGGUCCCCAUGCUG | 326 | 1994 | 2016 |
| AD-53761.1 | A-110639.1 | CCCACAAGCCGCCUGUGCUGA | 106 | A-109433.2 | UCAGCACAGGCGGCUUGUGGGUG | 327 | 2078 | 2100 |
| AD-53767.1 | A-110640.1 | GAGGCCACGAGGUCAGCCCAA | 107 | A-109435.2 | UUGGGCUGACCUCGUGGCCUCAG | 328 | 2097 | 2119 |
| AD-53773.1 | A-110641.1 | CACGAGGUCAGCCCAACCAGU | 108 | A-109437.2 | ACUGGUUGGGCUGACCUCGUGGC | 329 | 2102 | 2124 |
| AD-53779.1 | A-110642.1 | GGGAGGCCAGCAUCCACGCUU | 109 | A-109439.2 | AAGCGUGGAUGCUGGCCUCCCUG | 330 | 2135 | 2157 |
| AD-53785.1 | A-110643.1 | AUCCACGCUUCCUGCUGCCAU | 110 | A-109441.2 | AUGGCAGCAGGAAGCGUGGAUGC | 331 | 2146 | 2168 |
| AD-53744.1 | A-110644.1 | GGAAUGCAAAGUCAAGGAGCA | 111 | A-109443.2 | UGCUCCUUGACUUUGCAUUCCAG | 332 | 2178 | 2200 |
| AD-53750.1 | A-110645.1 | AAUCCCGGCCCCUCAGGAGCA | 112 | A-109445.2 | UGCUCCUGAGGGGCCGGGAUUCC | 333 | 2202 | 2224 |
| AD-53762.1 | A-110647.1 | GCUGGGGCUGAGCUUUAAAAU | 113 | A-109449.2 | AUUUUAAAGCUCAGCCCCAGCCC | 334 | 2479 | 2501 |
| AD-53768.1 | A-110648.1 | GGAGGUGCCAGGAAGCUCCCU | 114 | A-109451.2 | AGGGAGCUUCCUGGCACCUCCAC | 335 | 2648 | 2670 |
| AD-53774.1 | A-110649.1 | ACUGUGGGGCAUUUCACCAUU | 115 | A-109453.2 | AAUGGUGAAAUGCCCCACAGUGA | 336 | 2674 | 2696 |
| AD-53780.1 | A-110650.1 | CCACCAAGGAGGCAGGAUUCU | 116 | A-109455.2 | AGAAUCCUGCCUCCUUGGUGGAG | 337 | 2811 | 2833 |
| AD-53786.1 | A-110651.1 | CACCAAGGAGGCAGGAUUCUU | 117 | A-109457.2 | AAGAAUCCUGCCUCCUUGGUGGA | 338 | 2812 | 2834 |
| AD-53804.1 | A-110701.1 | ACCAAGGAGGCAGGAUUCUUU | 118 | A-109557.2 | AAAGAAUCCUGCCUCCUUGGUGG | 339 | 2813 | 2835 |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53810.1 | A-110702.1 | GGAGGCAGGAUUCUUCCCAUU | 119 | A-109559.2 | AAUGGGAAGAAUCCUGCCUCCUU | 340 | 2818 | 2840 |
| AD-53816.1 | A-110703.1 | GAGGCAGGAUUCUUCCCAUGA | 120 | A-109561.2 | UCAUGGGAAGAAUCCUGCCUCCU | 341 | 2819 | 2841 |
| AD-53745.1 | A-110652.1 | UGAUGGCCCUCAUCUCCAGCU | 121 | A-109459.2 | AGCUGGAGAUGAGGGCCAUCAGC | 342 | 2904 | 2926 |
| AD-53822.1 | A-110704.1 | CUUUCUGGAUGGCAUCUAGCA | 122 | A-109563.2 | UGCUAGAUGCCAUCCAGAAAGCU | 343 | 2971 | 2993 |
| AD-53751.1 | A-110653.1 | UUUCUGGAUGGCAUCUAGCCA | 123 | A-109461.2 | UGGCUAGAUGCCAUCCAGAAAGC | 344 | 2972 | 2994 |
| AD-53827.1 | A-110705.1 | UUCUGGAUGGCAUCUAGCCAA | 124 | A-109565.2 | UUGGCUAGAUGCCAUCCAGAAAG | 345 | 2973 | 2995 |
| AD-53757.1 | A-110654.1 | UCUGGAUGGCAUCUAGCCAGA | 125 | A-109463.2 | UCUGGCUAGAUGCCAUCCAGAAA | 346 | 2974 | 2996 |
| AD-53833.1 | A-110706.1 | CUGGAUGGCAUCUAGCCAGAA | 126 | A-109567.2 | UUCUGGCUAGAUGCCAUCCAGAA | 347 | 2975 | 2997 |
| AD-53793.1 | A-110707.1 | CUUUACUCUGCUCUAUGCCAA | 127 | A-109569.2 | UUGGCAUAGAGCAGAGUAAAGGU | 348 | 3053 | 3075 |
| AD-53799.1 | A-110708.1 | UUUACUCUGCUCUAUGCCAGA | 128 | A-109571.2 | UCUGGCAUAGAGCAGAGUAAAGG | 349 | 3054 | 3076 |
| AD-53763.1 | A-110655.1 | GCUCUAUGCCAGGCUGUGCUA | 129 | A-109465.2 | UAGCACAGCCUGGCAUAGAGCAG | 350 | 3062 | 3084 |
| AD-53769.1 | A-110656.1 | CUCAGCCAACCCGCUCCACUA | 130 | A-109467.2 | UAGUGGAGCGGGUUGGCUGAGAC | 351 | 3158 | 3180 |
| AD-53805.1 | A-110709.1 | UCAGCCAACCCGCUCCACUAA | 131 | A-109573.2 | UUAGUGGAGCGGGUUGGCUGAGA | 352 | 3159 | 3181 |
| AD-53811.1 | A-110710.1 | CCUGCCAAGCUCACACAGCAA | 132 | A-109575.2 | UUGCUGUGUGAGCUUGGCAGGCA | 353 | 3245 | 3267 |
| AD-53781.1 | A-110658.1 | GCCAAGCUCACACAGCAGGAA | 133 | A-109471.2 | UUCCUGCUGUGUGAGCUUGGCAG | 354 | 3248 | 3270 |
| AD-53817.1 | A-110711.1 | CCAAGCUCACACAGCAGGAAA | 134 | A-109577.2 | UUUCCUGCUGUGUGAGCUUGGCA | 355 | 3249 | 3271 |
| AD-53787.1 | A-110659.1 | CAAGCUCACACAGCAGGAACU | 135 | A-109473.2 | AGUUCCUGCUGUGUGAGCUUGGC | 356 | 3250 | 3272 |
| AD-53823.1 | A-110712.1 | AAGCUCACACAGCAGGAACUU | 136 | A-109579.2 | AAGUUCCUGCUGUGUGAGCUUGG | 357 | 3251 | 3273 |
| AD-53746.1 | A-110660.1 | CUGAAGCCAAGCCUCUUCUUA | 137 | A-109475.2 | UAAGAAGAGGCUUGGCUUCAGAG | 358 | 3298 | 3320 |
| AD-53828.1 | A-110713.1 | UGAAGCCAAGCCUCUUCUUAA | 138 | A-109581.2 | UUAAGAAGAGGCUUGGCUUCAGA | 359 | 3299 | 3321 |
| AD-53752.1 | A-110661.1 | GAAGCCAAGCCUCUUCUUACU | 139 | A-109477.2 | AGUAAGAAGAGGCUUGGCUUCAG | 360 | 3300 | 3322 |
| AD-53758.1 | A-110662.1 | AAGCCAAGCCUCUUCUUACUU | 140 | A-109479.2 | AAGUAAGAAGAGGCUUGGCUUCA | 361 | 3301 | 3323 |
| AD-53834.1 | A-110714.1 | AGUGAGGCUGGGAAGGGGAAA | 141 | A-109583.2 | UUUCCCCUUCCCAGCCUCACUGU | 362 | 3355 | 3377 |
| AD-53764.1 | A-110663.1 | GUGAGGCUGGGAAGGGGAACA | 142 | A-109481.2 | UGUUCCCCUUCCCAGCCUCACUG | 363 | 3356 | 3378 |
| AD-53770.1 | A-110664.1 | GGCUGGGAAGGGGAACACAGA | 143 | A-109483.2 | UCUGUGUUCCCCUUCCCAGCCUC | 364 | 3360 | 3382 |
| AD-53776.1 | A-110665.1 | GAAGGGGAACACAGACCAGGA | 144 | A-109485.2 | UCCUGGUCUGUGUUCCCCUUCCC | 365 | 3366 | 3388 |
| AD-53782.1 | A-110666.1 | AAGGGGAACACAGACCAGGAA | 145 | A-109487.2 | UUCCUGGUCUGUGUUCCCCUUCC | 366 | 3367 | 3389 |
| AD-53794.1 | A-110715.1 | AGGGGAACACAGACCAGGAAA | 146 | A-109585.2 | UUUCCUGGUCUGUGUUCCCCUUC | 367 | 3368 | 3390 |
| AD-53788.1 | A-110667.1 | GGGAACACAGACCAGGAAGCU | 147 | A-109489.2 | AGCUUCCUGGUCUGUGUUCCCCU | 368 | 3370 | 3392 |
| AD-53747.1 | A-110668.1 | ACUGUCCCUCCUUGAGCACCA | 148 | A-109491.2 | UGGUGCUCAAGGAGGGACAGUUG | 369 | 3509 | 3531 |
| AD-53753.1 | A-110669.1 | CCAGCCCCACCCAAGCAAGCA | 149 | A-109493.2 | UGCUUGCUUGGGUGGGGCUGGUG | 370 | 3527 | 3549 |
| AD-53759.1 | A-110670.1 | CCCCACCCAAGCAAGCAGACA | 150 | A-109495.2 | UGUCUGCUUGCUUGGGUGGGGCU | 371 | 3531 | 3553 |
| AD-53765.1 | A-110671.1 | CCCACCCAAGCAAGCAGACAU | 151 | A-109497.2 | AUGUCUGCUUGCUUGGGUGGGGC | 372 | 3532 | 3554 |
| AD-53771.1 | A-110672.1 | CCACCCAAGCAAGCAGACAUU | 152 | A-109499.2 | AAUGUCUGCUUGCUUGGGUGGGG | 373 | 3533 | 3555 |
| AD-53777.1 | A-110673.1 | CACCCAAGCAAGCAGACAUUU | 153 | A-109501.2 | AAAUGUCUGCUUGCUUGGGUGGG | 374 | 3534 | 3556 |
| AD-53783.1 | A-110674.1 | ACCCAAGCAAGCAGACAUUUA | 154 | A-109503.2 | UAAAUGUCUGCUUGCUUGGGUGG | 375 | 3535 | 3557 |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53789.1 | A-110675.1 | CCCAAGCAAGCAGACAUUUAU | 155 | A-109505.2 | AUAAAUGUCUGCUUGCUUGGGUG | 376 | 3536 | 3558 |
| AD-53800.1 | A-110716.1 | CCAAGCAAGCAGACAUUUAUU | 156 | A-109587.2 | AAUAAAUGUCUGCUUGCUUGGGU | 377 | 3537 | 3559 |
| AD-53748.1 | A-110676.1 | CAAGCAAGCAGACAUUUAUCU | 157 | A-109507.2 | AGAUAAAUGUCUGCUUGCUUGGG | 378 | 3538 | 3560 |
| AD-53754.1 | A-110677.1 | AAGCAAGCAGACAUUUAUCUU | 158 | A-109509.2 | AAGAUAAAUGUCUGCUUGCUUGG | 379 | 3539 | 3561 |
| AD-53760.1 | A-110678.1 | AGCAAGCAGACAUUUAUCUUU | 159 | A-109511.2 | AAAGAUAAAUGUCUGCUUGCUUG | 380 | 3540 | 3562 |
| AD-53806.1 | A-110717.1 | CAAGCAGACAUUUAUCUUUUU | 160 | A-109589.2 | AAAAAGAUAAAUGUCUGCUUGCU | 381 | 3542 | 3564 |
| AD-56975.1 | A-116394.4 | Same | 160 | A-109589.5 | Same | 381 | Same | Same |
| AD-56976.1 | A-116407.1 | | 160 | A-109589.11 | | 381 | | |
| AD-56977.1 | A-116406.2 | | 160 | A-109589.11 | | 381 | | |
| AD-56978.1 | A-116418.1 | | 160 | A-109589.18 | | 381 | | |
| AD-56979.1 | A-116393.1 | | 160 | A-109589.6 | | 381 | | |
| AD-56980.1 | A-116408.1 | Same | 160 | A-109589.12 | Same | 381 | Same | Same |
| AD-56981.1 | A-116419.1 | | 160 | A-109589.19 | | 381 | | |
| AD-56982.1 | A-116426.1 | | 160 | A-109589.19 | | 381 | | |
| AD-56983.1 | A-116400.1 | | 160 | A-109589.7 | | 381 | | |
| AD-56984.1 | A-116409.1 | | 160 | A-109589.13 | | 381 | | |
| AD-56985.1 | A-116420.1 | | 160 | A-109589.20 | | 381 | | |
| AD-56986.1 | A-116428.1 | | 160 | A-109589.20 | | 381 | | |
| AD-56986.2 | A-116428.2 | | 160 | A-109589.17 | | 381 | | |
| AD-56987.1 | A-116410.1 | | 160 | A-109589.14 | | 381 | | |
| AD-56988.1 | A-116421.1 | | 160 | A-109589.21 | | 381 | | |
| AD-56989.1 | A-116430.1 | | 160 | A-109589.21 | | 381 | | |
| AD-56990.1 | A-116432.1 | | 160 | A-109589.9 | | 381 | | |
| AD-56991.1 | A-116415.1 | | 160 | A-109589.15 | | 381 | | |
| AD-56992.1 | A-116434.1 | | 160 | A-109589.15 | | 381 | | |
| AD-56993.1 | A-116416.1 | | 160 | A-109589.16 | | 381 | | |
| AD-56994.1 | A-116436.1 | | 160 | A-109589.22 | | 381 | | |
| AD-56995.1 | A-116417.1 | | 160 | A-109589.17 | | 381 | | |
| AD-56996.1 | A-116438.1 | | 160 | A-109589.17 | | 381 | | |
| AD-56997.1 | A-116450.1 | | 160 | A-109589.17 | | 381 | | |
| AD-56998.1 | A-116471.1 | | 160 | A-109589.17 | | 381 | | |
| AD-56999.1 | A-116479.2 | | 160 | A-109589.17 | | 381 | | |
| AD-57000.1 | A-116492.3 | | 160 | A-109589.17 | | 381 | | |
| AD-57001.1 | A-116440.1 | | 160 | A-109589.17 | | 381 | | |
| AD-57002.1 | A-116452.1 | | 160 | A-109589.17 | | 381 | | |
| AD-57003.1 | A-116460.1 | | 160 | A-109589.17 | | 381 | | |
| AD-57004.1 | A-116473.1 | | 160 | A-109589.17 | | 381 | | |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-57005.1 | A-116486.1 | | 160 | A-109589.17 | | 381 | | |
| AD-57006.1 | A-116494.3 | | 160 | A-109589.17 | | 381 | | |
| AD-57007.1 | A-116442.1 | | 160 | A-109589.17 | | 381 | | |
| AD-57008.1 | A-116453.1 | | 160 | A-109589.17 | | 381 | | |
| AD-57009.1 | A-116462.1 | | 160 | A-109589.17 | | 381 | | |
| AD-57010.1 | A-116475.1 | | 160 | A-109589.17 | | 381 | | |
| AD-57011.1 | A-116488.1 | | 160 | A-109589.17 | | 381 | | |
| AD-57012.1 | A-116498.1 | | 160 | A-109589.17 | | 381 | | |
| AD-57013.1 | A-116444.1 | | 160 | A-109589.17 | | 381 | | |
| AD-57014.1 | A-116454.1 | | 160 | A-109589.17 | | 381 | | |
| AD-57015.1 | A-116464.1 | | 160 | A-109589.17 | | 381 | | |
| AD-57016.1 | A-116477.1 | | 160 | A-109589.17 | | 381 | | |
| AD-57017.1 | A-116490.1 | | 160 | A-109589.17 | | 381 | | |
| AD-57018.1 | A-116500.1 | | 160 | A-109589.17 | | 381 | | |
| AD-57019.1 | A-116446.1 | | 160 | A-109589.17 | | 381 | | |
| AD-57020.1 | A-116455.1 | | 160 | A-109589.23 | | 381 | | |
| AD-57021.1 | A-116481.1 | | 160 | A-109589.23 | | 381 | | |
| AD-57022.1 | A-116448.1 | | 160 | A-109589.23 | | 381 | | |
| AD-57023.1 | A-116467.1 | | 160 | A-109589.23 | | 381 | | |
| AD-57024.1 | A-116483.1 | | 160 | A-109589.23 | | 381 | | |
| AD-57025.1 | A-116449.1 | | 160 | A-109589.23 | | 381 | | |
| AD-57026.1 | A-116457.1 | | 160 | A-109589.23 | | 381 | | |
| AD-57027.1 | A-116469.1 | | 160 | A-109589.23 | | 381 | | |
| AD-53812.1 | A-110718.1 | AAGCAGACAUUUAUCUUUUGA | 161 | A-109591.2 | UCAAAAGAUAAAUGUCUGCUUGC | 382 | 3543 | 3565 |
| AD-53818.1 | A-110719.1 | AGCAGACAUUUAUCUUUUGGA | 162 | A-109593.2 | UCCAAAAGAUAAAUGUCUGCUUG | 383 | 3544 | 3566 |
| AD-53766.1 | A-110679.1 | GCAGACAUUUAUCUUUUGGGU | 163 | A-109513.2 | ACCCAAAAGAUAAAUGUCUGCUU | 384 | 3545 | 3567 |
| AD-53772.1 | A-110680.1 | AGACAUUUAUCUUUUGGGUCU | 164 | A-109515.2 | AGACCCAAAAGAUAAAUGUCUGC | 385 | 3547 | 3569 |
| AD-53824.1 | A-110720.1 | GACAUUUAUCUUUUGGGUCUU | 165 | A-109595.2 | AAGACCCAAAAGAUAAAUGUCUG | 386 | 3548 | 3570 |
| AD-53778.1 | A-110681.1 | ACAUUUAUCUUUUGGGUCUGU | 166 | A-109517.2 | ACAGACCCAAAAGAUAAAUGUCU | 387 | 3549 | 3571 |
| AD-53784.1 | A-110682.1 | UUUAUCUUUUGGGUCUGUCCU | 167 | A-109519.2 | AGGACAGACCCAAAAGAUAAAUG | 388 | 3552 | 3574 |
| AD-53829.1 | A-110721.1 | UUAUCUUUUGGGUCUGUCCUU | 168 | A-109597.2 | AAGGACAGACCCAAAAGAUAAAU | 389 | 3553 | 3575 |
| AD-53790.1 | A-110683.1 | UAUCUUUUGGGUCUGUCCUCU | 169 | A-109521.2 | AGAGGACAGACCCAAAAGAUAAA | 390 | 3554 | 3576 |
| AD-53835.1 | A-110722.1 | AUCUUUUGGGUCUGUCCUCUU | 170 | A-109599.2 | AAGAGGACAGACCCAAAAGAUAA | 391 | 3555 | 3577 |
| AD-53796.1 | A-110684.1 | UCUUUUGGGUCUGUCCUCUCU | 171 | A-109523.2 | AGAGAGGACAGACCCAAAAGAUA | 392 | 3556 | 3578 |
| AD-53802.1 | A-110685.1 | UUUUGGGUCUGUCCUCUCUGU | 172 | A-109525.2 | ACAGAGAGGACAGACCCAAAAGA | 393 | 3558 | 3580 |
| AD-53808.1 | A-110686.1 | UUUGGGUCUGUCCUCUCUGUU | 173 | A-109527.2 | AACAGAGAGGACAGACCCAAAAG | 394 | 3559 | 3581 |

TABLE 1-continued

| PCSK9 unmodified sequences | | | | | | | | | |
|---|---|---|---|---|---|---|---|---|---|
| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
| AD-53795.1 | A-110723.1 | UUGGGUCUGUCCUCUCUGUUU | 174 | A-109601.2 | AAACAGAGAGGACAGACCCAAAA | 395 | 3560 | 3582 |
| AD-53801.1 | A-110724.1 | UGGGUCUGUCCUCUCUGUUGA | 175 | A-109603.2 | UCAACAGAGAGGACAGACCCAAA | 396 | 3561 | 3583 |
| AD-53807.1 | A-110725.1 | GGGUCUGUCCUCUCUGUUGCA | 176 | A-109605.2 | UGCAACAGAGAGGACAGACCCAA | 397 | 3562 | 3584 |
| AD-53814.1 | A-110687.1 | GGUCUGUCCUCUCUGUUGCCU | 177 | A-109529.2 | AGGCAACAGAGAGGACAGACCCA | 398 | 3563 | 3585 |
| AD-53820.1 | A-110688.1 | GUCUGUCCUCUCUGUUGCCUU | 178 | A-109531.2 | AAGGCAACAGAGAGGACAGACCC | 399 | 3564 | 3586 |
| AD-53825.1 | A-110689.1 | UCUGUCCUCUCUGUUGCCUUU | 179 | A-109533.2 | AAAGGCAACAGAGAGGACAGACC | 400 | 3565 | 3587 |
| AD-53831.1 | A-110690.1 | CUGUCCUCUCUGUUGCCUUUU | 180 | A-109535.2 | AAAAGGCAACAGAGAGGACAGAC | 401 | 3566 | 3588 |
| AD-53791.1 | A-110691.1 | UGUCCUCUCUGUUGCCUUUUU | 181 | A-109537.2 | AAAAAGGCAACAGAGAGGACAGA | 402 | 3567 | 3589 |
| AD-53797.1 | A-110692.1 | GUCCUCUCUGUUGCCUUUUUA | 182 | A-109539.2 | UAAAAAGGCAACAGAGAGGACAG | 403 | 3568 | 3590 |
| AD-48400.1 | A-98247.2 | UUUUCUAGACCUGUUUUGCUU | 183 | A-93455.4 | AAGCAAAACAGGUCUAGAAAAGU | 404 | 3597 | 3619 |
| AD-53830.1 | A-110872.1 | | | A-110873.1 | | | | |
| AD-53803.1 | A-110693.1 | UUUCUAGACCUGUUUUGCUUU | 184 | A-109541.2 | AAAGCAAAACAGGUCUAGAAAAG | 405 | 3598 | 3620 |
| AD-53809.1 | A-110694.1 | UUCUAGACCUGUUUUGCUUUU | 185 | A-109543.2 | AAAAGCAAAACAGGUCUAGAAAA | 406 | 3599 | 3621 |
| AD-53813.1 | A-110726.1 | UCUAGACCUGUUUUGCUUUUU | 186 | A-109607.2 | AAAAAGCAAAACAGGUCUAGAAA | 407 | 3600 | 3622 |
| AD-53815.1 | A-110695.1 | CUAGACCUGUUUUGCUUUUGU | 187 | A-109545.2 | ACAAAAGCAAAACAGGUCUAGAA | 408 | 3601 | 3623 |
| AD-56610.1 | A-115523.2 | Same | 187 | A-115525.1 | Same | 408 | | Same |
| AD-56611.1 | A-115533.2 | | 187 | A-115534.1 | | 408 | | |
| AD-56612.1 | A-115536.2 | | 187 | A-115540.3 | | 408 | | |
| AD-56613.1 | A-115538.3 | | 187 | A-115541.5 | | 408 | | |
| AD-56614.1 | A-110695.9 | | 187 | A-115548.1 | | 408 | | |
| AD-56615.1 | A-110695.5 | | 187 | A-115519.1 | | 408 | | |
| AD-56616.1 | A-115523.3 | | 187 | A-115526.1 | | 408 | | |
| AD-56617.1 | A-115535.1 | | 187 | A-109545.7 | | 408 | | |
| AD-56618.1 | A-115537.2 | | 187 | A-115540.4 | | 408 | | |
| AD-56619.1 | A-115539.3 | | 187 | A-115541.6 | | 408 | | |
| AD-56620.1 | A-115542.2 | | 187 | A-115548.2 | | 408 | | |
| AD-56621.1 | A-115520.1 | | 187 | A-115519.2 | | 408 | | |
| AD-56622.1 | A-115527.1 | | 187 | A-115526.2 | | 408 | | |
| AD-56623.1 | A-115536.1 | | 187 | A-109545.8 | | 408 | | |
| AD-56624.1 | A-115538.2 | | 187 | A-115540.5 | | 408 | | |
| AD-56625.1 | A-115542.1 | | 187 | A-109545.12 | | 408 | | |
| AD-56626.1 | A-115543.2 | | 187 | A-115548.3 | | 408 | | |
| AD-56627.1 | A-115521.1 | | 187 | A-115519.3 | | 408 | | |
| AD-56628.1 | A-115527.2 | | 187 | A-115528.1 | | 408 | | |
| AD-56629.1 | A-115537.1 | | 187 | A-109545.9 | | 408 | | |
| AD-56630.1 | A-115539.2 | | 187 | A-115540.6 | | 408 | | |
| AD-56631.1 | A-115543.1 | | 187 | A-109545.13 | | 408 | | |

TABLE 1-continued

| PCSK9 unmodified sequences | | | | | | | | | |
|---|---|---|---|---|---|---|---|---|---|
| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
| AD-56632.1 | A-115544.2 | | 187 | A-115548.4 | | 408 | | |
| AD-56633.1 | A-115520.2 | | 187 | A-109545.6 | | 408 | | |
| AD-56634.1 | A-115529.1 | | 187 | A-115530.1 | | 408 | | |
| AD-56635.1 | A-115538.1 | | 187 | A-109545.10 | | 408 | | |
| AD-56636.1 | A-110695.8 | | 187 | A-115541.1 | | 408 | | |
| AD-56637.1 | A-115544.1 | Same | 187 | A-109545.14 | Same | 408 | | |
| AD-56638.1 | A-115545.2 | | 187 | A-115548.5 | | 408 | | |
| AD-56639.1 | A-115520.3 | | 187 | A-115522.1 | | 408 | | |
| AD-56640.1 | A-115529.2 | | 187 | A-115531.1 | | 408 | | |
| AD-56641.1 | A-115539.1 | | 187 | A-109545.11 | | 408 | | |
| AD-56642.1 | A-115535.3 | | 187 | A-115541.2 | | 408 | | |
| AD-56643.1 | A-115545.1 | | 187 | A-109545.15 | | 408 | | |
| AD-56644.1 | A-115546.2 | | 187 | A-115548.6 | | 408 | | |
| AD-56645.1 | A-110695.6 | | 187 | A-115522.2 | | 408 | | |
| AD-56646.1 | A-115529.3 | | 187 | A-115532.1 | | 408 | | |
| AD-56647.1 | A-110695.7 | | 187 | A-115540.1 | | 408 | | |
| AD-56648.1 | A-115536.3 | | 187 | A-115541.3 | | 408 | | |
| AD-56649.1 | A-115546.1 | | 187 | A-109545.16 | | 408 | | |
| AD-56650.1 | A-115547.2 | | 187 | A-115548.7 | | 408 | | |
| AD-56651.1 | A-115523.1 | | 187 | A-115524.1 | | 408 | | |
| AD-56652.1 | A-115533.1 | | 187 | A-115532.2 | | 408 | | |
| AD-56653.1 | A-115535.2 | | 187 | A-115540.2 | | 408 | | |
| AD-56654.1 | A-115537.3 | | 187 | A-115541.4 | | 408 | | |
| AD-56655.1 | A-115547.1 | | 187 | A-109545.17 | | 408 | | |
| AD-56656.1 | A-110695.10 | | 187 | A-115549.1 | | 408 | | |
| AD-56657.1 | A-115550.1 | | 187 | A-115551.1 | | 408 | | |
| AD-56658.1 | A-115564.1 | | 187 | A-115565.1 | | 408 | | |
| AD-56659.1 | A-110695.12 | | 187 | A-115579.1 | | 408 | | |
| AD-56662.1 | A-115542.3 | | 187 | A-115549.2 | | 408 | | |
| AD-56663.1 | A-115552.1 | | 187 | A-115553.1 | | 408 | | |
| AD-56664.1 | A-115566.1 | | 187 | A-115567.1 | | 408 | | |
| AD-56668.1 | A-115543.3 | Same | 187 | A-115549.3 | Same | 408 | | |
| AD-56669.1 | A-115554.1 | | 187 | A-115555.1 | | 408 | | |
| AD-56670.1 | A-115568.1 | | 187 | A-115569.1 | | 408 | | |
| AD-56673.1 | A-115544.3 | | 187 | A-115549.4 | | 408 | | |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-56674.1 | A-115556.1 | | 187 | A-115557.1 | | 408 | | |
| AD-56678.1 | A-115545.3 | | 187 | A-115549.5 | | 408 | | |
| AD-56679.1 | A-115558.1 | | 187 | A-115559.1 | | 408 | | |
| AD-56680.1 | A-115572.1 | | 187 | A-115573.1 | | 408 | | |
| AD-56683.1 | A-115546.3 | | 187 | A-115549.6 | | 408 | | |
| AD-56684.1 | A-115560.1 | | 187 | A-115561.1 | | 408 | | |
| AD-56685.1 | A-115574.1 | | 187 | A-115575.1 | | 408 | | |
| AD-56688.1 | A-115547.3 | | 187 | A-115549.7 | | 408 | | |
| AD-56689.1 | A-115535.4 | | 187 | A-115562.1 | | 408 | | |
| AD-56690.1 | A-115542.4 | | 187 | A-115576.1 | | 408 | | |
| AD-56693.1 | A-115520.4 | | 187 | A-115563.1 | | 408 | | |
| AD-56694.1 | A-115577.1 | | 187 | A-115578.1 | | 408 | | |
| AD-53821.1 | A-110696.1 | UAGACCUGUUUUGCUUUUGUA | 188 | A-109547.2 | UACAAAAGCAAAACAGGUCUAGA | 409 | 3602 | 3624 |
| AD-56660.1 | A-115594.1 | AGACCUGUUUUGCUUUUGU | 189 | A-115595.1 | ACAAAAGCAAAACAGGUCUAG | 410 | 3603 | 3623 |
| AD-56661.1 | A-115580.2 | Same | 189 | A-115610.1 | Same | 410 | | |
| AD-56665.1 | A-115580.1 | | 189 | A-115581.1 | | 410 | | |
| AD-56666.1 | A-115596.1 | | 189 | A-115597.1 | | 410 | | |
| AD-56667.1 | A-115611.1 | GACCUGUUUUGCUUUUGU | 190 | A-115612.1 | ACAAAAGCAAAACAGGUCAUA | 411 | 3603 | 3623 |
| AD-56671.1 | A-115582.1 | AGACCUGUUUUGCUUUUGU | 191 | A-115583.1 | ACAAAAGCAAAACAGGUCUAG | 412 | 3603 | 3623 |
| AD-56672.1 | A-115598.1 | Same | 191 | A-115599.1 | Same | 412 | Same | Same |
| AD-56676.1 | A-115584.1 | | 191 | A-115585.1 | | 412 | | |
| AD-56677.1 | A-115600.1 | | 191 | A-115601.1 | | 412 | | |
| AD-56681.1 | A-115586.1 | Same | 191 | A-115587.1 | Same | 412 | | |
| AD-56682.1 | A-115602.1 | | 191 | A-115603.1 | | 412 | | |
| AD-56686.1 | A-115588.1 | | 191 | A-115589.1 | | 412 | | |
| AD-56687.1 | A-115604.1 | | 191 | A-115605.1 | | 412 | | |
| AD-56691.1 | A-115590.1 | | 191 | A-115591.1 | | 412 | | |
| AD-56692.1 | A-115606.1 | | 191 | A-115607.1 | | 412 | | |
| AD-56695.1 | A-115592.1 | | 191 | A-115593.1 | | 412 | | |
| AD-56696.1 | A-115608.1 | | 191 | A-115609.1 | | 412 | | |
| AD-53826.1 | A-110697.1 | UUUUGUAACUUGAAGAUAUUU | 192 | A-109549.2 | AAAUAUCUUCAAGUUACAAAAGC | 413 | 3616 | 3638 |
| AD-53832.1 | A-110698.1 | UUUGUAACUUGAAGAUAUUUA | 193 | A-109551.2 | UAAAUAUCUUCAAGUUACAAAAG | 414 | 3617 | 3639 |
| AD-53792.1 | A-110699.1 | UUGUAACUUGAAGAUAUUUAU | 194 | A-109553.2 | AUAAAUAUCUUCAAGUUACAAAA | 415 | 3618 | 3640 |
| AD-53798.1 | A-110700.1 | UGUAACUUGAAGAUAUUUAUU | 195 | A-109555.2 | AAUAAAUAUCUUCAAGUUACAAA | 416 | 3619 | 3641 |
| AD-53819.1 | A-110727.1 | GUAACUUGAAGAUAUUUAUUU | 196 | A-109609.2 | AAAUAAAUAUCUUCAAGUUACAA | 417 | 3620 | 3642 |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-53815.1 | | CUAGACCUGUUUUGCUUUUGU | 197 | | ACAAAAGCAAAACAGGUCUAGAA | 418 | 3601 | |
| AD-57928.40 | | Same | 197 | | Same | 418 | | |
| AD-59182.5 | | | 197 | | | 418 | | |
| AD-59184.3 | | | 197 | | | 418 | | |
| AD-59186.3 | | | 197 | | | 418 | | |
| AD-59171.13 | | | 197 | | | 418 | | |
| AD-59176.7 | | | 197 | | | 418 | | |
| AD-59170.7 | | | 197 | | | 418 | | |
| AD-59175.7 | | Same | 197 | | Same | 418 | | |
| AD-59179.7 | | | 197 | | | 418 | | |
| AD-59218.1 | | | 197 | | | 418 | | |
| AD-59222.1 | | | 197 | | | 418 | | |
| AD-59226.1 | | | 197 | | | 418 | | |
| AD-59230.1 | | | 197 | | | 418 | | |
| AD-59235.1 | | | 197 | | | 418 | | |
| AD-59207.1 | | | 197 | | | 418 | | |
| AD-59211.1 | | | 197 | | | 418 | | |
| AD-59215.1 | | | 197 | | | 418 | | |
| AD-59219.1 | | | 197 | | | 418 | | |
| AD-59223.1 | | | 197 | | | 418 | | |
| AD-59181.5 | | | 197 | | | 418 | | |
| AD-59172.5 | | | 197 | | | 418 | | |
| AD-59177.5 | | | 197 | | | 418 | | |
| AD-59180.5 | | | 197 | | | 418 | | |
| AD-59183.5 | | | 197 | | | 418 | | |
| AD-59185.5 | | | 197 | | | 418 | | |
| AD-59173.5 | | | 197 | | | 418 | | |
| AD-59232.1 | | CUAGACCUGUUUUGCUUUUGU | 198 | | ACAAAAGCAAAACAGGUCUAGAA | 419 | 3600 | |
| AD-59236.1 | | Same | 198 | | Same | 419 | Same | |
| AD-59216.1 | | | 198 | | | 419 | | |
| AD-59220.1 | | | 198 | | | 419 | | |
| AD-59224.1 | | | 198 | | | 419 | | |
| AD-59228.1 | | | 198 | | | 419 | | |
| AD-59233.1 | | | 198 | | | 419 | | |
| AD-59237.1 | | | 198 | | | 419 | | |
| AD-59209.1 | | | 198 | | | 419 | | |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-59208.1 | | | 198 | | | 419 | | |
| AD-59212.1 | | CUAGACCUGUUUUGCUUUUGU | 199 | | ACAAAAGCAAAACAGGUCUAGAA | 420 | 3600 | |
| AD-59210.1 | | CUAGACCUGUUUUGCUUUUGU | 200 | | ACAAAAGCAAAACAGGUCUAGAA | 421 | 3601 | |
| AD-59214.1 | | AGACCUGUUUUGCUUUUGU | 201 | | ACAAAAGCAAAACAGGUCUAG | 422 | 3603 | |
| AD-59227.1 | | Same | 201 | | Same | 422 | | |
| AD-59231.1 | | | 201 | | | 422 | | |
| AD-59198.3 | | | 201 | | | 422 | | |
| AD-59200.3 | | | 201 | | | 422 | | |
| AD-59203.3 | | Same | 201 | | Same | 422 | | |
| AD-59204.3 | | | 201 | | | 422 | | |
| AD-59188.3 | | | 201 | | | 422 | | |
| AD-59191.3 | | | 201 | | | 422 | | |
| AD-59213.1 | | | 201 | | | 422 | | |
| AD-59217.1 | | | 201 | | | 422 | | |
| AD-59221.1 | | | 201 | | | 422 | | |
| AD-59225.1 | | | 201 | | | 422 | | |
| AD-59229.1 | | | 201 | | | 422 | | |
| AD-59234.1 | | | 201 | | | 422 | | |
| AD-59238.1 | | | 201 | | | 422 | | |
| AD-59241.1 | | | 201 | | | 422 | | |
| AD-59245.1 | | | 201 | | | 422 | | |
| AD-59250.1 | | | 201 | | | 422 | | |
| AD-59246.1 | | CUAGACCUGUUUUGCUUUUGU | 202 | | ACAAAAGCAAAACAGGUCUAGA | 423 | 3602 | |
| AD-59253.2 | | UAGACCUGUUUUGCUUUUGU | 203 | | ACAAAAGCAAAACAGGUCUAGA | 424 | 3602 | |
| AD-59242.1 | | AGACCUGUUUUGCUUUUGU | 204 | | ACAAAAGCAAAACAGGUCUAGA | 425 | 3602 | |
| AD-59253.1 | | UAGACCUGUUUUGCUUUUGU | 205 | | ACAAAAGCAAAACAGGUCUAGA | 426 | 3602 | |
| AD-59258.1 | | UAGACCUGUUUUGCUUUUGU | 206 | | ACAAAAGCAAAACAGGUCUAGA | 427 | 3602 | |
| AD-59251.1 | | CUAGACCUGUUUUGCUUUUGU | 207 | | ACAAAAGCAAAACAGGUCUAG | 428 | 3603 | |
| AD-59256.1 | | UAGACCUGUUUUGCUUUUGU | 208 | | ACAAAAGCAAAACAGGUCUA | 429 | 3604 | |
| AD-59260.1 | | AGACCUGUUUUGCUUUUGU | 209 | | ACAAAAGCAAAACAGGUCU | 430 | 3605 | |
| AD-59248.1 | | GACCUGUUUUGCUUUUGU | 210 | | ACAAAAGCAAAACAGGUCU | 431 | 3605 | |
| AD-59247.1 | | GACCUGUUUUGCUUUUGU | 211 | | ACAAAAGCAAAACAGGUCUA | 432 | 3604 | |
| AD-59252.1 | | AGACCUGUUUUGCUUUUGU | 212 | | ACAAAAGCAAAACAGGUCUA | 433 | 3604 | |
| AD-59257.1 | | UAGACCUGUUUUGCUUUUGU | 213 | | ACAAAAGCAAAACAGGUCUA | 434 | 3604 | |
| AD-59261.1 | | AGACCUGUUUUGCUUUUGU | 214 | | ACAAAAGCAAAACAGGUCUAG | 435 | 3603 | |
| AD-59262.1 | | UAGACCUGUUUUGCUUUUGU | 215 | | ACAAAAGCAAAACAGGUCUAG | 436 | 3603 | |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| AD-59265.1 | | CUAGACCUGUUUUGCUUUUGU | 216 | | ACAAAAGCAAAACAGGUCUAG | 437 | 3603 | |
| AD-59196.13 | | UAGACCUGUUUUGCUUUUGU | 217 | | ACAAAAGCAAAACAGGUCUAGAA | 438 | 3601 | |
| AD-59189.11 | | AGACCUGUUUUGCUUUUGU | 218 | | ACAAAAGCAAAACAGGUCUAGAA | 439 | 3601 | |
| AD-59190.3 | | UCUAGACCUGUUUUGCUUUUGU | 219 | | ACAAAAGCAAAACAGGUCUAGAA | 440 | 3601 | |
| AD-59192.3 | | UUCUAGACCUGUUUUGCUUUUGU | 220 | | ACAAAAGCAAAACAGGUCUAGAA | 441 | 3601 | |
| AD-59240.1 | | Same | 220 | | Same | 441 | Same | |
| AD-59244.1 | | | 220 | | | 441 | | |
| AD-59202.7 | | | 220 | | | 441 | | |
| AD-59195.5 | | | 220 | | | 441 | | |
| AD-59249.1 | | | 220 | | | 441 | | |
| AD-59254.1 | | | 220 | | | 441 | | |
| AD-59259.1 | | | 220 | | | 441 | | |
| AD-59264.1 | | | 220 | | | 441 | | |
| AD-59264.2 | | | 220 | | | 441 | | |
| AD-59255.1 | | | 220 | | | 441 | | |
| AD-57928.1 | | | 220 | | | 441 | | |
| AD-58893.1 | | | 220 | | | 441 | | |
| AD-58894.1 | | | 220 | | | 441 | | |
| AD-58895.1 | | | 220 | | | 441 | | |
| AD-58896.1 | | | 220 | | | 441 | | |
| AD-58897.1 | | | 220 | | | 441 | | |
| AD-58898.1 | | | 220 | | | 441 | | |
| AD-58899.1 | | | 220 | | | 441 | | |
| AD-58900.1 | | CAAGCAGACAUUUAUCUUUUU | 221 | | AAAAAGAUAAAUGUCUGCUUGCU | 442 | N/A | |
| AD-58902.1 | | UUUUCUAGACCUGUUUUGCUU | 222 | | AAGCAAAACAGGUCUAGAAAAGU | 443 | 3597 | |
| | | AGACCUGUUUUGCUUUUGU | 223 | | ACAAAAGCAAAACAGGUCUAG | 444 | | |
| | | AGACCUGUUUUGCUUUUGU | 224 | | ACAAAAGCAAAACAGGUCUAG | 445 | | |
| | | AGACCUGUUUUGCUUUUGU | 225 | | ACAAAAGCAAAACAGGUCUAG | 446 | | |
| | | AGACCUGUUUUGCUUUUGU | 226 | | ACAAAAGCAAAACAGGUCUAG | 447 | | |
| | | AGACCUGUUUUGCUUUUGU | 227 | | ACAAAAGCAAAACAGGUCUAG | 448 | | |
| | | AGACCUGUUUUGCUUUUGU | 228 | | ACAAAAGCAAAACAGGUCUAG | 449 | | |
| | | CUAGACCUGUUUUGCUUUUGU | 229 | | ACAAAAGCAAAACAGGUCUAGAA | 450 | | |
| | | Same | 229 | | Same | 450 | | |
| | | | 229 | | | 450 | | |
| | | | 229 | | | 450 | | |

TABLE 1-continued

| PCSK9 unmodified sequences | | | | | | | | |
|---|---|---|---|---|---|---|---|---|
| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
| | | | 229 | | | 450 | | |
| | | | 229 | | | 450 | | |
| | | | 229 | | | 450 | | |
| | | | 229 | | | 450 | | |
| | | | 229 | | | 450 | | |
| | | | 229 | | | 450 | | |
| | | | 229 | | | 450 | | |
| | | | 229 | | | 450 | | |
| | | AGACCUGUUUUGCUUUUGU | 230 | | ACAAAAGCAAAACAGGUCUAG | 451 | | |
| | | AGACCUGUUUUGCUUUUGU | 231 | | ACAAAAGCAAAACAGGUCUAG | 452 | | |
| | | CUAGACCUGUUUUGCUUUUGU | 232 | | ACAAAAGCAAAACAGGUCUAGAA | 453 | | |
| | | Same | 232 | | Same | 453 | | |
| | | | 232 | | | 453 | | |
| | | | 232 | | | 453 | | |
| | | | 232 | | | 453 | | |
| | | | 232 | | | 453 | | |
| | | CUAGACCUGUUUUGCUUUUGU | 233 | | ACAAAAGCAAAACAGGUCUAGAA | 454 | | |
| | | Same | 233 | | Same | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | Same | 233 | | Same | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |

TABLE 1-continued

PCSK9 unmodified sequences

| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
|---|---|---|---|---|---|---|---|---|
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | Same | 233 | | Same | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | Same | 233 | | Same | 454 | | |
| | | | 233 | | | 454 | | |
| | | | 233 | | | 454 | | |

TABLE 1-continued

| PCSK9 unmodified sequences | | | | | | | | |
|---|---|---|---|---|---|---|---|---|
| Duplex Name | Sense Oligo Name | Sense Trans Seq | SEQ ID NO: | Antisense Oligo Name | Antisense Trans Seq | SEQ ID NO: | Start In NM_174936.3 | End In NM_174936.3 |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |
| | | | 233 | | | 454 | | |

TABLE 2

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| AD-53649.1 | A-110542.1 | CfgAfgGfaCfgGfCfGfaCfuAfcGfaGfgAfL96 | 455 | 461 | A-109239.2 | uCfcUfcGfuAfgUfcgcCfgUfcCfuCfgsUfsc | 1006 |
| AD-53650.1 | A-110550.1 | GfcCfgGfgGfaUfAfCfcUfcAfcCfaAfgAfL96 | 456 | 673 | A-109255.2 | uCfuUfgGfuGfaGfguaUfcCfcCfgGfcsGfsg | 1007 |
| AD-53651.1 | A-110558.1 | GfcCfcCfaUfgUfCfGfaCfuAfcAfuCfgAfL96 | 457 | 773 | A-109271.2 | uCfgAfuGfuAfgUfcgaCfaUfgGfgGfcsAfsa | 1008 |
| AD-53652.1 | A-110566.1 | CfcUfgGfuGfgAfGfGfuGfuAfuCfuCfcUfL96 | 458 | 896 | A-109287.2 | aGfgAfgAfuAfcAfccuCfcAfcCfaGfgsCfsu | 1009 |
| AD-53653.1 | A-110574.1 | UfcCfuAfgAfcAfCfCfaGfcAfuAfcAfgAfL96 | 459 | 913 | A-109303.2 | uCfuGfuAfuGfcUfgguGfuCfuAfgGfasGfsa | 1010 |
| AD-53654.1 | A-110582.1 | GfcAfgGfgUfcAfUfGfgUfcAfcCfgAfcUfL96 | 460 | 955 | A-109319.2 | aGfuCfgGfuGfaCfcauGfaCfcCfuGfcsCfsc | 1011 |
| AD-53696.1 | A-110589.1 | CfcUfgCfgCfgUfGfCfuCfaAfcUfgCfcAfL96 | 461 | 1109 | A-109333.2 | uGfgCfaGfuUfgAfgcaCfgCfgCfaGfgsCfsu | 1012 |
| AD-53697.1 | A-110597.1 | UfaGfgCfcUfgGfAfGfuUfuAfuUfcGfgAfL96 | 462 | 1159 | A-109349.2 | uCfcGfaAfuAfaAfcucCfaGfgCfcUfasUfsg | 1013 |
| AD-53698.1 | A-110605.1 | GfgGfaCfgAfuGfCfCfuGfcCfuCfuAfcUfL96 | 463 | 1318 | A-109365.2 | aGfuAfgAfgGfcAfggcAfuCfgUfcCfcsGfsg | 1014 |
| AD-53699.1 | A-110613.1 | GfcAfuUfgCfaGfCfCfaUfgAfuGfcUfgUfL96 | 464 | 1543 | A-109381.2 | aCfaGfcAfuCfaUfggcUfgCfaAfuGfcsCfsa | 1015 |
| AD-53700.1 | A-110621.1 | GfgCfcUfgGfuUfCfCfcUfgAfgGfaCfcAfL96 | 465 | 1640 | A-109397.2 | uGfgUfcCfuCfaGfggaAfcCfaGfgCfcsUfsc | 1016 |
| AD-53701.1 | A-110629.1 | CfgCfuUfuUfgGfGfGfgUfgAfgGfgUfgUfL96 | 466 | 1901 | A-109413.2 | aCfaCfcCfuCfaCfcccCfaAfaAfgCfgsUfsu | 1017 |
| AD-48400.1 | A-98247.2 | UfuUfuCfuAfgAfcCfuGfuUfuUfgCfuUfL96 | 467 | | A-93455.4 | aAfgCfaAfaAfcAfgGfuCfuAfgAfaAfasGfsu | 1018 |
| AD-53656.1 | A-110551.1 | CfcGfgGfgAfuAfCfCfuCfaCfcAfaGfaUfL96 | 468 | 674 | A-109257.2 | aUfcUfuGfgUfgAfgguAfuCfcCfcGfgsCfsg | 1019 |
| AD-53657.1 | A-110559.1 | CfcAfuGfuCfgAfCfUfaCfaUfcGfaGfgAfL96 | 469 | 776 | A-109273.2 | uCfcUfcGfaUfgUfaguCfgAfcAfuGfgsGfsg | 1020 |
| AD-53658.1 | A-110567.1 | CfuGfgUfgGfaGfGfUfgUfaUfcUfcCfuAfL96 | 470 | 897 | A-109289.2 | uAfgGfaGfaUfaCfaccUfcCfaCfcAfgsGfsc | 1021 |
| AD-53659.1 | A-110575.1 | AfgAfcAfcCfaGfCfAfuAfcAfgAfgUfgAfL96 | 471 | 917 | A-109305.2 | uCfaCfuCfuGfuAfugcUfgGfuGfuCfusAfsg | 1022 |
| AD-53660.1 | A-110583.1 | CfaGfgGfuCfaUfGfGfuCfaCfcGfaCfuUfL96 | 472 | 956 | A-109321.2 | aAfgUfcGfgUfgAfccaUfgAfcCfcUfgsCfsc | 1023 |
| AD-53702.1 | A-110590.1 | CfuGfcGfcGfuGfCfUfcAfaCfuGfcCfaAfL96 | 473 | 1110 | A-109335.2 | uUfgGfcAfgUfuGfagcAfcGfcGfcAfgsGfsc | 1024 |
| AD-53703.1 | A-110598.1 | AfgGfcCfuGfgAfGfUfuUfaUfuCfgGfaAfL96 | 474 | 1160 | A-109351.2 | uUfcCfgAfaUfaAfacuCfcAfgGfcCfusAfsu | 1025 |
| AD-53704.1 | A-110606.1 | CfaAfcUfuUfgGfCfCfgCfuGfuGfuGfgAfL96 | 475 | 1421 | A-109367.2 | uCfcAfcAfcAfgCfggcCfaAfaGfuUfgsGfsu | 1026 |
| AD-53705.1 | A-110614.1 | GfuUfgAfgGfcAfGfAfgAfcUfgAfuCfcAfL96 | 476 | 1592 | A-109383.2 | uGfgAfuCfaGfuCfucuGfcCfuCfaAfcsUfsc | 1027 |

TABLE 2-continued

PCSK9- modified sequences

| Duplex Name | Sense Oligo Name | Sense Oligo Sequence | SEQ ID NO: | Position relative to NM_174936.3 | Antisense Oligo | Antisense Oligo Sequence | SEQ ID NO: |
|---|---|---|---|---|---|---|---|
| AD-53706.1 | A-110622.1 | GfgUfaCfuGfaCfCfCfcCfaAfcCfuGfgUfL96 | 477 | 1664 | A-109399.2 | aCfcAfgGfuUfgGfgggUfcAfgUfaCfcsCfsg | 1028 |
| AD-53707.1 | A-110630.1 | CfuUfuUfgGfgGfGfUfgAfgGfgUfgUfcUfL96 | 478 | 1903 | A-109415.2 | aGfaCfaCfcCfuCfaccCfcCfaAfaAfgsCfsg | 1029 |
| AD-53661.1 | A-110544.1 | AfcCfgCfuGfcGfCfCfaAfgGfaUfcCfgUfL96 | 479 | 556 | A-109243.2 | aCfgGfaUfcCfuUfggcGfcAfgCfgGfusGfsg | 1030 |
| AD-53663.1 | A-110560.1 | UfcGfaCfuAfcAfUfCfgAfgGfaGfgAfcUfL96 | 480 | 781 | A-109275.2 | aGfuCfcUfcCfuCfgauGfuAfgUfcGfasCfsa | 1031 |
| AD-53664.1 | A-110568.1 | GfgUfgGfaGfgUfGfUfaUfcUfcCfuAfgAfL96 | 481 | 899 | A-109291.2 | uCfuAfgGfaGfaUfacaCfcUfcCfaCfcsAfsg | 1032 |
| AD-53665.1 | A-110576.1 | CfaCfcAfgCfaUfAfCfaGfaGfuGfaCfcAfL96 | 482 | 920 | A-109307.2 | uGfgUfcAfcUfcUfguaUfgCfuGfgUfgsUfsc | 1033 |
| AD-53666.1 | A-110584.1 | GfgUfcAfuGfgUfCfAfcCfgAfcUfuCfgAfL96 | 483 | 959 | A-109323.2 | uCfgAfaGfuCfgGfugaCfcAfuGfaCfcsCfsu | 1034 |
| AD-53708.1 | A-110591.1 | CfgUfgCfuCfaAfCfUfgCfcAfaGfgGfaAfL96 | 484 | 1115 | A-109337.2 | uUfcCfcUfuGfgCfaguUfgAfgCfaCfgsCfsg | 1035 |
| AD-53709.1 | A-110599.1 | GfgCfcUfgGfaGfUfUfuAfuUfcGfgAfaAfL96 | 485 | 1161 | A-109353.2 | uUfuCfcGfaAfuAfaacUfcCfaGfgCfcsUfsa | 1036 |
| AD-53710.1 | A-110607.1 | UfuGfgCfcGfcUfGfUfgUfgGfaCfcUfcUfL96 | 486 | 1426 | A-109369.2 | aGfaGfgUfcCfaCfacaGfcGfgCfcAfasAfsg | 1037 |
| AD-53711.1 | A-110615.1 | UfgAfgGfcAfgAfGfAfcUfgAfuCfcAfcUfL96 | 487 | 1594 | A-109385.2 | aGfuGfgAfuCfaGfucuCfuGfcCfuCfasAfsc | 1038 |
| AD-53712.1 | A-110623.1 | GfuUfgGfcAfgCfUfGfuUfuUfgCfaGfgAfL96 | 488 | 1717 | A-109401.2 | uCfcUfgCfaAfaAfcagCfuGfcCfaAfcsCfsu | 1039 |
| AD-53713.1 | A-110631.1 | UfuUfuGfgGfgGfUfGfaGfgGfuGfuGfuAfL96 | 489 | 1904 | A-109417.2 | uAfgAfcAfcCfcUfcacCfcCfcAfaAfasGfsc | 1040 |
| AD-53667.1 | A-110545.1 | GfcUfgCfgCfcAfAfGfgAfuCfcGfuGfgAfL96 | 490 | 559 | A-109245.2 | uCfcAfcGfgAfuCfcuuGfgCfgCfaGfcsGfsg | 1041 |
| AD-53668.1 | A-110553.1 | AfuAfcCfuCfaCfCfAfaGfaUfcCfuGfcAfL96 | 491 | 680 | A-109261.2 | uGfcAfgGfaUfcUfuggUfgAfgGfuAfusCfsc | 1042 |
| AD-53669.1 | A-110561.1 | AfcUfaCfaUfcGfAfGfgAfgGfaCfuCfcUfL96 | 492 | 784 | A-109277.2 | aGfgAfgUfcCfuCfcucGfaUfgUfaGfusCfsg | 1043 |
| AD-53670.1 | A-110569.1 | UfgGfaGfgUfgUfAfUfcUfcCfuAfgAfcAfL96 | 493 | 901 | A-109293.2 | uGfuCfuAfgGfaGfauaCfaCfcUfcCfasCfsc | 1044 |
| AD-53671.1 | A-110577.1 | UfaCfaGfaGfuGfAfCfcAfcCfgGfgAfaAfL96 | 494 | 928 | A-109309.2 | uUfuCfcCfgGfuGfgucAfcUfcUfgUfasUfsg | 1045 |
| AD-53672.1 | A-110585.1 | UfcAfuGfgUfcAfCfCfgAfcUfuCfgAfgAfL96 | 495 | 961 | A-109325.2 | uCfuCfgAfaGfuCfgguGfaCfcAfuGfasCfsc | 1046 |
| AD-53714.1 | A-110592.1 | CfaCfcCfuCfaUfAfGfgCfcUfgGfaGfuUfL96 | 496 | 1151 | A-109339.2 | aAfcUfcCfaGfgCfcuaUfgAfgGfgUfgsCfsc | 1047 |
| AD-53715.1 | A-110600.1 | GfcCfuGfgAfgUfUfUfaUfuCfgGfaAfaAfL96 | 497 | 1162 | A-109355.2 | uUfuUfcCfgAfaUfaaaCfuCfcAfgGfcsCfsu | 1048 |
| AD-53716.1 | A-110608.1 | UfgGfcCfgCfuGfUfGfuGfgAfcCfuCfuUfL96 | 498 | 1427 | A-109371.2 | aAfgAfgGfuCfcAfcacAfgCfgGfcCfasAfsa | 1049 |
| AD-53717.1 | A-110616.1 | GfaGfgCfaGfaGfAfCfuGfaUfcCfaCfuUfL96 | 499 | 1595 | A-109387.2 | aAfgUfgGfaUfcAfgucUfcUfgCfcUfcsAfsa | 1050 |

TABLE 2-continued

PCSK9- modified sequences

| Duplex Name | Sense Oligo Name | Sense Oligo Sequence | SEQ ID NO: | Position relative to NM_174936.3 | Antisense Oligo | Antisense Oligo Sequence | SEQ ID NO: |
|---|---|---|---|---|---|---|---|
| AD-53718.1 | A-110624.1 | UfgGfcAfgCfuGfUfUfuUfgCfaGfgAfcUfL96 | 500 | 1719 | A-109403.2 | aGfuCfcUfgCfaAfaacAfgCfuGfcCfasAfsc | 1051 |
| AD-53719.1 | A-110632.1 | GfgGfgUfgAfgGfGfUfgUfcUfaCfgCfcAfL96 | 501 | 1909 | A-109419.2 | uGfgCfgUfaGfaCfaccCfuCfaCfcCfcsCfsa | 1052 |
| AD-53674.1 | A-110554.1 | CfaCfcAfaGfaUfCfCfuGfcAfuGfuCfuUfL96 | 502 | 686 | A-109263.2 | aAfgAfcAfuGfcAfggaUfcUfuGfgUfgsAfsg | 1053 |
| AD-53675.1 | A-110562.1 | UfaCfaUfcGfaGfGfAfgGfaCfuCfcUfcUfL96 | 503 | 786 | A-109279.2 | aGfaGfgAfgUfcCfuccUfcGfaUfgUfasGfsu | 1054 |
| AD-53676.1 | A-110570.1 | AfgGfuGfuAfuCfUfCfcUfaGfaCfaCfcAfL96 | 504 | 904 | A-109295.2 | uGfgUfgUfcUfaGfgagAfuAfcAfcCfusCfsc | 1055 |
| AD-53677.1 | A-110578.1 | AfcAfgAfgUfgAfCfCfaCfcGfgGfaAfaUfL96 | 505 | 929 | A-109311.2 | aUfuUfcCfcGfgUfgguCfaCfuCfuGfusAfsu | 1056 |
| AD-53678.1 | A-110586.1 | AfgGfaCfgGfgAfCfCfcGfcUfuCfcAfcAfL96 | 506 | 994 | A-109327.2 | uGfuGfgAfaGfcGfgguCfcCfgUfcCfusCfsc | 1057 |
| AD-53720.1 | A-110593.1 | AfcCfcUfcAfuAfGfGfcCfuGfgAfgUfuUfL96 | 507 | 1152 | A-109341.2 | aAfaCfuCfcAfgGfccuAfuGfaGfgGfusGfsc | 1058 |
| AD-53721.1 | A-110601.1 | GfgAfgUfuUfaUfUfCfgGfaAfaAfgCfcAfL96 | 508 | 1166 | A-109357.2 | uGfgCfuUfuUfcCfgaaUfaAfaCfuCfcsAfsg | 1059 |
| AD-53722.1 | A-110609.1 | GfgCfcGfcUfgUfGfUfgGfaCfcUfcUfuUfL96 | 509 | 1428 | A-109373.2 | aAfaGfaGfgUfcCfacaCfaGfcGfgCfcsAfsa | 1060 |
| AD-53723.1 | A-110617.1 | GfgCfaGfaGfaCfUfGfaUfcCfaCfuUfcUfL96 | 510 | 1597 | A-109389.2 | aGfaAfgUfgGfaUfcagUfcUfcUfgCfcsUfsc | 1061 |
| AD-53724.1 | A-110625.1 | GfcAfgCfuGfuUfUfUfgCfaGfgAfcUfgUfL96 | 511 | 1721 | A-109405.2 | aCfaGfuCfcUfgCfaaaAfcAfgCfuGfcsCfsa | 1062 |
| AD-53725.1 | A-110633.1 | GfgGfuGfaGfgGfUfGfuCfuAfcGfcCfaUfL96 | 512 | 1910 | A-109421.2 | aUfgGfcGfuAfgAfcacCfcUfcAfcCfcsCfsc | 1063 |
| AD-53679.1 | A-110547.1 | CfuAfcGfuGfgUfGfGfuGfcUfgAfaGfgAfL96 | 513 | 593 | A-109249.2 | uCfcUfuCfaGfcAfccaCfcAfcGfuAfgsGfsu | 1064 |
| AD-53680.1 | A-110555.1 | CfaAfgAfuCfcUfGfCfaUfgUfcUfuCfcAfL96 | 514 | 689 | A-109265.2 | uGfgAfaGfaCfaUfgcaGfgAfuCfuUfgsGfsu | 1065 |
| AD-53681.1 | A-110563.1 | UfcGfaGfgAfgGfAfCfuCfcUfcUfgUfcUfL96 | 515 | 790 | A-109281.2 | aGfaCfaGfaGfgAfgucCfuCfcUfcGfasUfsg | 1066 |
| AD-53682.1 | A-110571.1 | GfuAfuCfuCfcUfAfGfaCfaCfcAfgCfaUfL96 | 516 | 908 | A-109297.2 | aUfgCfuGfgUfgUfcuaGfgAfgAfuAfcsAfsc | 1067 |
| AD-53683.1 | A-110579.1 | GfaGfuGfaCfcAfCfCfgGfgAfaAfuCfgAfL96 | 517 | 932 | A-109313.2 | uCfgAfuUfuCfcCfgguGfgUfcAfcUfcsUfsg | 1068 |
| AD-53684.1 | A-110587.1 | CfgGfgAfcCfcGfCfUfuCfcAfcAfgAfcAfL96 | 518 | 998 | A-109329.2 | uGfuCfuGfuGfgAfagcGfgGfuCfcCfgsUfsc | 1069 |
| AD-53726.1 | A-110594.1 | CfcCfuCfaUfaGfGfCfcUfgGfaGfuUfuAfL96 | 519 | 1153 | A-109343.2 | uAfaAfcUfcCfaGfgccUfaUfgAfgGfgsUfsg | 1070 |
| AD-53727.1 | A-110602.1 | GfuUfuAfuUfcGfGfAfaAfaGfcCfaGfcUfL96 | 520 | 1169 | A-109359.2 | aGfcUfgGfcUfuUfuccGfaAfuAfaAfcsUfsc | 1071 |
| AD-53728.1 | A-110610.1 | UfgUfgUfgGfaCfCfUfcUfuUfgCfcCfcAfL96 | 521 | 1434 | A-109375.2 | uGfgGfgCfaAfaGfaggUfcCfaCfaCfasGfsc | 1072 |
| AD-53729.1 | A-110618.1 | CfaGfaGfaCfuGfAfUfcCfaCfuUfcUfcUfL96 | 522 | 1599 | A-109391.2 | aGfaGfaAfgUfgGfaucAfgUfcUfcUfgsCfsc | 1073 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-53730.1 | A-110626.1 | UfcUfgCfcGfgGfCfCfcAfcAfaCfgCfuUfL96 | 523 | 1885 | A-109407.2 | aAfgCfgUfuGfuGfggcCfcGfgCfaGfasCfsc | 1074 |
| AD-53731.1 | A-110634.1 | GfgUfgAfgGfgUfGfUfcUfaCfgCfcAfuUfL96 | 524 | 1911 | A-109423.2 | aAfuGfgCfgUfaGfacaCfcCfuCfaCfcsCfsc | 1075 |
| AD-53685.1 | A-110548.1 | CfcCfgCfcGfgGfGfAfuAfcCfuCfaCfcAfL96 | 525 | 670 | A-109251.2 | uGfgUfgAfgGfuAfuccCfcGfgCfgGfgsCfsa | 1076 |
| AD-53687.1 | A-110564.1 | CfgAfgGfaGfgAfCfUfcCfuCfuGfuCfuUfL96 | 526 | 791 | A-109283.2 | aAfgAfcAfgAfgGfaguCfcUfcCfuCfgsAfsu | 1077 |
| AD-53688.1 | A-110572.1 | UfaUfcUfcCfuAfGfAfcAfcCfaGfcAfuAfL96 | 527 | 909 | A-109299.2 | uAfuGfcUfgGfuGfucuAfgGfaGfaUfasCfsa | 1078 |
| AD-53689.1 | A-110580.1 | GfgAfaAfuCfgAfGfGfgCfaGfgGfuCfaUfL96 | 528 | 944 | A-109315.2 | aUfgAfcCfcUfgCfccuCfgAfuUfuCfcsCfsg | 1079 |
| AD-53690.1 | A-110588.1 | UfcCfaCfaGfaCfAfGfgCfcAfgCfaAfgUfL96 | 529 | 1009 | A-109331.2 | aCfuUfgCfuGfgCfcugUfcUfgUfgGfasAfsg | 1080 |
| AD-53732.1 | A-110595.1 | CfcUfcAfuAfgGfCfCfuGfgAfgUfuUfaUfL96 | 530 | 1154 | A-109345.2 | aUfaAfaCfuCfcAfggcCfuAfuGfaGfgsGfsu | 1081 |
| AD-53733.1 | A-110603.1 | GfgGfcUfgGfgGfUfCfgUfgCfuGfgUfcAfL96 | 531 | 1279 | A-109361.2 | uGfaCfcAfgCfaCfgacCfcCfaGfcCfcsUfsc | 1082 |
| AD-53734.1 | A-110611.1 | GfgGfaGfgAfcAfUfCfaUfuGfgUfgCfcUfL96 | 532 | 1456 | A-109377.2 | aGfgCfaCfcAfaUfgauGfuCfcUfcCfcsCfsu | 1083 |
| AD-53735.1 | A-110619.1 | AfcUfgAfuCfcAfCfUfuCfuCfuGfcCfaAfL96 | 533 | 1604 | A-109393.2 | uUfgGfcAfgAfgAfaguGfgAfuCfaGfusCfsu | 1084 |
| AD-53736.1 | A-110627.1 | CfuGfcCfgGfgCfCfCfaCfaAfcGfcUfuUfL96 | 534 | 1886 | A-109409.2 | aAfaGfcGfuUfgUfgggCfcCfgGfcAfgsAfsc | 1085 |
| AD-53737.1 | A-110635.1 | AfgGfgUfgUfcUfAfCfgCfcAfuUfgCfcAfL96 | 535 | 1915 | A-109425.2 | uGfgCfaAfuGfgCfguaGfaCfaCfcCfusCfsa | 1086 |
| AD-53691.1 | A-110549.1 | CfcGfcCfgGfgGfAfUfaCfcUfcAfcCfaAfL96 | 536 | 671 | A-109253.2 | uUfgGfuGfaGfgUfaucCfcCfgGfcGfgsGfsc | 1087 |
| AD-53692.1 | A-110557.1 | GfuUfgCfcCfcAfUfGfuCfgAfcUfaCfaUfL96 | 537 | 770 | A-109269.2 | aUfgUfaGfuCfgAfcauGfgGfgCfaAfcsUfsu | 1088 |
| AD-53693.1 | A-110565.1 | GfuAfcCfgGfgCfGfGfaUfgAfaUfaCfcAfL96 | 538 | 857 | A-109285.2 | uGfgUfaUfuCfaUfccgCfcCfgGfuAfcsCfsg | 1089 |
| AD-53694.1 | A-110573.1 | UfcUfcCfuAfgAfCfAfcCfaGfcAfuAfcAfL96 | 539 | 911 | A-109301.2 | uGfuAfuGfcUfgGfuguCfuAfgGfaGfasUfsa | 1090 |
| AD-53695.1 | A-110581.1 | AfaUfcGfaGfgGfCfAfgGfgUfcAfuGfgUfL96 | 540 | 947 | A-109317.2 | aCfcAfuGfaCfcCfugcCfcUfcGfaUfusUfsc | 1091 |
| AD-53738.1 | A-110596.1 | CfuCfaUfaGfgCfCfUfgGfaGfuUfuAfuUfL96 | 541 | 1155 | A-109347.2 | aAfuAfaAfcUfcCfaggCfcUfaUfgAfgsGfsg | 1092 |
| AD-53739.1 | A-110604.1 | GfgUfcAfcCfgCfUfGfcCfgGfcAfaCfuUfL96 | 542 | 1295 | A-109363.2 | aAfgUfuGfcCfgGfcagCfgGfuGfaCfcsAfsg | 1093 |
| AD-53740.1 | A-110612.1 | AfcUfgCfaGfcAfCfCfuGfcUfuUfgUfgUfL96 | 543 | 1483 | A-109379.2 | aCfaCfaAfaGfcAfgguGfcUfgCfaGfusCfsg | 1094 |
| AD-53741.1 | A-110620.1 | AfuCfcAfcUfuCfUfCfuGfcCfaAfaGfaUfL96 | 544 | 1608 | A-109395.2 | aUfcUfuUfgGfcAfgagAfaGfuGfgAfusCfsa | 1095 |
| AD-53742.1 | A-110628.1 | GfcCfcAfcAfaCfGfCfuUfuUfgGfgGfgUfL96 | 545 | 1893 | A-109411.2 | aCfcCfcCfaAfaAfgcgUfuGfuGfgGfcsCfsc | 1096 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-53743.1 | A-110636.1 | GfuGfuCfuAfcGfCfCfaUfuGfcCfaGfgUfL96 | 546 | 1918 | A-109427.2 | aCfcUfgGfcAfaUfggcGfuAfgAfcAfcsCfsc | 1097 |
| AD-53744.1 | A-110644.1 | GfgAfaUfgCfaAfAfGfuCfaAfgGfaGfcAfL96 | 547 | 2180 | A-109443.2 | uGfcUfcCfuUfgAfcuuUfgCfaUfuCfcsAfsg | 1098 |
| AD-53745.1 | A-110652.1 | UfgAfuGfgCfcCfUfCfaUfcUfcCfaGfcUfL96 | 548 | 2906 | A-109459.2 | aGfcUfgGfaGfaUfgagGfgCfcAfuCfasGfsc | 1099 |
| AD-53746.1 | A-110660.1 | CfuGfaAfgCfcAfAfGfcCfuCfuUfcUfuAfL96 | 549 | 3300 | A-109475.2 | uAfaGfaAfgAfgGfcuuGfgCfuUfcAfgsAfsg | 1100 |
| AD-53747.1 | A-110668.1 | AfcUfgUfcCfcUfCfCfuUfgAfgCfaCfcAfL96 | 550 | 3511 | A-109491.2 | uGfgUfgCfuCfaAfggaGfgGfaCfaGfusUfsg | 1101 |
| AD-53748.1 | A-110676.1 | CfaAfgCfaAfgCfAfGfaCfaUfuUfaUfcUfL96 | 551 | 3540 | A-109507.2 | aGfaUfaAfaUfgUfcugCfuUfgCfuUfgsGfsg | 1102 |
| AD-53790.1 | A-110683.1 | UfaUfcUfuUfuGfGfGfuCfuGfuCfcUfcUfL96 | 552 | 3556 | A-109521.2 | aGfaGfgAfcAfgAfcccAfaAfaGfaUfasAfsa | 1103 |
| AD-53791.1 | A-110691.1 | UfgUfcCfuCfuCfUfGfuUfgCfcUfuUfuUfL96 | 553 | 3569 | A-109537.2 | aAfaAfaGfgCfaAfcagAfgAfgGfaCfasGfsa | 1104 |
| AD-53792.1 | A-110699.1 | UfuGfuAfaCfuUfGfAfaGfaUfaUfuUfaUfL96 | 554 | 3620 | A-109553.2 | aUfaAfaUfaUfcUfucaAfgUfuAfcAfasAfsa | 1105 |
| AD-53793.1 | A-110707.1 | CfuUfuAfcUfcUfGfCfuCfuAfuGfcCfaAfL96 | 555 | 3055 | A-109569.2 | uUfgGfcAfuAfgAfgcaGfaGfuAfaAfgsGfsu | 1106 |
| AD-53794.1 | A-110715.1 | AfgGfgGfaAfcAfCfAfgAfcCfaGfgAfaAfL96 | 556 | 3370 | A-109585.2 | uUfuCfcUfgGfuCfuguGfuUfcCfcCfusUfsc | 1107 |
| AD-53795.1 | A-110723.1 | UfuGfgGfuCfuGfUfCfcUfaffcUfgUfuUfL96 | 557 | 3562 | A-109601.2 | aAfaCfaGfaGfaGfgacAfgAfcCfcAfasAfsa | 1108 |
| AD-53749.1 | A-110637.1 | UfgCfaGfcGfuCfCfAfcAfcAfgCfuCfcAfL96 | 558 | 1962 | A-109429.2 | uGfgAfgCfuGfuGfuggAfcGfcUfgCfasGfsu | 1109 |
| AD-53750.1 | A-110645.1 | AfaUfcCfcGfgCfCfCfcUfcAfgGfaGfcAfL96 | 559 | 2204 | A-109445.2 | uGfcUfcCfuGfaGfgggCfcGfgGfaUfusCfsc | 1110 |
| AD-53751.1 | A-110653.1 | UfuUfcUfgGfaUfGfGfcAfuCfuAfgCfcAfL96 | 560 | 2974 | A-109461.2 | uGfgCfuAfgAfuGfccaUfcCfaGfaAfasGfsc | 1111 |
| AD-53752.1 | A-110661.1 | GfaAfgCfcAfaGfCfCfuCfuUfcUfuAfcUfL96 | 561 | 3302 | A-109477.2 | aGfuAfaGfaAfgAfggcUfuGfgCfuUfcsAfsg | 1112 |
| AD-53753.1 | A-110669.1 | CfcAfgCfcCfcAfCfCfcAfaGfcAfaGfcAfL96 | 562 | 3529 | A-109493.2 | uGfcUfuGfcUfuGfgguGfgGfgCfuGfgsUfsg | 1113 |
| AD-53754.1 | A-110677.1 | AfaGfcAfaGfcAfGfAfcAfuUfuAfuCfuUfL96 | 563 | 3541 | A-109509.2 | aAfgAfuAfaAfuGfucuGfcUfuGfcUfusGfsg | 1114 |
| AD-53796.1 | A-110684.1 | UfcUfuUfuGfgGfUfCfuGfuCfcUfcUfcUfL96 | 564 | 3558 | A-109523.2 | aGfaGfaGfgAfcAfgacCfcAfaAfaGfasUfsa | 1115 |
| AD-53797.1 | A-110692.1 | GfuCfcUfcUfcUfGfUfuGfcCfuUfuUfuAfL96 | 565 | 3570 | A-109539.2 | uAfaAfaAfgGfcAfacaGfaGfaGfgAfcsAfsg | 1116 |
| AD-53798.1 | A-110700.1 | UfgUfaAfcUfuGfAfAfgAfuAfuUfuAfuUfL96 | 566 | 3621 | A-109555.2 | aAfuAfaAfuAfuCfuucAfaGfuUfaCfasAfsa | 1117 |
| AD-53799.1 | A-110708.1 | UfuUfaCfuCfuGfCfUfcUfaUfgCfcAfgAfL96 | 567 | 3056 | A-109571.2 | uCfuGfgCfaUfaGfagcAfgAfgUfaAfasGfsg | 1118 |
| AD-53800.1 | A-110716.1 | CfcAfaGfcAfaGfCfAfgAfcAfuUfuAfuUfL96 | 568 | 3539 | A-109587.2 | aAfuAfaAfuGfuCfugcUfuGfcUfuGfgsGfsu | 1119 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-53801.1 | A-110724.1 | UfgGfgUfcUfgUfCfCfuCfuCfuGfuUfgAfL96 | 569 | 3563 | A-109603.2 | uCfaAfcAfgAfgAfggaCfaGfaCfcCfasAfsa | 1120 |
| AD-53755.1 | A-110638.1 | GfcAfuGfgGfgAfCfCfcGfuGfuCfcAfcUfL96 | 570 | 1996 | A-109431.2 | aGfuGfgAfcAfcGfgguCfcCfcAfuGfcsUfsg | 1121 |
| AD-53757.1 | A-110654.1 | UfcUfgGfaUfgGfCfAfuCfuAfgCfcAfgAfL96 | 571 | 2976 | A-109463.2 | uCfuGfgCfuAfgAfugcCfaUfcCfaGfasAfsa | 1122 |
| AD-53758.1 | A-110662.1 | AfaGfcCfaAfgCfCfUfcUfuCfuUfaCfuUfL96 | 572 | 3303 | A-109479.2 | aAfgUfaAfgAfaGfaggCfuUfgGfcUfusCfsa | 1123 |
| AD-53759.1 | A-110670.1 | CfcCfcAfcCfcAfAfGfcAfaGfcAfgAfcAfL96 | 573 | 3533 | A-109495.2 | uGfuCfuGfcUfuGfcuuGfgGfuGfgGfgsCfsu | 1124 |
| AD-53760.1 | A-110678.1 | AfgCfaAfgCfaGfAfCfaUfuUfaUfcUfuUfL96 | 574 | 3542 | A-109511.2 | aAfaGfaUfaAfaUfgucUfgCfuUfgCfusUfsg | 1125 |
| AD-53802.1 | A-110685.1 | UfuUfuGfgGfuCfUfGfuCfcUfcUfcUfgUfL96 | 575 | 3560 | A-109525.2 | aCfaGfaGfaGfgAfcagAfcCfcAfaAfasGfsa | 1126 |
| AD-53803.1 | A-110693.1 | UfuUfcUfaGfaCfCfUfgUfuUfuGfcUfuUfL96 | 576 | 3600 | A-109541.2 | aAfaGfcAfaAfaCfaggUfcUfaGfaAfasAfsg | 1127 |
| AD-53804.1 | A-110701.1 | AfcCfaAfgGfaGfGfCfaGfgAfuUfcUfuUfL96 | 577 | 2815 | A-109557.2 | aAfaGfaAfuCfcUfgccUfcCfuUfgGfusGfsg | 1128 |
| AD-53805.1 | A-110709.1 | UfcAfgCfcAfaCfCfCfgCfuCfcAfcUfaAfL96 | 578 | 3161 | A-109573.2 | uUfaGfuGfgAfgCfgggUfuGfgCfuGfasGfsa | 1129 |
| AD-53806.1 | A-110717.1 | CfaAfgCfaGfaCfAfUfuUfaUfcUfuUfuUfL96 | 579 | 3544 | A-109589.2 | aAfaAfaGfaUfaAfaugUfcUfgCfuUfgsCfsu | 1130 |
| AD-53807.1 | A-110725.1 | GfgGfuCfuGfuCfCfUfcUfcUfgUfuGfcAfL96 | 580 | 3564 | A-109605.2 | uGfcAfaCfaGfaGfaggAfcAfgAfcCfcsAfsa | 1131 |
| AD-53761.1 | A-110639.1 | CfcCfaCfaAfgCfCfGfcCfuGfuGfcUfgAfL96 | 581 | 2080 | A-109433.2 | uCfaGfcAfcAfgGfcggCfuUfgUfgGfgsUfsg | 1132 |
| AD-53762.1 | A-110647.1 | GfcUfgGfgGfcUfGfAfgCfuUfuAfaAfaUfL96 | 582 | 2481 | A-109449.2 | aUfuUfuAfaAfgCfucaGfcCfcCfaGfcsCfsc | 1133 |
| AD-53763.1 | A-110655.1 | GfcUfcUfaUfgCfCfAfgGfcUfgUfgCfuAfL96 | 583 | 3064 | A-109465.2 | uAfgCfaCfaGfcCfuggCfaUfaGfaGfcsAfsg | 1134 |
| AD-53764.1 | A-110663.1 | GfuGfaGfgCfuGfGfGfaAfgGfgGfaAfcAfL96 | 584 | 3358 | A-109481.2 | uGfuUfcCfcCfuUfcccAfgCfcUfcAfcsUfsg | 1135 |
| AD-53765.1 | A-110671.1 | CfcCfaCfcCfaAfGfCfaAfgCfaGfaCfaUfL96 | 585 | 3534 | A-109497.2 | aUfgUfcUfgCfuUfgcuUfgGfgUfgGfgsGfsc | 1136 |
| AD-53766.1 | A-110679.1 | GfcAfgAfcAfuUfUfAfuCfuUfuUfgGfgUfL96 | 586 | 3547 | A-109513.2 | aCfcCfaAfaAfgAfuaaAfuGfuCfuGfcsUfsu | 1137 |
| AD-53808.1 | A-110686.1 | UfuUfgGfgUfcUfGfUfcCfuCfuCfuGfuUfL96 | 587 | 3561 | A-109527.2 | aAfcAfgAfgAfgGfacaGfaCfcCfaAfasAfsg | 1138 |
| AD-53809.1 | A-110694.1 | UfuCfuAfgAfcCfUfGfuUfuUfgCfuUfuUfL96 | 588 | 3601 | A-109543.2 | aAfaAfgCfaAfaAfcagGfuCfuAfgAfasAfsa | 1139 |
| AD-53810.1 | A-110702.1 | GfgAfgGfcAfgGfAfUfuCfuUfcCfcAfuUfL96 | 589 | 2820 | A-109559.2 | aAfuGfgGfaAfgAfaucCfuGfcCfuCfcsUfsu | 1140 |
| AD-53811.1 | A-110710.1 | CfcUfgCfcAfaGfCfUfcAfcAfcAfgCfaAfL96 | 590 | 3247 | A-109575.2 | uUfgCfuGfuGfuGfagcUfuGfgCfaGfgsCfsa | 1141 |
| AD-53812.1 | A-110718.1 | AfaGfcAfgAfcAfUfUfuAfuCfuUfuUfgAfL96 | 591 | 3545 | A-109591.2 | uCfaAfaAfgAfuAfaauGfuCfuGfcUfusGfsc | 1142 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-53813.1 | A-110726.1 | UfcUfaGfaCfcUfGfUfuUfuGfcUfuUfuUfL96 | 592 | 3602 | A-109607.2 | aAfaAfaGfcAfaAfacaGfgUfcUfaGfasAfsa | 1143 |
| AD-53767.1 | A-110640.1 | GfaGfgCfcAfcGfAfGfgUfcAfgCfcCfaAfL96 | 593 | 2099 | A-109435.2 | uUfgGfgCfuGfaCfcucGfuGfgCfcUfcsAfsg | 1144 |
| AD-53768.1 | A-110648.1 | GfgAfgGfuGfcCfAfGfgAfaGfcUfcCfcUfL96 | 594 | 2650 | A-109451.2 | aGfgGfaGfcUfuCfcugGfcAfcCfuCfcsAfsc | 1145 |
| AD-53769.1 | A-110656.1 | CfuCfaGfcCfaAfCfCfcGfcUfcCfaCfuAfL96 | 595 | 3160 | A-109467.2 | uAfgUfgGfaGfcGfgguUfgGfcUfgAfgsAfsc | 1146 |
| AD-53770.1 | A-110664.1 | GfgCfuGfgGfaAfGfGfgGfaAfcAfcAfgAfL96 | 596 | 3362 | A-109483.2 | uCfuGfuGfuUfcCfccuUfcCfcAfgCfcsUfsc | 1147 |
| AD-53771.1 | A-110672.1 | CfcAfcCfcAfaGfCfAfaGfcAfgAfcAfuUfL96 | 597 | 3535 | A-109499.2 | aAfuGfuCfuGfcUfugcUfuGfgGfuGfgsGfsg | 1148 |
| AD-53772.1 | A-110680.1 | AfgAfcAfuUfuAfUfCfuUfuUfgGfgUfcUfL96 | 598 | 3549 | A-109515.2 | aGfaCfcCfaAfaAfgauAfaAfuGfuCfusGfsc | 1149 |
| AD-53814.1 | A-110687.1 | GfgUfcUfgUfcCfUfCfuCfuGfuUfgCfcUfL96 | 599 | 3565 | A-109529.2 | aGfgCfaAfcAfgAfgagGfaCfaGfaCfcsCfsa | 1150 |
| AD-53815.1 | A-110695.1 | CfuAfgAfcCfuGfUfUfuUfgCfuUfuUfgUfL96 | 600 | 3603 | A-109545.2 | aCfaAfaAfgCfaAfaacAfgGfuCfuAfgsAfsa | 1151 |
| AD-53816.1 | A-110703.1 | GfaGfgCfaGfgAfUfUfcUfuCfcCfaUfgAfL96 | 601 | 2821 | A-109561.2 | uCfaUfgGfgAfaGfaauCfcUfgCfcUfcsCfsu | 1152 |
| AD-53817.1 | A-110711.1 | CfcAfaGfcUfcAfCfAfcAfgCfaGfgAfaAfL96 | 602 | 3251 | A-109577.2 | uUfuCfcUfgCfuGfuguGfaGfcUfuGfgsCfsa | 1153 |
| AD-53818.1 | A-110719.1 | AfgCfaGfaCfaUfUfUfaUfcUfuUfuGfgAfL96 | 603 | 3546 | A-109593.2 | uCfcAfaAfaGfaUfaaaUfgUfcUfgCfusUfsg | 1154 |
| AD-53819.1 | A-110727.1 | GfuAfaCfuUfgAfAfGfaUfaUfuUfaUfuUfL96 | 604 | 3622 | A-109609.2 | aAfaUfaAfaUfaUfcuuCfaAfgUfuAfcsAfsa | 1155 |
| AD-53773.1 | A-110641.1 | CfaCfgAfgGfuCfAfGfcCfcAfaCfcAfgUfL96 | 605 | 2104 | A-109437.2 | aCfuGfgUfuGfgGfcugAfcCfuCfgUfgsGfsc | 1156 |
| AD-53774.1 | A-110649.1 | AfcUfgUfgGfgGfCfAfuUfuCfaCfcAfuUfL96 | 606 | 2676 | A-109453.2 | aAfuGfgUfgAfaAfugcCfcCfaCfaGfusGfsa | 1157 |
| AD-53776.1 | A-110665.1 | GfaAfgGfgGfaAfCfAfcAfgAfcCfaGfgAfL96 | 607 | 3368 | A-109485.2 | uCfcUfgGfuCfuGfuguUfcCfcCfuUfcsCfsc | 1158 |
| AD-53777.1 | A-110673.1 | CfaCfcCfaAfgCfAfAfgCfaGfaCfaUfuUfL96 | 608 | 3536 | A-109501.2 | aAfaUfgUfcUfgCfuugCfuUfgGfgUfgsGfsg | 1159 |
| AD-53778.1 | A-110681.1 | AfcAfuUfuAfuCfUfUfuUfgGfgUfcUfgUfL96 | 609 | 3551 | A-109517.2 | aCfaGfaCfcCfaAfaagAfuAfaAfuGfusCfsu | 1160 |
| AD-53820.1 | A-110688.1 | GfuCfuGfuCfcUfCfUfcUfgUfuGfcCfuUfL96 | 610 | 3566 | A-109531.2 | aAfgGfcAfaCfaGfagaGfgAfcAfgAfcsCfsc | 1161 |
| AD-53821.1 | A-110696.1 | UfaGfaCfcUfgUfUfUfuGfcUfuUfuGfuAfL96 | 611 | 3604 | A-109547.2 | uAfcAfaAfaGfcAfaaaCfaGfgUfcUfasGfsa | 1162 |
| AD-53822.1 | A-110704.1 | CfuUfuCfuGfgAfUfGfgCfaUfcUfaGfcAfL96 | 612 | 2973 | A-109563.2 | uGfcUfaGfaUfgCfcauCfcAfgAfaAfgsCfsu | 1163 |
| AD-53823.1 | A-110712.1 | AfaGfcUfcAfcAfCfAfgCfaGfgAfaCfuUfL96 | 613 | 3253 | A-109579.2 | aAfgUfuCfcUfgCfuguGfuGfaGfcUfusGfsg | 1164 |
| AD-53824.1 | A-110720.1 | GfaCfaUfuUfaUfCfUfuUfuGfgGfuCfuUfL96 | 614 | 3550 | A-109595.2 | aAfgAfcCfcAfaAfagaUfaAfaUfgUfcsUfsg | 1165 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-48400.4 | A-98247.3 | UfuUfuCfuAfgAfcCfuGfuUfuUfgCfuUfL96 | 615 | | A-93455.5 | aAfgCfaAfaAfcAfgGfuCfuAfgAfaAfasGfsu | 1166 |
| AD-53779.1 | A-110642.1 | GfgGfaGfgCfcAfGfCfaUfcCfaCfgCfuUfL96 | 616 | 2137 | A-109439.2 | aAfgCfgUfgGfaUfgcuGfgCfcUfcCfcsUfsg | 1167 |
| AD-53780.1 | A-110650.1 | CfcAfcCfaAfgGfAfGfgCfaGfgAfuUfcUfL96 | 617 | 2813 | A-109455.2 | aGfaAfuCfcUfgCfcucCfuUfgGfuGfgsAfsg | 1168 |
| AD-53781.1 | A-110658.1 | GfcCfaAfgCfuCfAfCfaCfaGfcAfgGfaAfL96 | 618 | 3250 | A-109471.2 | uUfcCfuGfcUfgUfgugAfgCfuUfgGfcsAfsg | 1169 |
| AD-53782.1 | A-110666.1 | AfaGfgGfgAfaCfAfCfaGfaCfcAfgGfaAfL96 | 619 | 3369 | A-109487.2 | uUfcCfuGfgUfcUfgugUfuCfcCfcUfusCfsc | 1170 |
| AD-53783.1 | A-110674.1 | AfcCfcAfaGfcAfAfGfcAfgAfcAfuUfuAfL96 | 620 | 3537 | A-109503.2 | uAfaAfuGfuCfuGfcuuGfcUfuGfgGfusGfsg | 1171 |
| AD-53784.1 | A-110682.1 | UfuUfaUfcUfuUfUfGfgGfuCfuGfuCfcUfL96 | 621 | 3554 | A-109519.2 | aGfgAfcAfgAfcCfcaaAfaGfaUfaAfasUfsg | 1172 |
| AD-53825.1 | A-110689.1 | UfcUfgUfcCfuCfUfCfuGfuUfgCfcUfuUfL96 | 622 | 3567 | A-109533.2 | aAfaGfgCfaAfcAfgagAfgGfaCfaGfasCfsc | 1173 |
| AD-53826.1 | A-110697.1 | UfuUfuGfuAfaCfUfUfgAfaGfaUfaUfuUfL96 | 623 | 3618 | A-109549.2 | aAfaUfaUfcUfuCfaagUfuAfcAfaAfasGfsc | 1174 |
| AD-53827.1 | A-110705.1 | UfuCfuGfgAfuGfGfCfaUfcUfaGfcCfaAfL96 | 624 | 2975 | A-109565.2 | uUfgGfcUfaGfaUfgccAfuCfcAfgAfasAfsg | 1175 |
| AD-53828.1 | A-110713.1 | UfgAfaGfcCfaAfGfCfcUfcUfuCfuUfaAfL96 | 625 | 3301 | A-109581.2 | uUfaAfgAfaGfaGfgcuUfgGfcUfuCfasGfsa | 1176 |
| AD-53829.1 | A-110721.1 | UfuAfuCfuUfuUfGfGfgUfcUfgUfcCfuUfL96 | 626 | 3555 | A-109597.2 | aAfgGfaCfaGfaCfccaAfaAfgAfuAfasAfsu | 1177 |
| AD-53830.1 | A-110872.1 | UfuUfuCfuAfgAfCfCfuGfuUfuUfgCfuUfL96 | 627 | | A-110873.1 | aAfgCfaAfaAfcAfgguCfuAfgAfaAfasGfsu | 1178 |
| AD-53785.1 | A-110643.1 | AfuCfcAfcGfcUfUfCfcUfgCfuGfcCfaUfL96 | 628 | 2148 | A-109441.2 | aUfgGfcAfgCfaGfgaaGfcGfuGfgAfusGfsc | 1179 |
| AD-53786.1 | A-110651.1 | CfaCfcAfaGfgAfGfGfcAfgGfaUfuCfuUfL96 | 629 | 2814 | A-109457.2 | aAfgAfaUfcCfuGfccuCfcUfuGfgUfgsGfsa | 1180 |
| AD-53787.1 | A-110659.1 | CfaAfgCfuCfaCfAfCfaGfcAfgGfaAfcUfL96 | 630 | 3252 | A-109473.2 | aGfuUfcCfuGfcUfgugUfgAfgCfuUfgsGfsc | 1181 |
| AD-53788.1 | A-110667.1 | GfgGfaAfcAfcAfGfAfcCfaGfgAfaGfcUfL96 | 631 | 3372 | A-109489.2 | aGfcUfuCfcUfgGfucuGfuGfuUfcCfcsCfsu | 1182 |
| AD-53789.1 | A-110675.1 | CfcCfaAfgCfaAfGfCfaGfaCfaUfuUfaUfL96 | 632 | 3538 | A-109505.2 | aUfaAfaUfgUfcUfgcuUfgCfuUfgGfgsUfsg | 1183 |
| AD-53831.1 | A-110690.1 | CfuGfuCfcUfcUfCfUfgUfuGfcCfuUfuUfL96 | 633 | 3568 | A-109535.2 | aAfaAfgGfcAfaCfagaGfaGfgAfcAfgsAfsc | 1184 |
| AD-53832.1 | A-110698.1 | UfuUfgUfaAfcUfUfGfaAfgAfuAfuUfuAfL96 | 634 | 3619 | A-109551.2 | uAfaAfuAfuCfuUfcaaGfuUfaCfaAfasAfsg | 1185 |
| AD-53833.1 | A-110706.1 | CfuGfgAfuGfgCfAfUfcUfaGfcCfaGfaAfL96 | 635 | 2977 | A-109567.2 | uUfcUfgGfcUfaGfaugCfcAfuCfcAfgsAfsa | 1186 |
| AD-53834.1 | A-110714.1 | AfgUfgAfgGfcUfGfGfgAfaGfgGfgAfaAfL96 | 636 | 3357 | A-109583.2 | uUfuCfcCfcUfuCfccaGfcCfuCfaCfusGfsu | 1187 |
| AD-53835.1 | A-110722.1 | AfuCfuUfuUfgGfGfUfcUfgUfcCfuCfuUfL96 | 637 | 3557 | A-109599.2 | aAfgAfgGfaCfaGfaccCfaAfaAfgAfusAfsa | 1188 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-48399.1 | A-100981.1 | CfaCfuUfaCfgCfuGfaGfuAfcUfuCfgAfL96 | 638 | | A-100982.1 | uCfgAfaGfuAfcUfcAfgCfgUfaAfgUfgsAfsu | 1189 |
| AD-53815.5 | A-110695.11 | CfuAfgAfcCfuGfUfUfuUfgCfuUfuUfgUfL96 | 639 | 3603 | A-109545.18 | aCfaAfaAfgCfaAfaacAfgGfuCfuAfgsAfsa | 1190 |
| AD-53815.4 | A-110695.4 | CfuAfgAfcCfuGfUfUfuUfgCfuUfuUfgUfL96 | 640 | 3603 | A-109545.5 | aCfaAfaAfgCfaAfaacAfgGfuCfuAfgsAfsa | 1191 |
| AD-56633.1 | A-115520.2 | cuAfgAfcCfuGfUfUfuUfgCfuUfuUfgUfL96 | 641 | 3603 | A-109545.6 | aCfaAfaAfgCfaAfaacAfgGfuCfuAfgsAfsa | 1192 |
| AD-56617.1 | A-115535.1 | CfuagAfcCfuGfUfUfuUfgCfuUfuUfgUfL96 | 642 | 3603 | A-109545.7 | aCfaAfaAfgCfaAfaacAfgGfuCfuAfgsAfsa | 1193 |
| AD-56623.1 | A-115536.1 | CfuagAfcCfuGfUfUfuUfgcuUfuUfguL96 | 643 | 3603 | A-109545.8 | aCfaAfaAfgCfaAfaacAfgGfuCfuAfgsAfsa | 1194 |
| AD-56629.1 | A-115537.1 | CfuagAfccuGfUfUfuUfgcuUfuUfguL96 | 644 | 3603 | A-109545.9 | aCfaAfaAfgCfaAfaacAfgGfuCfuAfgsAfsa | 1195 |
| AD-56635.1 | A-115538.1 | CfuagAfccuGfUfUfuugcuUfuuguL96 | 645 | 3603 | A-109545.10 | aCfaAfaAfgCfaAfaacAfgGfuCfuAfgsAfsa | 1196 |
| AD-56641.1 | A-115539.1 | CfuagaccuGfUfUfuugcuuuuguL96 | 646 | 3603 | A-109545.11 | aCfaAfaAfgCfaAfaacAfgGfuCfuAfgsAfsa | 1197 |
| AD-56625.1 | A-115542.1 | CfuAfGfAfcCfuGfUfUfuUfgCfuUfuUfgUfL96 | 647 | 3603 | A-109545.12 | aCfaAfaAfgCfaAfaacAfgGfuCfuAfgsAfsa | 1198 |
| AD-56631.1 | A-115543.1 | CfuAfGfAfcCfuGfUfUfuUfGfCfuUfuUfgUfL96 | 648 | 3603 | A-109545.13 | aCfaAfaAfgCfaAfaacAfgGfuCfuAfgsAfsa | 1199 |
| AD-56637.1 | A-115544.1 | CfuAfGfAfcCfuGfUfUfuUfGfCfuUfUfUfgUfL96 | 649 | 3603 | A-109545.14 | aCfaAfaAfgCfaAfaacAfgGfuCfuAfgsAfsa | 1200 |
| AD-56643.1 | A-115545.1 | CfuAfGfAfCfCfuGfUfUfuUfGfCfuUfUfUfGfUfL96 | 650 | 3603 | A-109545.15 | aCfaAfaAfgCfaAfaacAfgGfuCfuAfgsAfsa | 1201 |
| AD-56649.1 | A-115546.1 | CfUfAfGfAfCfCfuGfUfUfuUfGfCfUfUfUfUfGfUfL96 | 651 | 3603 | A-109545.16 | aCfaAfaAfgCfaAfaacAfgGfuCfuAfgsAfsa | 1202 |
| AD-56655.1 | A-115547.1 | CfUfAfGfAfCfCfUfGfUfUfUfUfGfCfUfUfUfUfGfUfL96 | 652 | 3603 | A-109545.17 | aCfaAfaAfgCfaAfaacAfgGfuCfuAfgsAfsa | 1203 |
| AD-56615.1 | A-110695.5 | CfuAfgAfcCfuGfUfUfuUfgCfuUfuUfgUfL96 | 653 | 3603 | A-115519.1 | acaAfaAfgcaAfaacAfgGfuCfuAfgsAfsa | 1204 |
| AD-56621.1 | A-115520.1 | cuAfgAfcCfuGfUfUfuUfgCfuUfuUfgUfL96 | 654 | 3603 | A-115519.2 | acaAfaAfgcaAfaacAfgGfuCfuAfgsAfsa | 1205 |
| AD-56627.1 | A-115521.1 | cuAfgAfcCfuGfUfUfuugCfuUfuugUfL96 | 655 | 3603 | A-115519.3 | acaAfaAfgcaAfaacAfgGfuCfuAfgsAfsa | 1206 |
| AD-56639.1 | A-115520.3 | cuAfgAfcCfuGfUfUfuUfgCfuUfuUfgUfL96 | 656 | 3603 | A-115522.1 | ACfaAfaAfgCfaAfaacAfgGfuCfuAfgsAfsa | 1207 |
| AD-56645.1 | A-110695.6 | CfuAfgAfcCfuGfUfUfuUfgCfuUfuUfgUfL96 | 657 | 3603 | A-115522.2 | ACfaAfaAfgCfaAfaacAfgGfuCfuAfgsAfsa | 1208 |
| AD-56651.1 | A-115523.1 | (iC)uAfgAfcCfuGfUfUfuUfgCfuUfuUfgUfL96 | 658 | 3603 | A-115524.1 | (iA)CfaAfaAfgCfaAfaacAfgGfuCfuAfgsAfs(iA) | 1209 |
| AD-56610.1 | A-115523.2 | (iC)uAfgAfcCfuGfUfUfuUfgCfuUfuUfgUfL96 | 659 | 3603 | A-115525.1 | aCfaAfaAfgCfaAfaacAfgGfuCfuAfgsAfs(iA) | 1210 |
| AD-56616.1 | A-115523.3 | (iC)uAfgAfcCfuGfUfUfuUfgCfuUfuUfgUfL96 | 660 | 3603 | A-115526.1 | acaAfaAfgcaAfaacAfgGfuCfuAfgsAfs(iA) | 1211 |

TABLE 2-continued

PCSK9- modified sequences

| Duplex Name | Sense Oligo Name | Sense Oligo Sequence | SEQ ID NO: | Position relative to NM_174936.3 | Antisense Oligo | Antisense Oligo Sequence | SEQ ID NO: |
|---|---|---|---|---|---|---|---|
| AD-56622.1 | A-115527.1 | (iC)uAfgAfcCfuGfUfUfuUfgCfuUfuugUfL96 | 661 | 3603 | A-115526.2 | acaAfaAfgcaAfaacAfgGfuCfuAfgsAfs(iA) | 1212 |
| AD-56628.1 | A-115527.2 | (iC)uAfgAfcCfuGfUfUfuUfgCfuUfuugUfL96 | 662 | 3603 | A-115528.1 | (iA)caAfaAfgcaAfaacAfgGfuCfuAfgsAfs(iA) | 1213 |
| AD-56634.1 | A-115529.1 | CbuAfgAfcCfuGfUfUfuUfgCfuUfuUfgUfL96 | 663 | 3603 | A-115530.1 | AbCfaAfaAfgCfaAfaacAfgGfuCfuAfgsAfsAb | 1214 |
| AD-56640.1 | A-115529.2 | CbuAfgAfcCfuGfUfUfuUfgCfuUfuUfgUfL96 | 664 | 3603 | A-115531.1 | aCfaAfaAfgCfaAfaacAfgGfuCfuAfgsAfsAb | 1215 |
| AD-56646.1 | A-115529.3 | CbuAfgAfcCfuGfUfUfuUfgCfuUfuUfgUfL96 | 665 | 3603 | A-115532.1 | acaAfaAfgcaAfaacAfgGfuCfuAfgsAfsAb | 1216 |
| AD-56652.1 | A-115533.1 | CbuAfgAfcCfuGfUfUfuUfgCfuUfuugUfL96 | 666 | 3603 | A-115532.2 | acaAfaAfgcaAfaacAfgGfuCfuAfgsAfsAb | 1217 |
| AD-56611.1 | A-115533.2 | CbuAfgAfcCfuGfUfUfuUfgCfuUfuugUfL96 | 667 | 3603 | A-115534.1 | (iA)caAfaAfgcaAfaacAfgGfuCfuAfgsAfsAb | 1218 |
| AD-56647.1 | A-110695.7 | CfuAfgAfcCfuGfUfUfuUfgCfuUfuUfgUfL96 | 668 | 3603 | A-115540.1 | aCfaaaAfgCfaAfaacAfgGfuCfuAfgsasa | 1219 |
| AD-56653.1 | A-115535.2 | CfuagAfcCfuGfUfUfuUfgCfuUfuUfgUfL96 | 669 | 3603 | A-115540.2 | aCfaaaAfgCfaAfaacAfgGfuCfuAfgsasa | 1220 |
| AD-56612.1 | A-115536.2 | CfuagAfcCfuGfUfUfuUfgcuUfuUfguL96 | 670 | 3603 | A-115540.3 | aCfaaaAfgCfaAfaacAfgGfuCfuAfgsasa | 1221 |
| AD-56618.1 | A-115537.2 | CfuagAfccuGfUfUfuUfgcuUfuUfguL96 | 671 | 3603 | A-115540.4 | aCfaaaAfgCfaAfaacAfgGfuCfuAfgsasa | 1222 |
| AD-56624.1 | A-115538.2 | CfuagAfccuGfUfUfuugcuUfuuguL96 | 672 | 3603 | A-115540.5 | aCfaaaAfgCfaAfaacAfgGfuCfuAfgsasa | 1223 |
| AD-56630.1 | A-115539.2 | CfuagaccuGfUfUfuugcuuuuguL96 | 673 | 3603 | A-115540.6 | aCfaaaAfgCfaAfaacAfgGfuCfuAfgsasa | 1224 |
| AD-56636.1 | A-110695.8 | CfuAfgAfcCfuGfUfUfuUfgCfuUfuUfgUfL96 | 674 | 3603 | A-115541.1 | aCfaaaAfgCfaAfaacAfgguCfuAfgsasa | 1225 |
| AD-56642.1 | A-115535.3 | CfuagAfcCfuGfUfUfuUfgCfuUfuUfgUfL96 | 675 | 3603 | A-115541.2 | aCfaaaAfgCfaAfaacAfgguCfuAfgsasa | 1226 |
| AD-56648.1 | A-115536.3 | CfuagAfcCfuGfUfUfuUfgcuUfuUfguL96 | 676 | 3603 | A-115541.3 | aCfaaaAfgCfaAfaacAfgguCfuAfgsasa | 1227 |
| AD-56654.1 | A-115537.3 | CfuagAfccuGfUfUfuUfgcuUfuUfguL96 | 677 | 3603 | A-115541.4 | aCfaaaAfgCfaAfaacAfgguCfuAfgsasa | 1228 |
| AD-56613.1 | A-115538.3 | CfuagAfccuGfUfUfuugcuUfuuguL96 | 678 | 3603 | A-115541.5 | aCfaaaAfgCfaAfaacAfgguCfuAfgsasa | 1229 |
| AD-56619.1 | A-115539.3 | CfuagaccuGfUfUfuugcuuuuguL96 | 679 | 3603 | A-115541.6 | aCfaaaAfgCfaAfaacAfgguCfuAfgsasa | 1230 |
| AD-56614.1 | A-110695.9 | CfuAfgAfcCfuGfUfUfuUfgCfuUfuUfgUfL96 | 680 | 3603 | A-115548.1 | aCfaAfAfAfgCfaAfaacAfgGfUfCfuAfgsAfsa | 1231 |
| AD-56620.1 | A-115542.2 | CfuAfGfAfcCfuGfUfUfuUfgCfuUfuUfgUfL96 | 681 | 3603 | A-115548.2 | aCfaAfAfAfgCfaAfaacAfgGfUfCfuAfgsAfsa | 1232 |
| AD-56626.1 | A-115543.2 | CfuAfGfAfcCfuGfUfUfuUfGfCfuUfuUfgUfL96 | 682 | 3603 | A-115548.3 | aCfaAfAfAfgCfaAfaacAfgGfUfCfuAfgsAfsa | 1233 |
| AD-56632.1 | A-115544.2 | CfuAfGfAfcCfuGfUfUfuUfGfCfuUfUfUfgUfL96 | 683 | 3603 | A-115548.4 | aCfaAfAfAfgCfaAfaacAfgGfUfCfuAfgsAfsa | 1234 |

TABLE 2-continued

| Duplex Name | Sense Oligo Name | Sense Oligo Sequence | SEQ ID NO: | Position relative to NM_174936.3 | Antisense Oligo | Antisense Oligo Sequence | SEQ ID NO: |
|---|---|---|---|---|---|---|---|
| PCSK9- modified sequences | | | | | | | |
| AD-56638.1 | A-115545.2 | CfuAfGfAfCfCfuGfUfUfuUfGfCfuUfUfUfGfUfL96 | 684 | 3603 | A-115548.5 | aCfaAfAfAfgCfaAfaacAfgGfUfCfuAfgsAfsa | 1235 |
| AD-56644.1 | A-115546.2 | CfUfAfGfAfCfCfuGfUfUfuUfGfCfUfUfUfUfGfUfL96 | 685 | 3603 | A-115548.6 | aCfaAfAfAfgCfaAfaacAfgGfUfCfuAfgsAfsa | 1236 |
| AD-56650.1 | A-115547.2 | CfUfAfGfAfCfCfUfGfUfUfUfUfGfCfUfUfUfUfGfUfL96 | 686 | 3603 | A-115548.7 | aCfaAfAfAfgCfaAfaacAfgGfUfCfuAfgsAfsa | 1237 |
| AD-56656.1 | A-110695.10 | CfuAfgAfcCfuGfUfUfuUfgCfuUfuUfgUfL96 | 687 | 3603 | A-115549.1 | aCfaAfAfAfGfCfaAfaacAfgGfUfCfuAfgsAfsa | 1238 |
| AD-56662.1 | A-115542.3 | CfuAfGfAfcCfuGfUfUfuUfgCfuUfuUfgUfL96 | 688 | 3603 | A-115549.2 | aCfaAfAfAfGfCfaAfaacAfgGfUfCfuAfgsAfsa | 1239 |
| AD-56668.1 | A-115543.3 | CfuAfGfAfcCfuGfUfUfuUfGfCfuUfuUfgUfL96 | 689 | 3603 | A-115549.3 | aCfaAfAfAfGfCfaAfaacAfgGfUfCfuAfgsAfsa | 1240 |
| AD-56673.1 | A-115544.3 | CfuAfGfAfcCfuGfUfUfuUfGfCfuUfUfUfgUfL96 | 690 | 3603 | A-115549.4 | aCfaAfAfAfGfCfaAfaacAfgGfUfCfuAfgsAfsa | 1241 |
| AD-56678.1 | A-115545.3 | CfuAfGfAfCfCfuGfUfUfuUfGfCfuUfUfUfGfUfL96 | 691 | 3603 | A-115549.5 | aCfaAfAfAfGfCfaAfaacAfgGfUfCfuAfgsAfsa | 1242 |
| AD-56683.1 | A-115546.3 | CfUfAfGfAfCfCfuGfUfUfuUfGfCfUfUfUfUfGfUfL96 | 692 | 3603 | A-115549.6 | aCfaAfAfAfGfCfaAfaacAfgGfUfCfuAfgsAfsa | 1243 |
| AD-56688.1 | A-115547.3 | CfUfAfGfAfCfCfUfGfUfUfUfUfGfCfUfUfUfUfGfUfL96 | 693 | 3603 | A-115549.7 | aCfaAfAfAfGfCfaAfaacAfgGfUfCfuAfgsAfsa | 1244 |
| AD-56657.1 | A-115550.1 | CfuAfgAfcCfuGfUfUfuUfgCfuUfuugUfL96 | 694 | 3603 | A-115551.1 | aCfAfAfaAfgCfaAfaacAfgGfuCfuAfgsAfsa | 1245 |
| AD-56663.1 | A-115552.1 | CfuAfgAfcCfuGfUfUfuUfgCfuuuUfgUfL96 | 695 | 3603 | A-115553.1 | aCfaAfAfAfgCfaAfaacAfgGfuCfuAfgsAfsa | 1246 |
| AD-56669.1 | A-115554.1 | CfuAfgAfcCfuGfUfUfuUfgcuUfuUfgUfL96 | 696 | 3603 | A-115555.1 | aCfaAfaAfGfCfaAfaacAfgGfuCfuAfgsAfsa | 1247 |
| AD-56674.1 | A-115556.1 | CfuAfgAfcCfuGfUfUfuugCfuUfuUfgUfL96 | 697 | 3603 | A-115557.1 | aCfaAfaAfgCfAfAfaacAfgGfuCfuAfgsAfsa | 1248 |
| AD-56679.1 | A-115558.1 | CfuAfgAfccuGfUfUfuUfgCfuUfuUfgUfL96 | 698 | 3603 | A-115559.1 | aCfaAfaAfgCfaAfaacAfGfGfuCfuAfgsAfsa | 1249 |
| AD-56684.1 | A-115560.1 | CfuAfgacCfuGfUfUfuUfgCfuUfuUfgUfL96 | 699 | 3603 | A-115561.1 | aCfaAfaAfgCfaAfaacAfgGfUfCfuAfgsAfsa | 1250 |
| AD-56689.1 | A-115535.4 | CfuagAfcCfuGfUfUfuUfgCfuUfuUfgUfL96 | 700 | 3603 | A-115562.1 | aCfaAfaAfgCfaAfaacAfgGfuCfUfAfgsAfsa | 1251 |
| AD-56693.1 | A-115520.4 | cuAfgAfcCfuGfUfUfuUfgCfuUfuUfgUfL96 | 701 | 3603 | A-115563.1 | aCfaAfaAfgCfaAfaacAfgGfuCfuAfGfsAfsa | 1252 |
| AD-56658.1 | A-115564.1 | CfuAfgAfcCfuGfUfUfuUfgCfuUfUfUfgUfL96 | 702 | 3603 | A-115565.1 | aCfaaaAfgCfaAfaacAfgGfuCfuAfgsAfsa | 1253 |
| AD-56664.1 | A-115566.1 | CfuAfgAfcCfuGfUfUfuUfgCfUfUfuUfgUfL96 | 703 | 3603 | A-115567.1 | aCfaAfaagCfaAfaacAfgGfuCfuAfgsAfsa | 1254 |
| AD-56670.1 | A-115568.1 | CfuAfgAfcCfuGfUfUfuUfGfCfuUfuUfgUfL96 | 704 | 3603 | A-115569.1 | aCfaAfaAfgcaAfaacAfgGfuCfuAfgsAfsa | 1255 |
| AD-56680.1 | A-115572.1 | CfuAfgAfcCfUfGfUfUfuUfgCfuUfuUfgUfL96 | 705 | 3603 | A-115573.1 | aCfaAfaAfgCfaAfaacagGfuCfuAfgsAfsa | 1256 |
| AD-56685.1 | A-115574.1 | CfuAfgAfCfCfuGfUfUfuUfgCfuUfuUfgUfL96 | 706 | 3603 | A-115575.1 | aCfaAfaAfgCfaAfaacAfgguCfuAfgsAfsa | 1257 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-56690.1 | A-115542.4 | CfuAfGfAfcCfuGfUfUfuUfgCfuUfuUfgUfL96 | 707 | 3603 | A-115576.1 | aCfaAfaAfgCfaAfaacAfgGfucuAfgsAfsa | 1258 |
| AD-56694.1 | A-115577.1 | CfUfAfgAfcCfuGfUfUfuUfgCfuUfuUfgUfL96 | 708 | 3603 | A-115578.1 | aCfaAfaAfgCfaAfaacAfgGfuCfuagsAfsa | 1259 |
| AD-56659.1 | A-110695.12 | CfuAfgAfcCfuGfUfUfuUfgCfuUfuUfgUfL96 | 709 | 3603 | A-115579.1 | aCfaAfaAfgCfaAfaacAfgGfuCfuAfgsasa | 1260 |
| AD-56665.1 | A-115580.1 | AfgAfcCfuGfUfUfuUfgCfuUfuUfgUfL96 | 710 | 3605 | A-115581.1 | aCfaAfaAfgCfaAfaacAfgGfuCfusAfsg | 1261 |
| AD-56671.1 | A-115582.1 | AfgAfcCfuGfUfUfuUfgCfuUfuugUfL96 | 711 | 3605 | A-115583.1 | aCfAfAfaAfgCfaAfaacAfgGfuCfusAfsg | 1262 |
| AD-56676.1 | A-115584.1 | AfgAfcCfuGfUfUfuUfgCfuuuUfgUfL96 | 712 | 3605 | A-115585.1 | aCfaAfAfAfgCfaAfaacAfgGfuCfusAfsg | 1263 |
| AD-56681.1 | A-115586.1 | AfgAfcCfuGfUfUfuUfgcuUfuUfgUfL96 | 713 | 3605 | A-115587.1 | aCfaAfaAfGfCfaAfaacAfgGfuCfusAfsg | 1264 |
| AD-56686.1 | A-115588.1 | AfgAfcCfuGfUfUfuugCfuUfuUfgUfL96 | 714 | 3605 | A-115589.1 | aCfaAfaAfgCfAfAfaacAfgGfuCfusAfsg | 1265 |
| AD-56691.1 | A-115590.1 | AfgAfccuGfUfUfuUfgCfuUfuUfgUfL96 | 715 | 3605 | A-115591.1 | aCfaAfaAfgCfaAfaacAfGfGfuCfusAfsg | 1266 |
| AD-56695.1 | A-115592.1 | AfgacCfuGfUfUfuUfgCfuUfuUfgUfL96 | 716 | 3605 | A-115593.1 | aCfaAfaAfgCfaAfaacAfgGfUfCfusAfsg | 1267 |
| AD-56660.1 | A-115594.1 | agAfcCfuGfUfUfuUfgCfuUfuUfgUfL96 | 717 | 3605 | A-115595.1 | aCfaAfaAfgCfaAfaacAfgGfuCfUfsAfsg | 1268 |
| AD-56666.1 | A-115596.1 | AfgAfcCfuGfUfUfuUfgCfuUfUfUfgUfL96 | 718 | 3605 | A-115597.1 | aCfaaaAfgCfaAfaacAfgGfuCfusAfsg | 1269 |
| AD-56672.1 | A-115598.1 | AfgAfcCfuGfUfUfuUfgCfUfUfuUfgUfL96 | 719 | 3605 | A-115599.1 | aCfaAfaagCfaAfaacAfgGfuCfusAfsg | 1270 |
| AD-56677.1 | A-115600.1 | AfgAfcCfuGfUfUfuUfGfCfuUfuUfgUfL96 | 720 | 3605 | A-115601.1 | aCfaAfaAfgcaAfaacAfgGfuCfusAfsg | 1271 |
| AD-56682.1 | A-115602.1 | AfgAfcCfuGfUfUfUfUfgCfuUfuUfgUfL96 | 721 | 3605 | A-115603.1 | aCfaAfaAfgCfaaaacAfgGfuCfusAfsg | 1272 |
| AD-56687.1 | A-115604.1 | AfgAfcCfUfGfUfUfuUfgCfuUfuUfgUfL96 | 722 | 3605 | A-115605.1 | aCfaAfaAfgCfaAfaacagGfuCfusAfsg | 1273 |
| AD-56692.1 | A-115606.1 | AfgAfCfCfuGfUfUfuUfgCfuUfuUfgUfL96 | 723 | 3605 | A-115607.1 | aCfaAfaAfgCfaAfaacAfgguCfusAfsg | 1274 |
| AD-56696.1 | A-115608.1 | AfGfAfcCfuGfUfUfuUfgCfuUfuUfgUfL96 | 724 | 3605 | A-115609.1 | aCfaAfaAfgCfaAfaacAfgGfucusAfsg | 1275 |
| AD-56661.1 | A-115580.2 | AfgAfcCfuGfUfUfuUfgCfuUfuUfgUfL96 | 725 | 3605 | A-115610.1 | aCfaAfaAfgCfaAfaacAfgGfuCfusasg | 1276 |
| AD-56667.1 | A-115611.1 | gAfcCfuGfUfUfuUfgCfuUfuUfgUfL96 | 726 | 3605 | A-115612.1 | aCfaAfaAfgCfaAfaacAfgGfuCfausa | 1277 |
| AD-53806.11 | A-110717.10 | CfaAfgCfaGfaCfAfUfuUfaUfcUfuUfuUfL96 | 727 | 3544 | A-109589.15 | aAfaAfaGfaUfaAfaugUfcUfgCfuUfgsCfsu | 1278 |
| AD-53806.13 | A-110717.11 | CfaAfgCfaGfaCfAfUfuUfaUfcUfuUfuUfL96 | 728 | 3544 | A-109589.10 | aAfaAfaGfaUfaAfaugUfcUfgCfuUfgsCfsu | 1279 |
| AD-53806.12 | A-110717.12 | CfaAfgCfaGfaCfAfUfuUfaUfcUfuUfuUfL96 | 729 | 3544 | A-109589.22 | aAfaAfaGfaUfaAfaugUfcUfgCfuUfgsCfsu | 1280 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| AD-53806.5 | A-110717.4 | CfaAfgCfaGfaCfAfUfuUfaUfcUfuUfuUfL96 | 730 | 3544 | A-109589.5 | aAfaAfaGfaUfaAfaugUfcUfgCfuUfgsCfsu | 1281 |
| AD-53806.6 | A-110717.5 | CfaAfgCfaGfaCfAfUfuUfaUfcUfuUfuUfL96 | 731 | 3544 | A-109589.7 | aAfaAfaGfaUfaAfaugUfcUfgCfuUfgsCfsu | 1282 |
| AD-53806.7 | A-110717.6 | CfaAfgCfaGfaCfAfUfuUfaUfcUfuUfuUfL96 | 732 | 3544 | A-109589.8 | aAfaAfaGfaUfaAfaugUfcUfgCfuUfgsCfsu | 1283 |
| AD-53806.8 | A-110717.7 | CfaAfgCfaGfaCfAfUfuUfaUfcUfuUfuUfL96 | 733 | 3544 | A-109589.9 | aAfaAfaGfaUfaAfaugUfcUfgCfuUfgsCfsu | 1284 |
| AD-53806.9 | A-110717.8 | CfaAfgCfaGfaCfAfUfuUfaUfcUfuUfuUfL96 | 734 | 3544 | A-109589.9 | aAfaAfaGfaUfaAfaugUfcUfgCfuUfgsCfsu | 1285 |
| AD-53806.10 | A-110717.9 | CfaAfgCfaGfaCfAfUfuUfaUfcUfuUfuUfL96 | 735 | 3544 | A-109589.9 | aAfaAfaGfaUfaAfaugUfcUfgCfuUfgsCfsu | 1286 |
| AD-56979.1 | A-116393.1 | caAfgCfaGfaCfAfUfuUfaUfcUfuUfuUfL96 | 736 | 3544 | A-109589.6 | aAfaAfaGfaUfaAfaugUfcUfgCfuUfgsCfsu | 1287 |
| AD-56979.2 | A-116393.2 | caAfgCfaGfaCfAfUfuUfaUfcUfuUfuUfL96 | 737 | 3544 | A-109589.17 | aAfaAfaGfaUfaAfaugUfcUfgCfuUfgsCfsu | 1288 |
| AD-56975.3 | A-116394.1 | (iC)aAfgCfaGfaCfAfUfuUfaUfcUfuUfuUfL96 | 738 | 3544 | A-109589.9 | aAfaAfaGfaUfaAfaugUfcUfgCfuUfgsCfsu | 1289 |
| AD-56975.4 | A-116394.2 | (iC)aAfgCfaGfaCfAfUfuUfaUfcUfuUfuUfL96 | 739 | 3544 | A-109589.15 | aAfaAfaGfaUfaAfaugUfcUfgCfuUfgsCfsu | 1290 |
| AD-56975.5 | A-116394.3 | (iC)aAfgCfaGfaCfAfUfuUfaUfcUfuUfuUfL96 | 740 | 3544 | A-109589.22 | aAfaAfaGfaUfaAfaugUfcUfgCfuUfgsCfsu | 1291 |
| AD-56975.1 | A-116394.4 | (iC)aAfgCfaGfaCfAfUfuUfaUfcUfuUfuUfL96 | 741 | 3544 | A-109589.5 | aAfaAfaGfaUfaAfaugUfcUfgCfuUfgsCfsu | 1292 |
| AD-56975.2 | A-116394.5 | (iC)aAfgCfaGfaCfAfUfuUfaUfcUfuUfuUfL96 | 742 | 3544 | A-109589.6 | aAfaAfaGfaUfaAfaugUfcUfgCfuUfgsCfsu | 1293 |
| AD-56983.1 | A-116400.1 | CbaAfgCfaGfaCfAfUfuUfaUfcUfuUfuUfL96 | 743 | 3544 | A-109589.7 | aAfaAfaGfaUfaAfaugUfcUfgCfuUfgsCfsu | 1294 |
| AD-56983.2 | A-116400.2 | CbaAfgCfaGfaCfAfUfuUfaUfcUfuUfuUfL96 | 744 | 3544 | A-109589.8 | aAfaAfaGfaUfaAfaugUfcUfgCfuUfgsCfsu | 1295 |
| AD-56983.3 | A-116400.3 | CbaAfgCfaGfaCfAfUfuUfaUfcUfuUfuUfL96 | 745 | 3544 | A-109589.9 | aAfaAfaGfaUfaAfaugUfcUfgCfuUfgsCfsu | 1296 |
| AD-56983.4 | A-116400.4 | CbaAfgCfaGfaCfAfUfuUfaUfcUfuUfuUfL96 | 746 | 3544 | A-109589.9 | aAfaAfaGfaUfaAfaugUfcUfgCfuUfgsCfsu | 1297 |
| AD-56983.5 | A-116400.5 | CbaAfgCfaGfaCfAfUfuUfaUfcUfuUfuUfL96 | 747 | 3544 | A-109589.15 | aAfaAfaGfaUfaAfaugUfcUfgCfuUfgsCfsu | 1298 |
| AD-56977.3 | A-116406.1 | CfaagCfaGfaCfAfUfuUfaUfcUfuUfuUfL96 | 748 | 3544 | A-109589.10 | aAfaAfaGfaUfaAfaugUfcUfgCfuUfgsCfsu | 1299 |
| AD-56977.1 | A-116406.2 | CfaagCfaGfaCfAfUfuUfaUfcUfuUfuUfL96 | 749 | 3544 | A-109589.11 | aAfaAfaGfaUfaAfaugUfcUfgCfuUfgsCfsu | 1300 |
| AD-56977.2 | A-116406.3 | CfaagCfaGfaCfAfUfuUfaUfcUfuUfuUfL96 | 750 | 3544 | A-109589.18 | aAfaAfaGfaUfaAfaugUfcUfgCfuUfgsCfsu | 1301 |
| AD-56976.1 | A-116407.1 | CfaagCfaGfaCfAfUfuUfaucUfuUfuUfL96 | 751 | 3544 | A-109589.11 | aAfaAfaGfaUfaAfaugUfcUfgCfuUfgsCfsu | 1302 |
| AD-56976.2 | A-116407.2 | CfaagCfaGfaCfAfUfuUfaucUfuUfuUfL96 | 752 | 3544 | A-109589.12 | aAfaAfaGfaUfaAfaugUfcUfgCfuUfgsCfsu | 1303 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-56980.1 | A-116408.1 | CfaagCfagaCfAfUfuUfaucUfuUfuUfL96 | 753 | 3544 | A-109589.12 | aAfaAfaGfaUfaAfaugUfcUfgCfuUfgsCfsu | 1304 |
| AD-56980.2 | A-116408.2 | CfaagCfagaCfAfUfuUfaucUfuUfuUfL96 | 754 | 3544 | A-109589.13 | aAfaAfaGfaUfaAfaugUfcUfgCfuUfgsCfsu | 1305 |
| AD-56984.1 | A-116409.1 | CfaagCfagaCfAfUfuUfaucUfuuuUfL96 | 755 | 3544 | A-109589.13 | aAfaAfaGfaUfaAfaugUfcUfgCfuUfgsCfsu | 1306 |
| AD-56984.2 | A-116409.2 | CfaagCfagaCfAfUfuUfaucUfuuuUfL96 | 756 | 3544 | A-109589.14 | aAfaAfaGfaUfaAfaugUfcUfgCfuUfgsCfsu | 1307 |
| AD-56987.1 | A-116410.1 | CfaagCfagaCfAfUfuUfaucUfuuuuL96 | 757 | 3544 | A-109589.14 | aAfaAfaGfaUfaAfaugUfcUfgCfuUfgsCfsu | 1308 |
| AD-56987.2 | A-116410.2 | CfaagCfagaCfAfUfuUfaucUfuuuuL96 | 758 | 3544 | A-109589.9 | aAfaAfaGfaUfaAfaugUfcUfgCfuUfgsCfsu | 1309 |
| AD-56991.1 | A-116415.1 | CfaagCfagaCfAfUfuUfaucuuuuuL96 | 759 | 3544 | A-109589.15 | aAfaAfaGfaUfaAfaugUfcUfgCfuUfgsCfsu | 1310 |
| AD-56993.1 | A-116416.1 | CfaagcagaCfAfUfuUfaucuuuuuL96 | 760 | 3544 | A-109589.16 | aAfaAfaGfaUfaAfaugUfcUfgCfuUfgsCfsu | 1311 |
| AD-56995.1 | A-116417.1 | CfaagcagaCfAfUfuuaucuuuuuL96 | 761 | 3544 | A-109589.17 | aAfaAfaGfaUfaAfaugUfcUfgCfuUfgsCfsu | 1312 |
| AD-56978.1 | A-116418.1 | CfaAfGfCfaGfaCfAfUfuUfaUfcUfuUfuUfL96 | 762 | 3544 | A-109589.18 | aAfaAfaGfaUfaAfaugUfcUfgCfuUfgsCfsu | 1313 |
| AD-56978.2 | A-116418.2 | CfaAfGfCfaGfaCfAfUfuUfaUfcUfuUfuUfL96 | 763 | 3544 | A-109589.17 | aAfaAfaGfaUfaAfaugUfcUfgCfuUfgsCfsu | 1314 |
| AD-56981.1 | A-116419.1 | CfaAfGfCfaGfaCfAfUfuUfAfUfcUfuUfuUfL96 | 764 | 3544 | A-109589.19 | aAfaAfaGfaUfaAfaugUfcUfgCfuUfgsCfsu | 1315 |
| AD-56985.1 | A-116420.1 | CfaAfGfCfaGfaCfAfUfuUfAfUfCfUfuUfuUfL96 | 765 | 3544 | A-109589.20 | aAfaAfaGfaUfaAfaugUfcUfgCfuUfgsCfsu | 1316 |
| AD-56988.1 | A-116421.1 | CfaAfGfCfAfGfaCfAfUfuUfAfUfCfUfuUfuUfL96 | 766 | 3544 | A-109589.21 | aAfaAfaGfaUfaAfaugUfcUfgCfuUfgsCfsu | 1317 |
| AD-56988.2 | A-116421.2 | CfaAfGfCfAfGfaCfAfUfuUfAfUfCfUfuUfuUfL96 | 767 | 3544 | A-109589.9 | aAfaAfaGfaUfaAfaugUfcUfgCfuUfgsCfsu | 1318 |
| AD-56988.3 | A-116421.3 | CfaAfGfCfAfGfaCfAfUfuUfAfUfCfUfuUfuUfL96 | 768 | 3544 | A-109589.15 | aAfaAfaGfaUfaAfaugUfcUfgCfuUfgsCfsu | 1319 |
| AD-56982.1 | A-116426.1 | CfaAfgcaGfaCfAfUfuUfaUfcUfuUfuUfL96 | 769 | 3544 | A-109589.19 | aAfaAfaGfaUfaAfaugUfcUfgCfuUfgsCfsu | 1320 |
| AD-56982.2 | A-116426.2 | CfaAfgcaGfaCfAfUfuUfaUfcUfuUfuUfL96 | 770 | 3544 | A-109589.23 | aAfaAfaGfaUfaAfaugUfcUfgCfuUfgsCfsu | 1321 |
| AD-56986.1 | A-116428.1 | CfaAfgCfagaCfAfUfuUfaUfcUfuUfuUfL96 | 771 | 3544 | A-109589.20 | aAfaAfaGfaUfaAfaugUfcUfgCfuUfgsCfsu | 1322 |
| AD-56986.2 | A-116428.2 | CfaAfgCfagaCfAfUfuUfaUfcUfuUfuUfL96 | 772 | 3544 | A-109589.17 | aAfaAfaGfaUfaAfaugUfcUfgCfuUfgsCfsu | 1323 |
| AD-56989.1 | A-116430.1 | CfaAfgCfaGfacAfUfuUfaUfcUfuUfuUfL96 | 773 | 3544 | A-109589.21 | aAfaAfaGfaUfaAfaugUfcUfgCfuUfgsCfsu | 1324 |
| AD-56990.1 | A-116432.1 | CfaAfgCfaGfaCfAfuuUfaUfcUfuUfuUfL96 | 774 | 3544 | A-109589.9 | aAfaAfaGfaUfaAfaugUfcUfgCfuUfgsCfsu | 1325 |
| AD-56992.1 | A-116434.1 | CfaAfgCfaGfaCfAfUfuUfaucUfuUfuUfL96 | 775 | 3544 | A-109589.15 | aAfaAfaGfaUfaAfaugUfcUfgCfuUfgsCfsu | 1326 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-56992.2 | A-116434.2 | CfaAfgCfaGfaCfAfUfuUfaucUfuUfuUfL96 | 776 | 3544 | A-109589.17 | aAfaAfaGfaUfaAfaugUfcUfgCfuUfgsCfsu | 1327 |
| AD-56994.1 | A-116436.1 | CfaAfgCfaGfaCfAfUfuUfaUfcUfuuuUfL96 | 777 | 3544 | A-109589.22 | aAfaAfaGfaUfaAfaugUfcUfgCfuUfgsCfsu | 1328 |
| AD-56994.2 | A-116436.2 | CfaAfgCfaGfaCfAfUfuUfaUfcUfuuuUfL96 | 778 | 3544 | A-109589.23 | aAfaAfaGfaUfaAfaugUfcUfgCfuUfgsCfsu | 1329 |
| AD-56996.1 | A-116438.1 | caagCfaGfaCfAfUfuUfaUfcUfuUfuUfL96 | 779 | 3544 | A-109589.17 | aAfaAfaGfaUfaAfaugUfcUfgCfuUfgsCfsu | 1330 |
| AD-57001.1 | A-116440.1 | CfaAfgcagaCfAfUfuUfaUfcUfuUfuUfL96 | 780 | 3544 | A-109589.17 | aAfaAfaGfaUfaAfaugUfcUfgCfuUfgsCfsu | 1331 |
| AD-57007.1 | A-116442.1 | CfaAfgCfaGfaCfAfuuuaUfcUfuUfuUfL96 | 781 | 3544 | A-109589.17 | aAfaAfaGfaUfaAfaugUfcUfgCfuUfgsCfsu | 1332 |
| AD-57013.1 | A-116444.1 | CfaAfgCfaGfaCfAfUfuUfaucuuUfuUfL96 | 782 | 3544 | A-109589.17 | aAfaAfaGfaUfaAfaugUfcUfgCfuUfgsCfsu | 1333 |
| AD-57019.1 | A-116446.1 | CfaAfgCfaGfaCfAfUfuUfaUfcUfuuuuL96 | 783 | 3544 | A-109589.17 | aAfaAfaGfaUfaAfaugUfcUfgCfuUfgsCfsu | 1334 |
| AD-57022.1 | A-116448.1 | CfaAfgCfaGfaCfAfUfuUfaUfcUfUfUfuUfL96 | 784 | 3544 | A-109589.23 | aAfaAfaGfaUfaAfaugUfcUfgCfuUfgsCfsu | 1335 |
| AD-57025.1 | A-116449.1 | CfaAfgCfaGfaCfAfUfuUfaUfCfUfuUfuUfL96 | 785 | 3544 | A-109589.23 | aAfaAfaGfaUfaAfaugUfcUfgCfuUfgsCfsu | 1336 |
| AD-56997.1 | A-116450.1 | CfaAfgCfaGfaCfAfUfuUfAfUfcUfuUfuUfL96 | 786 | 3544 | A-109589.17 | aAfaAfaGfaUfaAfaugUfcUfgCfuUfgsCfsu | 1337 |
| AD-57002.1 | A-116452.1 | CfaAfgCfaGfaCfAfUfUfUfaUfcUfuUfuUfL96 | 787 | 3544 | A-109589.17 | aAfaAfaGfaUfaAfaugUfcUfgCfuUfgsCfsu | 1338 |
| AD-57008.1 | A-116453.1 | CfaAfgCfaGfAfCfAfUfuUfaUfcUfuUfuUfL96 | 788 | 3544 | A-109589.17 | aAfaAfaGfaUfaAfaugUfcUfgCfuUfgsCfsu | 1339 |
| AD-57014.1 | A-116454.1 | CfaAfgCfAfGfAfCfAfUfuUfaUfcUfuUfuUfL96 | 789 | 3544 | A-109589.17 | aAfaAfaGfaUfaAfaugUfcUfgCfuUfgsCfsu | 1340 |
| AD-57020.1 | A-116455.1 | CfAfAfgCfaGfaCfAfUfuUfaUfcUfuUfuUfL96 | 790 | 3544 | A-109589.23 | aAfaAfaGfaUfaAfaugUfcUfgCfuUfgsCfsu | 1341 |
| AD-57020.2 | A-116455.2 | CfAfAfgCfaGfaCfAfUfuUfaUfcUfuUfuUfL96 | 791 | 3544 | A-109589.23 | aAfaAfaGfaUfaAfaugUfcUfgCfuUfgsCfsu | 1342 |
| AD-57026.1 | A-116457.1 | CfaAfgCfaGfaCfAfUfuUfaUfcuuUfuUfL96 | 792 | 3544 | A-109589.23 | aAfaAfaGfaUfaAfaugUfcUfgCfuUfgsCfsu | 1343 |
| AD-57003.1 | A-116460.1 | CfaAfgCfaGfaCfAfUfuuaUfcUfuUfuUfL96 | 793 | 3544 | A-109589.17 | aAfaAfaGfaUfaAfaugUfcUfgCfuUfgsCfsu | 1344 |
| AD-57009.1 | A-116462.1 | CfaAfgCfaGfaCfauuUfaUfcUfuUfuUfL96 | 794 | 3544 | A-109589.17 | aAfaAfaGfaUfaAfaugUfcUfgCfuUfgsCfsu | 1345 |
| AD-57015.1 | A-116464.1 | CfaAfgCfaGfacaUfuUfaUfcUfuUfuUfL96 | 795 | 3544 | A-109589.17 | aAfaAfaGfaUfaAfaugUfcUfgCfuUfgsCfsu | 1346 |
| AD-57023.1 | A-116467.1 | CfaAfgCfaGfaCfAfUfuUfaucUfUfUfuUfL96 | 796 | 3544 | A-109589.23 | aAfaAfaGfaUfaAfaugUfcUfgCfuUfgsCfsu | 1347 |
| AD-57027.1 | A-116469.1 | CfaAfgCfaGfaCfAfUfuuaUfcUfUfUfuUfL96 | 797 | 3544 | A-109589.23 | aAfaAfaGfaUfaAfaugUfcUfgCfuUfgsCfsu | 1348 |
| AD-56998.1 | A-116471.1 | CfaAfgCfagaCfAfUfuUfaUfcUfUfUfuUfL96 | 798 | 3544 | A-109589.17 | aAfaAfaGfaUfaAfaugUfcUfgCfuUfgsCfsu | 1349 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| AD-57004.1 | A-116473.1 | CfaAfgcaGfaCfAfUfuUfaUfcUfUfUfuUfL96 | 799 | 3544 | A-109589.17 | aAfaAfaGfaUfaAfaugUfcUfgCfuUfgsCfsu | 1350 |
| AD-57010.1 | A-116475.1 | CfaagCfaGfaCfAfUfuUfaUfcUfUfUfuUfL96 | 800 | 3544 | A-109589.17 | aAfaAfaGfaUfaAfaugUfcUfgCfuUfgsCfsu | 1351 |
| AD-57016.1 | A-116477.1 | caAfgCfaGfaCfAfUfuUfaUfcUfUfUfuUfL96 | 801 | 3544 | A-109589.17 | aAfaAfaGfaUfaAfaugUfcUfgCfuUfgsCfsu | 1352 |
| AD-56999.2 | A-116479.1 | CfaAfgCfaGfaCfAfUfuUfAfUfcUfUfUfuUfL96 | 802 | 3544 | A-109589.17 | aAfaAfaGfaUfaAfaugUfcUfgCfuUfgsCfsu | 1353 |
| AD-56999.1 | A-116479.2 | CfaAfgCfaGfaCfAfUfuUfAfUfcUfUfUfuUfL96 | 803 | 3544 | A-109589.17 | aAfaAfaGfaUfaAfaugUfcUfgCfuUfgsCfsu | 1354 |
| AD-57021.1 | A-116481.1 | CfaAfgCfAfGfaCfAfUfuUfaUfcUfUfUfuUfL96 | 804 | 3544 | A-109589.23 | aAfaAfaGfaUfaAfaugUfcUfgCfuUfgsCfsu | 1355 |
| AD-57024.1 | A-116483.1 | CfaAfGfCfaGfaCfAfUfuUfaUfcUfUfUfuUfL96 | 805 | 3544 | A-109589.23 | aAfaAfaGfaUfaAfaugUfcUfgCfuUfgsCfsu | 1356 |
| AD-57005.1 | A-116486.1 | CfaAfgCfaGfaCfAfUfuUfaUfCfUfuuuUfL96 | 806 | 3544 | A-109589.17 | aAfaAfaGfaUfaAfaugUfcUfgCfuUfgsCfsu | 1357 |
| AD-57011.1 | A-116488.1 | CfaAfgCfaGfaCfAfUfuuaUfCfUfuUfuUfL96 | 807 | 3544 | A-109589.17 | aAfaAfaGfaUfaAfaugUfcUfgCfuUfgsCfsu | 1358 |
| AD-57017.1 | A-116490.1 | CfaAfGfCfagaCfAfUfuUfaUfcUfuUfuUfL96 | 808 | 3544 | A-109589.17 | aAfaAfaGfaUfaAfaugUfcUfgCfuUfgsCfsu | 1359 |
| AD-57000.2 | A-116492.1 | Cf(Aeo)Af(Geo)CfaGfaCfAfUfuUfaUfcUf(Teo)Uf (Teo)UfL96 | 809 | 3544 | A-109589.17 | aAfaAfaGfaUfaAfaugUfcUfgCfuUfgsCfsu | 1360 |
| AD-57000.3 | A-116492.2 | Cf(Aeo)Af(Geo)CfaGfaCfAfUfuUfaUfcUf(Teo)Uf (Teo)UfL96 | 810 | 3544 | A-109589.23 | aAfaAfaGfaUfaAfaugUfcUfgCfuUfgsCfsu | 1361 |
| AD-57000.1 | A-116492.3 | Cf(Aeo)Af(Geo)CfaGfaCfAfUfuUfaUfcUf(Teo)Uf (Teo)UfL96 | 811 | 3544 | A-109589.17 | aAfaAfaGfaUfaAfaugUfcUfgCfuUfgsCfsu | 1362 |
| AD-57006.2 | A-116494.1 | Cf(Aeo)Af(Geo)CfaGfaCfAfUfuUf(Aeo)Uf(m5Ceo)Uf (Teo)Uf(Teo)UfL96 | 812 | 3544 | A-109589.23 | aAfaAfaGfaUfaAfaugUfcUfgCfuUfgsCfsu | 1363 |
| AD-57006.3 | A-116494.2 | Cf(Aeo)Af(Geo)CfaGfaCfAfUfuUf(Aeo)Uf(m5Ceo)Uf (Teo)Uf(Teo)UfL96 | 813 | 3544 | A-109589.23 | aAfaAfaGfaUfaAfaugUfcUfgCfuUfgsCfsu | 1364 |
| AD-57006.1 | A-116494.3 | Cf(Aeo)Af(Geo)CfaGfaCfAfUfuUf(Aeo)Uf(m5Ceo)Uf (Teo)Uf(Teo)UfL96 | 814 | 3544 | A-109589.17 | aAfaAfaGfaUfaAfaugUfcUfgCfuUfgsCfsu | 1365 |
| AD-57012.1 | A-116498.1 | Cf(Aeo)Af(Geo)CfaGfaCfAfUfuUfaUfcUf(Teo)Uf (Teo)UbL96 | 815 | 3544 | A-109589.17 | aAfaAfaGfaUfaAfaugUfcUfgCfuUfgsCfsu | 1366 |
| AD-57018.1 | A-116500.1 | Cf(Aeo)Af(Geo)CfaGfaCfAfUfuUf(Aeo)Uf(m5Ceo)Uf (Teo)Uf(Teo)UbL96 | 816 | 3544 | A-109589.17 | aAfaAfaGfaUfaAfaugUfcUfgCfuUfgsCfsu | 1367 |
| AD-53815.1 | | CfuAfgAfcCfuGfUfUfuUfgCfuUfuUfgUfL96 | 817 | 3601 | | aCfaAfaAfgCfaAfaacAfgGfuCfuAfgsAfsa | 1368 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| AD-57928.40 | | CfsusAfgAfcCfuGfUfUfuUfgCfuUfuUfgUfL96 | 818 | 3601 | | asCfsaAfaAfgCfaAfaacAfgGfuCfuAfgsasa | 1369 |
| AD-59182.5 | | CfsusAfgAfcCfuGfUfUfuugCfuuuuguL96 | 819 | 3601 | | asCfsaAfaAfgCfaAfaacAfgGfuCfuAfgsasa | 1370 |
| AD-59184.3 | | CfsusAfgAfcCfuGfuUfuugCfuuuuguL96 | 820 | 3601 | | asCfsaAfaAfgCfaAfaacAfgGfuCfuAfgsasa | 1371 |
| AD-59186.3 | | CfsusAfgAfcCfuGfUfuuugCfuuuuguL96 | 821 | 3601 | | asCfsaAfaAfgCfaAfaacAfgGfuCfuAfgsasa | 1372 |
| AD-59171.13 | | CfsusAfgAfcCfuGfuuuugCfuuuuguL96 | 822 | 3601 | | asCfsaAfaAfgCfaAfaacAfgGfuCfuAfgsasa | 1373 |
| AD-59176.7 | | CfsusAfgAfcCfuGfuuuugcuuuuguL96 | 823 | 3601 | | asCfsaAfaAfgCfaAfaacAfgGfuCfuAfgsasa | 1374 |
| AD-59170.7 | | CfsusagacCfuGfuuuugCfuuuuguL96 | 824 | 3601 | | asCfsaAfaAfgCfaAfaacAfgGfuCfuAfgsasa | 1375 |
| AD-59175.7 | | CfsusagacCfuGfuuuugcuuuuguL96 | 825 | 3601 | | asCfsaAfaAfgCfaAfaacAfgGfuCfuAfgsasa | 1376 |
| AD-59179.7 | | csusagacCfuGfuuuugcuuuuguL96 | 826 | 3601 | | asCfsaAfaAfgCfaAfaacAfgGfuCfuAfgsasa | 1377 |
| AD-59218.1 | | CfsusAfgAfcCfuGfuuuugCfuuuuguL96 | 827 | 3601 | | asCfsaAfaAfgCfaAfAfAfcAfgGfuCfuAfgsasa | 1378 |
| AD-59222.1 | | CfsusAfgAfcCfuGfuuuugcuuuuguL96 | 828 | 3601 | | asCfsaAfaAfgCfaAfAfAfcAfgGfuCfuAfgsasa | 1379 |
| AD-59226.1 | | CfsusagacCfuGfuuuugCfuuuuguL96 | 829 | 3601 | | asCfsaAfaAfgCfaAfAfAfcAfgGfuCfuAfgsasa | 1380 |
| AD-59230.1 | | CfsusagacCfuGfuuuugcuuuuguL96 | 830 | 3601 | | asCfsaAfaAfgCfaAfAfAfcAfgGfuCfuAfgsasa | 1381 |
| AD-59235.1 | | csusagacCfuGfuuuugcuuuuguL96 | 831 | 3601 | | asCfsaAfaAfgCfaAfAfAfcAfgGfuCfuAfgsasa | 1382 |
| AD-59207.1 | | CfsusAfgAfcCfuGfuuuugCfuuuuguL96 | 832 | 3601 | | asCfsaAfAfAfgCfaAfaAfcAfgGfuCfuagsasa | 1383 |
| AD-59211.1 | | CfsusAfgAfcCfuGfuuuugcuuuuguL96 | 833 | 3601 | | asCfsaAfAfAfgCfaAfaAfcAfgGfuCfuagsasa | 1384 |
| AD-59215.1 | | CfsusagacCfuGfuuuugCfuuuuguL96 | 834 | 3601 | | asCfsaAfAfAfgCfaAfaAfcAfgGfuCfuagsasa | 1385 |
| AD-59219.1 | | CfsusagacCfuGfuuuugcuuuuguL96 | 835 | 3601 | | asCfsaAfAfAfgCfaAfaAfcAfgGfuCfuagsasa | 1386 |
| AD-59223.1 | | csusagacCfuGfuuuugcuuuuguL96 | 836 | 3601 | | asCfsaAfAfAfgCfaAfaAfcAfgGfuCfuagsasa | 1387 |
| AD-59181.5 | | CfsusAfgAfcCfuGfUfUfuUfgCfuUfuUfgsUfL96 | 837 | 3601 | | asCfsaAfaAfgCfaAfaacAfgGfuCfuAfgsasa | 1388 |
| AD-59172.5 | | CfsusAfgAfcCfuGfUfUfuUfgCfuUfuUfsgsUfL96 | 838 | 3601 | | asCfsaAfaAfgCfaAfaacAfgGfuCfuAfgsasa | 1389 |
| AD-59177.5 | | CfsusAfgAfcCfuGfUfUfuUfgCfsuUfsuUfsgsUfL96 | 839 | 3601 | | asCfsaAfaAfgCfaAfaacAfgGfuCfuAfgsasa | 1390 |
| AD-59180.5 | | CfsusAfgAfcCfuGfUfUfuUfgCfsuUfsuUfsgsUfsL96 | 840 | 3601 | | asCfsaAfaAfgCfaAfaacAfgGfuCfuAfgsasa | 1391 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-59183.5 | | CfsusAfgAfcCfuGfUfUfuUfgCfuUfuUfsgsUfsL96 | 841 | 3601 | | asCfsaAfaAfgCfaAfaacAfgGfuCfuAfgsasa | 1392 |
| AD-59185.5 | | CfsusAfgAfcCfuGfUfUfuUfgCfuUfuUfgUfsL96 | 842 | 3601 | | asCfsaAfaAfgCfaAfaacAfgGfuCfuAfgsasa | 1393 |
| AD-59173.5 | | CfsusAfgAfcCfuGfUfUfuugCfuuuugsuL96 | 843 | 3601 | | asCfsaAfaAfgCfaAfaacAfgGfuCfuAfgsasa | 1394 |
| AD-59232.1 | | CfsusAfgAfcCfuGfUfUfuUfgCfuUfuUfgUfL96 | 844 | 3600 | | PasCfsaAfaAfgCfaAfaacAfgGfuCfuAfgsasa | 1395 |
| AD-59236.1 | | CfsusAfgAfcCfuGfUfUfuUfgCfuUfuUfgUfL96 | 845 | 3601 | | asCfsaAfaAfsgCfaAfaacAfgGfuCfsuAfgsasa | 1396 |
| AD-59216.1 | | CfsusAfgAfcCfuGfUfUfuUfgCfuUfuUfgsUfL96 | 846 | 3601 | | asCfsaAfaAfsgCfaAfaacAfgGfuCfsuAfgsasa | 1397 |
| AD-59220.1 | | CfsusAfgAfcCfuGfUfUfuUfgCfuUfuUfsgsUfL96 | 847 | 3601 | | asCfsaAfaAfsgCfaAfaacAfgGfuCfsuAfgsasa | 1398 |
| AD-59224.1 | | CfsusAfgAfcCfuGfUfUfuUfgCfsuUfsuUfsgsUfL96 | 848 | 3601 | | asCfsaAfaAfsgCfaAfaacAfgGfuCfsuAfgsasa | 1399 |
| AD-59228.1 | | CfsusAfgAfcCfuGfUfUfuUfgCfsuUfsuUfsgsUfsL96 | 849 | 3601 | | asCfsaAfaAfsgCfaAfaacAfgGfuCfsuAfgsasa | 1400 |
| AD-59233.1 | | CfsusAfgAfcCfuGfUfUfuUfgCfuUfuUfsgsUfsL96 | 850 | 3601 | | asCfsaAfaAfsgCfaAfaacAfgGfuCfsuAfgsasa | 1401 |
| AD-59237.1 | | CfsusAfgAfcCfuGfUfUfuUfgCfuUfuUfgUfsL96 | 851 | 3601 | | asCfsaAfaAfsgCfaAfaacAfgGfuCfsuAfgsasa | 1402 |
| AD-59209.1 | | CfsusAfgAfcCfuGfUfUfuugCfuuuugsuL96 | 852 | 3601 | | asCfsaAfaAfsgCfaAfaacAfgGfuCfsuAfgsasa | 1403 |
| AD-59208.1 | | CfsusAfgAfcCfuGfUfUfuUfgCfuUfuUfgUfL96 | 853 | 3601 | | asCfsaAfaAfsgCfaAfaacAfgGfuCfsusAfgsasa | 1404 |
| AD-59212.1 | | CfsusAfgAfcCfuGfUfUfuUfgCfuUfuUfgUfL96 | 854 | 3600 | | PasCfsaAfaAfsgCfaAfaacAfgGfuCfsuAfgsasa | 1405 |
| AD-59210.1 | | csusAGAccuGuuuuGcuuuuGuL96 | 855 | 3601 | | AscsAAAAGcAAAAcAGGucuAGsasa | 1406 |
| AD-59214.1 | | AsGsAccuGuuuuGcuuuuGuL96 | 856 | 3603 | | AscsAAAAGcAAAAcAGGucusAsG | 1407 |
| AD-59227.1 | | CfsusAfGfAfccuGfuuuuGfcuuuuGfuL96 | 857 | 3601 | | asCfsAfAfAfAfGfcAfAfAfAfcAfGfGfucuAfGfsasa | 1408 |
| AD-59231.1 | | CfsusAfGfAfccuGfuuuuGfcuuuuGfuL96 | 858 | 3601 | | asCfsAfAfAfAfGfcAfAfaacAfGfGfucuAfGfsasa | 1409 |
| AD-59198.3 | | (C3m)usAfgAfcCfuGfUfUfuUfgCfuUfuUfgUfL96 | 859 | 3601 | | asCfsaAfaAfgCfaAfaacAfgGfuCfuAfgsasa | 1410 |
| AD-59200.3 | | (C3m)(U3m)AfgAfcCfuGfUfUfuUfgCfuUfuUfgUfL96 | 860 | 3601 | | asCfsaAfaAfgCfaAfaacAfgGfuCfuAfgsasa | 1411 |
| AD-59203.3 | | (m5Cam)usAfgAfcCfuGfUfUfuUfgCfuUfuUfgUfL96 | 861 | 3601 | | asCfsaAfaAfgCfaAfaacAfgGfuCfuAfgsasa | 1412 |
| AD-59204.3 | | (m5Cam)(Tam)AfgAfcCfuGfUfUfuUfgCfuUfuUfgUfL96 | 862 | 3601 | | asCfsaAfaAfgCfaAfaacAfgGfuCfuAfgsasa | 1413 |
| AD-59188.3 | | (m5Cams)(Tams)AfgAfcCfuGfUfUfuUfgCfuUfuUfgUfL96 | 863 | 3601 | | asCfsaAfaAfgCfaAfaacAfgGfuCfuAfgsasa | 1414 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| AD-59191.3 | | (m5Cams)usAfgAfcCfuGfUfUfuUfgCfuUfuUfgUfL96 | 864 | 3601 | | asCfsaAfaAfgCfaAfaacAfgGfuCfuAfgsasa | 1415 |
| AD-59213.1 | | CfsusAfgAfcCfuGfUfUfuUfgCfuUfuUfgUfL96 | 865 | 3601 | | asCfsaAfaAfgCfaAfaacAfgGfuCfuAfgs(A3m)a | 1416 |
| AD-59217.1 | | CfsusAfgAfcCfuGfUfUfuUfgCfuUfuUfgUfL96 | 866 | 3601 | | asCfsaAfaAfgCfaAfaacAfgGfuCfuAf(G3m)(A3m)a | 1417 |
| AD-59221.1 | | CfsusAfgAfcCfuGfUfUfuUfgCfuUfuUfgUfL96 | 867 | 3601 | | asCfsaAfaAfgCfaAfaacAfgGfuCfuAfgs(Aam)a | 1418 |
| AD-59225.1 | | CfsusAfgAfcCfuGfUfUfuUfgCfuUfuUfgUfL96 | 868 | 3601 | | asCfsaAfaAfgCfaAfaacAfgGfuCfuAf(Gam)(Aam)a | 1419 |
| AD-59229.1 | | CfsusAfgAfcCfuGfUfUfuUfgCfuUfuUfgUfL96 | 869 | 3601 | | asCfsaAfaAfgCfaAfaacAfgGfuCfuAfgs(Aams)a | 1420 |
| AD-59234.1 | | CfsusAfgAfcCfuGfUfUfuUfgCfuUfuUfgUfL96 | 870 | 3601 | | asCfsaAfaAfgCfaAfaacAfgGfuCfuAf(Gams)(Aams)a | 1421 |
| AD-59238.1 | | CfsusAfgAfcCfuGfUfUfuUfgCfuUfuUfgUfL96 | 871 | 3601 | | (A3m)CfsaAfaAfgCfaAfaacAfgGfuCfuAfgsasa | 1422 |
| AD-59241.1 | | CfsusAfgAfcCfuGfUfUfuUfgCfuUfuUfgUfL96 | 872 | 3601 | | as(C3m)aAfaAfgCfaAfaacAfgGfuCfuAfgsasa | 1423 |
| AD-59245.1 | | CfsusAfgAfcCfuGfUfUfuUfgCfuUfuUfgUfL96 | 873 | 3601 | | (Aam)CfsaAfaAfgCfaAfaacAfgGfuCfuAfgsasa | 1424 |
| AD-59250.1 | | CfsusAfgAfcCfuGfUfUfuUfgCfuUfuUfgUfL96 | 874 | 3601 | | as(m5Cam)aAfaAfgCfaAfaacAfgGfuCfuAfgsasa | 1425 |
| AD-59246.1 | | CfsusAfgAfcCfuGfUfUfuUfgCfuUfuUfgUfL96 | 875 | 3602 | | asCfsaAfaAfgCfaAfaacAfgGfuCfuAfsgsa | 1426 |
| AD-59253.2 | | usAfsgAfcCfuGfUfUfuUfgCfuUfuUfgUfL96 | 876 | 3602 | | asCfsaAfaAfgCfaAfaacAfgGfuCfuAfsgsa | 1427 |
| AD-59242.1 | | AfsgsAfcCfuGfUfUfuUfgCfuUfuUfgUfL96 | 877 | 3602 | | asCfsaAfaAfgCfaAfaacAfgGfuCfuAfsgsa | 1428 |
| AD-59253.1 | | usAfsgAfcCfuGfUfUfuUfgCfuUfuUfgUfL96 | 878 | 3602 | | asCfsaAfaAfgCfaAfaacAfgGfuCfuAfsgsa | 1429 |
| AD-59258.1 | | usasgAfcCfuGfUfUfuUfgCfuUfuUfgUfL96 | 879 | 3602 | | asCfsaAfaAfgCfaAfaacAfgGfuCfuAfsgsa | 1430 |
| AD-59251.1 | | CfsusAfgAfcCfuGfUfUfuUfgCfuUfuUfgUfL96 | 880 | 3603 | | asCfsaAfaAfgCfaAfaacAfgGfuCfusAfsg | 1431 |
| AD-59256.1 | | usAfsgAfcCfuGfUfUfuUfgCfuUfuUfgUfL96 | 881 | 3604 | | asCfsaAfaAfgCfaAfaacAfgGfuCfsusAf | 1432 |
| AD-59260.1 | | AfsgsAfcCfuGfUfUfuUfgCfuUfuUfgUfL96 | 882 | 3605 | | asCfsaAfaAfgCfaAfaacAfgGfusCfsu | 1433 |
| AD-59248.1 | | gsAfscCfuGfUfUfuUfgCfuUfuUfgUfL96 | 883 | 3605 | | asCfsaAfaAfgCfaAfaacAfgGfusCfsu | 1434 |
| AD-59247.1 | | gsAfscCfuGfUfUfuUfgCfuUfuUfgUfL96 | 884 | 3604 | | asCfsaAfaAfgCfaAfaacAfgGfuCfsusa | 1435 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| AD-59252.1 | | AfsgsAfcCfuGfUfUfuUfgCfuUfuUfgUfL96 | 885 | 3604 | | asCfsaAfaAfgCfaAfaacAfgGfuCfsusa | 1436 |
| AD-59257.1 | | usAfsgAfcCfuGfUfUfuUfgCfuUfuUfgUfL96 | 886 | 3604 | | asCfsaAfaAfgCfaAfaacAfgGfuCfsusa | 1437 |
| AD-59261.1 | | AfsgsAfcCfuGfUfUfuUfgCfuUfuUfgUfL96 | 887 | 3603 | | asCfsaAfaAfgCfaAfaacAfgGfuCfusasg | 1438 |
| AD-59262.1 | | usAfsgAfcCfuGfUfUfuUfgCfuUfuUfgUfL96 | 888 | 3603 | | asCfsaAfaAfgCfaAfaacAfgGfuCfusasg | 1439 |
| AD-59265.1 | | csusAfgAfcCfuGfUfUfuUfgCfuUfuUfgUfL96 | 889 | 3603 | | asCfsaAfaAfgCfaAfaacAfgGfuCfusasg | 1440 |
| AD-59196.13 | | usAfsgAfcCfuGfUfUfuUfgCfuUfuUfgUfL96 | 890 | 3601 | | asCfsaAfaAfgCfaAfaacAfgGfuCfuAfgsasa | 1441 |
| AD-59189.11 | | AfsgsAfcCfuGfUfUfuUfgCfuUfuUfgUfL96 | 891 | 3601 | | asCfsaAfaAfgCfaAfaacAfgGfuCfuAfgsasa | 1442 |
| AD-59190.3 | | usCfsuAfgAfcCfuGfUfUfuUfgCfuUfuUfgUfL96 | 892 | 3601 | | asCfsaAfaAfgCfaAfaacAfgGfuCfuAfgsasa | 1443 |
| AD-59192.3 | | UfsusCfuAfgAfcCfuGfUfUfuUfgCfuUfuUfgUfL96 | 893 | 3601 | | asCfsaAfaAfgCfaAfaacAfgGfuCfuAfgsasa | 1444 |
| AD-59240.1 | | CfsusAfgAfcCfuGfuuuugCfuuuuguL96 | 894 | 3601 | | asCfsaAfaAfsgCfaAfaacAfgGfuCfuAfgs(A3m)a | 1445 |
| AD-59244.1 | | CfsusAfgAfcCfuGfuuuugCfuuuuguL96 | 895 | 3601 | | asCfsaAfaAfsgCfaAfaacAfgGfuCfuAfgsasa | 1446 |
| AD-59202.7 | | (C3m)usagaccuguuuugcuuuuguL96 | 896 | 3601 | | asCfsaAfaAfgCfaAfaacAfgGfuCfuAfgsasa | 1447 |
| AD-59195.5 | | (C3m)usAfgAfcCfuGfuuuugCfuuuuguL96 | 897 | 3601 | | asCfsaAfaAfgCfaAfaacAfgGfuCfuAfgsasa | 1448 |
| AD-59249.1 | | CfsusAfgAfcCfuGfUfUfuugCfuuuuguL96 | 898 | 3601 | | asCfsaAfaAfgCfaAfaacAfgGfuCfuAfgs(A3m)a | 1449 |
| AD-59254.1 | | CfsusAfgAfcCfuGfuuuugCfuuuuguL96 | 899 | 3601 | | asCfsaAfaAfgCfaAfaacAfgGfuCfuAfgs(A3m)a | 1450 |
| AD-59259.1 | | (C3m)usAfgAfcCfuGfuuuugCfuuuuguL96 | 900 | 3601 | | asCfsaAfaAfgCfaAfaacAfgGfuCfuAfgs(A3m)a | 1451 |
| AD-59264.1 | | (C3m)usagaccuguuuugcuuuuguL96 | 901 | 3601 | | asCfsaAfaAfgCfaAfaacAfgGfuCfuAfgs(A3m)a | 1452 |
| AD-59264.2 | | (C3m)usagaccuguuuugcuuuuguL96 | 902 | 3601 | | asCfsaAfaAfgCfaAfaacAfgGfuCfuAfgs(A3m)a | 1453 |
| AD-59255.1 | | CsusagaccuGfUfUfuugcuuuuguL96 | 903 | 3601 | | asCfsaAfaAfgCfaAfaacAfgGfuCfuAfgs(A3m)a | 1454 |
| AD-57928.1 | | CfsusAfgAfcCfuGfUfUfuUfgCfuUfuUfgUfL96 | 904 | 3601 | | asCfsaAfaAfgCfaAfaacAfgGfuCfuAfgsasa | 1455 |
| AD-58893.1 | | CfsuAfgAfcCfuGfUfUfuUfgCfuUfuUfgUfL96 | 905 | 3601 | | asCfaAfaAfgCfaAfaacAfgGfuCfuAfgasa | 1456 |
| AD-58894.1 | | CfusAfgAfcCfuGfUfUfuUfgCfuUfuUfgUfL96 | 906 | 3601 | | aCfsaAfaAfgCfaAfaacAfgGfuCfuAfgsaa | 1457 |
| AD-58895.1 | | CfuAfgAfcCfuGfUfUfuUfgCfuUfuUfgUfL96 | 907 | 3601 | | asCfsaAfaAfgCfaAfaacAfgGfuCfuAfgsasa | 1458 |

TABLE 2-continued

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| PCSK9- modified sequences | | | | | | | |
| AD-58896.1 | | CfsusAfgAfcCfuGfUfUfuUfgCfuUfuUfgUfL96 | 908 | 3601 | | aCfaAfaAfgCfaAfaacAfgGfuCfuAfgaa | 1459 |
| AD-58897.1 | | CfsusAfsgAfcCfuGfUfUfuUfgCfuUfuUfgUfL96 | 909 | 3601 | | asCfsasAfaAfgCfaAfaacAfgGfuCfuAfsgsasa | 1460 |
| AD-58898.1 | | CfsusAfsgAfcCfuGfUfUfuUfgCfuUfuUfgUfL96 | 910 | 3601 | | asCfsaAfaAfgCfsaAfaacAfsgGfuCfuAfsgsasa | 1461 |
| AD-58899.1 | | CfsusAfsgAfcCfuGfUfUfuUfgCfuUfuUfsgUfL96 | 911 | 3601 | | asCfsaAfaAfgCfsaAfaacAfsgGfuCfuAfsgsasa | 1462 |
| AD-58900.1 | | CfsasAfgCfaGfaCfAfUfuUfaUfcUfuUfuUfL96 | 912 | NA | | asAfsaAfaGfaUfaAfaugUfcUfgCfuUfgscsu | 1463 |
| AD-58902.1 | | UfsusUfuCfuAfgAfCfCfuGfuUfuUfgCfuUfL96 | 913 | 3597 | | asAfsgCfaAfaAfcAfgguCfuAfgAfaAfasgsu | 1464 |
| | | (A3mx)(G3mx)AfcCfuGfUfUfuUfgCfuUfuUfgUfL96 | 914 | | | asCfsaAfaAfgCfaAfaacAfgGfuCfusasg | 1465 |
| | | (A3mx)(G3mx)AfcCfuGfUfUfuUfgCfuUfuUfgUfL96 | 915 | | | (A3mx)CfaAfaAfgCfaAfaacAfgGfuCfusasg | 1466 |
| | | (A3mx)(G3mx)AfcCfuGfUfUfuUfgCfuUfuUfgUfL96 | 916 | | | (A3mx)CfaAfaAfgCfaAfaacAfgGfuCfu(A3mx)g | 1467 |
| | | (A3mx)gAfcCfuGfUfUfuUfgCfuUfuUfgUfL96 | 917 | | | asCfsaAfaAfgCfaAfaacAfgGfuCfusasg | 1468 |
| | | (A3mx)gAfcCfuGfUfUfuUfgCfuUfuUfgUfL96 | 918 | | | (A3mx)CfaAfaAfgCfaAfaacAfgGfuCfusasg | 1469 |
| | | (A3mx)gAfcCfuGfUfUfuUfgCfuUfuUfgUfL96 | 919 | | | (A3mx)CfaAfaAfgCfaAfaacAfgGfuCfu(A3mx)g | 1470 |
| | | (C3mx)(U3mx)AfgAfcCfuGfUfUfuUfgCfuUfuUfgUfL96 | 920 | | | asCfsaAfaAfgCfaAfaacAfgGfuCfuAfgsasa | 1471 |
| | | (C3mx)(U3mx)AfgAfcCfuGfUfUfuUfgCfuUfuUfgUfL96 | 921 | | | (A3mx)CfaAfaAfgCfaAfaacAfgGfuCfuAf(G3mx)(A3mx)a | 1472 |
| | | (C3mx)uAfgAfcCfuGfUfUfuUfgCfuUfuUfgUfL96 | 922 | | | asCfsaAfaAfgCfaAfaacAfgGfuCfuAfgsasa | 1473 |
| | | (C3mx)uAfgAfcCfuGfUfUfuUfgCfuUfuUfgUfL96 | 923 | | | (A3mx)CfaAfaAfgCfaAfaacAfgGfuCfuAfgsasa | 1474 |
| | | (C3mx)uAfgAfcCfuGfUfUfuUfgCfuUfuUfgUfL96 | 924 | | | (A3mx)CfaAfaAfgCfaAfaacAfgGfuCfuAfg(A3mx)a | 1475 |
| | | (C3mx)uAfgAfcCfuGfUfUfuUfgCfuUfuUfgUfL96 | 925 | | | (A3mx)CfaAfaAfgCfaAfaacAfgGfuCfuAf(G3mx)(A3mx)a | 1476 |
| | | (C3mx)usAfgAfcCfuGfUfUfuUfgCfuUfuUfgUfL96 | 926 | | | asCfsaAfaAfgCfaAfaacAfgGfuCfuAfgsasa | 1477 |
| | | (Chd)susAfgAfcCfuGfUfUfuUfgCfuUfuUfgUfL96 | 927 | | | asCfsaAfaAfgCfaAfaacAfgGfuCfuAfgsasa | 1478 |
| | | (phe)CfsuAfgAfcCfuGfUfUfuUfgCfuUfuUfgUfL96 | 928 | | | asCfsaAfaAfgCfaAfaacAfgGfuCfuAfgsasa | 1479 |
| | | (phe)CfuAfgAfcCfuGfUfUfuUfgCfuUfuUfgUfL96 | 929 | | | asCfsaAfaAfgCfaAfaacAfgGfuCfuAfgsasa | 1480 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| | | (pshe)CfsuAfgAfcCfuGfUfUfuUfgCfuUfuUfgUfL96 | 930 | | | asCfsaAfaAfgCfaAfaacAfgGfuCfuAfgsasa | 1481 |
| | | (pshe)CfuAfgAfcCfuGfUfUfuUfgCfuUfuUfgUfL96 | 931 | | | asCfsaAfaAfgCfaAfaacAfgGfuCfuAfgsasa | 1482 |
| | | AfsgsAfcCfuGfUfUfuUfgCfuUfuUfgUfL96 | 932 | | | (A3mx)CfaAfaAfgCfaAfaacAfgGfuCfusasg | 1483 |
| | | AfsgsAfcCfuGfUfUfuUfgCfuUfuUfgUfL96 | 933 | | | (A3mx)CfaAfaAfgCfaAfaacAfgGfuCfu(A3mx)g | 1484 |
| | | Cfs(Uhd)sAfgAfcCfuGfUfUfuUfgCfuUfuUfgUfL96 | 934 | | | asCfsaAfaAfgCfaAfaacAfgGfuCfuAfgsasa | 1485 |
| | | CfsusAfgAf(Chd)CfuGfUfUfuUfgCfuUfuUfgUfL96 | 935 | | | asCfsaAfaAfgCfaAfaacAfgGfuCfuAfgsasa | 1486 |
| | | CfsusAfgAfc(Chd)uGfUfUfuUfgCfuUfuUfgUfL96 | 936 | | | asCfsaAfaAfgCfaAfaacAfgGfuCfuAfgsasa | 1487 |
| | | CfsusAfgAfcCf(Uhd)GfUfUfuUfgCfuUfuUfgUfL96 | 937 | | | asCfsaAfaAfgCfaAfaacAfgGfuCfuAfgsasa | 1488 |
| | | CfsusAfgAfcCfuGfUfUf(Uhd)UfgCfuUfuUfgUfL96 | 938 | | | asCfsaAfaAfgCfaAfaacAfgGfuCfuAfgsasa | 1489 |
| | | CfsusAfgAfcCfuGfUfUfuUf(Ggn)CfuUfuUfgUfL96 | 939 | | | asCfsaAfaAfgCfaAfaacAfgGfuCfuAfgsasa | 1490 |
| | | CfsusAfgAfcCfuGfUfUfuUfg(Cgn)uUfuUfgUfL96 | 940 | | | asCfsaAfaAfgCfaAfaacAfgGfuCfuAfgsasa | 1491 |
| | | CfsusAfgAfcCfuGfUfUfuUfg(Chd)uUfuUfgUfL96 | 941 | | | asCfsaAfaAfgCfaAfaacAfgGfuCfuAfgsasa | 1492 |
| | | CfsusAfgAfcCfuGfUfUfuUfgCf(Tgn)UfuUfgUfL96 | 942 | | | asCfsaAfaAfgCfaAfaacAfgGfuCfuAfgsasa | 1493 |
| | | CfsusAfgAfcCfuGfUfUfuUfgCf(Uhd)UfuUfgUfL96 | 943 | | | asCfsaAfaAfgCfaAfaacAfgGfuCfuAfgsasa | 1494 |
| | | CfsusAfgAfcCfuGfUfUfuUfgCfu(Tgn)uUfgUfL96 | 944 | | | asCfsaAfaAfgCfaAfaacAfgGfuCfuAfgsasa | 1495 |
| | | CfsusAfgAfcCfuGfUfUfuUfgCfuUf(Tgn)UfgUfL96 | 945 | | | asCfsaAfaAfgCfaAfaacAfgGfuCfuAfgsasa | 1496 |
| | | CfsusAfgAfcCfuGfUfUfuUfgCfuUf(Uhd)UfgUfL96 | 946 | | | asCfsaAfaAfgCfaAfaacAfgGfuCfuAfgsasa | 1497 |
| | | CfsusAfgAfcCfuGfUfUfuUfgCfuUfu(Tgn)gUfL96 | 947 | | | asCfsaAfaAfgCfaAfaacAfgGfuCfuAfgsasa | 1498 |
| | | CfsusAfgAfcCfuGfUfUfuUfgCfuUfu(Uhd)gUfL96 | 948 | | | asCfsaAfaAfgCfaAfaacAfgGfuCfuAfgsasa | 1499 |
| | | CfsusAfgAfcCfuGfUfUfuUfgCfuUfuUf(Ggn)UfL96 | 949 | | | asCfsaAfaAfgCfaAfaacAfgGfuCfuAfgsasa | 1500 |
| | | CfsusAfgAfcCfuGfUfUfuUfgCfuUfuUfg(Tgn)L96 | 950 | | | asCfsaAfaAfgCfaAfaacAfgGfuCfuAfgsasa | 1501 |
| | | CfsusAfgAfcCfuGfUfUfuUfgCfuUfuUfg(Uhd)L96 | 951 | | | asCfsaAfgAfgCfaAfaacAfgGfuCfuAfgsasa | 1502 |
| | | CfsusAfgAfcCfuGfUfUfuUfgCfuUfuUfgUfL96 | 952 | | | asCfsaAfaAfgCfaAfaacAfgGfuCfuAfgsasa | 1503 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| | | CfsusAfgAfcCfuGfUfUfuUfgCfuUfuUfgUfL96 | 953 | | | (Agn)CfsaAfaAfgCfaAfaacAfgGfuCfuAfgsasa | 1504 |
| | | CfsusAfgAfcCfuGfUfUfuUfgCfuUfuUfgUfL96 | 954 | | | (Agn)CfaAfaAfgCfaAfaacAfgGfuCfuAfgsasa | 1505 |
| | | CfsusAfgAfcCfuGfUfUfuUfgCfuUfuUfgUfL96 | 955 | | | P(Agn)CfaAfaAfgCfaAfaacAfgGfuCfuAfgsasa | 1506 |
| | | CfsusAfgAfcCfuGfUfUfuUfgCfuUfuUfgUfL96 | 956 | | | as(Cgn)aAfaAfgCfaAfaacAfgGfuCfuAfgsasa | 1507 |
| | | CfsusAfgAfcCfuGfUfUfuUfgCfuUfuUfgUfL96 | 957 | | | asCfs(Agn)AfaAfgCfaAfaacAfgGfuCfuAfgsasa | 1508 |
| | | CfsusAfgAfcCfuGfUfUfuUfgCfuUfuUfgUfL96 | 958 | | | asCfsa(Agn)aAfgCfaAfaacAfgGfuCfuAfgsasa | 1509 |
| | | CfsusAfgAfcCfuGfUfUfuUfgCfuUfuUfgUfL96 | 959 | | | asCfsaAf(Agn)AfgCfaAfaacAfgGfuCfuAfgsasa | 1510 |
| | | CfsusAfgAfcCfuGfUfUfuUfgCfuUfuUfgUfL96 | 960 | | | asCfsaAfa(Agn)gCfaAfaacAfgGfuCfuAfgsasa | 1511 |
| | | CfsusAfgAfcCfuGfUfUfuUfgCfuUfuUfgUfL96 | 961 | | | asCfsaAfaAf(Ggn)CfaAfaacAfgGfuCfuAfgsasa | 1512 |
| | | CfsusAggAfcCfuGfUfUfuUfgCfuUfuUfgUfL96 | 962 | | | asCfsaAfaAfg(Cgn)aAfaacAfgGfuCfuAfgsasa | 1513 |
| | | CfsusAfgAfcCfuGfUfUfuUfgCfuUfuUfgUfL96 | 963 | | | asCfsaAfaAfgCf(Agn)AfaacAfgGfuCfuAfgsasa | 1514 |
| | | CfsusAfgAfcCfuGfUfUfuUfgCfuUfuUfgUfL96 | 964 | | | asCfsaAfaAfgCfa(Agn)aacAfgGfuCfuAfgsasa | 1515 |
| | | CfsusAfgAfcCfuGfUfUfuUfgCfuUfuUfgUfL96 | 965 | | | asCfsaAfaAfgCfaAf(Agn)acAfgGfuCfuAfgsasa | 1516 |
| | | CfsusAfgAfcCfuGfUfUfuUfgCfuUfuUfgUfL96 | 966 | | | asCfsaAfaAfgCfaAfa(Agn)cAfgGfuCfuAfgsasa | 1517 |
| | | CfsusAfgAfcCfuGfUfUfuUfgCfuUfuUfgUfL96 | 967 | | | asCfsaAfaAfgCfaAfaa(Cgn)AfgGfuCfuAfgsasa | 1518 |
| | | CfsusAfgAfcCfuGfUfUfuUfgCfuUfuUfgUfL96 | 968 | | | asCfsaAfaAfiCfaAfaacAfiGfuCfuAfisasa | 1519 |
| | | CfsusAfgAfcCfuGfUfUfuUfgCfuUfuUfgUfL96 | 969 | | | asCfsaAfaAfgCfaAfaacAfgGfuCfuAfg(A3mx)a | 1520 |
| | | CfsusAfgAfcCfuGfUfUfuUfgCfuUfuUfgUfL96 | 970 | | | asCfsaAfaAfgCfaAfaacAfgGfuCfuAfgs(A3mx)a | 1521 |
| | | CfsusAfgAfcCfuGfUfUfuUfgCfuUfuUfgUfL96 | 971 | | | asCfsaAfaAfgCfaAfaacAfgGfuCfuAf(G3mx)(A3mx)a | 1522 |
| | | CfsusAfgAfcCfuGfUfUfuUfgCfuUfuUfgUfL96 | 972 | | | (A3mx)CfaAfaAfgCfaAfaacAfgGfuCfuAfgsasa | 1523 |
| | | CfsusAfgAfcCfuGfUfUfuUfgCfuUfuUfgUfL96 | 973 | | | (A3mx)CfsaAfaAfgCfaAfaacAfgGfuCfuAfgsasa | 1524 |
| | | CfsusAfgAfcCfuGfUfUfuUfgCfuUfuUfgUfL96 | 974 | | | P(A3mx)CfaAfaAfgCfaAfaacAfgGfuCfuAfgsasa | 1525 |

TABLE 2-continued

| PCSK9- modified sequences | | | | | | | |
|---|---|---|---|---|---|---|---|
| Duplex Name | Sense Oligo Name | Sense Oligo Sequence | SEQ ID NO: | Position relative to NM_ 174936.3 | Antisense Oligo | Antisense Oligo Sequence | SEQ ID NO: |
| | | CfsusAfgAfcCfuGfUfUfuUfgCfuUfuUfgUfL96 | 975 | | | a(C3mx)aAfaAfgCfaAfaacAfgGfuCfuAfgsasa | 1526 |
| | | CfsusAfgAfcCfuGfUfUfuUfgCfuUfuUfgUfL96 | 976 | | | as(C3mx)aAfaAfgCfaAfaacAfgGfuCfuAfgsasa | 1527 |
| | | CfsusAfgAfcCfuGfUfUfuUfgCfuUfuUfgUfL96 | 977 | | | (A3mx)<br>(C3mx)aAfaAfgCfaAfaacAfgGfuCfuAfgsasa | 1528 |
| | | CfsusAfgAfcCfuGfUfUfuUfgCfuUfuUfgUfL96 | 978 | | | (A3mx)CfaAfaAfgCfaAfaacAfgGfuCfuAfg<br>(A3mx)a | 1529 |
| | | CfsusAfgAfcCfuGfUfUfuUfgCfuUfuUfgUfL96 | 979 | | | (A3mx)CfsaAfaAfgCfaAfaacAfgGfuCfuAfgs<br>(A3mx)a | 1530 |
| | | CfsusAfgAfcCfuGfUfUfuUfgCfuUfuUfgUfL96 | 980 | | | (A3mx)CfaAfaAfgCfaAfaacAfgGfuCfuAf(G3mx)<br>(A3mx)a | 1531 |
| | | CfsusAfgAfcCfuGfUfUfuUfgCfuUfuUfgUfL96 | 981 | | | asCfsaAfaAfgCfaAfaacAfgGfuCfuAfgasas(phe) | 1532 |
| | | CfsusAfgAfcCfuGfUfUfuUfgCfuUfuUfgUfL96 | 982 | | | asCfsaAfaAfgCfaAfaacAfgGfuCfuAfgaas(phe) | 1533 |
| | | CfsusAfgAfcCfuGfUfUfuUfgCfuUfuUfgUfL96 | 983 | | | asCfsaAfaAfgCfaAfaacAfgGfuCfuAfgaa(phe) | 1534 |
| | | CfsusAfgAfcCfuGfUfUfuUfgCfuUfuUfgUfL96 | 984 | | | asCfsaAfaAfgCfaAfaacAfgGfuCfuAfgsas(phe) | 1535 |
| | | CfsusAfgAfcCfuGfUfUfuUfgCfuUfuUfgUfL96 | 985 | | | asCfsaAfaAfgCfaAfaacAfgGfuCfuAfgas(phe) | 1536 |
| | | CfsusAfgAfcCfuGfUfUfuUfgCfuUfuUfgUfL96 | 986 | | | asCfsaAfaAfgCfaAfaacAfgGfuCfuAfga(phe) | 1537 |
| | | CfsusAfgAfcCfuGfUfUfuUfgCfuUfuUfgUfL96 | 987 | | | asCfsaAfaAfgCfaAfaacAfgGf(Uhd)CfuAfgsasa | 1538 |
| | | CfsusAfgAfcCfuGfUfUfuUfgCfuUfuUfgUfL96 | 988 | | | asCfsaAfaAfgCfaAfaacAfgGfuCf(Uhd)Afgsasa | 1539 |
| | | CfsusAfgAfcCfuGfUfUfuUfgCfuUfuUfgUfL96 | 989 | | | asCfsaAfaAfg(Chd)aAfaacAfgGfuCfuAfgsasa | 1540 |
| | | CfsusAfgAfcCfuGfUfUfuUfgCfuUfuUfgUfL96 | 990 | | | asCfsaAfaagCfaAfaacAfgGfucuAfgsasa | 1541 |
| | | CfsusAfgAfcCfuGfUfUfuUfgCfuUfuUfguL96 | 991 | | | asCfsaAfaAfgCfaAfaacAfgGfuCfuAfgsasa | 1542 |
| | | CfsusAfgAfcCfuGfUfUfuUfgCfuUfuUfguL96 | 992 | | | asCfsaAfaagCfaAfaacAfgGfucuAfgsasa | 1543 |
| | | CfsusAfgAfcCfuGfUfUfuUfgCfuUfuugUfL96 | 993 | | | asCfsaAfaAfgCfaAfaacAfgGfuCfuAfgsasa | 1544 |
| | | CfsusAfgAfcCfuGfUfUfuUfgCfuUfuugUfL96 | 994 | | | asCfsaAfaagCfaAfaacAfgGfucuAfgsasa | 1545 |
| | | CfsusAfgAfcCfuGfUfUfuUfgCfuUfuuguL96 | 995 | | | asCfsaAfaAfgCfaAfaacAfgGfuCfuAfgsasa | 1546 |

TABLE 2-continued

PCSK9- modified sequences

| Duplex Name | Sense Oligo Name | Sense Oligo Sequence | SEQ ID NO: | Position relative to NM_ 174936.3 | Antisense Oligo | Antisense Oligo Sequence | SEQ ID NO: |
|---|---|---|---|---|---|---|---|
| | | CfsusAfgAfcCfuGfUfUfuUfgCfuUfuuguL96 | 996 | | | asCfsaAfaagCfaAfaacAfgGfucuAfgsasa | 1547 |
| | | CfsusAfgAfcCfuGfUfUfuUfgcuuuugUfL96 | 997 | | | asCfsaAfaAfgCfaAfaacAfgGfuCfuAfgsasa | 1548 |
| | | CfsusAfgAfcCfuGfUfUfuUfgcuuuugUfL96 | 998 | | | asCfsaAfaagCfaAfaacAfgGfucuAfgsasa | 1549 |
| | | CfsusAfgAfcCfuGfUfUfuUfgcuuuuguL96 | 999 | | | asCfsaAfaAfgCfaAfaacAfgGfuCfuAfgsasa | 1550 |
| | | CfsusAfgAfcCfuGfUfUfuUfgcuuuuguL96 | 1000 | | | asCfsaAfaagCfaAfaacAfgGfucuAfgsasa | 1551 |
| | | CfsusAfgAfcCfuGfUfUfuUfgUfuUfuUfgUfL96 | 1001 | | | asCfsaAfaAfgCfaAfaacAfgGfuCfuAfgsasa | 1552 |
| | | CfsusAfgAfcCfuGfUfUfuUfiCfuUfuUfiUfL96 | 1002 | | | asCfsaAfaAfgCfaAfaacAfgGfuCfuAfgsasa | 1553 |
| | | CfsusAfgAfcCfuGfUfUfuUfiCfuUfuUfiUfL96 | 1003 | | | asCfsaAfaAfiCfaAfaacAfgGfuCfuAfgsasa | 1554 |
| | | CfsusAfgAfcCfuGfUfUfuUfiCfuUfuUfiUfL96 | 1004 | | | asCfsaAfaAfiCfaAfaacAfiGfuCfuAfisasa | 1555 |
| | | CfsusAfiAfcCfuGfUfUfuUfiCfuUfuUfiUfL96 | 1005 | | | asCfsaAfaAfiCfaAfaacAfiGfuCfuAfisasa | 1556 |

Example 2. In Vitro and In Vivo Screening

A subset of these duplexes was evaluated for efficacy in single dose free uptake assays in *Cynomolgus* monkey hepatocytes. Briefly, primary *Cynomolgus* monkey hepatocytes (PCH) were treated with the conjugated modified siRNA duplexes at three concentrations, 500 nM, 100 nM and 10 nM. The 100 nM and 10 nM free uptake assays were performed twice and the data are represented as average message remaining relative to control +/− the standard deviation (SD). The 500 nM screen was performed a single time. Table 3 shows the results of these assays.

TABLE 3

PCSK9 efficacy screen by free uptake in primary Cynomolgous monkey hepatocytes.

| DUPLEX ID | PCH 500 nM | PCH 100 nM Avg | PCH 10 nM Avg | PCH 100 nM SD | PCH 10 nM SD |
|---|---|---|---|---|---|
| AD-48399 | 1.08 | 1.03 | 0.98 | 0.09 | 0.02 |
| AD-48399 | 0.97 | 0.95 | 1.10 | 0.03 | 0.09 |
| AD-48399 | 0.89 | 0.98 | 1.02 | 0.06 | 0.06 |
| AD-48399 | 1.04 | 1.00 | 1.01 | 0.02 | 0.08 |
| AD-48399 | 0.92 | 1.03 | 0.96 | 0.02 | 0.09 |
| AD-48399 | 1.13 | 1.03 | 0.96 | 0.05 | 0.01 |
| AD-48400 | 0.48 | 0.63 | 0.90 | 0.04 | 0.00 |
| AD-48400.4 | 0.65 | 0.78 | 0.89 | 0.14 | 0.13 |
| AD-53649.1 | 0.96 | 0.96 | 1.14 | 0.02 | 0.07 |
| AD-53650.1 | 0.97 | 0.92 | 1.15 | 0.01 | 0.06 |
| AD-53651.1 | 1.02 | 0.98 | 1.15 | 0.13 | 0.10 |
| AD-53652.1 | 0.83 | 0.89 | 1.14 | 0.20 | 0.05 |
| AD-53653.1 | 0.85 | 0.95 | 1.26 | 0.04 | 0.07 |
| AD-53654.1 | 0.84 | 0.93 | 1.19 | 0.02 | 0.13 |
| AD-53656.1 | 0.92 | 0.92 | 1.07 | 0.05 | 0.03 |
| AD-53657.1 | 0.92 | 0.89 | 1.02 | 0.05 | 0.03 |
| AD-53658.1 | 0.89 | 0.83 | 0.97 | 0.04 | 0.14 |
| AD-53659.1 | 0.79 | 0.82 | 1.05 | 0.06 | 0.13 |
| AD-53660.1 | 0.89 | 0.86 | 0.98 | 0.07 | 0.07 |
| AD-53661.1 | 0.92 | 1.03 | 1.07 | 0.02 | 0.04 |
| AD-53663.1 | 0.88 | 0.90 | 1.08 | 0.03 | 0.02 |
| AD-53664.1 | 0.95 | 0.86 | 1.00 | 0.09 | 0.13 |
| AD-53665.1 | 0.92 | 0.91 | 1.05 | 0.01 | 0.13 |
| AD-53666.1 | 0.73 | 0.80 | 0.95 | 0.08 | 0.02 |
| AD-53667.1 | 0.95 | 0.96 | 1.12 | 0.06 | 0.03 |
| AD-53668.1 | 1.03 | 0.89 | 1.17 | 0.03 | 0.12 |
| AD-53669.1 | 1.12 | 0.90 | 1.05 | 0.01 | 0.15 |
| AD-53670.1 | 0.85 | 0.88 | 1.00 | 0.06 | 0.06 |
| AD-53671.1 | 0.87 | 0.90 | 0.93 | 0.02 | 0.04 |
| AD-53672.1 | 0.87 | 0.86 | 0.95 | 0.04 | 0.16 |
| AD-53674.1 | 0.69 | 0.75 | 0.92 | 0.08 | 0.02 |
| AD-53675.1 | 0.99 | 0.92 | 1.17 | 0.11 | 0.06 |
| AD-53676.1 | 0.90 | 0.87 | 1.10 | 0.03 | 0.08 |
| AD-53677.1 | 1.22 | 0.86 | 1.12 | 0.10 | 0.04 |
| AD-53678.1 | 1.01 | 0.98 | 1.03 | 0.03 | 0.12 |
| AD-53679.1 | 0.96 | 0.85 | 1.02 | 0.04 | 0.11 |
| AD-53680.1 | 1.21 | 0.94 | 0.99 | 0.03 | 0.01 |
| AD-53681.1 | 1.02 | 0.94 | 1.01 | 0.01 | 0.11 |
| AD-53682.1 | 0.98 | 0.90 | 1.01 | 0.06 | 0.11 |
| AD-53683.1 | 0.95 | 0.90 | 1.01 | 0.02 | 0.08 |
| AD-53684.1 | 1.14 | 1.01 | 1.01 | 0.09 | 0.07 |
| AD-53685.1 | 0.96 | 0.92 | 1.03 | 0.00 | 0.07 |
| AD-53687.1 | 1.31 | 0.91 | 1.02 | 0.02 | 0.11 |
| AD-53688.1 | 0.90 | 0.95 | 0.96 | 0.03 | 0.03 |
| AD-53689.1 | 0.97 | 0.95 | 1.05 | 0.04 | 0.07 |
| AD-53690.1 | 0.82 | 0.97 | 0.99 | 0.13 | 0.08 |
| AD-53691.1 | 0.99 | 1.01 | 0.97 | 0.01 | 0.12 |
| AD-53692.1 | 1.11 | 0.91 | 1.00 | 0.04 | 0.03 |
| AD-53693.1 | 1.02 | 0.96 | 1.02 | 0.04 | 0.10 |
| AD-53694.1 | 1.12 | 0.98 | 0.97 | 0.07 | 0.06 |
| AD-53695.1 | 0.97 | 1.04 | 0.94 | 0.11 | 0.08 |
| AD-53696.1 | 0.85 | 0.91 | 1.23 | 0.10 | 0.01 |
| AD-53697.1 | 0.89 | 0.91 | 1.06 | 0.03 | 0.00 |
| AD-53698.1 | 0.90 | 0.86 | 1.15 | 0.06 | 0.01 |
| AD-53699.1 | 0.84 | 0.85 | 1.07 | 0.00 | 0.03 |
| AD-53700.1 | 0.93 | 1.02 | 1.21 | 0.02 | 0.15 |
| AD-53701.1 | 1.01 | 0.96 | 1.12 | 0.00 | 0.17 |
| AD-53702.1 | 0.95 | 0.94 | 1.06 | 0.05 | 0.15 |

TABLE 3-continued

PCSK9 efficacy screen by free uptake in primary Cynomolgous monkey hepatocytes.

| DUPLEX ID | PCH 500 nM | PCH 100 nM Avg | PCH 10 nM Avg | PCH 100 nM SD | PCH 10 nM SD |
|---|---|---|---|---|---|
| AD-53703.1 | 0.82 | 0.85 | 1.04 | 0.07 | 0.13 |
| AD-53704.1 | 0.92 | 0.97 | 0.94 | 0.04 | 0.02 |
| AD-53705.1 | 0.96 | 0.98 | 1.00 | 0.11 | 0.15 |
| AD-53706.1 | 0.90 | 0.97 | 1.03 | 0.01 | 0.20 |
| AD-53707.1 | 0.86 | 0.98 | 1.11 | 0.14 | 0.24 |
| AD-53708.1 | 1.10 | 0.94 | 1.05 | 0.02 | 0.15 |
| AD-53709.1 | 0.79 | 0.84 | 1.08 | 0.01 | 0.18 |
| AD-53710.1 | 1.03 | 0.91 | 1.06 | 0.01 | 0.09 |
| AD-53711.1 | 0.90 | 0.90 | 0.99 | 0.00 | 0.28 |
| AD-53712.1 | 0.97 | 0.92 | 0.97 | 0.00 | 0.12 |
| AD-53713.1 | 0.98 | 0.93 | 1.07 | 0.01 | 0.16 |
| AD-53714.1 | 1.09 | 0.86 | 0.99 | 0.03 | 0.09 |
| AD-53715.1 | 1.04 | 0.83 | 0.94 | 0.06 | 0.06 |
| AD-53716.1 | 0.82 | 0.85 | 1.02 | 0.05 | 0.14 |
| AD-53717.1 | 0.98 | 0.94 | 0.98 | 0.11 | 0.12 |
| AD-53718.1 | 0.89 | 1.04 | 1.01 | 0.18 | 0.01 |
| AD-53719.1 | 0.98 | 1.05 | 1.05 | 0.06 | 0.17 |
| AD-53720.1 | 1.02 | 0.88 | 1.08 | 0.01 | 0.15 |
| AD-53721.1 | 0.88 | 0.95 | 1.03 | 0.07 | 0.11 |
| AD-53722.1 | 0.98 | 0.95 | 1.01 | 0.06 | 0.12 |
| AD-53723.1 | 0.89 | 0.89 | 1.02 | 0.10 | 0.06 |
| AD-53724.1 | 0.98 | 0.93 | 1.00 | 0.13 | 0.01 |
| AD-53725.1 | 1.04 | 1.05 | 1.09 | 0.19 | 0.11 |
| AD-53726.1 | 0.87 | 0.88 | 0.88 | 0.00 | 0.02 |
| AD-53727.1 | 0.82 | 0.92 | 1.02 | 0.05 | 0.13 |
| AD-53728.1 | 0.86 | 0.93 | 1.06 | 0.03 | 0.08 |
| AD-53729.1 | 0.86 | 0.81 | 1.02 | 0.12 | 0.03 |
| AD-53730.1 | 1.01 | 0.95 | 1.02 | 0.07 | 0.01 |
| AD-53731.1 | 0.99 | 0.98 | 1.00 | 0.08 | 0.07 |
| AD-53732.1 | 0.93 | 0.86 | 1.01 | 0.12 | 0.11 |
| AD-53733.1 | 1.06 | 1.02 | 1.08 | 0.05 | 0.06 |
| AD-53734.1 | 0.95 | 0.93 | 1.04 | 0.12 | 0.05 |
| AD-53735.1 | 1.00 | 0.93 | 1.01 | 0.02 | 0.06 |
| AD-53736.1 | 0.90 | 1.09 | 1.16 | 0.05 | 0.01 |
| AD-53737.1 | 0.94 | 0.93 | 1.00 | 0.02 | 0.09 |
| AD-53738.1 | 0.93 | 0.79 | 0.93 | 0.03 | 0.01 |
| AD-53739.1 | 1.11 | 0.90 | 0.90 | 0.05 | 0.00 |
| AD-53740.1 | 0.86 | 0.92 | 0.97 | 0.08 | 0.01 |
| AD-53741.1 | 0.96 | 0.84 | 0.92 | 0.00 | 0.07 |
| AD-53742.1 | 1.03 | 0.93 | 1.03 | 0.04 | 0.06 |
| AD-53743.1 | 0.92 | 0.98 | 1.05 | 0.08 | 0.14 |
| AD-53744.1 | 0.95 | 1.02 | 1.03 | 0.08 | 0.12 |
| AD-53745.1 | 0.81 | 0.99 | 1.11 | 0.10 | 0.18 |
| AD-53746.1 | 0.65 | 0.83 | 1.04 | 0.07 | 0.16 |
| AD-53747.1 | 0.82 | 0.88 | 1.02 | 0.05 | 0.13 |
| AD-53748.1 | 0.46 | 0.59 | 0.72 | 0.06 | 0.07 |
| AD-53749.1 | 0.93 | 0.90 | 1.04 | 0.12 | 0.16 |
| AD-53750.1 | 0.90 | 1.02 | 0.97 | 0.02 | 0.10 |
| AD-53751.1 | 0.92 | 0.87 | 1.02 | 0.19 | 0.16 |
| AD-53752.1 | 0.73 | 0.88 | 0.99 | 0.06 | 0.18 |
| AD-53753.1 | 0.87 | 0.97 | 1.06 | 0.07 | 0.19 |
| AD-53754.1 | 0.43 | 0.58 | 0.72 | 0.10 | 0.05 |
| AD-53755.1 | 1.01 | 0.99 | 1.03 | 0.03 | 0.02 |
| AD-53757.1 | 0.98 | 0.91 | 1.07 | 0.05 | 0.13 |
| AD-53758.1 | 0.63 | 0.73 | 0.92 | 0.05 | 0.00 |
| AD-53759.1 | 0.91 | 0.92 | 0.99 | 0.02 | 0.08 |
| AD-53760.1 | 0.51 | 0.67 | 0.80 | 0.03 | 0.12 |
| AD-53761.1 | 0.89 | 1.07 | 1.10 | 0.11 | 0.18 |
| AD-53762.1 | 1.06 | 1.00 | 0.96 | 0.12 | 0.10 |
| AD-53763.1 | 0.95 | 1.10 | 1.00 | 0.07 | 0.09 |
| AD-53764.1 | 0.99 | 0.94 | 0.99 | 0.05 | 0.16 |
| AD-53765.1 | 0.92 | 0.87 | 0.86 | 0.09 | 0.11 |
| AD-53766.1 | 0.75 | 0.78 | 0.86 | 0.09 | 0.14 |
| AD-53767.1 | 1.01 | 1.02 | 0.97 | 0.05 | 0.18 |
| AD-53768.1 | 0.89 | 1.07 | 0.97 | 0.09 | 0.15 |
| AD-53769.1 | 0.89 | 1.11 | 0.95 | 0.05 | 0.11 |
| AD-53770.1 | 0.76 | 1.01 | 0.98 | 0.01 | 0.12 |
| AD-53771.1 | 0.70 | 0.74 | 0.84 | 0.06 | 0.12 |
| AD-53772.1 | 0.72 | 0.83 | 0.85 | 0.04 | 0.11 |
| AD-53773.1 | 0.96 | 1.00 | 0.98 | 0.05 | 0.07 |
| AD-53774.1 | 0.75 | 0.92 | 1.01 | 0.06 | 0.14 |
| AD-53776.1 | 0.78 | 0.94 | 0.97 | 0.11 | 0.08 |
| AD-53777.1 | 0.67 | 0.68 | 0.74 | 0.11 | 0.01 |
| AD-53778.1 | 0.74 | 0.73 | 0.92 | 0.13 | 0.14 |

TABLE 3-continued

PCSK9 efficacy screen by free uptake in primary Cynomolgous monkey hepatocytes.

| DUPLEX ID | PCH 500 nM | PCH 100 nM Avg | PCH 10 nM Avg | PCH 100 nM SD | PCH 10 nM SD |
|---|---|---|---|---|---|
| AD-53779.1 | 1.00 | 0.98 | 0.95 | 0.14 | 0.04 |
| AD-53780.1 | 0.90 | 0.92 | 0.98 | 0.12 | 0.05 |
| AD-53781.1 | 0.84 | 0.95 | 1.00 | 0.17 | 0.06 |
| AD-53782.1 | 0.87 | 0.92 | 0.90 | 0.11 | 0.02 |
| AD-53783.1 | 0.71 | 0.79 | 0.78 | 0.14 | 0.03 |
| AD-53784.1 | 0.68 | 0.82 | 0.86 | 0.10 | 0.10 |
| AD-53785.1 | 1.10 | 0.96 | 0.96 | 0.09 | 0.07 |
| AD-53786.1 | 0.98 | 0.89 | 0.95 | 0.20 | 0.14 |
| AD-53787.1 | 1.23 | 0.93 | 1.00 | 0.11 | 0.21 |
| AD-53788.1 | 0.95 | 0.90 | 0.94 | 0.17 | 0.08 |
| AD-53789.1 | 0.55 | 0.60 | 0.78 | 0.09 | 0.08 |
| AD-53790.1 | 0.70 | 0.91 | 1.04 | 0.08 | 0.16 |
| AD-53791.1 | 0.47 | 0.67 | 0.92 | 0.12 | 0.09 |
| AD-53792.1 | 0.52 | 0.75 | 0.89 | 0.06 | 0.04 |
| AD-53793.1 | 0.88 | 1.03 | 1.07 | 0.20 | 0.09 |
| AD-53794.1 | 0.85 | 1.00 | 1.09 | 0.17 | 0.22 |
| AD-53795.1 | 0.58 | 0.71 | 1.00 | 0.10 | 0.12 |
| AD-53796.1 | 0.62 | 0.78 | 0.96 | 0.07 | 0.12 |
| AD-53797.1 | 0.72 | 0.78 | 0.93 | 0.12 | 0.10 |
| AD-53798.1 | 0.50 | 0.55 | 0.76 | 0.08 | 0.03 |
| AD-53799.1 | 0.98 | 0.92 | 1.10 | 0.11 | 0.21 |
| AD-53800.1 | 0.59 | 0.65 | 0.87 | 0.15 | 0.14 |
| AD-53801.1 | 0.81 | 0.84 | 1.05 | 0.14 | 0.18 |
| AD-53802.1 | 0.68 | 0.79 | 1.03 | 0.13 | 0.13 |
| AD-53803.1 | 0.51 | 0.53 | 0.77 | 0.09 | 0.05 |
| AD-53804.1 | 0.94 | 0.86 | 1.05 | 0.15 | 0.15 |
| AD-53805.1 | 0.95 | 0.93 | 1.03 | 0.12 | 0.19 |
| AD-53806.1 | 0.38 | 0.45 | 0.78 | 0.05 | 0.12 |
| AD-53807.1 | 0.85 | 0.95 | 1.15 | 0.09 | 0.24 |
| AD-53808.1 | 0.81 | 0.85 | 0.93 | 0.08 | 0.11 |
| AD-53809.1 | 0.50 | 0.62 | 0.77 | 0.00 | 0.12 |
| AD-53810.1 | 0.84 | 0.82 | 0.98 | 0.16 | 0.22 |
| AD-53811.1 | 0.94 | 0.95 | 1.00 | 0.10 | 0.11 |
| AD-53812.1 | 0.61 | 0.76 | 0.97 | 0.14 | 0.22 |
| AD-53813.1 | 0.67 | 0.76 | 0.94 | 0.01 | 0.15 |
| AD-53814.1 | 0.58 | 0.67 | 0.84 | 0.11 | 0.19 |
| AD-53815.1 | 0.49 | 0.50 | 0.72 | 0.09 | 0.17 |

TABLE 3-continued

PCSK9 efficacy screen by free uptake in primary Cynomolgous monkey hepatocytes.

| DUPLEX ID | PCH 500 nM | PCH 100 nM Avg | PCH 10 nM Avg | PCH 100 nM SD | PCH 10 nM SD |
|---|---|---|---|---|---|
| AD-53816.1 | 0.82 | 0.91 | 0.93 | 0.08 | 0.10 |
| AD-53817.1 | 0.92 | 0.94 | 1.07 | 0.13 | 0.36 |
| AD-53818.1 | 0.83 | 0.99 | 0.99 | 0.07 | 0.41 |
| AD-53819.1 | 0.61 | 0.75 | 0.88 | 0.24 | 0.16 |
| AD-53820.1 | 0.71 | 0.81 | 0.92 | 0.17 | 0.04 |
| AD-53821.1 | 0.56 | 0.54 | 0.68 | 0.13 | 0.05 |
| AD-53822.1 | 1.24 | 0.88 | 1.05 | 0.12 | 0.17 |
| AD-53823.1 | 1.03 | 0.86 | 0.99 | 0.11 | 0.18 |
| AD-53824.1 | 0.76 | 0.73 | 0.93 | 0.16 | 0.11 |
| AD-53825.1 | 0.57 | 0.63 | 0.82 | 0.18 | 0.04 |
| AD-53826.1 | 0.54 | 0.51 | 0.78 | 0.08 | 0.07 |
| AD-53827.1 | 0.99 | 0.91 | 1.05 | 0.12 | 0.08 |
| AD-53828.1 | 0.69 | 0.77 | 0.87 | 0.09 | 0.16 |
| AD-53829.1 | 0.72 | 0.91 | 0.95 | 0.11 | 0.16 |
| AD-53830.1 | 0.48 | 0.73 | 0.76 | 0.11 | 0.01 |
| AD-53831.1 | 0.97 | 0.92 | 1.00 | 0.22 | 0.25 |
| AD-53832.1 | 0.68 | 0.63 | 0.81 | 0.15 | 0.02 |
| AD-53833.1 | 0.92 | 0.90 | 0.84 | 0.20 | 0.03 |
| AD-53834.1 | 1.15 | 0.93 | 0.86 | 0.16 | 0.02 |
| AD-53835.1 | 0.88 | 0.79 | 0.81 | 0.18 | 0.03 |
| PBS | 0.90 | 1.02 | 0.99 | 0.04 | 0.15 |

The modified and conjugated PCSK9 siRNA duplexes were also evaluated for efficacy by transfection assays in three human cell lines. PCSK9 siRNAs were transfected in three different cell lines, HeLa, Hep3B and HepG2 at two doses, 10 nM and 0.1 nM. The results of these assays are shown in Table 4 and the data are expressed as a fraction of the message remaining relative to control.

FIG. 1 shows that there is a general reproducibility in the silencing activity of the PCSK9 duplexes between the free uptake assays and the transfection assays.

The $IC_{50}$ values for selected duplexes by free-uptake in *Cynomologous* cells and by transfection in Hep3B cells are shown in Table 5.

TABLE 4

PCSK9 efficacy screen by transfection in human cell lines.

| DUPLEX ID | Hela, 10 nM | Hela, 0.1 nM | Hep3b, 10 nM | Hep3b, 0.1 nM | HepG2, 10 nM | HepG2, 0.1 nM |
|---|---|---|---|---|---|---|
| AD-48399 | 0.94 | 0.90 | 1.18 | 1.03 | 1.34 | 1.05 |
| AD-48399 | 0.90 | 1.03 | 0.87 | 0.88 | 0.84 | 0.91 |
| AD-48399 | 0.88 | 1.14 | 0.90 | 0.99 | 0.92 | 1.04 |
| AD-48399 | 1.22 | 0.97 | 0.95 | 0.98 | 0.81 | 0.92 |
| AD-48399 | 1.04 | 0.81 | 1.01 | 1.10 | 1.03 | 1.09 |
| AD-48399 | 1.06 | 1.20 | 1.14 | 1.04 | 1.16 | 1.01 |
| AD-48400 | 0.05 | 0.63 | 0.10 | 0.51 | 0.17 | 0.69 |
| AD-48400.4 | 0.06 | 0.28 | 0.14 | 0.31 | 0.13 | 0.32 |
| AD-53649.1 | 0.84 | 1.05 | 1.07 | 0.94 | 0.97 | 1.11 |
| AD-53650.1 | 0.16 | 0.87 | 0.41 | 0.87 | 0.52 | 1.12 |
| AD-53651.1 | 0.47 | 0.86 | 0.49 | 0.92 | 0.71 | 1.08 |
| AD-53652.1 | 0.34 | 0.93 | 0.50 | 0.96 | 0.40 | 1.21 |
| AD-53653.1 | 0.36 | 0.99 | 0.43 | 1.01 | 0.52 | 1.13 |
| AD-53654.1 | 0.85 | 1.06 | 0.99 | 0.92 | 0.95 | 1.06 |
| AD-53656.1 | 0.46 | 0.92 | 0.78 | 0.98 | 0.80 | 0.74 |
| AD-53657.1 | 0.71 | 0.97 | 0.75 | 1.01 | 0.81 | 0.94 |
| AD-53658.1 | 0.32 | 0.97 | 0.50 | 0.91 | 0.58 | 1.05 |
| AD-53659.1 | 0.11 | 0.86 | 0.24 | 0.93 | 0.22 | 0.94 |
| AD-53660.1 | 0.35 | 1.12 | 0.43 | 0.99 | 0.44 | 1.31 |
| AD-53661.1 | 0.94 | 1.07 | 0.85 | 0.95 | 0.88 | 0.92 |
| AD-53663.1 | 0.82 | 1.03 | 0.74 | 1.06 | 1.04 | 1.04 |
| AD-53664.1 | 0.60 | 0.94 | 0.61 | 1.06 | 0.85 | 1.28 |
| AD-53665.1 | 0.33 | 1.00 | 0.55 | 1.01 | 0.45 | 1.12 |
| AD-53666.1 | 0.09 | 0.98 | 0.22 | 0.97 | 0.21 | 1.08 |
| AD-53667.1 | 0.94 | 1.07 | 0.95 | 0.96 | 0.95 | 1.02 |
| AD-53668.1 | 0.27 | 0.88 | 0.36 | 1.07 | 0.35 | 1.13 |
| AD-53669.1 | 0.81 | 1.02 | 0.93 | 1.08 | 1.35 | 1.24 |
| AD-53670.1 | 0.55 | 0.94 | 0.52 | 0.48 | 0.45 | 1.13 |

TABLE 4-continued

PCSK9 efficacy screen by transfection in human cell lines.

| DUPLEX ID | Hela, 10 nM | Hela, 0.1 nM | Hep3b, 10 nM | Hep3b, 0.1 nM | HepG2, 10 nM | HepG2, 0.1 nM |
|---|---|---|---|---|---|---|
| AD-53671.1 | 0.68 | 1.07 | 0.78 | 1.02 | 0.82 | 1.27 |
| AD-53672.1 | 0.22 | 1.04 | 0.38 | 1.06 | 0.34 | 1.15 |
| AD-53674.1 | 0.08 | 0.67 | 0.15 | 0.85 | 0.15 | 0.80 |
| AD-53675.1 | 0.25 | 1.04 | 0.43 | 0.95 | 0.38 | 1.04 |
| AD-53676.1 | 0.81 | 0.94 | 0.90 | 1.14 | 0.98 | 1.06 |
| AD-53677.1 | 0.45 | 0.90 | 0.70 | 0.98 | 0.70 | 1.14 |
| AD-53678.1 | 0.41 | 1.02 | 0.72 | 1.04 | 0.70 | 1.15 |
| AD-53679.1 | 0.44 | 0.93 | 0.58 | 0.88 | 0.50 | 0.95 |
| AD-53680.1 | 0.36 | 0.99 | 0.55 | 0.98 | 0.52 | 0.96 |
| AD-53681.1 | 0.33 | 0.93 | 0.57 | 1.12 | 0.54 | 1.11 |
| AD-53682.1 | 0.84 | 0.94 | 0.85 | 1.06 | 0.93 | 1.13 |
| AD-53683.1 | 0.65 | 0.78 | 0.95 | 1.05 | 0.73 | 1.06 |
| AD-53684.1 | 0.57 | 0.98 | 0.79 | 0.92 | 0.62 | 1.08 |
| AD-53685.1 | 0.85 | 0.90 | 0.94 | 0.95 | 0.69 | 0.98 |
| AD-53687.1 | 0.15 | 0.83 | 0.39 | 1.09 | 0.34 | 1.23 |
| AD-53688.1 | 0.45 | 0.89 | 0.72 | 1.01 | 0.57 | 1.19 |
| AD-53689.1 | 0.56 | 0.93 | 1.04 | 1.14 | 0.59 | 1.24 |
| AD-53690.1 | 0.45 | 0.79 | 0.53 | 1.26 | 0.41 | 1.22 |
| AD-53691.1 | 0.82 | 1.03 | 0.91 | 1.22 | 0.57 | 1.05 |
| AD-53692.1 | 0.68 | 0.81 | 0.81 | 0.89 | 0.82 | 1.05 |
| AD-53693.1 | 0.61 | 0.92 | 0.85 | 0.81 | 0.53 | 1.03 |
| AD-53694.1 | 0.59 | 0.87 | 0.58 | 1.01 | 0.53 | 0.82 |
| AD-53695.1 | 0.91 | 0.78 | 1.02 | 1.23 | 1.14 | 1.11 |
| AD-53696.1 | 0.57 | 0.98 | 0.82 | 1.01 | 0.68 | 1.05 |
| AD-53697.1 | 0.31 | 1.04 | 0.40 | 0.95 | 0.24 | 0.90 |
| AD-53698.1 | 0.17 | 0.97 | 0.31 | 0.92 | 0.32 | 0.84 |
| AD-53699.1 | 0.29 | 1.00 | 0.47 | 0.90 | 0.47 | 1.23 |
| AD-53700.1 | 0.81 | 1.07 | 0.94 | 0.99 | 0.97 | 1.08 |
| AD-53701.1 | 0.89 | 1.07 | 0.96 | 0.84 | 0.65 | 0.93 |
| AD-53702.1 | 0.45 | 1.03 | 0.84 | 1.08 | 0.72 | 0.99 |
| AD-53703.1 | 0.18 | 0.79 | 0.28 | 0.97 | 0.29 | 0.90 |
| AD-53704.1 | 0.77 | 0.80 | 0.88 | 1.06 | 0.91 | 0.95 |
| AD-53705.1 | 0.63 | 0.89 | 0.81 | 1.06 | 0.76 | 0.97 |
| AD-53706.1 | 0.39 | 0.82 | 0.41 | 1.00 | 0.48 | 0.88 |
| AD-53707.1 | 0.42 | 0.97 | 0.60 | 0.83 | 0.54 | 0.80 |
| AD-53708.1 | 0.49 | 0.95 | 0.82 | 0.96 | 1.07 | 1.09 |
| AD-53709.1 | 0.19 | 0.90 | 0.43 | 0.85 | 0.38 | 1.05 |
| AD-53710.1 | 0.66 | 1.00 | 0.82 | 0.85 | 0.69 | 1.08 |
| AD-53711.1 | 0.40 | 0.90 | 0.45 | 0.95 | 0.23 | 1.03 |
| AD-53712.1 | 0.47 | 0.99 | 0.51 | 0.94 | 0.62 | 0.97 |
| AD-53713.1 | 0.52 | 1.05 | 0.69 | 0.83 | 0.79 | 0.94 |
| AD-53714.1 | 0.43 | 1.01 | 0.71 | 1.11 | 0.75 | 1.12 |
| AD-53715.1 | 0.23 | 0.99 | 0.58 | 1.24 | 0.58 | 1.09 |
| AD-53716.1 | 0.39 | 1.00 | 0.52 | 0.98 | 0.51 | 0.80 |
| AD-53717.1 | 0.20 | 0.84 | 0.33 | 1.02 | 0.41 | 1.09 |
| AD-53718.1 | 0.35 | 1.08 | 0.33 | 1.02 | 0.45 | 0.97 |
| AD-53719.1 | 0.58 | 0.96 | 0.74 | 0.84 | 0.79 | 1.01 |
| AD-53720.1 | 0.31 | 1.00 | 0.55 | 1.09 | 0.48 | 1.24 |
| AD-53721.1 | 0.26 | 1.02 | 0.62 | 0.92 | 0.49 | 0.94 |
| AD-53722.1 | 0.50 | 0.99 | 0.86 | 0.99 | 0.87 | 1.26 |
| AD-53723.1 | 0.28 | 0.86 | 0.37 | 0.92 | 0.54 | 1.11 |
| AD-53724.1 | 0.18 | 1.11 | 0.20 | 0.98 | 0.36 | 1.05 |
| AD-53725.1 | 0.47 | 1.00 | 0.63 | 0.95 | 0.60 | 1.04 |
| AD-53726.1 | 0.19 | 1.01 | 0.42 | 0.96 | 0.41 | 1.21 |
| AD-53727.1 | 0.55 | 0.82 | 0.77 | 1.08 | 0.68 | 1.35 |
| AD-53728.1 | 0.44 | 0.92 | 0.65 | 1.11 | 0.68 | 1.44 |
| AD-53729.1 | 0.11 | 0.92 | 0.25 | 0.94 | 0.11 | 1.01 |
| AD-53730.1 | 0.31 | 0.91 | 0.51 | 1.05 | 0.59 | 1.34 |
| AD-53731.1 | 0.26 | 0.63 | 0.42 | 0.95 | 0.44 | 1.07 |
| AD-53732.1 | 0.17 | 0.87 | 0.29 | 0.99 | 0.36 | 0.98 |
| AD-53733.1 | 1.06 | 0.72 | 1.21 | 1.14 | 1.07 | 1.28 |
| AD-53734.1 | 0.79 | 0.92 | 0.93 | 0.98 | 0.90 | 1.33 |
| AD-53735.1 | 0.54 | 0.87 | 0.83 | 1.12 | 0.66 | 1.24 |
| AD-53736.1 | 0.40 | 0.69 | 0.76 | 1.09 | 0.76 | 1.11 |
| AD-53737.1 | 0.29 | 0.82 | 0.41 | 1.04 | 0.39 | 0.96 |
| AD-53738.1 | 0.19 | 0.70 | 0.24 | 1.09 | 0.28 | 1.10 |
| AD-53739.1 | 0.91 | 0.94 | 0.72 | 1.07 | 0.78 | 1.09 |
| AD-53740.1 | 0.17 | 1.06 | 0.42 | 1.07 | 0.32 | 1.05 |
| AD-53741.1 | 0.17 | 0.91 | 0.32 | 0.99 | 0.41 | 1.05 |
| AD-53742.1 | 0.55 | 1.07 | 0.69 | 0.97 | 0.72 | 1.08 |
| AD-53743.1 | 0.71 | 0.99 | 0.75 | 0.76 | 0.58 | 1.08 |
| AD-53744.1 | 0.13 | 0.86 | 0.50 | 0.69 | 0.36 | 0.87 |
| AD-53745.1 | 0.46 | 0.91 | 0.78 | 0.72 | 0.87 | 0.94 |
| AD-53746.1 | 0.13 | 0.82 | 0.23 | 0.50 | 0.28 | 0.90 |
| AD-53747.1 | 0.29 | 1.08 | 0.54 | 0.77 | 0.50 | 1.07 |
| AD-53748.1 | 0.04 | 0.22 | 0.12 | 0.21 | 0.20 | 0.32 |

TABLE 4-continued

PCSK9 efficacy screen by transfection in human cell lines.

| DUPLEX ID | Hela, 10 nM | Hela, 0.1 nM | Hep3b, 10 nM | Hep3b, 0.1 nM | HepG2, 10 nM | HepG2, 0.1 nM |
|---|---|---|---|---|---|---|
| AD-53749.1 | 0.56 | 0.76 | 0.48 | 0.81 | 0.53 | 0.85 |
| AD-53750.1 | 0.61 | 0.75 | 0.69 | 0.81 | 0.81 | 1.07 |
| AD-53751.1 | 0.25 | 0.69 | 0.37 | 0.72 | 0.26 | 0.77 |
| AD-53752.1 | 0.11 | 0.43 | 0.13 | 0.40 | 0.16 | 0.61 |
| AD-53753.1 | 0.70 | 0.76 | 0.75 | 0.92 | 0.63 | 1.09 |
| AD-53754.1 | 0.06 | 0.31 | 0.10 | 0.34 | 0.12 | 0.40 |
| AD-53755.1 | 0.46 | 0.91 | 0.66 | 0.84 | 0.56 | 0.79 |
| AD-53757.1 | 0.61 | 0.90 | 0.50 | 0.89 | 0.44 | 0.91 |
| AD-53758.1 | 0.11 | 0.31 | 0.11 | 0.29 | 0.11 | 0.60 |
| AD-53759.1 | 0.61 | 0.87 | 0.57 | 0.84 | 0.56 | 0.98 |
| AD-53760.1 | 0.05 | 0.36 | 0.14 | 0.42 | 0.12 | 0.53 |
| AD-53761.1 | 0.95 | 0.99 | 0.76 | 0.72 | 0.55 | 0.61 |
| AD-53762.1 | 0.58 | 1.18 | 0.74 | 0.88 | 0.69 | 0.88 |
| AD-53763.1 | 0.16 | 0.86 | 0.19 | 0.64 | 0.21 | 0.75 |
| AD-53764.1 | 0.70 | 0.91 | 0.54 | 0.85 | 0.59 | 0.94 |
| AD-53765.1 | 0.16 | 0.63 | 0.38 | 0.64 | 0.30 | 0.87 |
| AD-53766.1 | 0.09 | 0.72 | 0.16 | 0.67 | 0.18 | 0.63 |
| AD-53767.1 | 0.30 | 1.14 | 0.69 | 0.83 | 0.71 | 0.83 |
| AD-53768.1 | 0.50 | 0.98 | 0.75 | 0.98 | 0.52 | 1.06 |
| AD-53769.1 | 0.36 | 1.07 | 0.26 | 0.62 | 0.39 | 0.83 |
| AD-53770.1 | 0.27 | 1.08 | 0.45 | 1.00 | 0.44 | 1.25 |
| AD-53771.1 | 0.18 | 0.62 | 0.19 | 0.44 | 0.21 | 0.65 |
| AD-53772.1 | 0.12 | 0.75 | 0.30 | 0.66 | 0.18 | 0.85 |
| AD-53773.1 | 0.39 | 0.98 | 0.60 | 0.84 | 0.19 | 1.00 |
| AD-53774.1 | 0.07 | 0.54 | 0.25 | 0.40 | 0.20 | 0.71 |
| AD-53776.1 | 0.33 | 0.97 | 0.45 | 0.94 | 0.34 | 0.95 |
| AD-53777.1 | 0.06 | 0.39 | 0.18 | 0.30 | 0.11 | 0.41 |
| AD-53778.1 | 0.09 | 0.72 | 0.24 | 0.69 | 0.23 | 0.78 |
| AD-53779.1 | 0.47 | 0.66 | 0.68 | 0.67 | 0.57 | 0.81 |
| AD-53780.1 | 0.29 | 0.93 | 0.61 | 0.71 | 0.42 | 0.92 |
| AD-53781.1 | 0.41 | 0.99 | 0.38 | 0.87 | 0.28 | 1.09 |
| AD-53782.1 | 0.56 | 0.47 | 0.56 | 0.89 | 0.41 | 1.16 |
| AD-53783.1 | 0.16 | 0.68 | 0.32 | 0.46 | 0.34 | 0.61 |
| AD-53784.1 | 0.15 | 0.71 | 0.27 | 0.72 | 0.25 | 0.80 |
| AD-53785.1 | 0.17 | 0.90 | 0.57 | 0.71 | 0.29 | 0.64 |
| AD-53786.1 | 0.11 | 0.78 | 0.28 | 0.48 | 0.24 | 0.74 |
| AD-53787.1 | 0.34 | 0.72 | 0.56 | 1.04 | 0.46 | 0.81 |
| AD-53788.1 | 0.36 | 0.83 | 0.46 | 0.95 | 0.32 | 0.65 |
| AD-53789.1 | 0.09 | 0.43 | 0.18 | 0.42 | 0.12 | 0.47 |
| AD-53790.1 | 0.10 | 0.74 | 0.30 | 0.65 | 0.31 | 0.81 |
| AD-53791.1 | 0.07 | 0.51 | 0.20 | 0.30 | 0.16 | 0.58 |
| AD-53792.1 | 0.05 | 0.40 | 0.11 | 0.30 | 0.17 | 0.64 |
| AD-53793.1 | 0.23 | 1.19 | 0.42 | 0.84 | 0.45 | 1.12 |
| AD-53794.1 | 0.43 | 1.15 | 0.65 | 0.67 | 0.42 | 0.95 |
| AD-53795.1 | 0.08 | 0.37 | 0.15 | 0.34 | 0.12 | 0.48 |
| AD-53796.1 | 0.07 | 0.33 | 0.19 | 0.49 | 0.15 | 0.58 |
| AD-53797.1 | 0.10 | 0.43 | 0.16 | 0.39 | 0.20 | 0.62 |
| AD-53798.1 | 0.04 | 0.31 | 0.09 | 0.29 | 0.16 | 0.60 |
| AD-53799.1 | 0.22 | 0.71 | 0.30 | 0.85 | 0.27 | 0.85 |
| AD-53800.1 | 0.09 | 0.34 | 0.16 | 0.35 | 0.14 | 0.51 |
| AD-53801.1 | 0.09 | 0.28 | 0.25 | 0.55 | 0.20 | 0.54 |
| AD-53802.1 | 0.10 | 0.31 | 0.20 | 0.40 | 0.15 | 0.72 |
| AD-53803.1 | 0.07 | 0.27 | 0.08 | 0.21 | 0.14 | 0.29 |
| AD-53804.1 | 0.18 | 0.57 | 0.29 | 0.47 | 0.27 | 0.79 |
| AD-53805.1 | 0.69 | 0.85 | 0.68 | 0.85 | 0.48 | 1.01 |
| AD-53806.1 | 0.07 | 0.38 | 0.18 | 0.43 | 0.13 | 0.50 |
| AD-53807.1 | 0.29 | 0.61 | 0.26 | 0.71 | 0.28 | 0.68 |
| AD-53808.1 | 0.15 | 0.68 | 0.26 | 0.50 | 0.28 | 0.72 |
| AD-53809.1 | 0.04 | 0.23 | 0.17 | 0.22 | 0.12 | 0.31 |
| AD-53810.1 | 0.31 | 0.88 | 0.30 | 0.55 | 0.36 | 0.85 |
| AD-53811.1 | 0.28 | 0.77 | 0.33 | 0.57 | 0.39 | 0.87 |
| AD-53812.1 | 0.12 | 0.69 | 0.16 | 0.62 | 0.22 | 0.79 |
| AD-53813.1 | 0.11 | 0.33 | 0.18 | 0.26 | 0.17 | 0.40 |
| AD-53814.1 | 0.12 | 0.59 | 0.57 | 0.60 | 0.29 | 0.57 |
| AD-53815.1 | 0.03 | 0.27 | 0.11 | 0.18 | 0.18 | 0.33 |
| AD-53816.1 | 0.16 | 0.89 | 0.24 | 0.62 | 0.32 | 0.75 |
| AD-53817.1 | 0.26 | 0.98 | 0.44 | 0.69 | 0.44 | 1.18 |
| AD-53818.1 | 0.12 | 0.71 | 0.21 | 0.55 | 0.21 | 0.70 |
| AD-53819.1 | 0.09 | 0.52 | 0.12 | 0.45 | 0.12 | 0.46 |
| AD-53820.1 | 0.20 | 0.96 | 0.27 | 0.67 | 0.34 | 0.74 |
| AD-53821.1 | 0.04 | 0.29 | 0.10 | 0.23 | 0.13 | 0.29 |
| AD-53822.1 | 0.54 | 1.05 | 0.60 | 0.91 | 0.48 | 0.96 |
| AD-53823.1 | 0.21 | 0.76 | 0.41 | 0.59 | 0.33 | 0.85 |
| AD-53824.1 | 0.16 | 0.78 | 0.40 | 0.51 | 0.36 | 0.70 |
| AD-53825.1 | 0.05 | 0.40 | 0.12 | 0.31 | 0.24 | 0.73 |
| AD-53826.1 | 0.04 | 0.34 | 0.10 | 0.21 | 0.20 | 0.34 |

TABLE 4-continued

| PCSK9 efficacy screen by transfection in human cell lines. | | | | | | |
|---|---|---|---|---|---|---|
| DUPLEX ID | Hela, 10 nM | Hela, 0.1 nM | Hep3b, 10 nM | Hep3b, 0.1 nM | HepG2, 10 nM | HepG2, 0.1 nM |
| AD-53827.1 | 0.40 | 1.11 | 0.40 | 0.84 | 0.31 | 1.15 |
| AD-53828.1 | 0.17 | 0.51 | 0.23 | 0.55 | 0.17 | 1.14 |
| AD-53829.1 | 0.06 | 0.71 | 0.21 | 0.58 | 0.24 | 1.21 |
| AD-53830.1 | 0.07 | 0.27 | 0.06 | 0.30 | 0.15 | 0.43 |
| AD-53831.1 | 0.09 | 0.56 | 0.21 | 0.39 | 0.16 | 0.95 |
| AD-53832.1 | 0.08 | 0.52 | 0.26 | 0.31 | 0.11 | 0.76 |
| AD-53833.1 | 1.04 | 1.05 | 0.74 | 1.24 | 0.60 | 1.58 |
| AD-53834.1 | 0.70 | 1.14 | 0.71 | 0.85 | 0.38 | 1.47 |
| AD-53835.1 | 0.11 | 0.43 | 0.33 | 0.35 | 0.09 | 0.53 |
| PBS | 0.67 | 1.13 | 0.90 | 0.90 | 0.99 | 0.99 |

TABLE 5

| PCSK9 $IC_{50}$ values for selected duplexes by free uptake in Cynomologous monkey cells and by transfection in the Hep3B human cell line. | | |
|---|---|---|
| Duplex | Transfection IC50, nM | Free uptake IC50, nM |
| AD-53806.1 | 0.07 | 18.00 |
| AD-53748.1 | 0.06 | 16.88 |
| AD-53815.1 | 0.05 | 39.21 |
| AD-53809.1 | 0.05 | 571.00 |
| AD-53821.1 | 0.05 | 55.41 |
| AD-53830.1 | 0.08 | ND |
| AD-53754.1 | 0.25 | 67.42 |
| AD-53800.1 | 0.30 | ND |
| AD-53798.1 | 0.04 | ND |
| AD-53789.1 | 0.37 | ND |
| AD-48400.4 | 0.23 | ND |

Figure 2A:
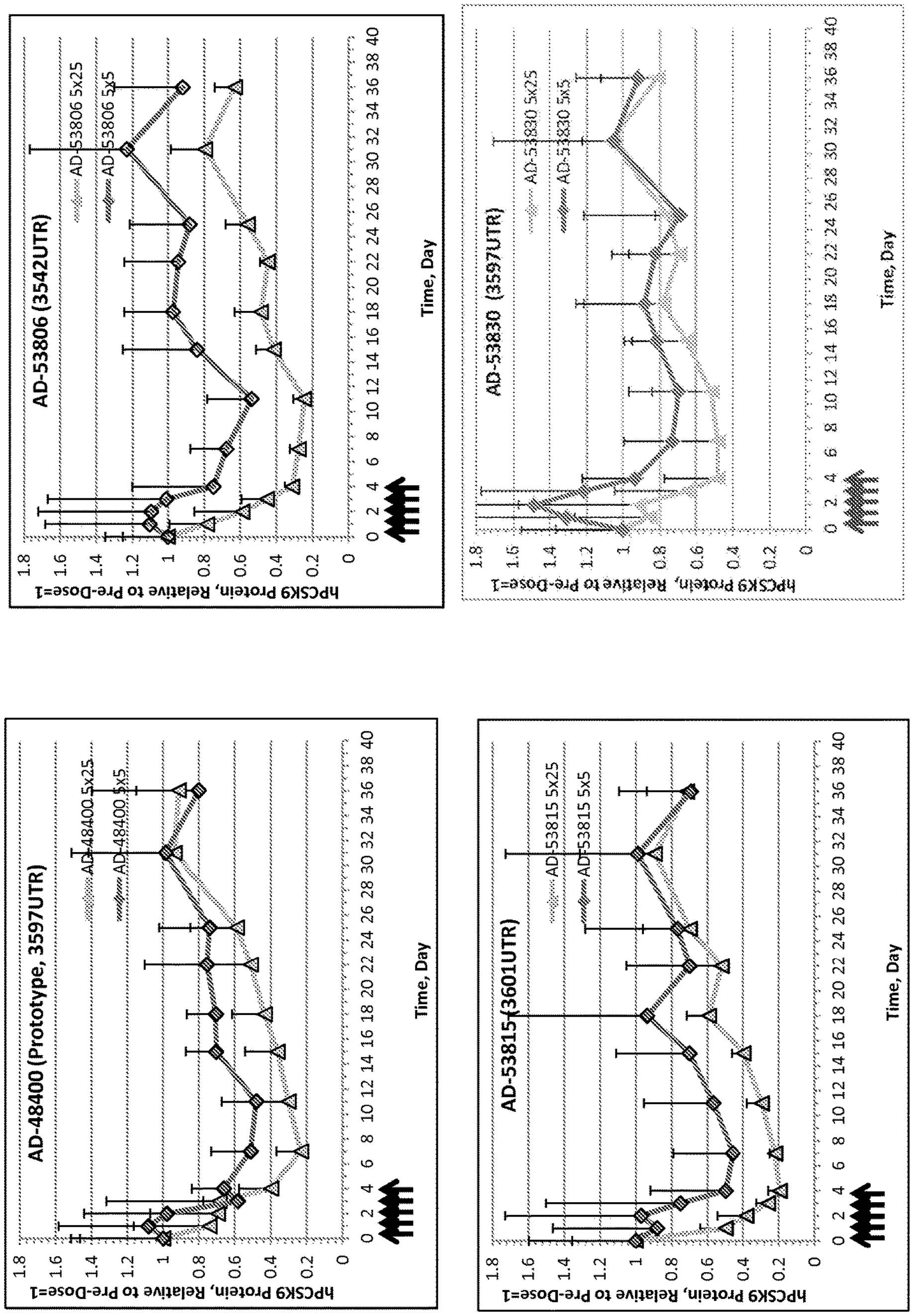
FIGS. 2A and 2B are graphs depicting the in vivo efficacy and duration of response for the indicated siRNAs.
Figure 2B:
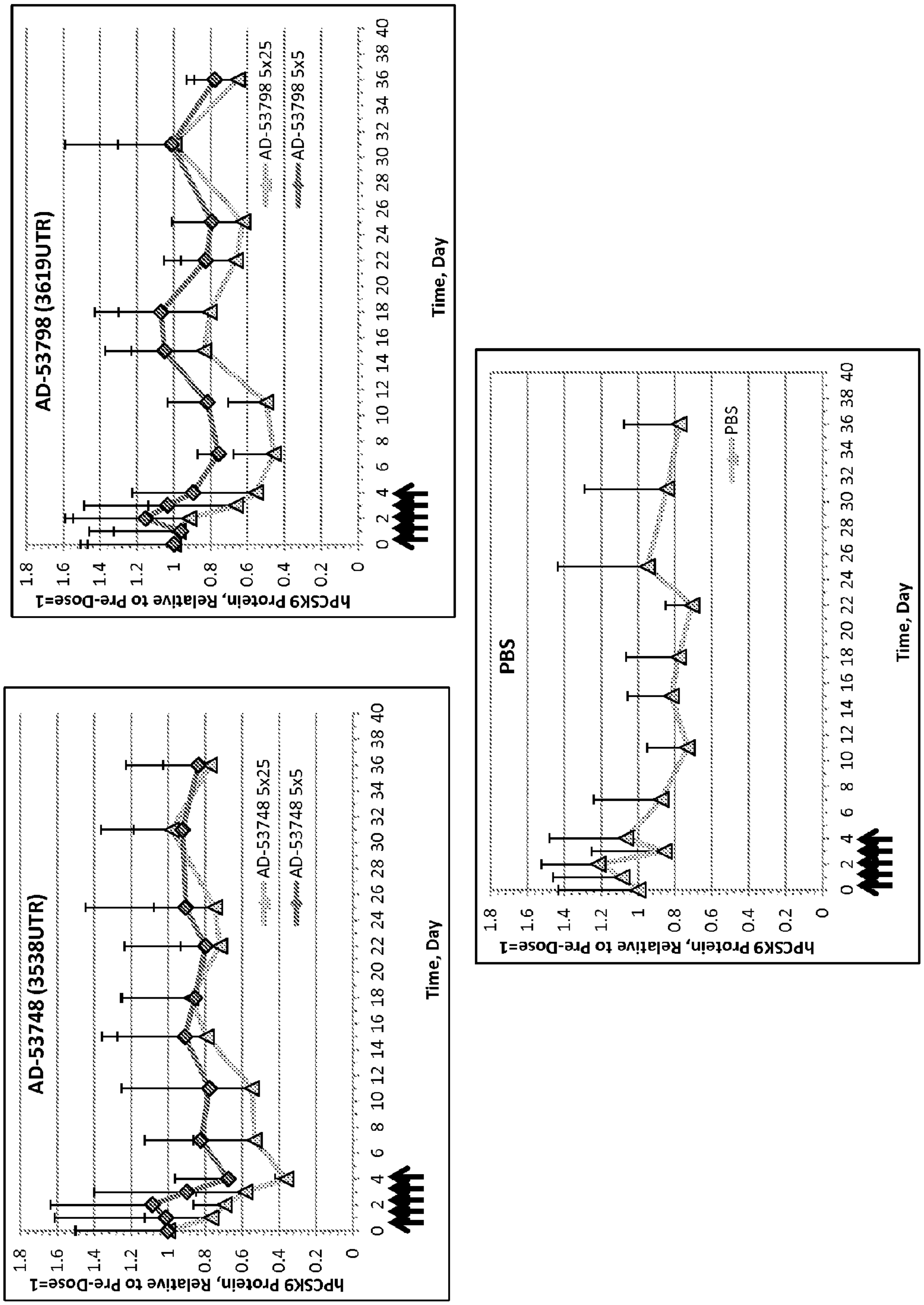

AD-48400 was also assayed for in vivo efficacy in female mice carrying a human PCSK9 transgene randomly inserted into the genome without disruption of the endogenous PCSK9 gene. Briefly, mice were injected subcutaneously with a single 20 mg/kg dose at Day 0, a single 100 mg/kg dose at Day 0, and five 20 mg/kg doses at Days 0, 1, 2, 3, 4, and 5. Serum was collected at Days −6, −3, 0, 1, 2, 3, 4, and 7 and the amount of PCSK9 protein was determined by ELISA assay. The results of these analyses are depicted in FIG. 2 and show that there is a dose response effect with AD-48400 conjugated to GalNAc at all three dosages tested.

The six most efficacious duplexes identified by the in vitro screens described above, were evaluated for in vivo efficacy and duration of response. Transgenic PCSK9 mice were injected at Days 0, 1, 2, 3, and 4 with either 5 mg/kg or 25 mg/kg of AD-48400, AD-53830, AD-53806, AD-53815, AD-53748, or AD-53798. Serum PCSK9 protein levels were determined by ELISA on Days −3, 0, 1, 2, 3, 4, 8, 11. 15. 18, 22, 26, 31, and 36. The results are depicted in FIGS. 3A and 3B.

Example 3. Lead Optimization

Based on the efficacy assays described in Example 2 above, PCSK9 siRNAs based on the parent sequences of AD-53815 and AD-53806 with a variety of chemical modifications were evaluated for efficacy in free uptake assays in primary *Cynomolgous* monkey hepatocytes (PCH) at 200 nM, 20 nM, 2 nM, and 0.2 nM. For all doses other than 0.2 nM dose, assays were performed twice and data are expressed as the average fraction message remaining relative to control. The 0.2 nM dose was assayed a single time. The results of these assays are shown in Table 6.

TABLE 6

| Efficacy screens for lead optimization of AD-53815 and AD-53806 by free uptake in Cynomolgous monkey hepatocytes. | | | | | | | | |
|---|---|---|---|---|---|---|---|---|
| Parent duplex | Duplex ID | 200 nM Avg | 20 nM Avg | 2 nM Avg | 0.2 nM-384 | 200 nM SD | 20 nM SD | 2 nM SD |
| AD-53815 | AD-53815.5 | 0.45 | 0.48 | 0.74 | 0.95 | 0.05 | 0.00 | 0.05 |
| AD-53815 | AD-53815.4 | 0.43 | 0.54 | 0.84 | 0.83 | 0.00 | 0.04 | 0.10 |
| AD-53815 | AD-56633.1 | 0.33 | 0.52 | 0.82 | 0.88 | 0.04 | 0.01 | 0.10 |
| AD-53815 | AD-56617.1 | 0.40 | 0.65 | 0.91 | 1.06 | 0.03 | 0.02 | 0.03 |
| AD-53815 | AD-56623.1 | 0.52 | 0.61 | 0.87 | 1.05 | 0.03 | 0.04 | 0.21 |
| AD-53815 | AD-56629.1 | 0.50 | 0.62 | 0.87 | 1.05 | 0.04 | 0.13 | 0.17 |
| AD-53815 | AD-56635.1 | 0.45 | 0.71 | 0.92 | 1.03 | 0.03 | 0.02 | 0.03 |
| AD-53815 | AD-56641.1 | 0.47 | 0.73 | 0.84 | 1.04 | 0.04 | 0.00 | 0.17 |
| AD-53815 | AD-56625.1 | 0.49 | 0.55 | 0.82 | 1.12 | 0.01 | 0.16 | 0.16 |
| AD-53815 | AD-56631.1 | 0.48 | 0.57 | 0.82 | 1.05 | 0.04 | 0.11 | 0.06 |
| AD-53815 | AD-56637.1 | 0.48 | 0.58 | 0.76 | 1.01 | 0.01 | 0.14 | 0.13 |
| AD-53815 | AD-56643.1 | 0.59 | 0.77 | 0.93 | 1.04 | 0.05 | 0.01 | 0.04 |
| AD-53815 | AD-56649.1 | 0.76 | 0.87 | 0.95 | 1.06 | 0.02 | 0.07 | 0.14 |
| AD-53815 | AD-56655.1 | 0.73 | 0.86 | 0.85 | 0.96 | 0.01 | 0.04 | 0.11 |
| AD-53815 | AD-56615.1 | 0.58 | 0.70 | 0.92 | 0.98 | 0.00 | 0.02 | 0.03 |
| AD-53815 | AD-56621.1 | 0.71 | 0.76 | 0.93 | 0.95 | 0.18 | 0.07 | 0.07 |
| AD-53815 | AD-56627.1 | 0.58 | 0.72 | 0.93 | 0.94 | 0.01 | 0.08 | 0.02 |
| AD-53815 | AD-56639.1 | 0.52 | 0.57 | 0.72 | 0.94 | 0.16 | 0.00 | 0.04 |
| AD-53815 | AD-56645.1 | 0.32 | 0.49 | 0.74 | 0.88 | 0.03 | 0.03 | 0.14 |
| AD-53815 | AD-56651.1 | 0.71 | 0.94 | 0.88 | 0.88 | 0.08 | 0.29 | 0.12 |
| AD-53815 | AD-56610.1 | 0.31 | 0.57 | 0.82 | 0.93 | 0.02 | 0.01 | 0.04 |
| AD-53815 | AD-56616.1 | 0.47 | 0.68 | 0.70 | 1.01 | 0.06 | 0.08 | 0.34 |

TABLE 6-continued

Efficacy screens for lead optimization of AD-53815 and AD-53806 by free uptake in Cynomolgous monkey hepatocytes.

| Parent duplex | Duplex ID | 200 nM Avg | 20 nM Avg | 2 nM Avg | 0.2 nM-384 | 200 nM SD | 20 nM SD | 2 nM SD |
|---|---|---|---|---|---|---|---|---|
| AD-53815 | AD-56622.1 | 0.47 | 0.66 | 0.88 | 0.95 | 0.06 | 0.10 | 0.10 |
| AD-53815 | AD-56628.1 | 1.02 | 1.15 | 1.04 | 0.99 | 0.00 | 0.12 | 0.02 |
| AD-53815 | AD-56634.1 | 0.75 | 0.90 | 0.97 | 1.03 | 0.11 | 0.04 | 0.07 |
| AD-53815 | AD-56640.1 | 0.58 | 0.76 | 0.81 | 1.01 | 0.10 | 0.05 | 0.12 |
| AD-53815 | AD-56646.1 | 0.77 | 0.94 | 0.82 | 0.99 | 0.09 | 0.12 | 0.14 |
| AD-53815 | AD-56652.1 | 0.61 | 0.74 | 0.78 | 0.89 | 0.00 | 0.00 | 0.03 |
| AD-53815 | AD-56611.1 | 0.93 | 1.02 | 1.16 | 0.89 | 0.05 | 0.15 | 0.05 |
| AD-53815 | AD-56647.1 | 0.38 | 0.58 | 0.79 | 0.94 | 0.05 | 0.08 | 0.00 |
| AD-53815 | AD-56653.1 | 0.47 | 0.46 | 0.63 | 0.84 | 0.12 | 0.04 | 0.04 |
| AD-53815 | AD-56612.1 | 0.41 | 0.61 | 0.88 | 0.85 | 0.03 | 0.09 | 0.09 |
| AD-53815 | AD-56618.1 | 0.64 | 0.60 | 1.03 | 1.08 | 0.21 | 0.09 | 0.01 |
| AD-53815 | AD-56624.1 | 0.46 | 0.61 | 0.85 | 1.05 | 0.04 | 0.17 | 0.15 |
| AD-53815 | AD-56630.1 | 0.49 | 0.69 | 0.87 | 1.01 | 0.01 | 0.00 | 0.15 |
| AD-53815 | AD-56636.1 | 0.49 | 0.57 | 0.82 | 1.13 | 0.01 | 0.05 | 0.03 |
| AD-53815 | AD-56642.1 | 0.43 | 0.55 | 0.82 | 1.09 | 0.00 | 0.08 | 0.03 |
| AD-53815 | AD-56648.1 | 0.48 | 0.66 | 0.80 | 0.96 | 0.00 | 0.04 | 0.08 |
| AD-53815 | AD-56654.1 | 0.43 | 0.53 | 0.72 | 0.84 | 0.01 | 0.00 | 0.07 |
| AD-53815 | AD-56613.1 | 0.54 | 0.61 | 0.81 | 0.91 | 0.16 | 0.08 | 0.19 |
| AD-53815 | AD-56619.1 | 0.55 | 0.67 | 1.02 | 1.06 | 0.04 | 0.07 | 0.07 |
| AD-53815 | AD-56614.1 | 0.42 | 0.56 | 0.86 | 0.90 | 0.05 | 0.04 | 0.10 |
| AD-53815 | AD-56620.1 | 0.41 | 0.52 | 0.85 | 0.84 | 0.01 | 0.12 | 0.08 |
| AD-53815 | AD-56626.1 | 0.59 | 0.68 | 0.90 | 1.12 | 0.01 | 0.03 | 0.10 |
| AD-53815 | AD-56632.1 | 0.60 | 0.73 | 0.91 | 1.05 | 0.04 | 0.09 | 0.10 |
| AD-53815 | AD-56638.1 | 0.68 | 0.89 | 0.94 | 1.19 | 0.03 | 0.03 | 0.18 |
| AD-53815 | AD-56644.1 | 0.84 | 0.89 | 1.09 | 1.09 | 0.08 | 0.08 | 0.06 |
| AD-53815 | AD-56650.1 | 0.86 | 0.95 | 1.05 | 1.05 | 0.10 | 0.01 | 0.10 |
| AD-53815 | AD-56656.1 | 0.53 | 0.64 | 0.92 | 0.88 | 0.09 | 0.04 | 0.14 |
| AD-53815 | AD-56662.1 | 0.55 | 0.61 | 0.96 | 1.03 | 0.02 | 0.09 | 0.01 |
| AD-53815 | AD-56668.1 | 0.76 | 0.79 | 0.99 | 1.10 | 0.07 | 0.11 | 0.06 |
| AD-53815 | AD-56673.1 | 0.81 | 0.87 | 1.12 | 1.09 | 0.01 | 0.15 | 0.13 |
| AD-53815 | AD-56678.1 | 0.84 | 0.76 | 1.12 | 1.05 | 0.04 | 0.24 | 0.05 |
| AD-53815 | AD-56683.1 | 0.88 | 0.93 | 1.08 | 1.06 | 0.05 | 0.10 | 0.06 |
| AD-53815 | AD-56688.1 | 0.80 | 0.86 | 0.93 | 0.99 | 0.10 | 0.11 | 0.19 |
| AD-53815 | AD-56657.1 | 0.45 | 0.63 | 0.84 | 0.88 | 0.20 | 0.04 | 0.09 |
| AD-53815 | AD-56663.1 | 0.35 | 0.49 | 0.77 | 1.03 | 0.00 | 0.07 | 0.04 |
| AD-53815 | AD-56669.1 | 0.53 | 0.68 | 0.99 | 1.11 | 0.00 | 0.18 | 0.03 |
| AD-53815 | AD-56674.1 | 0.44 | 0.64 | 0.84 | 1.03 | 0.06 | 0.01 | 0.17 |
| AD-53815 | AD-56679.1 | 0.52 | 0.67 | 0.77 | 1.01 | 0.01 | 0.06 | 0.14 |
| AD-53815 | AD-56684.1 | 0.43 | 0.59 | 0.84 | 1.08 | 0.01 | 0.03 | 0.04 |
| AD-53815 | AD-56689.1 | 0.55 | 0.57 | 0.73 | 0.95 | 0.09 | 0.01 | 0.11 |
| AD-53815 | AD-56693.1 | 0.45 | 0.48 | 0.65 | 0.84 | 0.04 | 0.02 | 0.11 |
| AD-53815 | AD-56658.1 | 0.46 | 0.55 | 0.85 | 0.84 | 0.21 | 0.09 | 0.07 |
| AD-53815 | AD-56664.1 | 0.35 | 0.60 | 0.80 | 0.91 | 0.13 | 0.03 | 0.14 |
| AD-53815 | AD-56670.1 | 0.62 | 0.61 | 0.90 | 1.11 | 0.17 | 0.06 | 0.00 |
| AD-53815 | AD-56680.1 | 0.74 | 0.90 | 1.00 | 0.91 | 0.05 | 0.01 | 0.05 |
| AD-53815 | AD-56685.1 | 0.64 | 0.64 | 0.77 | 1.07 | 0.15 | 0.01 | 0.15 |
| AD-53815 | AD-56690.1 | 0.39 | 0.61 | 0.75 | 0.97 | 0.13 | 0.03 | 0.08 |
| AD-53815 | AD-56694.1 | 0.41 | 0.53 | 0.67 | 0.94 | 0.01 | 0.00 | 0.04 |
| AD-53815 | AD-56659.1 | 0.57 | 0.58 | 0.84 | 0.95 | 0.25 | 0.09 | 0.05 |
| AD-53815 | AD-56665.1 | 0.38 | 0.51 | 0.78 | 1.01 | 0.05 | 0.07 | 0.17 |
| AD-53815 | AD-56671.1 | 0.32 | 0.45 | 0.78 | 0.94 | 0.03 | 0.05 | 0.01 |
| AD-53815 | AD-56676.1 | 0.31 | 0.55 | 0.81 | 1.02 | 0.03 | 0.13 | 0.02 |
| AD-53815 | AD-56681.1 | 0.54 | 0.75 | 0.88 | 1.02 | 0.02 | 0.07 | 0.11 |
| AD-53815 | AD-56686.1 | 0.50 | 0.74 | 0.86 | 1.03 | 0.01 | 0.10 | 0.10 |
| AD-53815 | AD-56691.1 | 0.44 | 0.56 | 0.79 | 1.03 | 0.01 | 0.00 | 0.05 |
| AD-53815 | AD-56695.1 | 0.37 | 0.70 | 0.67 | 0.89 | 0.01 | 0.29 | 0.11 |
| AD-53815 | AD-56660.1 | 0.36 | 0.73 | 0.83 | 0.93 | 0.02 | 0.22 | 0.10 |
| AD-53815 | AD-56666.1 | 0.39 | 0.47 | 0.74 | 0.94 | 0.02 | 0.05 | 0.13 |
| AD-53815 | AD-56672.1 | 0.63 | 0.55 | 0.87 | 1.03 | 0.25 | 0.10 | 0.04 |
| AD-53815 | AD-56677.1 | 0.54 | 0.70 | 0.85 | 0.99 | 0.24 | 0.11 | 0.00 |
| AD-53815 | AD-56682.1 | 0.48 | 0.57 | 0.90 | 0.96 | 0.11 | 0.09 | 0.05 |
| AD-53815 | AD-56687.1 | 0.81 | 0.94 | 1.06 | 1.08 | 0.07 | 0.02 | 0.05 |
| AD-53815 | AD-56692.1 | 0.45 | 0.64 | 0.73 | 0.95 | 0.03 | 0.13 | 0.05 |
| AD-53815 | AD-56696.1 | 0.40 | 0.48 | 0.66 | 0.95 | 0.01 | 0.04 | 0.06 |
| AD-53815 | AD-56661.1 | 0.52 | 0.54 | 0.75 | 0.98 | 0.22 | 0.06 | 0.04 |
| AD-53815 | AD-56667.1 | 0.40 | 0.68 | 0.87 | 1.03 | 0.03 | 0.03 | 0.11 |
| AD-53806 | AD-53806.11 | 0.28 | 0.44 | 0.74 | 0.98 | 0.05 | 0.01 | 0.13 |
| AD-53806 | AD-53806.13 | 0.31 | 0.36 | 0.65 | 0.92 | 0.01 | 0.08 | 0.06 |
| AD-53806 | AD-53806.12 | 0.53 | 0.56 | 0.70 | 1.04 | 0.00 | 0.01 | 0.15 |
| AD-53806 | AD-53806.5 | 0.34 | 0.54 | 0.85 | 0.87 | 0.01 | 0.00 | 0.10 |
| AD-53806 | AD-53806.6 | 0.41 | 0.51 | 0.77 | 0.91 | 0.05 | 0.04 | 0.08 |
| AD-53806 | AD-53806.7 | 0.39 | 0.58 | 0.75 | 0.97 | 0.02 | 0.16 | 0.14 |
| AD-53806 | AD-53806.8 | 0.35 | 0.49 | 0.69 | 0.91 | 0.06 | 0.03 | 0.09 |
| AD-53806 | AD-53806.9 | 0.36 | 0.55 | 0.77 | 1.01 | 0.04 | 0.07 | 0.13 |

TABLE 6-continued

Efficacy screens for lead optimization of AD-53815 and AD-53806 by free uptake in Cynomolgous monkey hepatocytes.

| Parent duplex | Duplex ID | 200 nM Avg | 20 nM Avg | 2 nM Avg | 0.2 nM-384 | 200 nM SD | 20 nM SD | 2 nM SD |
|---|---|---|---|---|---|---|---|---|
| AD-53806 | AD-53806.10 | 0.29 | 0.44 | 0.73 | 0.93 | 0.04 | 0.10 | 0.14 |
| AD-53806 | AD-56979.1 | 0.43 | 0.50 | 0.78 | 0.96 | 0.01 | 0.03 | 0.11 |
| AD-53806 | AD-56979.2 | 0.32 | 0.47 | 0.65 | 1.02 | 0.02 | 0.11 | 0.05 |
| AD-53806 | AD-56975.3 | 0.27 | 0.57 | 0.72 | 0.83 | 0.01 | 0.16 | 0.08 |
| AD-53806 | AD-56975.4 | 0.55 | 0.67 | 0.81 | 0.92 | 0.11 | 0.10 | 0.04 |
| AD-53806 | AD-56975.5 | 0.34 | 0.54 | 0.71 | 0.94 | 0.04 | 0.22 | 0.10 |
| AD-53806 | AD-56975.1 | 0.38 | 0.53 | 0.74 | 0.93 | 0.13 | 0.14 | 0.02 |
| AD-53806 | AD-56975.2 | 0.50 | 0.62 | 0.82 | 0.98 | 0.09 | 0.16 | 0.11 |
| AD-53806 | AD-56983.1 | 0.49 | 0.72 | 0.89 | 1.11 | 0.10 | 0.09 | 0.21 |
| AD-53806 | AD-56983.2 | 0.74 | 0.89 | 1.14 | 1.16 | 0.10 | 0.06 | 0.02 |
| AD-53806 | AD-56983.3 | 0.91 | 1.05 | 1.02 | 1.04 | 0.09 | 0.10 | 0.08 |
| AD-53806 | AD-56983.4 | 0.40 | 0.57 | 0.83 | 1.05 | 0.03 | 0.02 | 0.08 |
| AD-53806 | AD-56983.5 | 0.33 | 0.51 | 0.83 | 0.90 | 0.03 | 0.04 | 0.03 |
| AD-53806 | AD-56977.3 | 0.44 | 0.49 | 0.62 | 0.95 | 0.17 | 0.16 | 0.06 |
| AD-53806 | AD-56977.1 | 0.27 | 0.58 | 0.81 | 0.88 | 0.06 | 0.07 | 0.08 |
| AD-53806 | AD-56977.2 | 0.41 | 0.60 | 0.81 | 0.90 | 0.01 | 0.07 | 0.12 |
| AD-53806 | AD-56976.1 | 0.40 | 0.64 | 0.85 | 0.90 | 0.14 | 0.21 | 0.01 |
| AD-53806 | AD-56976.2 | 0.37 | 0.47 | 0.70 | 1.01 | 0.09 | 0.10 | 0.13 |
| AD-53806 | AD-56980.1 | 0.47 | 0.54 | 0.83 | 0.97 | 0.12 | 0.02 | 0.14 |
| AD-53806 | AD-56980.2 | 0.44 | 0.55 | 0.81 | 1.08 | 0.15 | 0.11 | 0.08 |
| AD-53806 | AD-56984.1 | 0.41 | 0.63 | 0.81 | 1.08 | 0.04 | 0.07 | 0.14 |
| AD-53806 | AD-56984.2 | 0.32 | 0.58 | 0.86 | 1.04 | 0.02 | 0.17 | 0.07 |
| AD-53806 | AD-56987.1 | 0.37 | 0.63 | 0.82 | 1.11 | 0.08 | 0.08 | 0.05 |
| AD-53806 | AD-56987.2 | 0.33 | 0.59 | 0.79 | 1.02 | 0.05 | 0.05 | 0.13 |
| AD-53806 | AD-56991.1 | 0.36 | 0.57 | 0.73 | 1.08 | 0.01 | 0.07 | 0.18 |
| AD-53806 | AD-56993.1 | 0.41 | 0.54 | 0.75 | 0.99 | 0.12 | 0.09 | 0.06 |
| AD-53806 | AD-56995.1 | 0.35 | 0.45 | 0.67 | 1.00 | 0.07 | 0.02 | 0.12 |
| AD-53806 | AD-56978.1 | 0.35 | 0.67 | 0.88 | 0.91 | 0.04 | 0.22 | 0.05 |
| AD-53806 | AD-56978.2 | 0.47 | 0.55 | 0.78 | 1.12 | 0.03 | 0.01 | 0.07 |
| AD-53806 | AD-56981.1 | 0.45 | 0.65 | 0.86 | 1.08 | 0.01 | 0.16 | 0.15 |
| AD-53806 | AD-56985.1 | 0.53 | 0.61 | 1.08 | 1.14 | 0.02 | 0.09 | 0.07 |
| AD-53806 | AD-56988.1 | 0.62 | 0.81 | 0.91 | 1.13 | 0.01 | 0.05 | 0.20 |
| AD-53806 | AD-56988.2 | 0.76 | 0.94 | 0.85 | 1.14 | 0.17 | 0.10 | 0.11 |
| AD-53806 | AD-56988.3 | 0.55 | 0.79 | 0.86 | 1.19 | 0.04 | 0.05 | 0.16 |
| AD-53806 | AD-56982.1 | 0.40 | 0.65 | 0.84 | 1.07 | 0.04 | 0.10 | 0.09 |
| AD-53806 | AD-56982.2 | 0.38 | 0.50 | 0.70 | 1.01 | 0.03 | 0.03 | 0.08 |
| AD-53806 | AD-56986.1 | 0.45 | 0.57 | 0.80 | 1.12 | 0.02 | 0.11 | 0.15 |
| AD-53806 | AD-56986.2 | 0.49 | 0.59 | 0.79 | 1.04 | 0.01 | 0.05 | 0.17 |
| AD-53806 | AD-56989.1 | 0.69 | 0.84 | 0.95 | 1.12 | 0.08 | 0.06 | 0.12 |
| AD-53806 | AD-56990.1 | 0.49 | 0.56 | 0.79 | 1.08 | 0.03 | 0.02 | 0.13 |
| AD-53806 | AD-56992.1 | 0.61 | 0.70 | 0.90 | 1.14 | 0.01 | 0.04 | 0.14 |
| AD-53806 | AD-56992.2 | 0.48 | 0.63 | 0.87 | 0.99 | 0.05 | 0.10 | 0.07 |
| AD-53806 | AD-56994.1 | 0.88 | 0.89 | 0.97 | 1.11 | 0.02 | 0.06 | 0.13 |
| AD-53806 | AD-56994.2 | 0.34 | 0.42 | 0.73 | 0.98 | 0.01 | 0.05 | 0.05 |
| AD-53806 | AD-56996.1 | 0.50 | 0.59 | 0.77 | 0.95 | 0.07 | 0.12 | 0.10 |
| AD-53806 | AD-57001.1 | 0.44 | 0.54 | 0.77 | 1.08 | 0.01 | 0.05 | 0.12 |
| AD-53806 | AD-57007.1 | 0.62 | 0.68 | 0.91 | 1.11 | 0.04 | 0.02 | 0.19 |
| AD-53806 | AD-57013.1 | 0.65 | 0.78 | 0.94 | 1.17 | 0.05 | 0.04 | 0.22 |
| AD-53806 | AD-57019.1 | 0.57 | 0.74 | 0.87 | 1.14 | 0.01 | 0.09 | 0.13 |
| AD-53806 | AD-57022.1 | 0.46 | 0.48 | 0.72 | 0.98 | 0.14 | 0.01 | 0.17 |
| AD-53806 | AD-57025.1 | 0.37 | 0.47 | 0.68 | 0.92 | 0.04 | 0.11 | 0.06 |
| AD-53806 | AD-56997.1 | 0.41 | 0.56 | 0.77 | 0.88 | 0.00 | 0.10 | 0.09 |
| AD-53806 | AD-57002.1 | 0.46 | 0.58 | 0.81 | 1.04 | 0.03 | 0.03 | 0.08 |
| AD-53806 | AD-57008.1 | 0.68 | 0.75 | 0.91 | 1.13 | 0.02 | 0.03 | 0.15 |
| AD-53806 | AD-57014.1 | 0.80 | 0.82 | 0.99 | 1.17 | 0.02 | 0.01 | 0.12 |
| AD-53806 | AD-57020.1 | 0.51 | 0.53 | 0.81 | 1.07 | 0.17 | 0.03 | 0.07 |
| AD-53806 | AD-57020.2 | 0.37 | 0.46 | 0.68 | 1.02 | 0.04 | 0.07 | 0.13 |
| AD-53806 | AD-57026.1 | 0.34 | 0.51 | 0.68 | 0.97 | 0.01 | 0.08 | 0.06 |
| AD-53806 | AD-57003.1 | 0.76 | 0.90 | 0.94 | 1.11 | 0.02 | 0.16 | 0.11 |
| AD-53806 | AD-57009.1 | 0.81 | 0.88 | 0.93 | 0.98 | 0.01 | 0.03 | 0.10 |
| AD-53806 | AD-57015.1 | 0.72 | 0.92 | 0.90 | 1.04 | 0.01 | 0.05 | 0.15 |
| AD-53806 | AD-57023.1 | 0.41 | 0.50 | 0.75 | 1.00 | 0.08 | 0.07 | 0.06 |
| AD-53806 | AD-57027.1 | 0.38 | 0.46 | 0.68 | 0.93 | 0.11 | 0.00 | 0.07 |
| AD-53806 | AD-56998.1 | 0.45 | 0.57 | 0.94 | 0.98 | 0.01 | 0.06 | 0.11 |
| AD-53806 | AD-57004.1 | 0.39 | 0.61 | 0.80 | 1.13 | 0.03 | 0.04 | 0.13 |
| AD-53806 | AD-57010.1 | 0.43 | 0.64 | 0.81 | 1.00 | 0.01 | 0.07 | 0.15 |
| AD-53806 | AD-57016.1 | 0.44 | 0.71 | 0.80 | 0.97 | 0.01 | 0.25 | 0.05 |
| AD-53806 | AD-56999.2 | 0.49 | 0.60 | 0.69 | 1.04 | 0.04 | 0.02 | 0.16 |
| AD-53806 | AD-56999.1 | 0.39 | 0.55 | 0.68 | 0.96 | 0.01 | 0.09 | 0.10 |
| AD-53806 | AD-57021.1 | 0.40 | 0.58 | 0.71 | 1.02 | 0.03 | 0.03 | 0.11 |
| AD-53806 | AD-57024.1 | 0.41 | 0.49 | 0.68 | 1.02 | 0.14 | 0.00 | 0.10 |
| AD-53806 | AD-57005.1 | 0.45 | 0.56 | 0.87 | 1.06 | 0.03 | 0.03 | 0.20 |
| AD-53806 | AD-57011.1 | 0.53 | 0.63 | 0.92 | 1.02 | 0.02 | 0.07 | 0.10 |
| AD-53806 | AD-57017.1 | 0.48 | 0.60 | 0.81 | 1.07 | 0.00 | 0.01 | 0.12 |

TABLE 6-continued

Efficacy screens for lead optimization of AD-53815 and AD-53806 by free uptake in Cynomolgous monkey hepatocytes.

| Parent duplex | Duplex ID | 200 nM Avg | 20 nM Avg | 2 nM Avg | 0.2 nM-384 | 200 nM SD | 20 nM SD | 2 nM SD |
|---|---|---|---|---|---|---|---|---|
| AD-53806 | AD-57000.2 | 0.50 | 0.60 | 0.74 | 0.93 | 0.04 | 0.01 | 0.02 |
| AD-53806 | AD-57000.3 | 0.54 | 0.49 | 0.72 | 0.97 | 0.22 | 0.08 | 0.00 |
| AD-53806 | AD-57000.1 | 0.70 | 0.76 | 0.80 | 0.95 | 0.02 | 0.05 | 0.04 |
| AD-53806 | AD-57006.2 | 0.48 | 0.75 | 0.76 | 0.94 | 0.00 | 0.31 | 0.12 |
| AD-53806 | AD-57006.3 | 0.45 | 0.57 | 0.71 | 0.98 | 0.08 | 0.09 | 0.12 |
| AD-53806 | AD-57006.1 | 0.64 | 0.76 | 0.84 | 0.97 | 0.00 | 0.11 | 0.10 |
| AD-53806 | AD-57012.1 | 0.53 | 0.83 | 0.79 | 0.93 | 0.04 | 0.42 | 0.02 |
| AD-53806 | AD-57018.1 | 0.67 | 0.73 | 0.72 | 0.93 | 0.07 | 0.04 | 0.03 |

siRNAs with a variety of chemical modifications based on the parent sequences of AD-53815 and AD-53806 were also screened for in vitro efficacy by transfection in Hep3B cells at 10 nM and 0.1 nM. The results of this structure-activity relationship screen are shown in Table 7, and are expressed as the average fraction message remaining relative to control +/−SD.

TABLE 7

Efficacy screens for lead optimization of AD-53815 and AD-53806 by transfection in a human cells.

| Parent duplex | Duplex ID | Trans 10 nM Avg | Trans 10 nM SD | Trans 0.1 nM Avg | Trans 0.1 nM SD |
|---|---|---|---|---|---|
| AD-53815 | AD-53815.5 | 0.14 | 0.05 | 0.24 | ND |
| AD-53815 | AD-53815.4 | 0.18 | 0.07 | 0.38 | ND |
| AD-53815 | AD-56633.1 | 0.18 | 0.10 | 0.24 | ND |
| AD-53815 | AD-56617.1 | 0.13 | 0.06 | 0.25 | ND |
| AD-53815 | AD-56623.1 | 0.14 | 0.05 | 0.24 | ND |
| AD-53815 | AD-56629.1 | 0.14 | 0.02 | 0.17 | ND |
| AD-53815 | AD-56635.1 | 0.12 | 0.02 | 0.22 | ND |
| AD-53815 | AD-56641.1 | 0.15 | 0.01 | 0.16 | ND |
| AD-53815 | AD-56625.1 | 0.12 | 0.03 | 0.29 | ND |
| AD-53815 | AD-56631.1 | 0.13 | 0.01 | 0.20 | ND |
| AD-53815 | AD-56637.1 | 0.22 | 0.14 | 0.16 | ND |
| AD-53815 | AD-56643.1 | 0.18 | 0.08 | 0.16 | ND |
| AD-53815 | AD-56649.1 | 0.16 | 0.00 | 0.19 | ND |
| AD-53815 | AD-56655.1 | 0.24 | 0.11 | 0.24 | ND |
| AD-53815 | AD-56615.1 | 0.15 | 0.00 | 0.32 | ND |
| AD-53815 | AD-56621.1 | 0.20 | 0.07 | 0.41 | ND |
| AD-53815 | AD-56627.1 | 0.17 | 0.04 | 0.31 | ND |
| AD-53815 | AD-56639.1 | 0.19 | 0.08 | 0.24 | ND |
| AD-53815 | AD-56645.1 | 0.19 | 0.09 | 0.27 | ND |
| AD-53815 | AD-56651.1 | 0.29 | 0.09 | 0.68 | ND |
| AD-53815 | AD-56610.1 | 0.21 | 0.11 | 0.23 | ND |
| AD-53815 | AD-56616.1 | 0.16 | 0.04 | 0.29 | ND |
| AD-53815 | AD-56622.1 | 0.18 | 0.07 | 0.36 | ND |
| AD-53815 | AD-56628.1 | 0.28 | 0.07 | 0.60 | ND |
| AD-53815 | AD-56634.1 | 0.16 | 0.04 | 0.29 | ND |
| AD-53815 | AD-56640.1 | 0.21 | 0.09 | 0.26 | ND |
| AD-53815 | AD-56646.1 | 0.27 | 0.21 | 0.37 | ND |
| AD-53815 | AD-56652.1 | 0.26 | 0.08 | 0.29 | ND |
| AD-53815 | AD-56611.1 | 0.35 | 0.11 | 0.96 | ND |
| AD-53815 | AD-56647.1 | 0.17 | 0.09 | 0.13 | ND |
| AD-53815 | AD-56653.1 | 0.17 | 0.09 | 0.28 | ND |
| AD-53815 | AD-56612.1 | 0.17 | 0.07 | 0.24 | ND |
| AD-53815 | AD-56618.1 | 0.14 | 0.00 | 0.26 | ND |
| AD-53815 | AD-56624.1 | 0.15 | 0.02 | 0.27 | ND |
| AD-53815 | AD-56630.1 | 0.13 | 0.01 | 0.24 | ND |
| AD-53815 | AD-56636.1 | 0.17 | 0.08 | 0.22 | ND |
| AD-53815 | AD-56642.1 | 0.12 | 0.03 | 0.13 | ND |
| AD-53815 | AD-56648.1 | 0.15 | 0.05 | 0.21 | ND |
| AD-53815 | AD-56654.1 | 0.22 | 0.10 | 0.24 | ND |
| AD-53815 | AD-56613.1 | 0.17 | 0.07 | 0.40 | ND |
| AD-53815 | AD-56619.1 | 0.21 | 0.12 | 0.30 | ND |
| AD-53815 | AD-56614.1 | 0.12 | 0.01 | 0.23 | ND |
| AD-53815 | AD-56620.1 | 0.12 | 0.02 | 0.15 | ND |
| AD-53815 | AD-56626.1 | 0.14 | 0.03 | 0.20 | ND |

TABLE 7-continued

Efficacy screens for lead optimization of AD-53815 and AD-53806 by transfection in a human cells.

| Parent duplex | Duplex ID | Trans 10 nM Avg | Trans 10 nM SD | Trans 0.1 nM Avg | Trans 0.1 nM SD |
|---|---|---|---|---|---|
| AD-53815 | AD-56632.1 | 0.12 | 0.02 | 0.21 | ND |
| AD-53815 | AD-56638.1 | 0.15 | 0.10 | 0.23 | ND |
| AD-53815 | AD-56644.1 | 0.23 | 0.11 | 0.17 | ND |
| AD-53815 | AD-56650.1 | 0.13 | 0.03 | 0.20 | ND |
| AD-53815 | AD-56656.1 | 0.26 | 0.03 | 0.27 | ND |
| AD-53815 | AD-56662.1 | 0.13 | 0.06 | 0.18 | ND |
| AD-53815 | AD-56668.1 | 0.19 | 0.05 | 0.20 | ND |
| AD-53815 | AD-56673.1 | 0.18 | 0.05 | 0.21 | ND |
| AD-53815 | AD-56678.1 | 0.17 | 0.00 | 0.20 | ND |
| AD-53815 | AD-56683.1 | 0.29 | 0.22 | 0.27 | ND |
| AD-53815 | AD-56688.1 | 0.19 | 0.02 | 0.18 | ND |
| AD-53815 | AD-56657.1 | 0.18 | 0.14 | 0.34 | ND |
| AD-53815 | AD-56663.1 | 0.11 | 0.04 | 0.18 | ND |
| AD-53815 | AD-56669.1 | 0.11 | 0.02 | 0.31 | ND |
| AD-53815 | AD-56674.1 | 0.14 | 0.00 | 0.21 | ND |
| AD-53815 | AD-56679.1 | 0.14 | 0.05 | 0.19 | ND |
| AD-53815 | AD-56684.1 | 0.14 | 0.03 | 0.19 | ND |
| AD-53815 | AD-56689.1 | 0.18 | 0.09 | 0.18 | ND |
| AD-53815 | AD-56693.1 | 0.19 | 0.11 | 0.21 | ND |
| AD-53815 | AD-56658.1 | 0.19 | 0.13 | 0.30 | ND |
| AD-53815 | AD-56664.1 | 0.15 | 0.07 | 0.20 | ND |
| AD-53815 | AD-56670.1 | 0.18 | 0.10 | 0.26 | ND |
| AD-53815 | AD-56680.1 | 0.27 | 0.05 | 0.31 | ND |
| AD-53815 | AD-56685.1 | 0.14 | 0.02 | 0.28 | ND |
| AD-53815 | AD-56690.1 | 0.10 | 0.03 | 0.18 | ND |
| AD-53815 | AD-56694.1 | 0.15 | 0.06 | 0.17 | ND |
| AD-53815 | AD-56659.1 | 0.16 | 0.04 | 0.27 | ND |
| AD-53815 | AD-56665.1 | 0.14 | 0.06 | 0.26 | ND |
| AD-53815 | AD-56671.1 | 0.11 | 0.01 | 0.29 | ND |
| AD-53815 | AD-56676.1 | 0.14 | 0.06 | 0.20 | ND |
| AD-53815 | AD-56681.1 | 0.15 | 0.03 | 0.30 | ND |
| AD-53815 | AD-56686.1 | 0.15 | 0.03 | 0.26 | ND |
| AD-53815 | AD-56691.1 | 0.11 | 0.02 | 0.16 | ND |
| AD-53815 | AD-56695.1 | 0.14 | 0.06 | 0.24 | ND |
| AD-53815 | AD-56660.1 | 0.10 | 0.03 | 0.37 | ND |
| AD-53815 | AD-56666.1 | 0.18 | 0.13 | 0.22 | ND |
| AD-53815 | AD-56672.1 | 0.14 | 0.02 | 0.35 | ND |
| AD-53815 | AD-56677.1 | 0.15 | 0.04 | 0.23 | ND |
| AD-53815 | AD-56682.1 | 0.14 | 0.06 | 0.28 | ND |
| AD-53815 | AD-56687.1 | 0.24 | 0.01 | 0.53 | ND |
| AD-53815 | AD-56692.1 | 0.09 | 0.01 | 0.36 | ND |
| AD-53815 | AD-56696.1 | 0.16 | 0.09 | 0.26 | ND |
| AD-53815 | AD-56661.1 | 0.21 | 0.15 | 0.48 | ND |
| AD-53815 | AD-56667.1 | 0.22 | 0.16 | 0.26 | ND |
| AD-53806 | AD-53806.11 | 0.19 | 0.05 | 0.25 | 0.06 |
| AD-53806 | AD-53806.13 | 0.21 | 0.07 | 0.21 | 0.16 |
| AD-53806 | AD-53806.12 | 0.21 | 0.08 | 0.21 | 0.02 |
| AD-53806 | AD-53806.5 | 0.22 | 0.01 | 0.29 | 0.06 |
| AD-53806 | AD-53806.6 | 0.24 | 0.07 | 0.33 | 0.12 |
| AD-53806 | AD-53806.7 | 0.19 | 0.02 | 0.24 | 0.11 |
| AD-53806 | AD-53806.8 | 0.20 | 0.01 | 0.23 | 0.05 |
| AD-53806 | AD-53806.9 | 0.22 | 0.01 | 0.19 | 0.06 |
| AD-53806 | AD-53806.10 | 0.17 | 0.01 | 0.21 | 0.07 |

TABLE 7-continued

Efficacy screens for lead optimization of AD-53815 and AD-53806 by transfection in a human cells.

| Parent duplex | Duplex ID | Trans 10 nM Avg | Trans 10 nM SD | Trans 0.1 nM Avg | Trans 0.1 nM SD |
|---|---|---|---|---|---|
| AD-53806 | AD-56979.1 | 0.18 | 0.00 | 0.29 | 0.14 |
| AD-53806 | AD-56979.2 | 0.24 | 0.11 | 0.24 | 0.12 |
| AD-53806 | AD-56975.3 | 0.26 | 0.09 | 0.28 | 0.18 |
| AD-53806 | AD-56975.4 | 0.35 | 0.02 | 0.50 | 0.23 |
| AD-53806 | AD-56975.5 | 0.17 | 0.01 | 0.21 | 0.18 |
| AD-53806 | AD-56975.1 | 0.24 | 0.09 | 0.32 | 0.12 |
| AD-53806 | AD-56975.2 | 0.19 | 0.04 | 0.16 | 0.02 |
| AD-53806 | AD-56983.1 | 0.17 | 0.01 | 0.32 | 0.18 |
| AD-53806 | AD-56983.2 | 0.28 | 0.07 | 0.63 | 0.15 |
| AD-53806 | AD-56983.3 | 1.22 | 0.61 | 0.83 | 0.02 |
| AD-53806 | AD-56983.4 | 0.25 | 0.10 | 0.24 | 0.10 |
| AD-53806 | AD-56983.5 | 0.17 | 0.01 | 0.26 | 0.15 |
| AD-53806 | AD-56977.3 | 0.31 | 0.11 | 0.28 | 0.23 |
| AD-53806 | AD-56977.1 | 0.22 | 0.04 | 0.34 | 0.12 |
| AD-53806 | AD-56977.2 | 0.22 | 0.05 | 0.29 | 0.16 |
| AD-53806 | AD-56976.1 | 0.21 | 0.09 | 0.34 | 0.20 |
| AD-53806 | AD-56976.2 | 0.17 | 0.03 | 0.25 | 0.04 |
| AD-53806 | AD-56980.1 | 0.22 | 0.04 | 0.20 | 0.02 |
| AD-53806 | AD-56980.2 | 0.19 | 0.01 | 0.20 | 0.06 |
| AD-53806 | AD-56984.1 | 0.24 | 0.11 | 0.22 | 0.10 |
| AD-53806 | AD-56984.2 | 0.19 | 0.01 | 0.21 | 0.10 |
| AD-53806 | AD-56987.1 | 0.19 | 0.05 | 0.29 | 0.19 |
| AD-53806 | AD-56987.2 | 0.24 | 0.03 | 0.24 | 0.09 |
| AD-53806 | AD-56991.1 | 0.17 | 0.01 | 0.17 | 0.08 |
| AD-53806 | AD-56993.1 | 0.14 | 0.09 | 0.22 | 0.06 |
| AD-53806 | AD-56995.1 | 0.19 | 0.07 | 0.27 | 0.13 |
| AD-53806 | AD-56978.1 | 0.27 | 0.12 | 0.36 | 0.12 |
| AD-53806 | AD-56978.2 | 0.24 | 0.03 | 0.20 | 0.01 |
| AD-53806 | AD-56981.1 | 0.22 | 0.03 | 0.28 | 0.17 |
| AD-53806 | AD-56985.1 | 0.21 | 0.00 | 0.28 | 0.04 |
| AD-53806 | AD-56988.1 | 0.20 | 0.02 | 0.24 | 0.02 |
| AD-53806 | AD-56988.2 | 0.20 | 0.03 | 0.27 | 0.13 |
| AD-53806 | AD-56988.3 | 0.23 | 0.03 | 0.27 | 0.01 |
| AD-53806 | AD-56982.1 | 0.23 | 0.06 | 0.24 | 0.00 |
| AD-53806 | AD-56982.2 | 0.21 | 0.06 | 0.18 | 0.07 |
| AD-53806 | AD-56986.1 | 0.23 | 0.05 | 0.20 | 0.06 |
| AD-53806 | AD-56986.2 | 0.24 | 0.04 | 0.25 | 0.13 |
| AD-53806 | AD-56989.1 | 0.31 | 0.02 | 0.43 | 0.00 |
| AD-53806 | AD-56990.1 | 0.27 | 0.00 | 0.28 | 0.10 |
| AD-53806 | AD-56992.1 | 0.27 | 0.06 | 0.31 | 0.01 |
| AD-53806 | AD-56992.2 | 0.22 | 0.10 | 0.30 | 0.14 |
| AD-53806 | AD-56994.1 | 0.97 | 0.05 | 0.85 | 0.09 |
| AD-53806 | AD-56994.2 | 0.22 | 0.09 | 0.26 | 0.01 |
| AD-53806 | AD-56996.1 | 0.18 | 0.04 | 0.31 | 0.08 |
| AD-53806 | AD-57001.1 | 0.24 | 0.09 | 0.23 | 0.08 |
| AD-53806 | AD-57007.1 | 0.25 | 0.01 | 0.27 | 0.03 |
| AD-53806 | AD-57013.1 | 0.30 | 0.08 | 0.33 | 0.02 |
| AD-53806 | AD-57019.1 | 0.29 | 0.03 | 0.28 | 0.02 |
| AD-53806 | AD-57022.1 | 0.20 | 0.06 | 0.21 | 0.05 |
| AD-53806 | AD-57025.1 | 0.23 | 0.12 | 0.25 | 0.15 |
| AD-53806 | AD-56997.1 | 0.20 | 0.05 | 0.25 | 0.11 |
| AD-53806 | AD-57002.1 | 0.21 | 0.07 | 0.28 | 0.01 |
| AD-53806 | AD-57008.1 | 0.26 | 0.01 | 0.31 | 0.01 |
| AD-53806 | AD-57014.1 | 0.32 | 0.03 | 0.43 | 0.05 |
| AD-53806 | AD-57020.1 | 0.19 | 0.00 | 0.23 | 0.01 |
| AD-53806 | AD-57020.2 | 0.20 | 0.08 | 0.28 | 0.22 |
| AD-53806 | AD-57026.1 | 0.34 | 0.24 | 0.37 | 0.24 |
| AD-53806 | AD-57003.1 | 0.34 | 0.04 | 0.45 | 0.15 |
| AD-53806 | AD-57009.1 | 0.30 | 0.07 | 0.40 | 0.02 |
| AD-53806 | AD-57015.1 | 0.32 | 0.01 | 0.47 | 0.04 |
| AD-53806 | AD-57023.1 | 0.17 | 0.06 | 0.27 | 0.13 |
| AD-53806 | AD-57027.1 | 0.20 | 0.03 | 0.19 | 0.11 |
| AD-53806 | AD-56998.1 | 0.23 | 0.09 | 0.29 | 0.24 |
| AD-53806 | AD-57004.1 | 0.24 | 0.13 | 0.30 | 0.12 |
| AD-53806 | AD-57010.1 | 0.23 | 0.09 | 0.23 | 0.11 |
| AD-53806 | AD-57016.1 | 0.21 | 0.03 | 0.23 | 0.06 |
| AD-53806 | AD-56999.2 | 0.25 | 0.10 | 0.35 | 0.05 |
| AD-53806 | AD-56999.1 | 0.24 | 0.08 | 0.28 | 0.21 |

TABLE 7-continued

Efficacy screens for lead optimization of AD-53815 and AD-53806 by transfection in a human cells.

| Parent duplex | Duplex ID | Trans 10 nM Avg | Trans 10 nM SD | Trans 0.1 nM Avg | Trans 0.1 nM SD |
|---|---|---|---|---|---|
| AD-53806 | AD-57021.1 | 0.18 | 0.04 | 0.29 | 0.17 |
| AD-53806 | AD-57024.1 | 0.20 | 0.09 | 0.28 | 0.11 |
| AD-53806 | AD-57005.1 | 0.18 | 0.10 | 0.29 | 0.17 |
| AD-53806 | AD-57011.1 | 0.21 | 0.07 | 0.26 | 0.12 |
| AD-53806 | AD-57017.1 | 0.20 | 0.07 | 0.29 | 0.21 |
| AD-53806 | AD-57000.2 | 0.20 | 0.04 | 0.29 | 0.21 |
| AD-53806 | AD-57000.3 | 0.22 | 0.11 | 0.30 | 0.16 |
| AD-53806 | AD-57000.1 | 0.25 | 0.14 | 0.38 | 0.33 |
| AD-53806 | AD-57006.2 | 0.22 | 0.14 | 0.31 | 0.18 |
| AD-53806 | AD-57006.3 | 0.19 | 0.09 | 0.31 | 0.25 |
| AD-53806 | AD-57006.1 | 0.20 | 0.12 | 0.41 | 0.29 |
| AD-53806 | AD-57012.1 | 0.16 | 0.05 | 0.36 | 0.17 |
| AD-53806 | AD-57018.1 | 0.20 | 0.37 | 0.10 | 0.14 |

Figure 4:
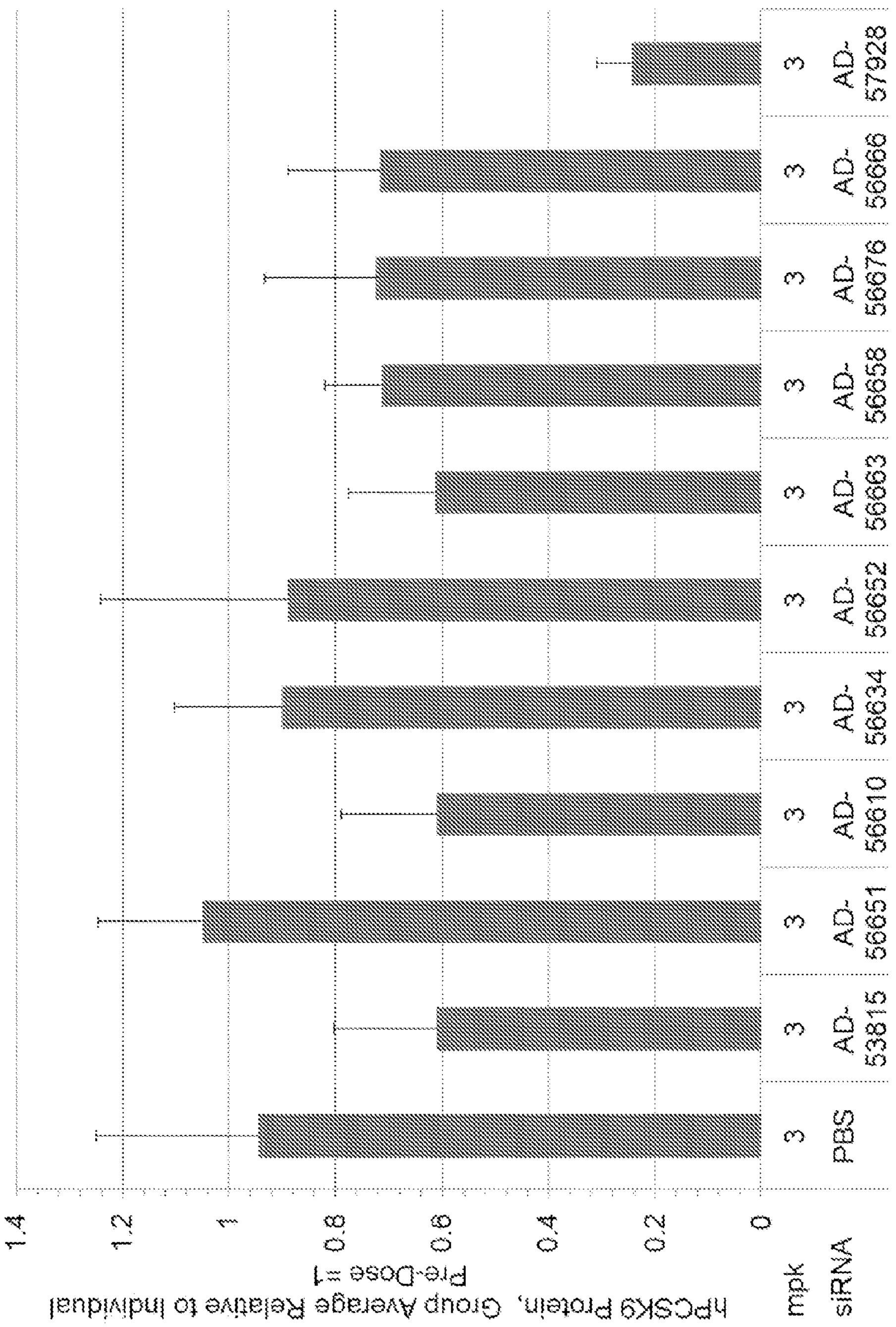
FIG. 4 is a graph depicting the results of the in vivo efficacy assays for lead optimization.
Figure 5:
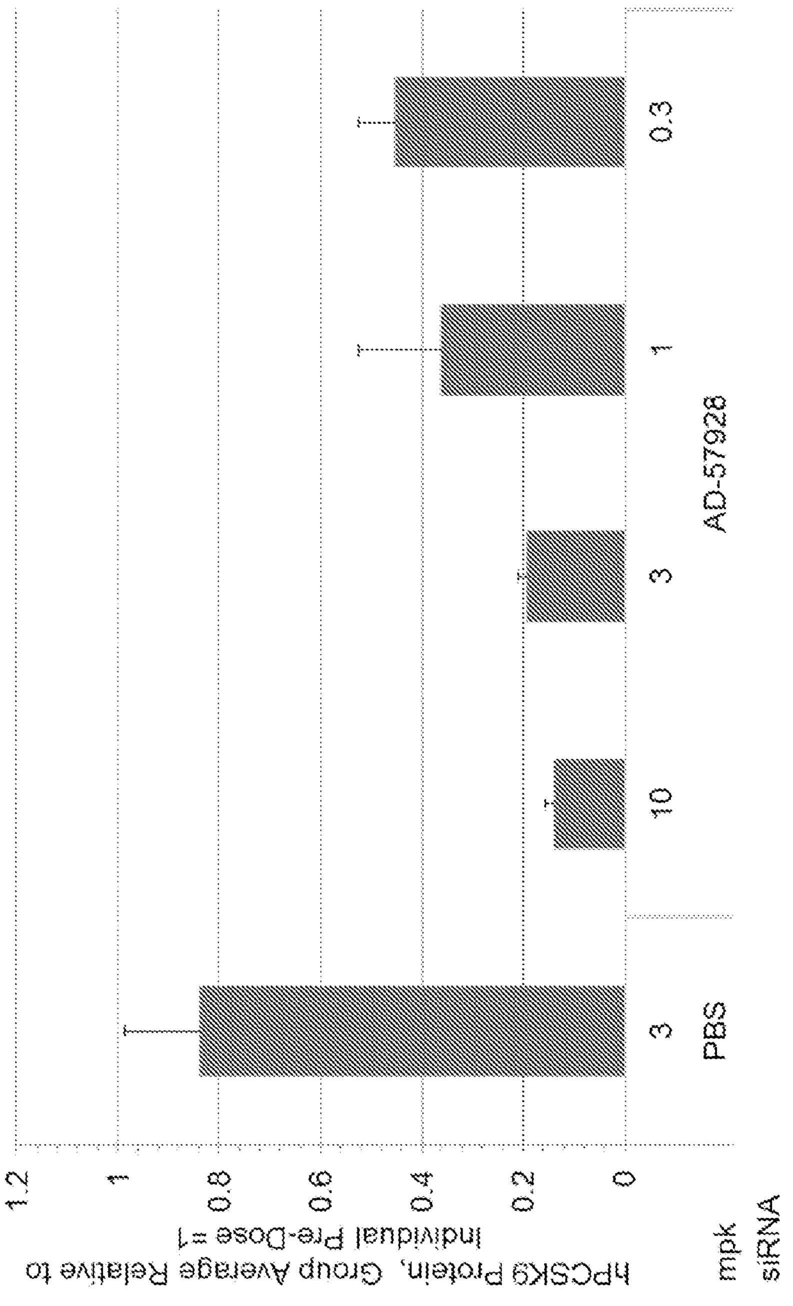
FIG. 5 is a graph depicting the results of the in vivo dose response assays performed in PCSK9 transgenic mice. Seventy-two hours after a single dose of 10 mg/kg, 3 mg/kg, 1 mg/kg, and 0.3 mg/kg of AD-57928, PCSK9 protein levels were determined by ELISA.
Figure 6:
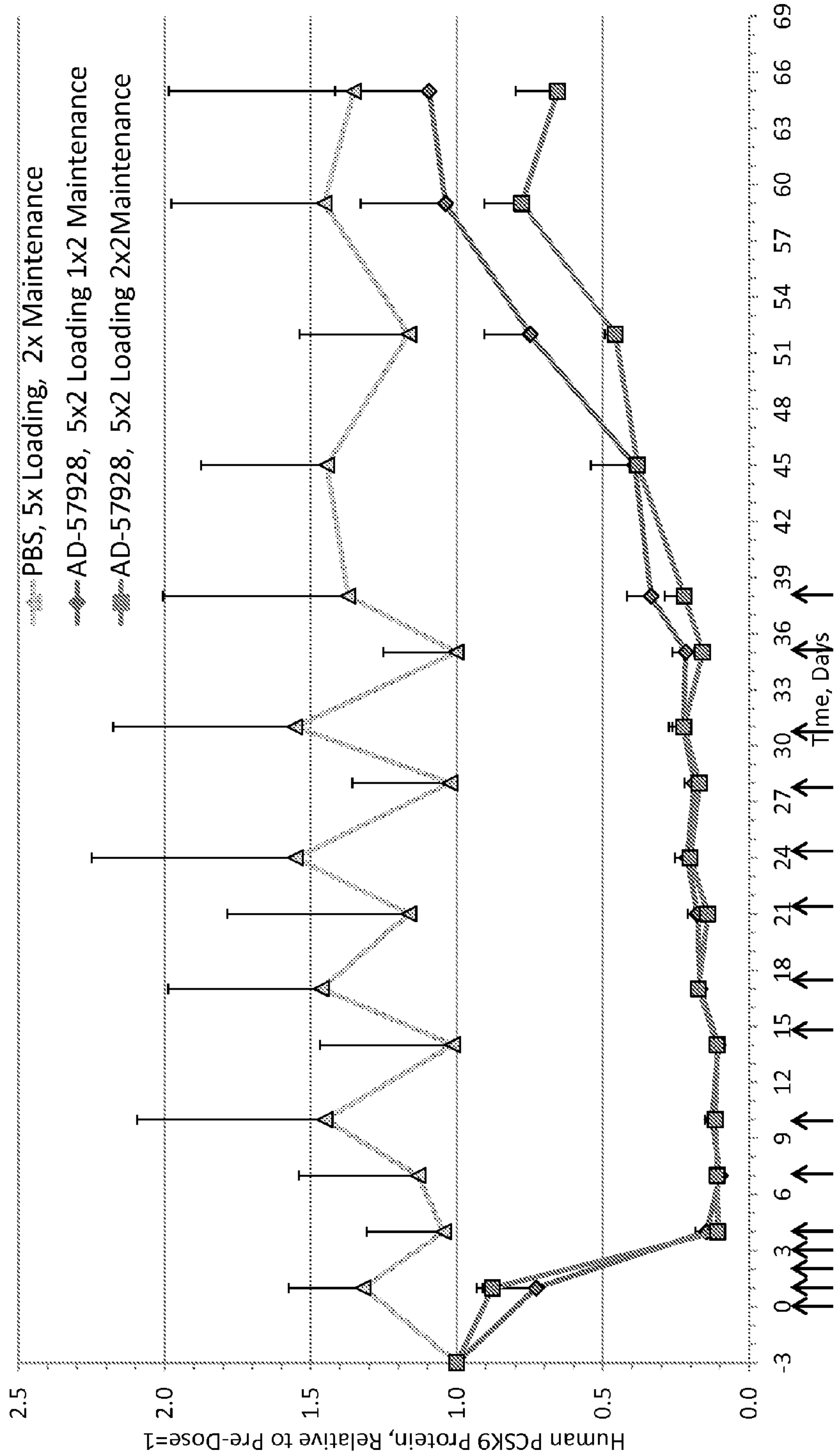
FIG. 6 is a graph depicting the levels of PCSK9 protein in serum of PCSK9 transgenic mice after administration of AD-57928 in 5×2 mg/kg doses during the "loading phase" and 1×2 mg/kg or 2×2 mg/kg doses during the "maintenance phase".

To determine whether any of the siRNAs from the in vitro SAR screen are more effective at silencing PCSK9 than the parent siRNA (AD-53815) PCSK9 transgenic mice were administered a single 3 mg/kg dose of the siRNAs shown in FIG. 4, and 72 hours post-dosing, PCSK9 protein levels were determined by ELISA assay. The results, shown in FIG. 5, demonstrate that AD-57928 is surprisingly effective at silencing PCSK9. FIG. 6 shows that, not only does a single dose of AD-57928 effectively knock-down PCSK9 protein, but there is also a dose response using AD-57928.

Example 4. Split Dosing Study Using AD-57928

The ability of AD-57928 to suppress expression of PCSK9 protein was assessed by measuring levels of human PCSK9 (hPCSK9) protein in serum of hPCSK9 transgenic mice following administration of AD-57928. AD-57928 was administered subcutaneously using six different dosing schedules that included a "loading phase" during the first week (one dose of 0.5 mg/kg, 1 mg/kg or 2 mg/kg daily for 5 subsequent days), followed by a "maintenance phase" (once or twice weekly dosing of either 0.5 mg/kg, 1 mg/kg or 2 mg/kg for 5 weeks), as is described in Table 8 below. The last dose was administered at day 38. Each dosing schedule was tested using a group of 3 mice that included two males and one female. A control group received injections with PBS.

TABLE 8

Dosing Schedules for administration of AD-57928

| Test Article | Week 1 Loading Dose (mg/kg) | Week 1 Total Dose (mg/kg) | Weeks 2-6 Maintenance dose (mg/kg) | Weeks 2-6 Total Weekly Dose (mg/kg) |
|---|---|---|---|---|
| PBS | 5x | 0 | 2x | 0 |
| AD-57928 | 5x2 | 10 | 2x2 | 4 |
| AD-57928 | 5x2 | 10 | 1x2 | 2 |
| AD-57928 | 5x1 | 5 | 2x1 | 2 |
| AD-57928 | 5x1 | 5 | 1x1 | 1 |
| AD-57928 | 5x0.5 | 2.5 | 2x0.5 | 1 |
| AD-57928 | 5x0.5 | 2.5 | 1x0.5 | 0.5 |

Figure 7:
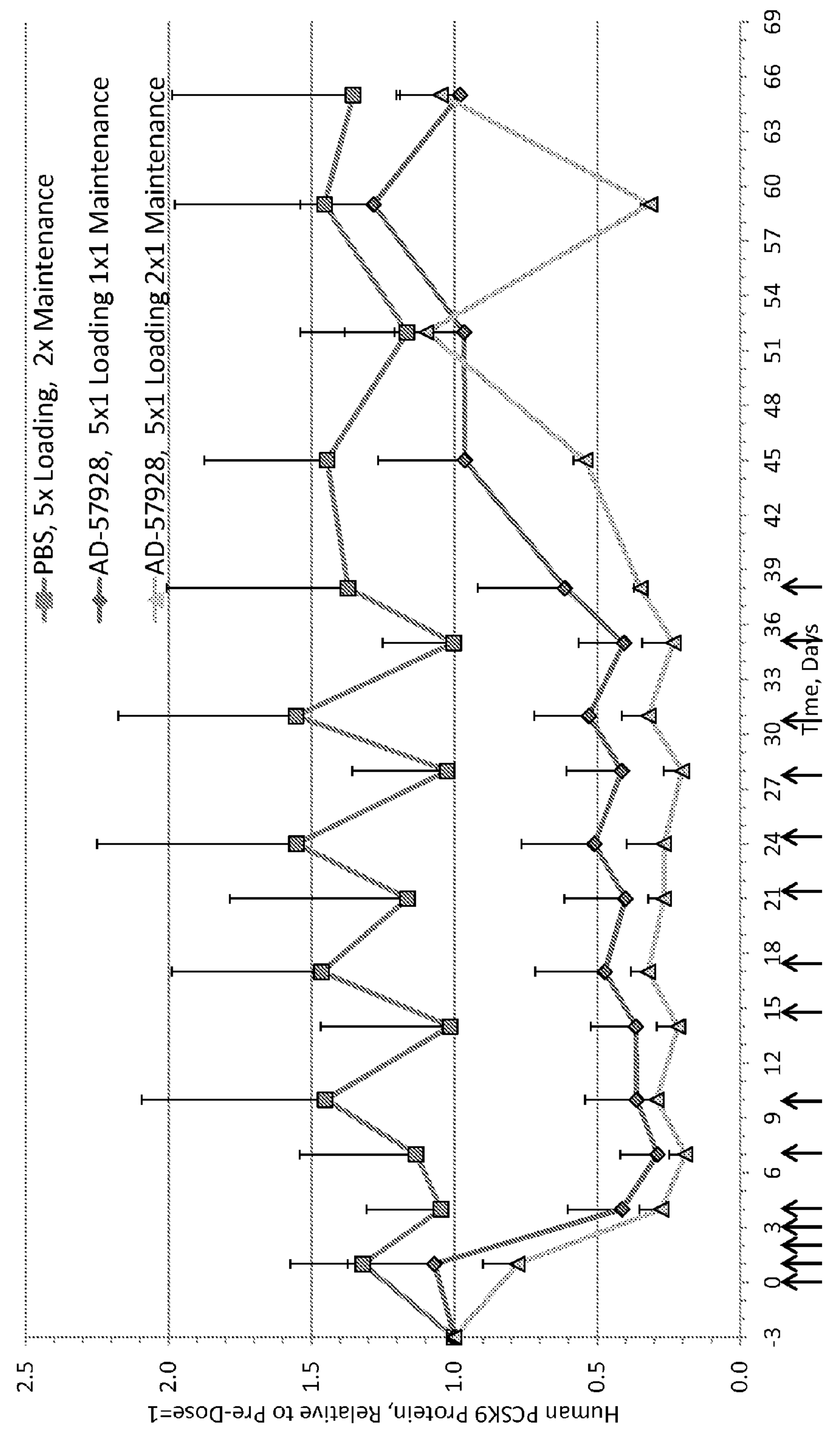
FIG. 7 is a graph depicting the levels of PCSK9 protein in serum of PCSK9 transgenic mice after administration of AD-57928 in 5×1 mg/kg doses during the "loading phase" and 1×1 mg/kg or 2×1 mg/kg doses during the "maintenance phase".
Figure 8:
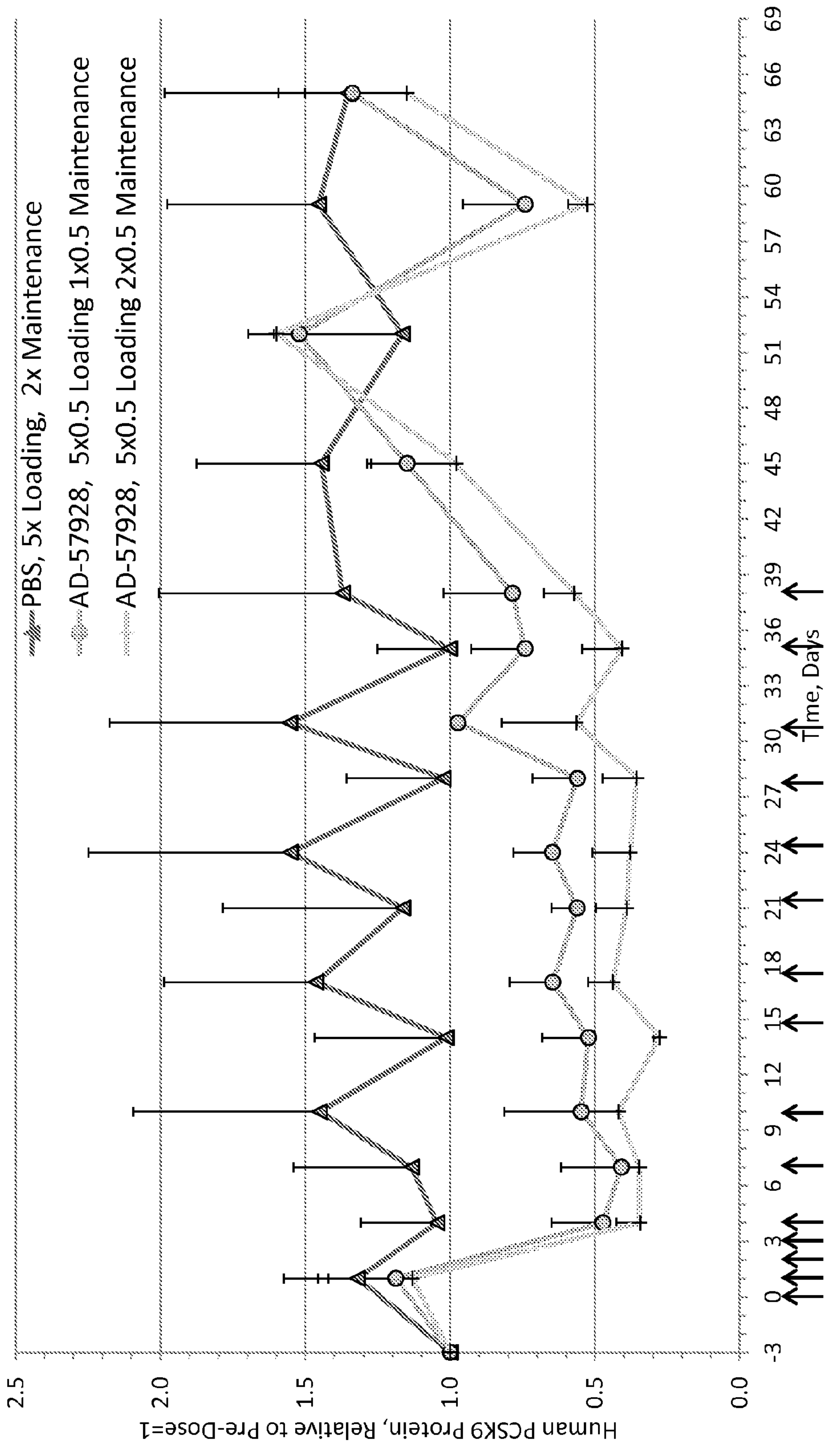
FIG. 8 is a graph depicting the levels of PCSK9 protein in serum of PCSK9 transgenic mice after administration of AD-57928 in 5×0.5 mg/kg doses during the "loading phase" and 1×0.5 mg/kg or 2×0.5 mg/kg doses during the "maintenance phase".

Serum was collected 3 days prior to administration of the first dose and on days 1, 4, 7, 10, 14, 17, 21, 24, 28, 31, 35, 38, 42, 45, 52, 59 and 65 after the first dose. PCSK9 protein levels in serum were assessed by ELISA assay. The results are shown in FIGS. 6, 7 and 8.

Reduced of hPCSK9 serum protein levels were observed 72 hours following the first dose, and were sustained through day 38. Administration of AD-57928 at the loading doses of 5×2 mg/kg, 5×1 mg/kg and 5×0.5 mg/kg resulted in ~90%, ~70% and ~60% reduction of hPCSK9 serum protein levels, respectively (see FIGS. 6-8). In the group dosed using the 2× maintenance dosing schedule, the reduced levels of hPCSK9 were sustained for 1 week longer than in the group dosed using the 1× maintenance dosing schedule, and returned to baseline 4 weeks after the last dose (see FIGS. 6-8).

Example 5. Phosphorothioate Titration

Figure 9:
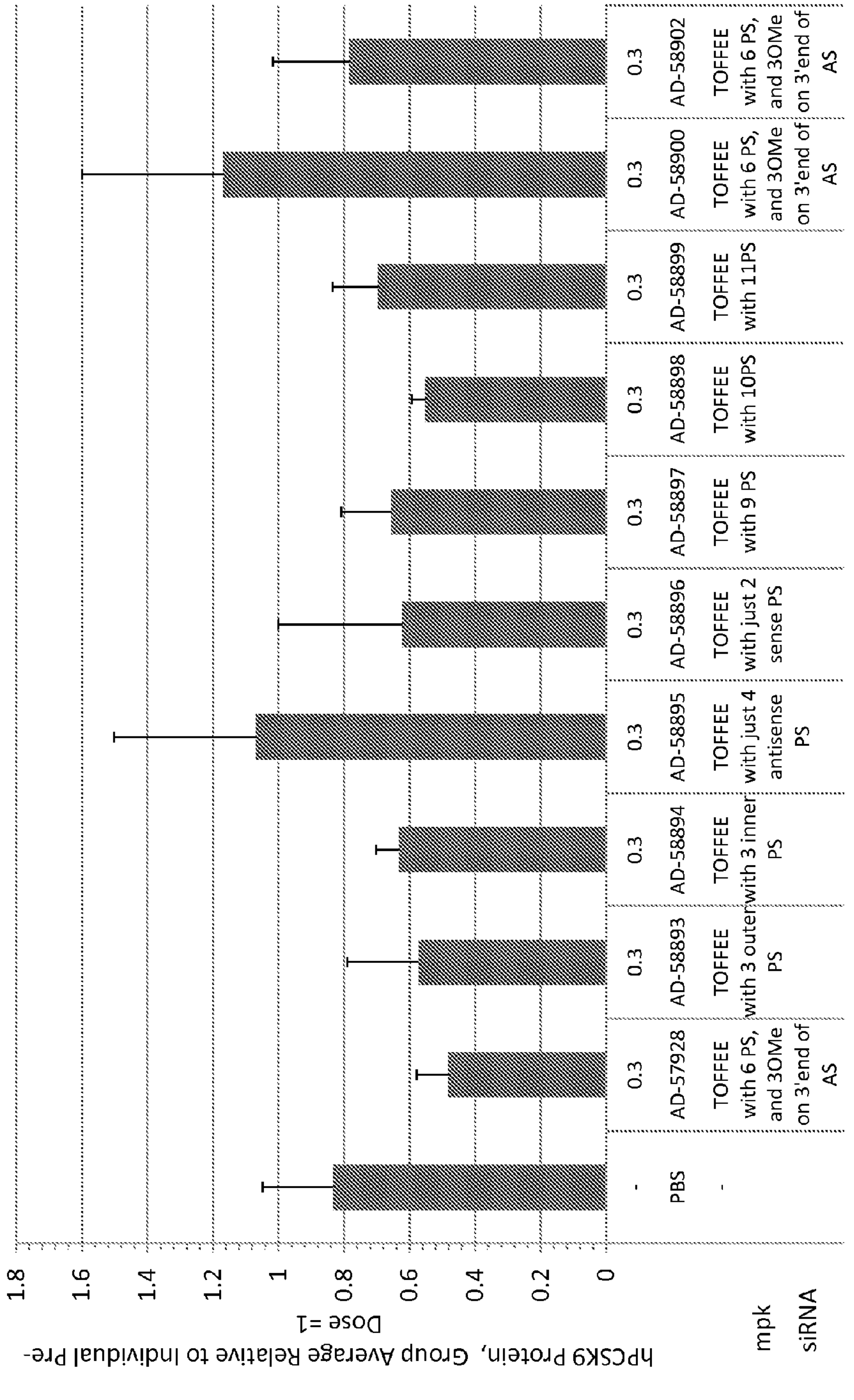
FIG. 9 is a graph depicting the results of the in vivo dose response assays performed in PCSK9 transgenic mice. Seventy-two hours after a single dose of 0.3 mg/kg of siRNAs, PCSK9 protein levels were determined by ELISA.

In order to determine the effect of the number and position of phosphorothioate modifications on the ability of dsRNA to inhibit the expression of PCSK9, a number of siRNAs based on the parent sequences of AD-57928, AD-53806 and AD-53830 as shown in Table 9 were prepared and tested. To determine whether any of the siRNAs are more effective at silencing PCSK9 than AD-57928, PCSK9 transgenic mice were administered a single 0.3 mg/kg dose of the siRNA in Table 9, and 72 hours post-dosing, PCSK9 protein levels were determined by ELISA assay. The results, shown in FIG. 9, demonstrate that AD-57928 is surprisingly effective at silencing PCSK9. AD-58893, AD-58894, AD-58896, AD-58897, AD-58898 and AD-58899 were also able to silence PCSK9 as compared to the control.

TABLE 9 siRNAs used in phosphorothiate titration experiment

| Duplex ID | Sense Sequence | SEQ ID NO: | Antisense Sequence | SEQ ID NO: | Chemistry |
|---|---|---|---|---|---|
| AD-57928 | CfsusAfgAfcCfuGfUfUfuUfgCfuUfuUfgUfL96 | 1557 | asCfsaAfaAfgCfaAfaacAfgGfuCfuAfgsasa | 1567 | TOFFEE with 6 PS, and 3OMe on 3'end of AS |
| AD-58893 | CfsuAfgAfcCfuGfUfUfuUfgCfuUfuUfgUfL96 | 1558 | asCfaAfaAfgCfaAfaacAfgGfuCfuAfgasa | 1568 | TOFFEE with 3 outer PS |
| AD-58894 | CfusAfgAfcCfuGfUfUfuUfgCfuUfuUfgUfL96 | 1559 | aCfsaAfaAfgCfaAfaacAfgGfuCfuAfgsaa | 1569 | TOFFEE with 3 inner PS |
| AD-58895 | CfuAfgAfcCfuGfUfUfuUfgCfuUfuUfgUfL96 | 1560 | asCfsaAfaAfgCfaAfaacAfgGfuCfuAfgsasa | 1570 | TOFFEE with just 4 antisense PS |
| AD-58896 | CfsusAfgAfcCfuGfUfUfuUfgCfuUfuUfgUfL96 | 1561 | aCfaAfaAfgCfaAfaacAfgGfuCfuAfgaa | 1571 | TOFFEE with just 2 sense PS |
| AD-58897 | CfsusAfsgAfcCfuGfUfUfuUfgCfuUfuUfgUfL96 | 1562 | asCfsasAfaAfgCfaAfaacAfgGfuCfuAfsgsasa | 1572 | TOFFEE with 9 PS |
| AD-58898 | CfsusAfsgAfcCfuGfUfUfuUfgCfuUfuUfgUfL96 | 1563 | asCfsaAfaAfgCfsaAfaacAfsgGfuCfuAfsgsasa | 1573 | TOFFEE with 10PS |
| AD-58899 | CfsusAfsgAfcCfuGfUfUfuUfgCfuUfuUfsgUfL96 | 1564 | asCfsaAfaAfgCfsaAfaacAfsgGfuCfuAfsgsasa | 1574 | TOFFEE with 11PS |
| AD-58900 | CfsasAfgCfaGfaCfAfUfuUfaUfcUfuUfuUfL96 | 1565 | asAfsaAfaGfaUfaAfaugUfcUfgCfuUfgscsu | 1575 | 6PS version of AD-53806 |
| AD-58902 | UfsusUfuCfuAfgAfCfCfuGfuUfuUfgCfuUfL96 | 1566 | asAfsgCfaAfaAfcAfgguCfuAfgAfaAfasgsu | 1576 | 6PS version of AD-53830 |

Example 6. Liver Drug Levels of AD-57928 and AD-58895

The goal of this study was to quantify siRNA levels in the liver of wild-type mice in order to define appropriate conditions for drug level screening. The siRNAs used in the experiment were AD-57928 and AD-58895 (that produced no decrease in PCSK9 protein level in Example 5). AD-58895 was used as a comparator to define timepoints at which a difference in drug level reflective of efficacy is observable.

Figure 10:
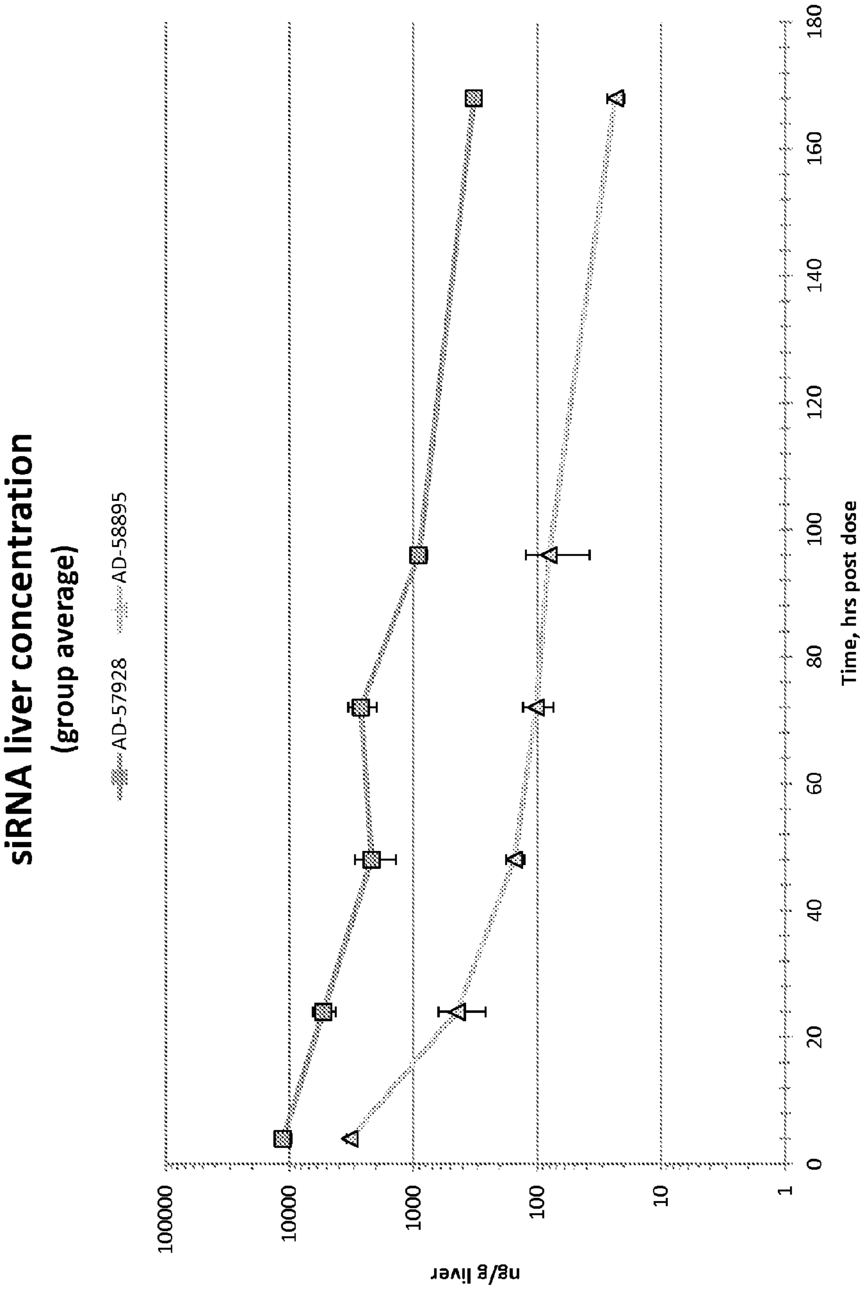
FIG. 10 is a graph showing the amount of AD-57928 and AD-58895 per nanogram of liver of C57B6 wild-type mice after administration of a single dose of 1 mg/kg of AD-57928 or AD-58895.
Figure 11:
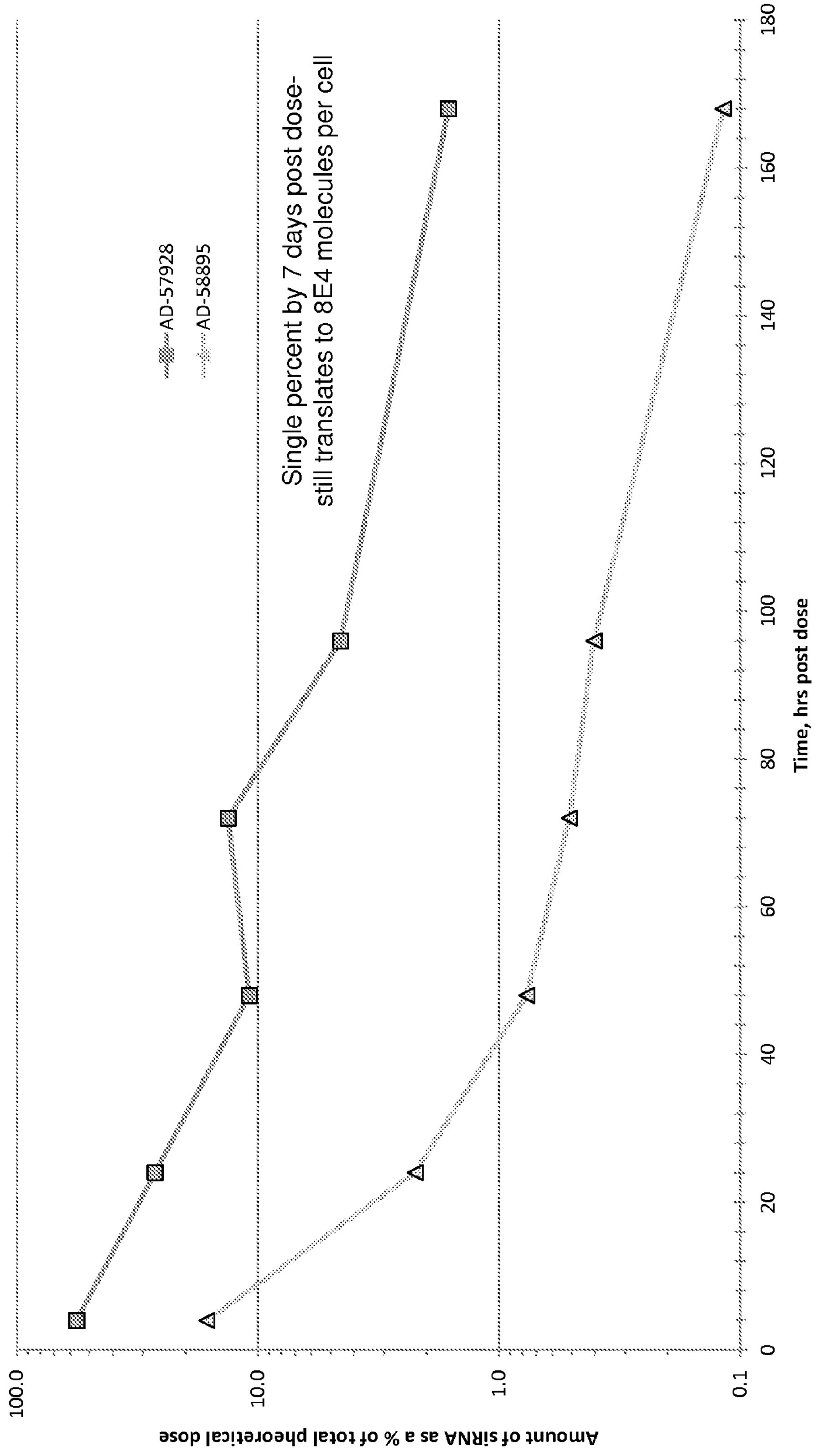
FIG. 11 is a graph showing the amount of AD-57928 and AD-58895 expressed as a % of theoretical amount in the liver of C57B6 wild-type mice after administration of a single dose of 1 mg/kg of AD-57928 or AD-58895.

A total of 33 C57B6 female mice were used in the experiment (3 mice per group). These mice were administered a single subcutaneous dose of either AD-57928, AD-58895 or PBS as a control. Livers were collected at 4, 24, 48, 72, 96 and 168 hours post-dose. Duplicate tissue aliquots per sample were collected, and the concentration of siRNA in the liver was measured using a newly designed antisense sequence specific qRT-PCR assay. The measured amount of AD-57928 and AD-58895 per gram of liver over time is shown in FIG. 10, and the amount of AD-57928 and AD-58895 expressed as a percentage of total theoretical dose is shown in FIG. 11. The limit of detection (LOD) of the qRT-PCR assay was ~1 ng/g of liver, and the assay showed good performance and accurate duplicates reproducibility. The results indicate that AD-57928 is more stable in the liver and AD-58895 is less stable, and both can be detected across all timepoints. At 7 days post dose, the level of AD-57928 is >100 fold above the LOD of the qRT-PCR assay, and the level of AD-58895 is >10 fold above LOD. The concentrations of AD-57928 and AD-58895 differ on average >10 fold according to their predicted stability and the observed efficacy. The timepoint between 72 and 120 hours post dose may be appropriate for siRNA concentration based screens.

Example 7. Optimization of AD-57928

In order to enhance the in vivo activity and stability of AD-57928, additional iRNA agents based on the parent sequences of AD-57928 were prepared and tested (Table 10; the "Sense" sequences in Table 10 are disclosed as SEQ ID NOS: 1653-1658, respectively, in order of appearance, and the "Antisense" sequences are disclosed as SEQ ID NOS: 1659-1664, respectively, in order of appearance; the same sense and antisense sequences disclosed in Table 10 are also disclosed in FIG. 12A).

The unmodified sense and antisense sequences for AD-60212 are:

```
                          (A-122088.3; SEQ ID NO: 1665)
Sense -         5'- CUAGACCUGUTUUGCUUUUGU -3';
and

                         (A-120190.19; SEQ ID NO: 1666)
Antisense -     5'- ACAAAAGCAAAACAGGUCUAGAA -3'.
```

In general, these compounds contained fewer 2'-fluro modifications and fluoro-modified uridines were removed. The in vitro potency of these duplexes was tested by transfection of HeLa and Hep3b cells. As shown in FIG. 12B, AD-59849, AD-59228, and AD-60212 have $IC_{50}$ values comparable to the parent (AD-57928).

Figure 13:
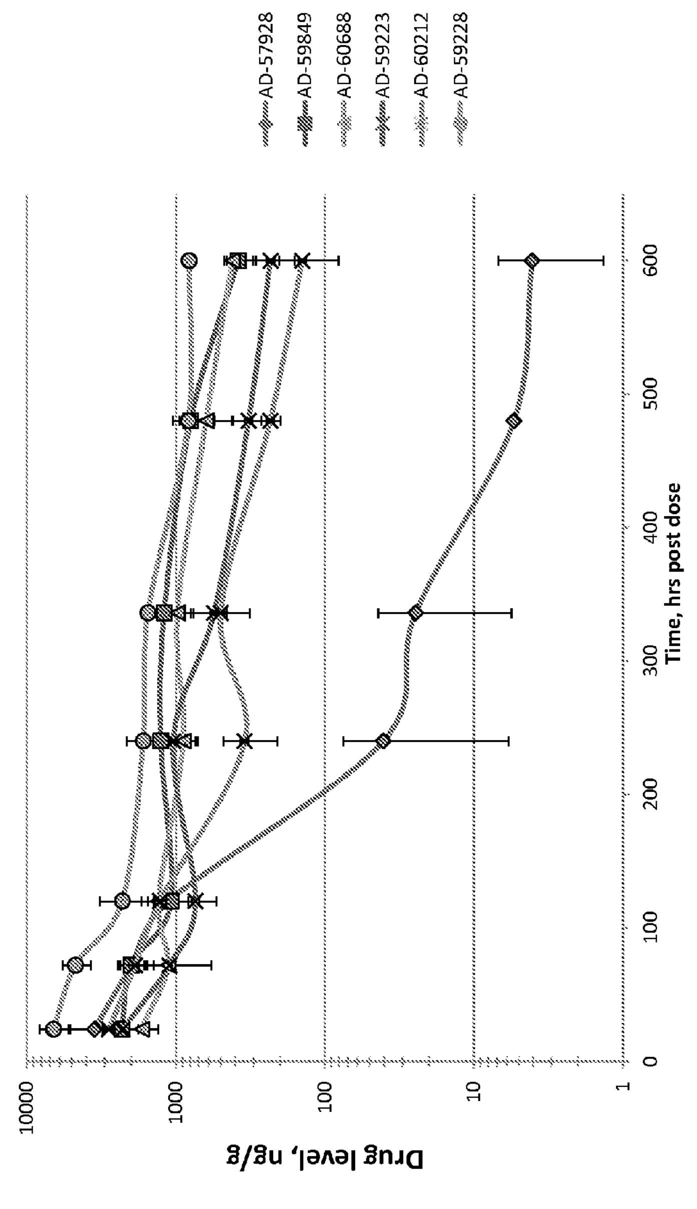
FIG. 13 is a graph showing the level of the indicated iRNA agents in the liver of wild-type mice following administration of a single 1 mg/kg dose of the indicated iRNA agent.

The ability of these duplexes to persist in vivo in the liver was also determined by administering 1 mg/kg of each duplex to wild-type mice and determining the siRNA level by quantitative PCR. As depicted in FIG. 13, all of the duplexes show greater persistence in the liver than the parent duplex starting at the post-120 hours administration timepoint.

The ability of these duplexes to suppress expression of PCSK9 protein was also assessed in vivo by measuring levels of PCSK9 protein, LDL, HDL, total cholesterol (Tc), triglycerides (Tgs), alanine transaminase (ALT), aspartate aminotransferase (AST), and alkaline phosphatase (ALP) in the serum of non-human primates (NHP). The presence of injection site reaction was also monitored. The duplexes were administered using a dosing schedule that included a "loading phase" during the first week (one dose of 2 mg/kg daily for 5 subsequent days, qdx5), followed by a "maintenance phase" (three weekly doses of 2 mg/kg for 3 weeks, qwx3), as is described in Table 11 below.

TABLE 11

Dosing Schedules

| Test Article | Group Number | N | Dose Level (mg/kg) | Dose Frequency | Cumulative dose (mg/kg) |
|---|---|---|---|---|---|
| AD-57928 | 1 | 3 | 2 | qdx5 + qwx3, 8 doses | 16 |
| AD-59849 | 2 | females | 2 | qdx5 + qwx3, 8 doses | 16 |
| AD-60688 | 3 | | 2 | qdx5 + qwx3, 8 doses | 16 |
| AD-59223 | 4 | | 2 | qdx5 + qwx3, 8 doses | 16 |
| AD-60212 | 5 | | 2 | qdx5 + qwx3, 8 doses | 16 |
| AD-59228 | 6 | | 2 | qdx5 + qwx3, 8 doses | 16 |

Blood: Days −9, −6, −3, 4, 7, 10, 14, 17, 21, 24, 28, 31, 35, 42, 49, 56, 63 (first dose, Day 1)

Injection site observation: Yes

Readouts: PCSK9 protein, LDL, HDL, Tc, Trigs, ALT, AST, ALP

Figure 14:
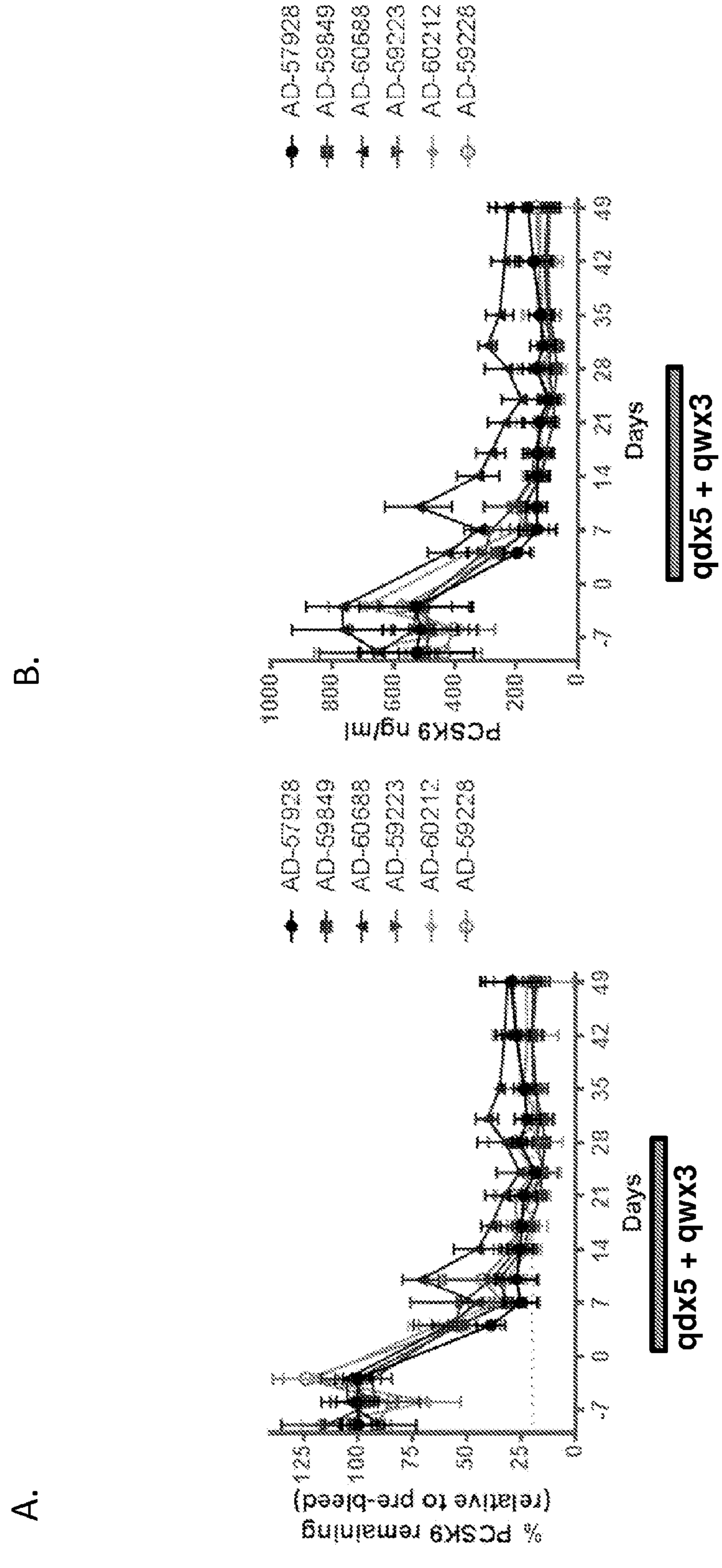
FIG. 14A is a graph showing the amount of PCSK9 protein in the serum of non-human primates expressed as percent of PCSK9 remaining relative to pre-bleed levels of PCSK9 after administration of the indicated iRNA agents at qdx5+qwx3.
FIG. 14B is a graph showing the absolute amount of PCSK9 protein in the serum of non-human primates after administration of the indicated iRNA agents at qdx5+qwx3.
Figure 15:
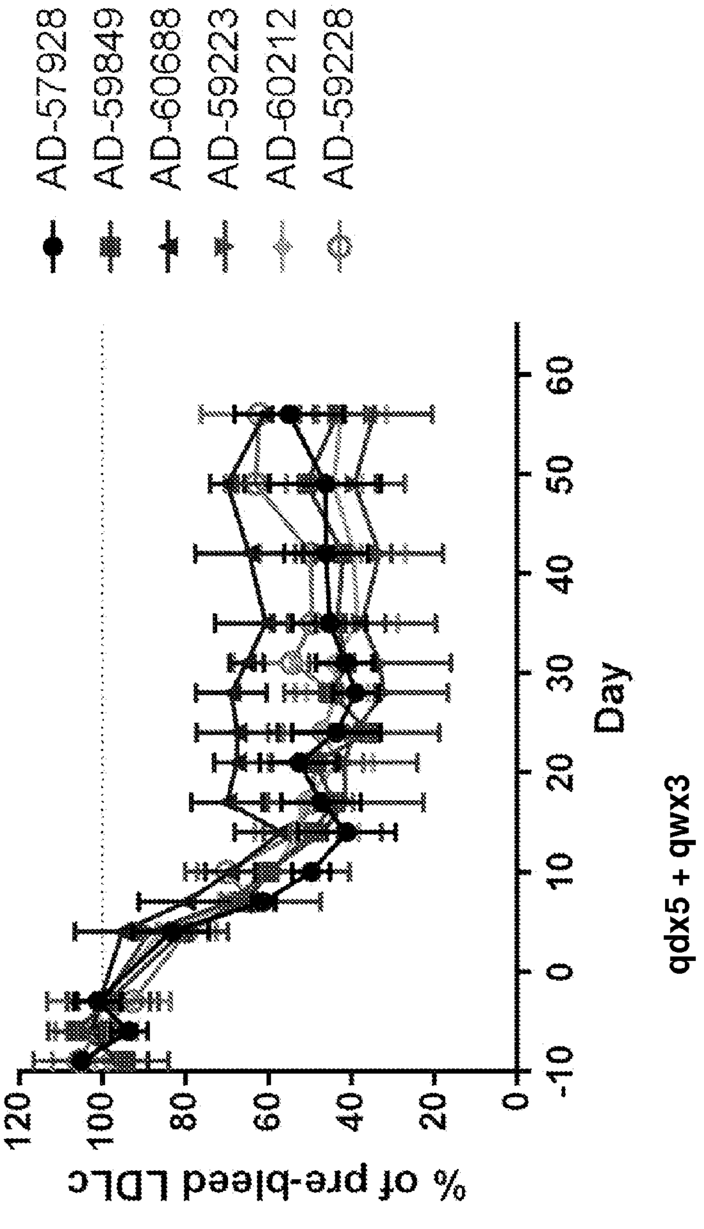
FIG. 15 is a graph showing the amount of low density lipoprotein cholesterol (LDL or LDLc) in the serum of non-human primates expressed as a percent of LDL remaining relative to pre-bleed levels of LDL after administration of the indicated iRNA agents at qdx5+qwx3.
Figure 18:
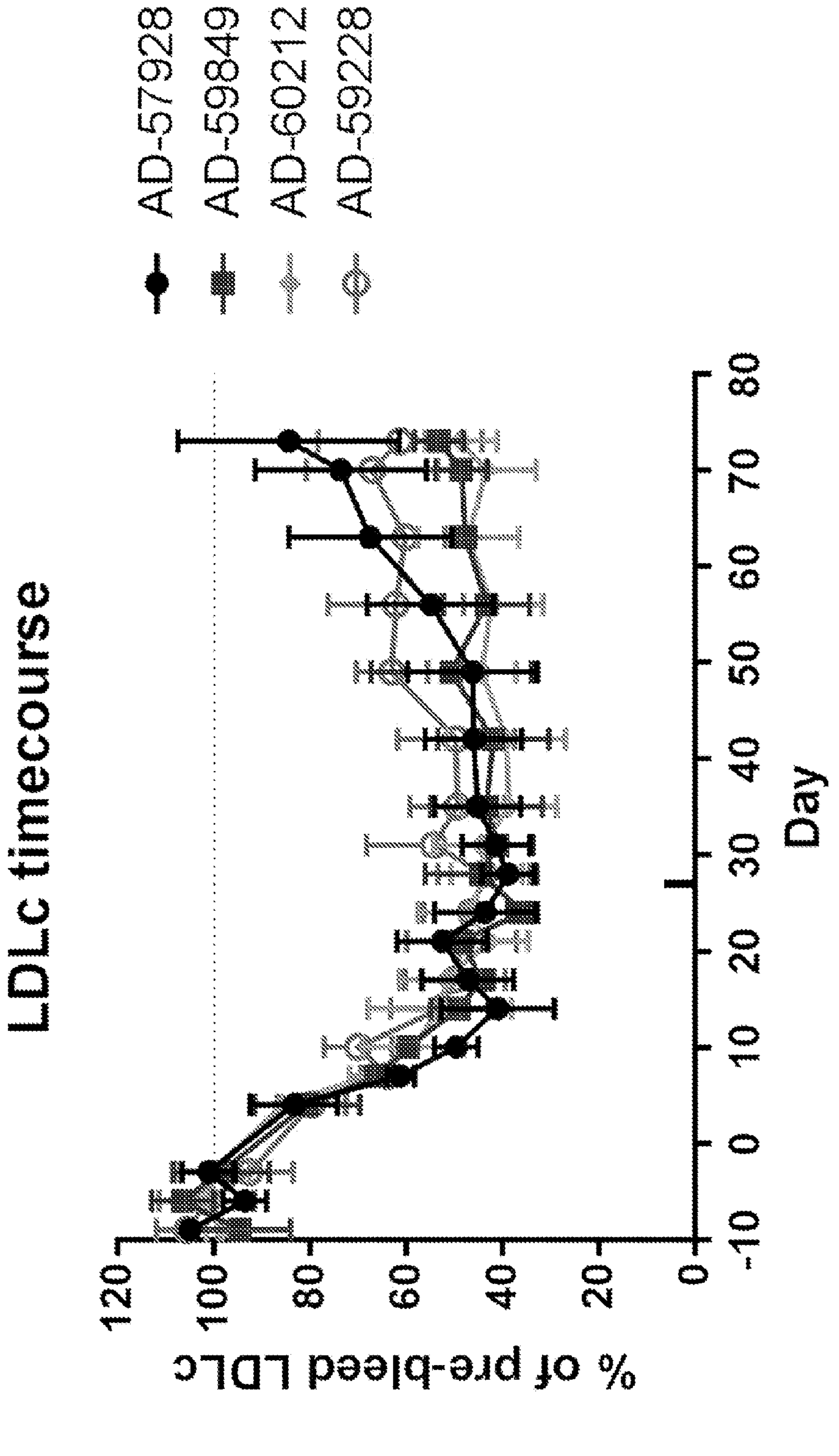
FIG. 18 is a graph showing the amount of low density lipoprotein cholesterol (LDL or LDLc) in the serum of non-human primates expressed as a percent of LDL remaining relative to pre-bleed levels of LDL after administration of the indicated iRNA agents at qdx5+qwx3.
Figure 19:
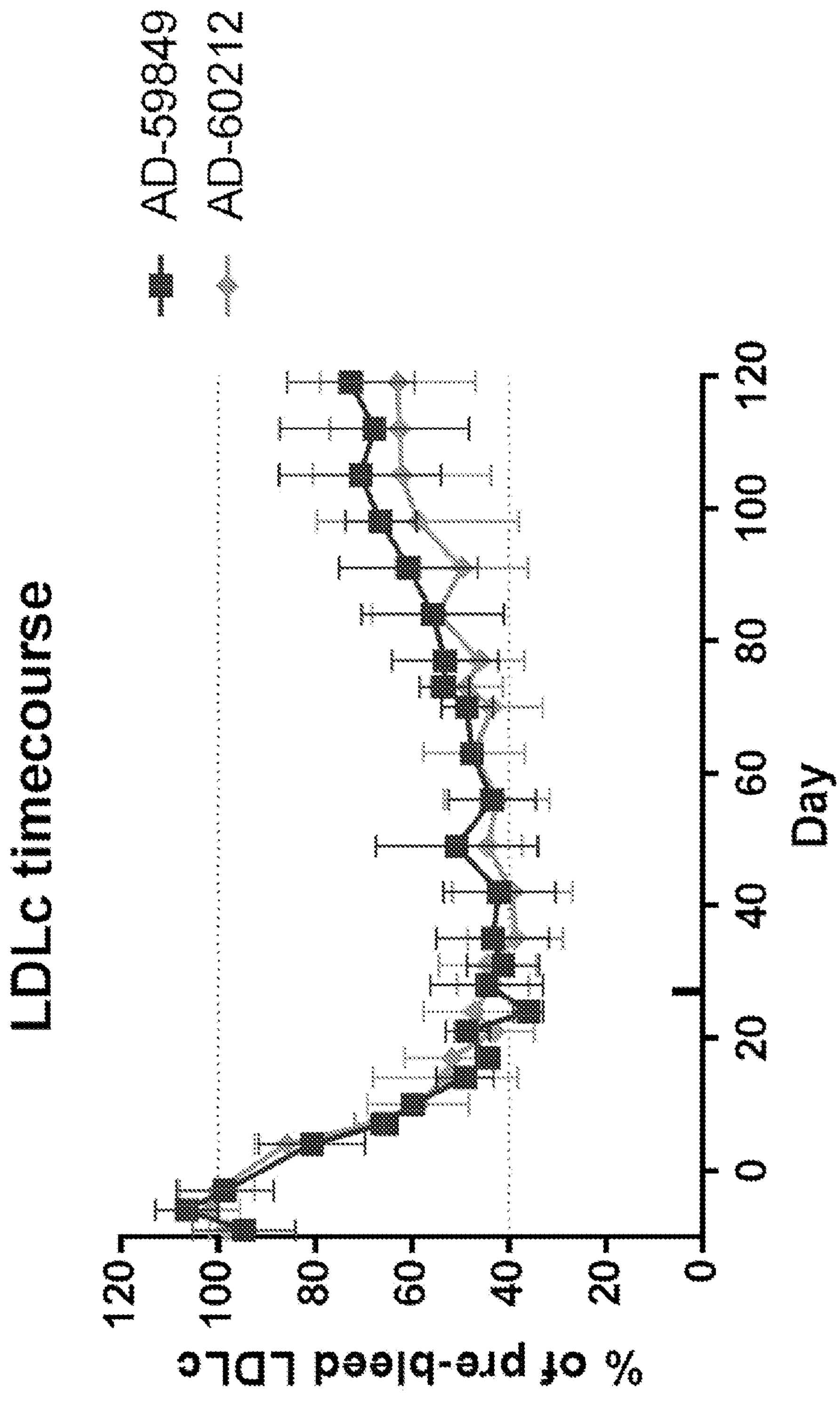
FIG. 19 is a graph showing the amount of low density lipoprotein cholesterol (LDL or LDLc) in the serum of non-human primates expressed as a percent of LDL remaining relative to pre-bleed levels of LDL after administration of the indicated iRNA agents at qdx5+qwx3.

As shown in FIGS. 14A and 14B, all compounds except for AD-60688 achieve greater than 80% PCSK9 silencing and individual animals in the AD-60212 group achieve greater than 90% PCSK9 silencing. FIG. 15 demonstrates that, in the absence of statins, all compounds except for AD-60688 achieve 60% LDL cholesterol lowering and individual animals in the AD-59223 group achieve up to 77% LDL cholesterol lowering. Surprisingly, and as depicted in FIG. 18, the indicated agents maintained cholesterol lowering 46 days following the last dose of the indicated agents. Even more surprisingly, and as depicted in FIG. 19, AD-60212 and AD-59849 maintain up to 60% LDL cholesterol lowering to at least day 120 (93 days after the final dose), longer than any effect observed for an RNAi agent in vivo, indicating that, following a loading phase, these compounds may be administered at a frequency of once a month, once every two months, once every three months, once every four months, once every five months, or once every six months during the maintenance phase.

TABLE 10

Additional iRNA Agents.

| Duplex | Sense ID | Sense | AntiSense ID | Antisense |
|---|---|---|---|---|
| AD-57928 (parent) | A-117428 | CfsusAfgAfcCfuGfUfUfuUfgCfuUfuUfgUfL96 | A-117429 | asCfsaAfaAfgCfaAfa acAfgGfuCfuAfgsasa |
| AD-59849 | A-121244 | CfsusAfgAfcCfuGfUfUfuUfgcuuuuguL96 | A-121239 | asCfsaAfaagCfaAfaa cAfgGfucuAfgsasa |
| AD-60688 | A-120188 | csusagacCfuGfuuuugcuuuuguL96 | A-121239 | asCfsaAfaagCfaAfaa cAfgGfucuAfgsasa |
| AD-59223 | A-120188 | csusagacCfuGfuuuugcuuuuguL96 | A-120190 | asCfsaAfAfAfgCfaAf aAfcAfgGfuCfuagsasa |
| AD-60212 | A-122088 | csusagacCfuGfudTuugcuuuuguL96 | A-120190 | asCfsaAfAfAfgCfaAf aAfcAfgGfuCfuagsasa |
| AD-59228 | A-120197 | CfsusAfgAfcCfuGfUfUfuUfgCfsuUfsuUfsgsUfsL96 | A-120202 | asCfsaAfaAfsgCfaAfa acAfgGfuCfsuAfgsasa |

Example 8. Preparation of Additional AD-57928-Based PCSK9 Sequences

Additional iRNA agents based on the parent sequences of AD-57928 were prepared (see Table 12, below) and tested in vitro for potency by transfecting HeLa and Hep3B cells with these agents. The $IC_{50}$ values for these agents are shown in Table 13.

TABLE 12

PCSK9 sequences

| Duplex ID | Sense strand | Sense (5' to 3') | SEQ ID NO: | Antisense | Antisense (5' to 3') | SEQ ID NO: |
|---|---|---|---|---|---|---|
| AD-57928.45 | A-117428.1 | CfsusAfgAfcCfuGfUfUfuUfgCfuUfuUfgUfL96 | 1577 | A-117429.1 | asCfsaAfaAfgCfaAfaacAfgGfuCfuAfgsasa | 1605 |
| AD-60928.1 | A-122701.2 | CfsusAfgAfcCfuGfUfUfuUfgCfuUfuUfgAfL96 | 1578 | A-122702.2 | usCfsaAfaAfgCfaAfaacAfgGfuCfuAfgsasa | 1606 |
| AD-60929.1 | A-122703.2 | GfsusAfgAfcCfuGfUfUfuUfgCfuUfuUfgUfL96 | 1579 | A-122704.2 | asCfsaAfaAfgCfaAfaacAfgGfuCfuAfcsusu | 1607 |
| AD-60930.1 | A-122705.2 | GfsasAfgAfcCfuGfUfUfuUfgCfuUfuUfgUfL96 | 1580 | A-122706.2 | asCfsaAfaAfgCfaAfaacAfgGfuCfuUfcsusu | 1608 |
| AD-60931.1 | A-122707.3 | GfsasUfgAfcCfuGfUfUfuUfgCfuUfuUfgUfL96 | 1581 | A-122708.2 | asCfsaAfaAfgCfaAfaacAfgGfuCfaUfcsusu | 1609 |
| AD-60932.1 | A-122707.4 | GfsasUfgAfcCfuGfUfUfuUfgCfuUfuUfgUfL96 | 1582 | A-122709.2 | asCfsaAfaAfgCfaAfaacAfgGfuCfaUfcsasa | 1610 |
| AD-60933.1 | A-122710.2 | CfsasUfcAfcCfuGfUfUfuUfgCfuUfuUfgUfL96 | 1583 | A-122711.2 | asCfsaAfaAfgCfaAfaacAfgGfuGfaUfgsasa | 1611 |
| AD-60934.1 | A-122712.2 | CfsusUfcUfcCfuGfUfUfuUfgCfuUfuUfgUfL96 | 1584 | A-122713.2 | asCfsaAfaAfgCfaAfaacAfgGfaGfaAfgsasa | 1612 |
| AD-60927.1 | A-122714.2 | CfsusAlcUfgCfuGfUfUfuUfgCfullfuUfgUfL96 | 1585 | A-122715.2 | asCfsaAfaAfgCfaAfaacAfgCfaGfuAfgsasa | 1613 |
| AD-57928.45 | A-117428.1 | CfsusAfgAfcCfuGfUfUfuUfgCfuUfuUfgUfL96 | 1586 | A-117429.1 | asCfsaAfaAfgCfaAfaacAfgGfuCfuAfgsasa | 1614 |
| AD-60906.1 | A-117428.1 | CfsusAfgAfcCfuGfUfUfuUfgCfuUfuUfgUfL96 | 1587 | A-122309.1 | asCfsaAfaAfgCf(Ayh)AfaacAfgGfuCfuAfgsasa | 1615 |
| AD-60907.1 | A-117428.1 | CfsusAfgAfcCfuGfUfUfuUfgCfuUfuUfgUfL96 | 1588 | A-122310.1 | asCfsaAfaAfgCfa(Ayh)aacAfgGfuCfuAfgsasa | 1616 |
| AD-60908.1 | A-117428.1 | CfsusAfgAfcCfuGfUfUfuUfgCfuUfuUfgUfL96 | 1589 | A-122311.1 | asCfsaAfaAfgCfaAf(Ayh)acAfgGfuCfuAfgsasa | 1617 |
| AD-60909.1 | A-117428.1 | CfsusAfgAfcCfuGfUfUfuUfgCfuUfuUfgUfL96 | 1590 | A-122312.1 | asCfsaAfaAfgCfaAfa(Ayh)cAfgGfuCfuAfgsasa | 1618 |
| AD-60910.1 | A-117428.1 | CfsusAfgAfcCfuGfUfUfuUfgCfuUfuUfgUfL96 | 1591 | A-122313.1 | asCfsaAfaAfgCf(Ayh)AfaacAf(Gyh)GfuCf(Uyh)Afgsasa | 1619 |
| AD-60911.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1592 | A-117429.1 | asCfsaAfaAfgCfaAfaacAfgGfuCfuAfgsasa | 1620 |
| AD-60912.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1593 | A-117429.1 | asCfsaAfaAfgCfaAfaacAfgGfuCfuAfgsasa | 1621 |
| AD-60913.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1594 | A-122309.1 | asCfsaAfaAfgCf(Ayh)AfaacAfgGfuCfuAfgsasa | 1622 |
| AD-60914.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1595 | A-122310.1 | asCfsaAfaAfgCfa(Ayh)aacAfgGfuCfuAfgsasa | 1623 |
| AD-60915.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1596 | A-122311.1 | asCfsaAfaAfgCfaAf(Ayh)acAfgGfuCfuAfgsasa | 1624 |
| AD-57928.45 | A-117428.1 | CfsusAfgAfcCfuGfUfUfuUfgCfuUfuUfgUfL96 | 1597 | A-117429.1 | asCfsaAfaAfgCfaAfaacAfgGfuCfuAfgsasa | 1625 |

TABLE 12-continued

| PCSK9 sequences | | | | | | |
|---|---|---|---|---|---|---|
| Duplex ID | Sense strand | Sense (5' to 3') | SEQ ID NO: | Antisense | Antisense (5' to 3') | SEQ ID NO: |
| AD-60916.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1598 | A-122312.1 | asCfsaAfaAfgCfaAfa(Ayh)cAfgGfuCfuAfgsasa | 1626 |
| AD-60917.1 | A-122307.1 | Cfsus(Ayh)(Gyh)(Ayh)(Cyh)CfuGfUfUfuUf(Gyh)Cf(Uyh)Uf(Uyh)Uf(Gyh)UfL96 | 1599 | A-122313.1 | asCfsaAfaAfgCf(Ayh)AfaacAf(Gyh)GfuCf(Uyh)Afgsasa | 1627 |
| AD-60918.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1600 | A-122309.1 | asCfsaAfaAfgCf(Ayh)AfaacAfgGfuCfuAfgsasa | 1628 |
| AD-60919.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1601 | A-122310.1 | asCfsaAfaAfgCfa(Ayh)aacAfgGfuCfuAfgsasa | 1629 |
| AD-60920.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1602 | A-122311.1 | asCfsaAfaAfgCfaAf(Ayh)acAfgGfuCfuAfgsasa | 1630 |
| AD-60921.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1603 | A-122312.1 | asCfsaAfaAfgCfaAfa(Ayh)cAfgGfuCfuAfgsasa | 1631 |
| AD-60922.1 | A-122308.1 | (Cyh)u(Ayh)(Gyh)(Ayh)(Cyh)CfuGfUfUfuUf(Gyh)Cf(Uyh)Uf(Uyh)Uf(Gyh)UfL96 | 1604 | A-122313.1 | asCfsaAfaAfgCf(Ayh)AfaacAf(Gyh)GfuCf(Uyh)Afgsasa | 1632 |

TABLE 13

| $IC_{50}$ values for the iRNA agents identified in Table 12. | | |
|---|---|---|
| Duplex ID | Hela $IC_{50}$(nM) | Hep3b $IC_{50}$(nM) |
| AD-57928.47 | 0.0026 | 0.0005 |
| AD-60928.1 | 0.0000 | 0.0009 |
| AD-60929.1 | 0.0010 | 0.0027 |
| AD-60930.1 | 0.0055 | 0.0019 |
| AD-60931.1 | 0.0028 | 0.0019 |
| AD-60932.1 | 0.0039 | 0.0036 |
| AD-60933.1 | 0.0349 | 0.1518 |
| AD-60934.1 | 0.2115 | 0.5420 |
| AD-60927.1 | >10 | — |
| AD-57928.45 | <3.57225e−005 | 0.0007 |
| AD-60906.1 | 0.0048 | 0.0007 |
| AD-60907.1 | 0.0001 | <3.57225e−005 |
| AD-60908.1 | 0.0003 | 0.0072 |
| AD-60909.1 | — | 0.0142 |
| AD-60910.1 | 0.0001 | 0.0030 |
| AD-60911.1 | 0.0955 | 0.1935 |
| AD-60912.1 | 0.1834 | 0.4106 |
| AD-60913.1 | 0.2693 | 0.5715 |
| AD-60914.1 | 0.2292 | 0.4319 |
| AD-60915.1 | 0.2069 | 0.3185 |
| AD-57928.45 | 0.0057 | 0.0027 |
| AD-60916.1 | 0.0802 | 0.2040 |
| AD-60917.1 | 0.1420 | 0.0976 |
| AD-60918.1 | 0.4101 | 0.3268 |
| AD-60919.1 | 0.3202 | 0.5143 |
| AD-60920.1 | 0.5199 | 0.5978 |
| AD-60921.1 | 0.7969 | 2.0875 |
| AD-60922.1 | 1.1078 | 1.0307 |

Example 9. Repeat-Dose Efficacy of AD-57928

The repeat-dose efficacy of AD-57928 in suppressing expression of PCSK9 protein was assessed in vivo by measuring the levels of PCSK9 protein, LDL, HDL, total cholesterol (Tc), triglycerides (Tgs), alanine transaminase (ALT), aspartate aminotransferase (AST), and alkaline phosphatase (ALP) in the serum of non-human primates (NHP). The presence of injection site reaction was also monitored. AD-57928 duplexes were subcutaneously administered using the dosing schedules described in Table 14 below. Group 5 animals were re-dosed with a single 25 mg/kg dose on day 92. One additional group of animals was administered a single dose of 25 mg/kg. "2xw" is two times per week; "q2w" is once every two weeks; and "q1w" is once per week.

TABLE 14

| Dosing Schedules | | | | | |
|---|---|---|---|---|---|
| Test Article | Group Number | N | Dose Level (mg/kg) | Dose Frequency | Cumulative dose (mg/kg) |
| AD-57928 | 1 | 3 | 1 | 2xw, 12 doses | 12 |
| | 2 | fe- | 2 | 2xw, 12 doses | 24 |
| | 3 | males | 1 | q2w, 6 doses | 6 |
| | 4 | | 2 | q2w, 6 doses | 12 |
| | 5 | | 0.5 | q1w, 6 doses | 3 |
| | 6 | | 1 | q1w, 10 doses | 10 |
| | 7 | | 2 | q1w, 10 doses | 20 |

Figure 16:
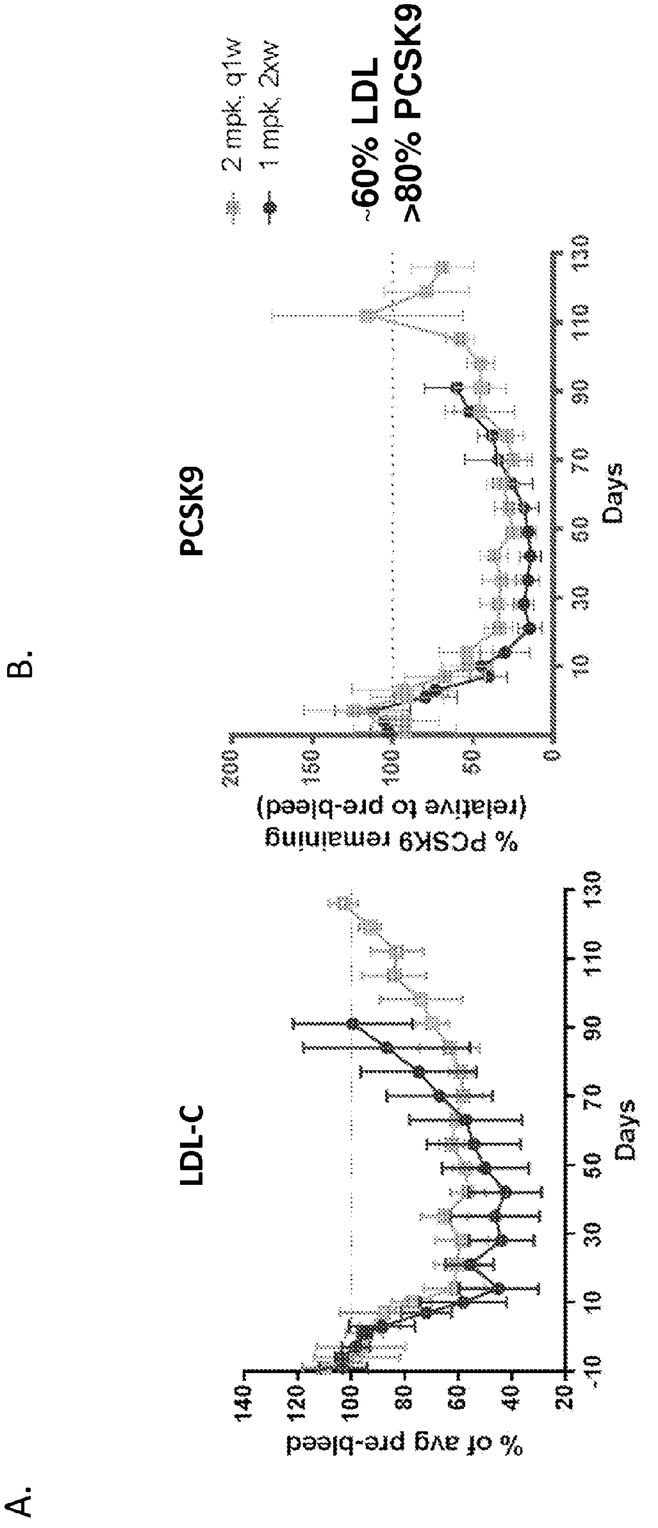
FIG. 16A is a graph showing the amount of low density lipoprotein cholesterol (LDL or LDLc) in the serum of non-human primates expressed as a percent of the average amount of pre-bleed levels of LDL after administration of AD-57928 at 2 mg/kg, q1w and 1 mg/kg, 2xw.
FIG. 16B is a graph showing the amount of PCSK9 protein relative to the pre-bleed amount in the serum of non-human primates after administration of AD-57928 at 2 mg/kg, q1w and 1 mg/kg, 2xw.

Blood: Days −9, −6, −3, 1 (pre-bleeds) 3-129 (efficacy bleeds)
Injection site observation: Yes
Readouts: PCSK9 protein, LDL, HDL, Tc, Trigs, ALT, AST, ALP As depicted in FIG. 16A, the most effective regimen for lowering LDL was a twice weekly regimen (2xw) which achieved about a 60% reduction in LDL levels. The same cumulative dose administered less frequently was less efficacious than the twice a week regimen. FIG. 16B demonstrates that the 2xw regimen achieved greater than 80% PCSK9 silencing.

Figure 17:
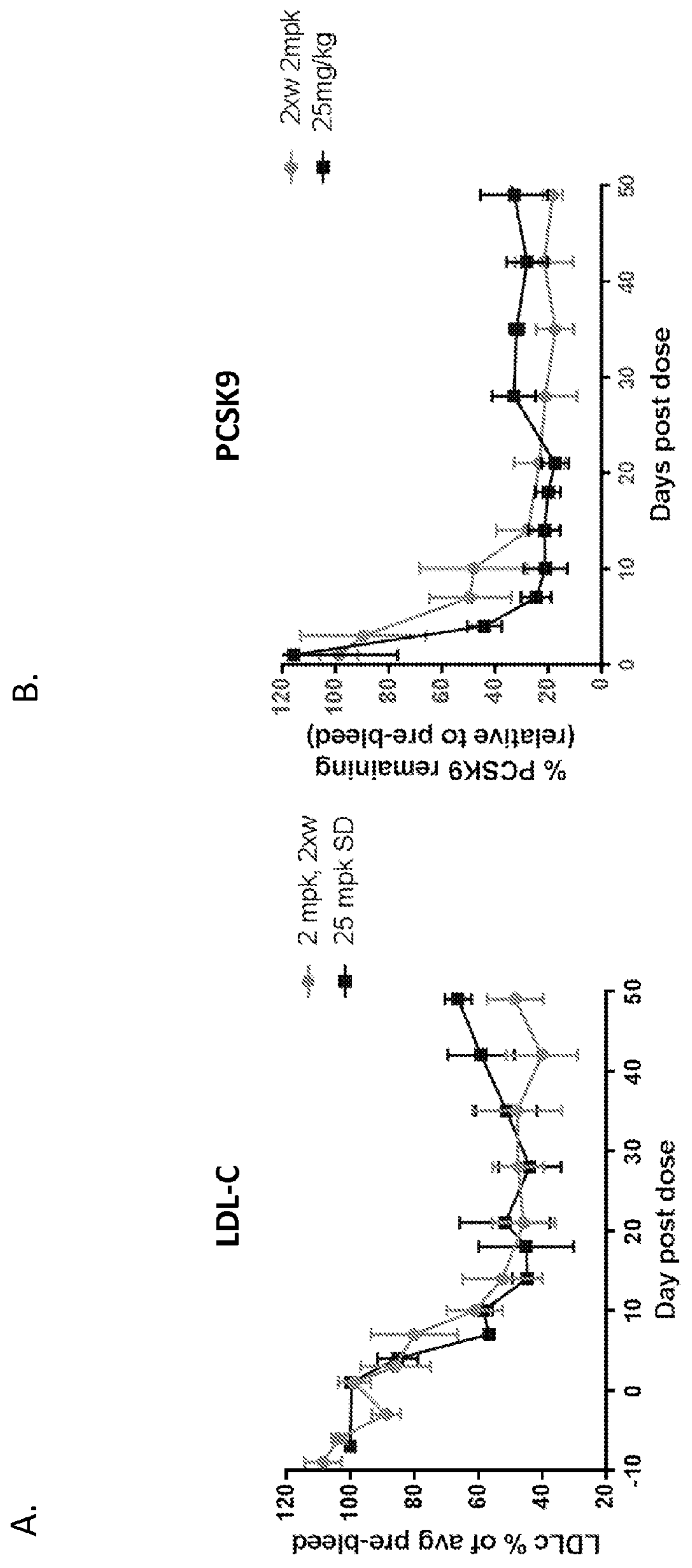
FIG. 17A is a graph showing the amount of low density lipoprotein cholesterol (LDL or LDLc) in the serum of non-human primates expressed as a percent of the average amount of pre-bleed levels of LDL after administration of AD-57928 at 2 mg/kg, 2xw and a single 25 mg/kg dose. The last dose for the 2 mg/kg, 2xw group was day 36.
FIG. 17B is a graph showing the amount of PCSK9 protein relative to the pre-bleed amount in the serum of non-human primates after administration of AD-57928 at 2 mg/kg, 2xw and a single 25 mg/kg dose.

FIGS. 17A and 17B demonstrate that a single 25 mg/kg dose of AD-57928 has the same onset of LDL and PCSK9 lowering, the same nadir of PCSK9 and LDL lowering, and equivalent rate of LDL lowering as a lower multiple-dose of 2 mg/kg AD-57928 administered two times per week (2xw). These graphs also demonstrate that there is a trend towards faster PCSK9 lowering with the single 25 mg/kg dose and that recovery of both PCSK9 levels and LDL levels starts about 20 days after nadir is reached (day 7) for the 25 mg/kg single dose. The nadir for the 25 mg/kg single dose is at Day 7.

Example 10. Tolerability of Optimized AD-57928 iRNA Agents

The additional iRNA agents prepared based on the parent sequences of AD-57928 described in FIG. 12A (and Table 10) were assessed for tolerability in rats. Male rats were subcutaneously administered 225 mg/kg of the indicated iRNA agents on days 1, 8, and 15, and sacrificed and necropsied on day 16 (see Table 15). The animals were observed for any clinical symptoms on a daily basis and the body weights of the animals were determined pre-study and weekly during the study. On day 16, blood from the animals was assessed hematologically, for coagulation and for serum chemistry; the drug metabolism and pharmacokinetics of the agents were determined using liver samples from the animals; and the heart, lungs (insufflated), kidneys, liver, spleen, testes, and first and last injection sites were analyzed for any changes. There were no changes in clinical signs, visual injection site observations, serum chemistry, coagulation or microscopic pathology of the liver, spleen lung, heart, or testes. Table 16 provides a summary of the liver weights, the final body weights, the results of the hematological analyses and the pathology severity scores for the final injection sites and kidneys for each agent tested.

TABLE 15

Dosing Schedules

| Dose Group | TA | Dose (mg/kg) | Dose Vol. (mL/kg) | No. Males | Dosing Schedule | Nx Day |
|---|---|---|---|---|---|---|
| 1 | PBS | 0 | 5 | 3 | SC on Days 1, 8, and 15 | Day 16 |
| 2 | AD-57928 (parent) | 225 | | 3 | | |
| 3 | AD-59849 | 225 | | 3 | | |
| 4 | AD-59223 | 225 | | 3 | | |
| 5 | AD-59228 | 225 | | 3 | | |
| 6 | AD-60688 | 225 | | 3 | | |
| 7 | AD-60212 | 225 | | 3 | | |

TABLE 16

Tolerability Summary

| | AD-57928 (parent) | AD-59849 | AD-59223 | AD-59228 | AD-60688 | AD-60212 |
|---|---|---|---|---|---|---|
| No. PS | 6 | 6 | 6 | 13 | 6 | 6 |
| No. 2'F | 21 | 15 | 12 | 21 | 9 | 12 |
| No. dT | 0 | 0 | 0 | 0 | 0 | 1 |
| [Liver] (μg/gl) | 907 ± 62 | 1139 ± 160 | 1277 ± 231 | 1999 ± 424 | 1624 ± 147 | 1258 ± 286 |
| Final BW (% from control) | −2.1% | −4.6% | −2.1% | −6.8% | −0.5% | −2.9% |
| Day 16 Hematology | No Change | No Change | ↑WBC, ↑LYM, hemolysis | No Change | No Change | No Change |
| Day 16 Final Inj. Site Inflammation | 3/3 (1.7) | 3/3 (1.3) | 2/3 (1.5) | 3/3 (2.3) | 2/3 (1.0) | 3/3 (1.3) |
| Day 16 Basophilic Granules, Kidney | 3/3 (2.0) | 3/3 (2.3) | 3/3 (1.0) | 3/3 (2.0) | 3/3 (1.3) | 3/3 (1.3) |

Pathology Severity Scores:
1 = minimal;
2 = slight;
3 = moderate
BW = Body Weight
WBC = White Blood Cell
LYM = Lymphocytes

We claim:

1. A double stranded RNAi agent that inhibits the expression of Proprotein convertase subtilisin kexin 9 (PCSK9) in a cell, wherein said double stranded RNAi agent comprises a sense strand complementary to an antisense strand forming a double stranded region, wherein said antisense strand comprises a region complementary to part of an mRNA encoding PCSK9, wherein each strand is independently about 14 to about 30 nucleotides in length, wherein said antisense strand comprises at least 19 contiguous nucleotides of the nucleotide sequence 5'-ACAAAAGCAAAACAGGUCUAG-3' (SEQ ID NO: 412) and said double stranded RNAi agent is represented by formula (III):

sense:
$5'\ n_p\text{-}N_a\text{-}(X\ X\ X)_i\text{-}N_b\text{-}Y\ Y\ Y\text{-}N_b\text{-}(Z\ Z\ Z)_j\text{-}N_a\text{-}n_q\ 3'$ antisense:
$3'\ n_p'\text{-}N_a'\text{-}(X'X'X')_k\text{-}N_b'\text{-}Y'Y'Y'\text{-}N_b'\text{-}(Z'Z'Z')_l\text{-}$ $N_a'\text{-}n_q'\ 5'$ (III)

wherein:

j, k, and l are each independently 0 or 1;

p, p', q, and q' are each independently 0-6;

each $N_a$ and each $N_a'$ independently represents an oligonucleotide sequence comprising 0-25 nucleotides, 2-20 of which are modified nucleotides, each sequence comprising at least two differently modified nucleotides, wherein the modified nucleotides are each independently selected from the group consisting of 2'-O-methyl, 2'-fluoro, and 2'-deoxythymidine (dT);

each $N_b$ and each $N_b'$ independently represents an oligonucleotide sequence comprising 0-10 nucleotides, 1-10 of which are modified nucleotides, wherein the modified nucleotides each independently comprise a nucleotide modification selected from the group consisting of 2'-O-methyl, 2'-fluoro, and 2'-deoxythymidine (dT);

wherein the double stranded RNAi agent comprises at least one phosphorothioate or methylphosphonate internucleotide linkage;

$n_p$, $n_p'$, $n_q$, and $n_q'$, each of which may or may not be present, each independently represents an overhang nucleotide;

XXX, YYY, ZZZ, X'X'X', Y'Y'Y', and Z'Z'Z' each independently represent one motif of three identical modifications on three consecutive nucleotides, wherein XXX is complementary to X'X'X', YYY is complementary to Y'Y'Y', and ZZZ is complementary to Z'Z'Z'; and wherein the sense strand is conjugated to at least one ligand which is one or more GalNAc derivatives attached through a bivalent or trivalent branched linker.

2. The double stranded RNAi agent of claim 1, wherein the YYY motif occurs at or near the cleavage site of the sense strand.

3. The double stranded RNAi agent of claim 1, wherein the Y'Y'Y' motif occurs at the 11, 12 and 13 positions of the antisense strand from the 5'-end.

4. The double stranded RNAi agent of claim 1, wherein the modifications on the XXX nucleotides are different than the modifications on the X'X'X' nucleotides, the modifications on the YYY nucleotides are different than the modifications on the Y'Y'Y' nucleotides, and the modifications on the ZZZ nucleotides are different than the modifications on the Z'Z'Z' nucleotides.

5. The double stranded RNAi agent of claim 1, wherein the modifications on the YYY nucleotides are different than the modifications on the Y'Y'Y' nucleotides.

6. The double stranded RNAi agent of claim 1, wherein p'>0 and at least one np' is linked to a neighboring nucleotide via a phosphorothioate linkage.

7. The double stranded RNAi agent of claim 1, wherein the phosphorothioate or methylphosphonate internucleotide linkage is at the 5'-terminus of the sense strand; the 5'-terminus of the antisense strand; or at both the 5'-terminus of the sense strand and 5'-terminus of the antisense one strand.

8. The double stranded RNAi agent of claim 7, wherein the antisense strand comprises two phosphorothioate internucleotide linkages between the 3'-end three terminal nucleotides and two phosphorothioate internucleotide linkages between the 5' end three terminal nucleotides; and wherein the sense strand comprises two phosphorothioate internucleotide linkages between the 5' end three terminal nucleotides.

9. The double stranded RNAi agent of claim 1, wherein the double-stranded region is 15-30 nucleotide pairs in length.

10. The double stranded RNAi agent of claim 1, wherein the double-stranded region is 17-23 nucleotide pairs in length.

11. The double stranded RNAi agent of claim 1, wherein the double-stranded region is 17-25 nucleotide pairs in length.

12. The double stranded RNAi agent of claim 1, wherein the double-stranded region is 23-27 nucleotide pairs in length.

13. The double stranded RNAi agent of claim 1, wherein the double-stranded region is 19-21 nucleotide pairs in length.

14. The double stranded RNAi agent of claim 1, wherein the double-stranded region is or 21-23 nucleotide pairs in length.

15. The double stranded RNAi agent of claim 1, wherein each strand has 15-30 nucleotides.

16. The double stranded RNAi agent of claim 1, wherein the sense strand has a total of 21 nucleotides and the antisense strand has a total of 23 nucleotides.

17. The double stranded RNAi agent of claim 1, wherein the region complementary to part of an mRNA encoding PCSK9 comprises the nucleotide sequence of 5'-ACAAAAGCAAAACAGGUCUAGAA-3'(SEQ ID NO:1666).

18. The double stranded RNAi agent of claim 1, wherein the sense strand comprises the nucleotide sequence of 5'-CUAGACCUGUTUUGCUUUUGU-3' (SEQ ID NO:1665) and the antisense strand comprises the nucleotide sequence of 5'-ACAAAAGCAAAACAGGUCUAGAA-3' (SEQ ID NO:1666).

19. The double stranded RNAi agent of claim 1, wherein the antisense strand comprises the nucleotide sequence 5'-ACAAAAGCAAAACAGGUCUAG-3' (SEQ ID NO: 412) and the sense strand comprises the nucleotide sequence 5'-AGACCUGUUUUGCUUUUGU-3' (SEQ ID NO: 191).

20. The double stranded RNAi agent of claim 1, wherein the antisense strand consists of the nucleotide sequence 5'-ACAAAAGCAAAACAGGUCUAGAA-3'(SEQ ID NO:1666) and the sense strand consists of the nucleotide sequence 5'-CUAGACCUGUTUUGCUUUUGU-3' (SEQ ID NO: 1665).

21. The double stranded RNAi agent of claim 1, wherein the sense strand comprises the nucleotide sequence of 5'-csusagacCfuGfudTuugcuuuugu-3' (SEQ ID NO:1657) and the antisense strand comprises the nucleotide sequence of 5'-asCfsaAfAfAfgCfaAfaAfcAfgGfuCfuagsasa-3' (SEQ ID NO:1663), wherein a, c, g, and u are 2'-O-methyl (2'-OMe) A, C, G, and U; Af, Cf, Gf and Uf are 2'-fluoro A, C, G and U; dT is 2'-deoxythymidine; and s is a phosphorothioate linkage.

22. The double stranded RNAi agent of claim 1, wherein the double stranded RNAi agent comprises:

(a) an antisense strand consisting of the nucleotide sequence 5'-aCfaAfaAfgCfaAfaacAfgGfuCfuAfg-sAfsa-3' (SEQ ID NO: 1151) and a sense strand consisting of the nucleotide sequence 5'-CfuAfgAfcCfuG-fUfUfuUfgCfuUfuUfgUf-3' (SEQ ID NO: 600);

(b) an antisense strand consisting of the nucleotide sequence 5'-aCfaAfAfAfgCfaAfaacAfgGfuCfuAfg-sAfsa-3' (SEQ ID NO: 1246) and a sense strand consisting of the nucleotide sequence 5'-CfuAfgAfcCfuG-fUfUfuUfgCfuuuUfgUf-3' (SEQ ID NO: 695);

(c) an antisense strand consisting of the nucleotide sequence 5'-aCfaaaAfgCfaAfaacAfgGfuCfuAfgsAfsa-3' (SEQ ID NO: 1253) and a sense strand consisting of the nucleotide sequence 5'-CfuAfgAfcCfuGfUfUfuUf-gCfuUfUfUfgUf-3' (SEQ ID NO: 702);

(d) an antisense strand consisting of the nucleotide sequence 5'-aCfaAfAfAfgCfaAfaacAfgGfuCfusAfsg-3' (SEQ ID NO: 1263) and a sense strand consisting of the nucleotide sequence 5'-AfgAfcCfuGfUfUfuUfgC-fuuuUfgUf-3' (SEQ ID NO: 712);

(e) an antisense strand consisting of the nucleotide sequence 5'-aCfaaaAfgCfaAfaacAfgGfuCfusAfsg-3' (SEQ ID NO: 1269) and a sense strand consisting of the nucleotide sequence 5'-AfgAfcCfuGfUfUfuUfgCfuU-fUfUfgUf-3' (SEQ ID NO: 718);

(f) an antisense strand consisting of the nucleotide sequence 5'-asCfsaAfaAfgCfaAfaacAfgGfuCfuAfg-sasa-3' (SEQ ID NO: 1369) and a sense strand consisting of the nucleotide sequence 5'-CfsusAfgAfcCfuG-fUfUfuUfgCfuUfuUfgUf-3' (SEQ ID NO: 818);

(g) an antisense strand consisting of the nucleotide sequence 5'-asCfsaAfaagCfaAfaacAfgGfucuAfgsasa-3' (SEQ ID NO:1660) and a sense strand consisting of the nucleotide sequence 5'-CfsusAfgAfcCfuGfUfU-fuUfgcuuuugu-3' SEQ ID NO:1654); or (h) an antisense strand consisting of the nucleotide sequence 5'-asCfsaAfaAfsgCfaAfaacAfgGfuCfsuAfg-sasa-3' (SEQ ID NO: 1400) and a sense strand consisting of the nucleotide sequence 5'-CfsusAfgAfcCfuG-fUfUfuUfgCfsuUfsuUfsgsUfs-3' (SEQ ID NO: 849);

wherein a, g, c, and u are 2'-O-methyl (2'-OMe) modified A, G, C, and U nucleotides, respectively; Af, Gf, Cf and Uf are 2' fluoro A, G, C and U modified nucleotides, respectively; dT is a 2'-deoxythymidine nucleotide and s is a phosphorothioate linkage.

23. A pharmaceutical composition comprising the double stranded RNAi agent of claim 1.

24. The pharmaceutical composition of claim 23, further comprising an unbuffered solution.

25. The pharmaceutical composition of claim 24, wherein the unbuffered solution is saline or water.

26. The pharmaceutical composition of claim 23, further comprising a buffer solution.

27. The pharmaceutical composition of claim 26, wherein the buffer solution comprises acetate, citrate, prolamine, carbonate, or phosphate or any combination thereof.

28. A double stranded RNAi agent that inhibits the expression of Proprotein convertase subtilisin kexin 9 (PCSK9) in a cell, wherein said double stranded RNAi agent comprises a sense strand complementary to an antisense strand forming a double stranded region, wherein said antisense strand comprises a region complementary to part of an mRNA encoding PCSK9, wherein each strand is independently about 14 to about 30 nucleotides in length, wherein said antisense strand comprises at least 19 contiguous nucleotides of the nucleotide sequence 5'-ACAAAAGCAAAACAGGUCUAG-3' (SEQ ID NO: 412) and said double stranded RNAi agent is represented by formula Ma:

sense: 5' $n_p$-$N_a$-Y Y Y-$N_a$-$n_q$ 3' antisense: 3' $n_p'$-$N_a'$-Y'Y'Y'-$N_a'$-$n_q'$ 5' (IIIa)

wherein $n_p$, $n_q$, $n_{p'}$, and $n_{q'}$, each of which may or may not be present, each independently represents an overhang nucleotide;

p, q, and q' are each independently 0-6;

$n_p'$>0 and at least one $n_p'$ is linked to a neighboring nucleotide via a phosphorothioate linkage;

each $N_a$ and each $N_a'$ independently represents an oligonucleotide sequence comprising 0-25 nucleotides, 2-20 of which are modified nucleotides, wherein the modified nucleotides are each independently selected from the group consisting of 2'-O-methyl, 2'-fluoro, and 2'-deoxythymidine (dT);

YYY and Y'Y'Y' each independently represent one motif of three identical modifications on three consecutive nucleotides, and wherein the modifications are 2'-O-methyl or 2'-fluoro modifications;

wherein YYY is complementary to Y'Y'Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

29. The double stranded RNAi agent of claim 28, wherein the YYY motif occurs at or near the cleavage site of the sense strand.

30. The double stranded RNAi agent of claim 1 or 28, wherein each $N_a$ and each $N_a'$ independently represents an oligonucleotide sequence comprising 0-25 nucleotides which are modified, each sequence comprising at least two differently modified nucleotides.

31. The double stranded RNAi agent of claim 1 or 28, wherein each $N_a$ and each $N_a'$ independently represents an oligonucleotide sequence comprising 0-25 nucleotides which are modified, each sequence comprising at least two differently modified nucleotides, wherein the modifications on the nucleotides are independently selected from the group consisting of 2'-O-methyl, 2'-fluoro, and 2'-deoxythymidine (dT).

32. The double stranded RNAi agent of claim 1 or 28, wherein each $N_b$ and each $N_b'$ independently represents an oligonucleotide sequence comprising 0-10 nucleotides which are modified.

34. The double stranded RNAi agent of claim 1 or 28, wherein substantially all of the nucleotides of the sense strand and substantially all of the nucleotides of the antisense strand are modified nucleotides.

35. The double stranded RNAi agent of claim 1 or 28, wherein all of the nucleotides of the sense strand and all of the nucleotides of the antisense strand are modified.

36. The double stranded RNAi agent of claim 1 or 28, wherein all of the nucleotides of the sense strand and all of the nucleotides of the antisense strand are modified, and wherein the modifications on the nucleotides are independently selected from the group consisting of 2'-O-methyl, 2'-fluoro, and 2'-deoxythymidine (dT).

37. The double stranded RNAi agent of any one of claims 1, 2, 6, 9, 28, and 10-12, wherein the Y nucleotides contain a 2'-O-methyl modification and the Y' nucleotides contain a 2'-fluoro modification.

38. The double stranded RNAi agent of claim 1 or 28, wherein each strand is about 19 to about 25 nucleotides in length.

39. The double stranded RNAi agent of claim 1 or 28, wherein each strand is about 19 to about 23 nucleotides in length.

40. The double stranded RNAi agent of claim 1 or 28, wherein each strand is about 17 to about 23 nucleotides in length.

41. The double stranded RNAi agent of claim 1 or 28, wherein each strand is about 21 to about 25 nucleotides in length.

42. The double stranded RNAi agent of claim 1 or 28, wherein the ligand is

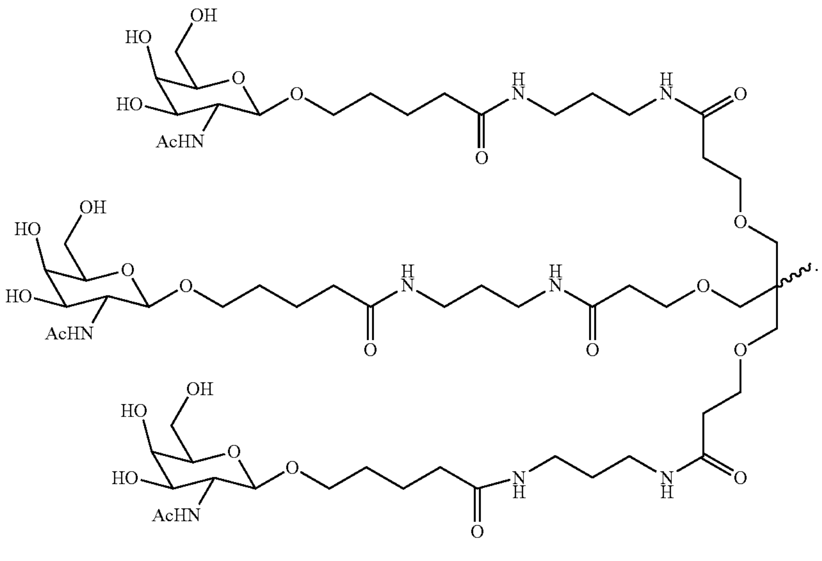 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

33. The double stranded RNAi agent of claim 1 or 28, wherein each $N_b$ and each $N_b'$ independently represents an oligonucleotide sequence comprising 0-10 nucleotides which are modified, wherein the modifications on the nucleotides are independently selected from the group consisting of 2'-O-methyl, 2'-fluoro, and 2'-deoxythymidine (dT).

43. The double stranded RNAi agent of claim 1 or 28, wherein the ligand is attached to the 3' end of the sense strand.

44. The double stranded RNAi agent of claim 43, wherein the RNAi agent is conjugated to the ligand as shown in the following schematic

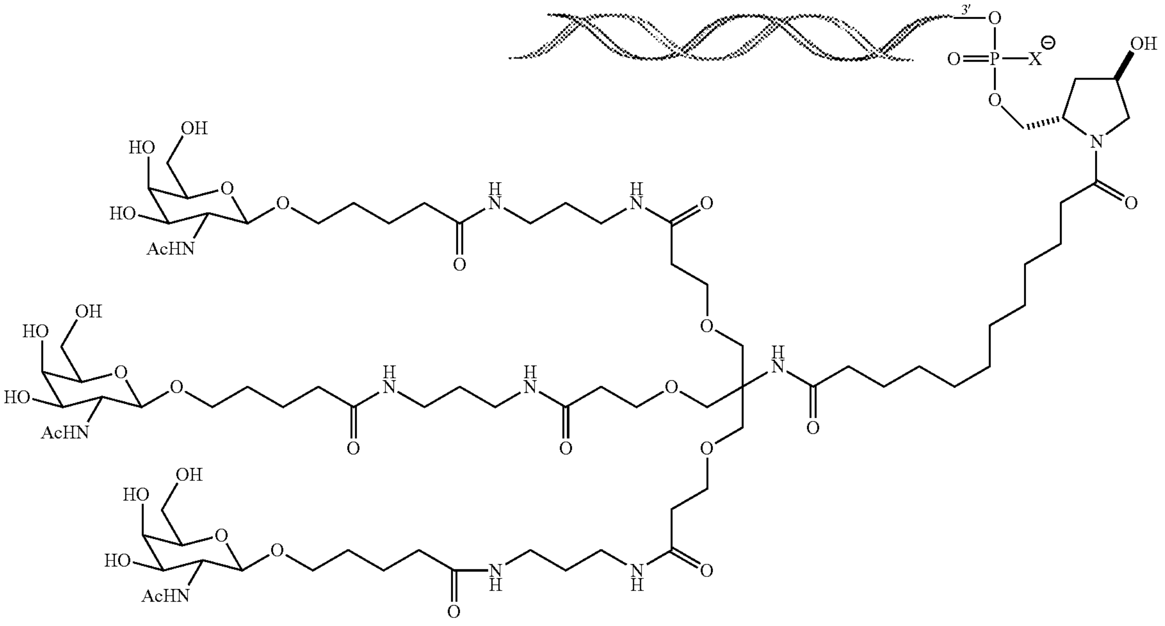

wherein X is O or S.

45. A pharmaceutical composition comprising the double stranded RNAi agent of claim 28.

46. A double stranded RNAi agent that inhibits the expression of Proprotein convertase subtilisin kexin 9 (PCSK9) in a cell, wherein said double stranded RNAi agent comprises a sense strand complementary to an antisense strand forming a double stranded region, wherein said antisense strand comprises a region complementary to part of an mRNA encoding PCSK9, wherein each strand is independently about 14 to about 30 nucleotides in length, wherein said antisense strand comprises at least 19 contiguous nucleotides of the nucleotide sequence 5'-ACAAAAGCAAAACAGGUCUAG-3' (SEQ ID NO: 412), wherein said double stranded RNAi agent comprises at least one modified nucleotide selected from the group consisting of 2'-O-methyl, 2'-fluoro, and 2'-deoxythymidine (dT);

wherein the antisense strand comprises two phosphorothioate internucleotide linkages between the 3'-end three terminal nucleotides and two phosphorothioate internucleotide linkages between the 5' end three terminal nucleotides;

wherein the sense strand comprises two phosphorothioate internucleotide linkages between the 5' end three terminal nucleotides; and wherein the sense strand is conjugated to a ligand comprising one or more GalNAc derivatives attached through a bivalent or trivalent branched linker.

47. The dsRNA agent of claim 46, wherein all of the nucleotides of the sense strand and all of the nucleotides of the antisense strand are modified nucleotides.

48. The double stranded RNAi agent of claim 46, wherein the ligand is

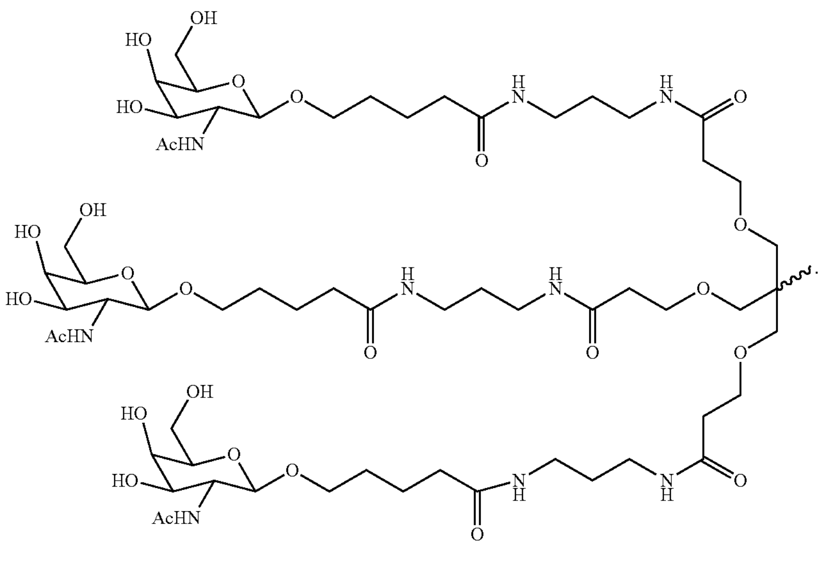 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

49. The double stranded RNAi agent of claim 46, wherein the ligand is attached to the 3' end of the sense strand.

50. The double stranded RNAi agent of claim 46, wherein the RNAi agent is conjugated to the ligand as shown in the following schematic

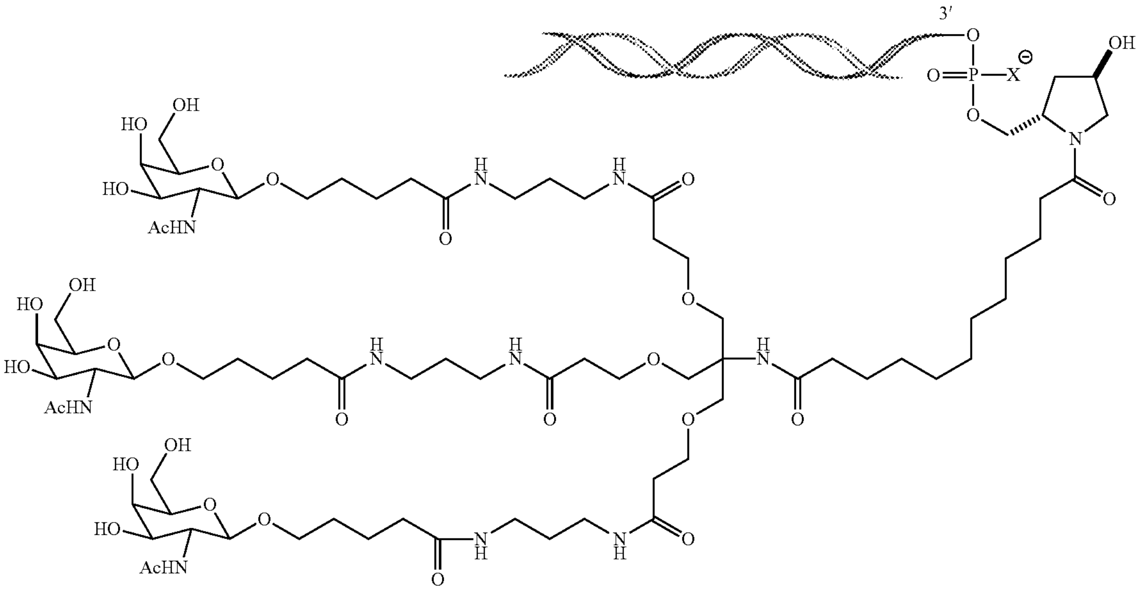

wherein X is O or S.

51. A pharmaceutical composition comprising the double stranded RNAi agent of claim 46.

52. A double stranded RNAi agent that inhibits the expression of Proprotein convertase subtilisin kexin 9 (PCSK9) in a cell, comprising a sense strand and an antisense strand, wherein the sense strand comprises the nucleotide sequence of 5'-csusagacCfuGfudTuugcuuuuguL96-3' (SEQ ID NO:1657) and the antisense strand comprises the nucleotide sequence of 5'-asCfsaAfAfAfgCfaAfaAfcAfgGfuCfuagsasa-3' (SEQ ID NO:1663), wherein a, c, g, and u are 2'-O-methyl (2'-OMe) A, C, G, and U; Af, Cf, Gf and Uf are 2'-fluoro A, C, G and U; s is a phosphorothioate linkage; dT is 2'-deoxythymidine; and L96 is N-[tris(GalNAc-alkyl)-amidodecanoyl)]-4-hydroxyprolinol.

53. An isolated cell containing the double stranded RNAi agent of claim 52.

54. A pharmaceutical composition comprising the double stranded RNAi agent of claim 52.

55. The pharmaceutical composition of claim 54, further comprising an unbuffered solution.

56. The pharmaceutical composition of claim 55, wherein the unbuffered solution is saline or water.

57. The pharmaceutical composition of claim 54, further comprising a buffer solution.

58. The pharmaceutical composition of claim 57, wherein the buffer solution comprises acetate, citrate, prolamine, carbonate, or phosphate or any combination thereof.

59. A double stranded RNAi agent that inhibits the expression of Proprotein convertase subtilisin kexin 9 (PCSK9) in a cell, comprising a sense strand and an antisense strand, wherein the sense strand consists of the nucleotide sequence of 5'-csusagacCfuGfudTuugcuuuuguL96-3' (SEQ ID NO:1657) and the antisense strand consists of the nucleotide sequence of 5'-asCfsaAfAfAfgCfaAfaAfcAfgGfuCfuagsasa-3' (SEQ ID NO:1663), wherein a, c, g, and u are 2'-O-methyl (2'-OMe) A, C, G, and U; Af, Cf, Gf, and Uf are 2'-fluoro A, C, G, and U; s is a phosphorothioate linkage; dT is 2'-deoxythymidine; and L96 is N-[tris(GalNAc-alkyl)-amidodecanoyl)]-4-hydroxyprolinol.

60. A pharmaceutical composition comprising the double stranded RNAi agent of claim 59.

61. A double stranded RNAi agent that inhibits the expression of Proprotein convertase subtilisin kexin 9 (PCSK9) in a cell, comprising a sense strand which differs by no more than 4 bases from the nucleotide sequence of 5'-asCfsaAfAfAfgCfaAfaAfcAfgGfuCfuagsasa-3' (SEQ ID NO:1663), and an antisense strand which differs by no more than 4 bases from the nucleotide sequence of 5'-csusagacCfuGfudTuugcuuuuguL96-3' (SEQ ID NO:1657), wherein a, c, g, and u are 2'-O-methyl (2'-OMe) A, C, G, and U; Af, Cf, Gf and Uf are 2'-fluoro A, C, G and U; s is a phosphorothioate linkage; dT is 2'-deoxythymidine; and L96 is N-[tris(GalNAc-alkyl)-amidodecanoyl)]-4-hydroxyprolinol.

62. The double stranded RNAi agent of claim 61, wherein the sense strand differs by no more than 3 bases from the nucleotide sequence of 5'-asCfsaAfAfAfgCfaAfaAfcAfgGfuCfuagsasa-3' (SEQ ID NO:1663), and the antisense strand differs by no more than 3 bases from the nucleotide sequence of 5'-csusagacCfuGfudTuugcuuuuguL96-3' (SEQ ID NO:1657).

63. The double stranded RNAi agent of claim 61, wherein the sense strand differs by no more than 2 bases from the nucleotide sequence of 5'-asCfsaAfAfAfgCfaAfaAfcAfgGfuCfuagsasa-3' (SEQ ID NO:1663), and the antisense strand differs by no more than 2 bases from the nucleotide sequence of 5'-csusagacCfuGfudTuugcuuuuguL96-3' (SEQ ID NO:1657).

64. An isolated cell containing the double stranded RNAi agent of any one of claims 1, 28, 46, 59, and 61.

65. A pharmaceutical composition comprising the double stranded RNAi agent of claim 61.

66. A method of inhibiting PCSK9 expression in a cell, the method comprising:

(a) contacting the cell with the double stranded RNAi agent of any one of claim, 1, 28, 17-16, 96, 10-14, 20, 59 or 61 or a pharmaceutical composition of any one of claim 23, 45, 51, 60 or 40; and (b) maintaining the cell produced in step (a) for a time sufficient to obtain degradation of the mRNA transcript of a PCSK9 gene, thereby inhibiting expression of the PCSK9 gene in the cell.

67. A method of treating a subject having lipidemia mediated by PCSK9 expression, comprising administering to the subject a therapeutically effective amount of the double stranded RNAi agent of any one of claim, 1, 28, 17-16, 46, 10-14, 20, 59 or 61 or a pharmaceutical composition of any one of claim 23, 45, 51, 60 or 40, thereby treating said subject.

68. The method of claim 67, wherein the subject is a human.

69. The method of claim 68, wherein the human has hypercholesterolemia.

70. The method of claim 67, wherein the double stranded RNAi agent is administered at a dose of about 0.01 mg/kg to about 10 mg/kg or about 0.5 mg/kg to about 50 mg/kg.

71. The method of claim 67, wherein the double stranded RNAi agent is administered in two or more doses.

72. The method of claim 71, wherein the double stranded RNAi agent is administered in a dosing regimen that includes a loading phase followed by a maintenance phase.

73. The method of claim 72, wherein the maintenance phase comprises administering a dose of the double stranded RNAi agent to the subject once every three months.

74. The method of claim 72, wherein the maintenance phase comprises administering a dose of the double stranded RNAi agent to the subject once every six months.

75. The method of claim 67, wherein the double stranded RNAi agent or the pharmaceutical composition is administered to the subject subcutaneously or intravenously.

76. A method of inhibiting PCSK9 expression in a cell, the method comprising:

(a) contacting the cell with the double stranded RNAi agent of claim 52 or the pharmaceutical composition of claim 54; and (b) maintaining the cell produced in step (a) for a time sufficient to obtain degradation of the mRNA transcript of a PCSK9 gene, thereby inhibiting expression of the PCSK9 gene in the cell.

77. A method of treating a subject having lipidemia mediated by PCSK9 expression, comprising administering to the subject a therapeutically effective amount of the double stranded RNAi agent of claim 52 or the pharmaceutical composition of claim 54, thereby treating said subject.

78. The method of claim 77, wherein the subject is a human.

79. The method of claim 78, wherein the human has hypercholesterolemia.

80. The method of claim 77, wherein the double stranded RNAi agent or the pharmaceutical composition is administered to the subject subcutaneously or intravenously.

81. The method of claim 77, wherein the double stranded RNAi agent is administered at a dose of about 0.01 mg/kg to about 10 mg/kg or about 0.5 mg/kg to about 50 mg/kg.

82. The method of claim 77, wherein the double stranded RNAi agent is administered in two or more doses.

83. The method of claim 77, wherein the double stranded RNAi agent is administered in a dosing regimen that includes a loading phase followed by a maintenance phase.

84. The method of claim 83, wherein the maintenance phase comprises administering a dose of the double stranded RNAi agent to the subject once every three months.

85. The method of claim 83, wherein the maintenance phase comprises administering a dose of the double stranded RNAi agent to the subject once every six months.

* * * * *

UNITED STATES PATENT AND TRADEMARK OFFICE
CERTIFICATE OF CORRECTION

PATENT NO. : 10,125,369 B2
APPLICATION NO. : 14/650128
DATED : November 13, 2018
INVENTOR(S) : Anna Borodovsky et al.

Page 1 of 1

It is certified that error appears in the above-identified patent and that said Letters Patent is hereby corrected as shown below:

In the Claims

At Column 753, Line 2, Claim number 14, delete "is or 21-23 nucleotide pairs" and replace it with --is 21-23 nucleotide pairs--

At Column 756, Lines 14-15, Claim number 37, delete "claims 1, 2, 6, 9, 28, and 10-12," and replace it with --claims 1-3, 9-12, or 28,--

At Column 761, Lines 4-5, Claim number 66, delete "claim, 1, 28, 17-16, 96, 10-14, 20, 59 or 61" and replace it with --claims 1, 10-14, 16-22, 28, 46, 59, or 61--

At Column 761, Line 6, Claim number 66, delete "claim 23, 45, 51, 60 or 40" and replace it with --claims 23, 45, 51, 60, or 65--

At Column 761, Line 11, Claim number 67, insert --a-- between "having" and "lipidemia"

At Column 761, Lines 14-15, Claim number 67, delete "claim, 1, 28, 17-16, 46, 10-14, 20, 59 or 61" and replace it with --claims 1, 10-14, 16-22, 28, 46, 59, or 61--

At Column 761, Line 16, Claim number 67, delete "claim 23, 45, 51, 60 or 40" and replace it with --claims 23, 45, 51, 60, or 65--

At Column 762, Line 10, Claim number 77, insert --a-- between "having" and "lipidemia"

Signed and Sealed this
Twenty-ninth Day of January, 2019

Andrei Iancu
*Director of the United States Patent and Trademark Office*

UNITED STATES PATENT AND TRADEMARK OFFICE
CERTIFICATE OF CORRECTION

PATENT NO. : 10,125,369 B2
APPLICATION NO. : 14/650128
DATED : November 13, 2018
INVENTOR(S) : Borodovsky et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this
Twenty-third Day of April, 2019

Andrei Iancu
*Director of the United States Patent and Trademark Office*

UNITED STATES PATENT AND TRADEMARK OFFICE
CERTIFICATE OF CORRECTION

PATENT NO. : 10,125,369 B2  
APPLICATION NO. : 14/650128  
DATED : November 13, 2018  
INVENTOR(S) : Anna Borodovsky et al.

Page 1 of 1

It is certified that error appears in the above-identified patent and that said Letters Patent is hereby corrected as shown below:

In the Claims

At Column 751, Line 41, Claim number 1, delete "j, k, and l" and replace it with --i, j, k, and l--

At Column 752, Line 43, Claim number 7, delete "antisense one strand." and replace it with --antisense strand.--

At Column 754, Line 50, Claim number 28, delete "Ma" and replace it with --IIIa--

At Column 760, Line 38, Claim number 61, delete "a sense" and replace it with --an antisense--

At Column 760, Line 41, Claim number 61, delete "an antisense" and replace it with --a sense--

At Column 760, Line 51, Claim number 62, delete "a sense" and replace it with --an antisense--

At Column 760, Line 53, Claim number 62, delete "an antisense" and replace it with --a sense--

At Column 760, Line 58, Claim number 63, delete "a sense" and replace it with --an antisense--

At Column 760, Line 60, Claim number 63, delete "an antisense" and replace it with --a sense--

Signed and Sealed this  
Seventh Day of April, 2020

Andrei Iancu  
*Director of the United States Patent and Trademark Office*